US010544151B2

(12) United States Patent
Ong et al.

(10) Patent No.: US 10,544,151 B2
(45) Date of Patent: *Jan. 28, 2020

(54) COMPOUNDS AND USES THEREOF

(71) Applicant: Kala Pharmaceuticals, Inc., Watertown, MA (US)

(72) Inventors: Winston Zapanta Ong, Waltham, MA (US); Pawel Wojciech Nowak, Waltham, MA (US); Ben C. Askew, Marshfield, MA (US); Andrew Good, Wallingford, CT (US)

(73) Assignee: Kala Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,937

(22) Filed: Jun. 21, 2018

(65) Prior Publication Data

US 2019/0023710 A1 Jan. 24, 2019

Related U.S. Application Data

(63) Continuation of application No. 15/970,740, filed on May 3, 2018, which is a continuation of application
(Continued)

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS 8,273,741 B2  9/2012 Sakai et al.
9,056,057 B2  6/2015 Popov et al.
(Continued)

FOREIGN PATENT DOCUMENTS

WO  2008/016131    2/2008
WO  2008/016192    2/2008
WO  2010/032880 A2  3/2010

OTHER PUBLICATIONS

U.S. Appl. No. 14/894,214, filed May 30, 2014, Novel Compounds and Uses Thereof.
(Continued)

*Primary Examiner* — Paul V Ward
(74) *Attorney, Agent, or Firm* — K&L Gates LLP; Louis C. Cullman; Michelle Glasky Bergman

(57) ABSTRACT

The present invention provides novel compounds of any one of Formulae (I)-(IV), and pharmaceutical compositions thereof. Also provided are particles (e.g., nanoparticles) comprising compounds of any one of Formulae (I)-(IV) and pharmaceutical compositions thereof that are mucus penetrating. The invention also provides methods and kits for using the inventive compounds, and pharmaceutical compositions thereof, for treating and/or preventing diseases associated with abnormal or pathological angiogenesis and/or aberrant signaling of a growth factor signaling pathway (e.g., vascular endothelial growth factor (VEGF), such as proliferative diseases (e.g., cancers, benign neoplasms, inflammatory diseases, autoimmune diseases) and ocular diseases (e.g., macular degeneration, glaucoma, diabetic retinopathy, retinoblastoma, edema, uveitis, dry eye, blepharitis, and post-surgical inflammation) in a subject in need thereof.

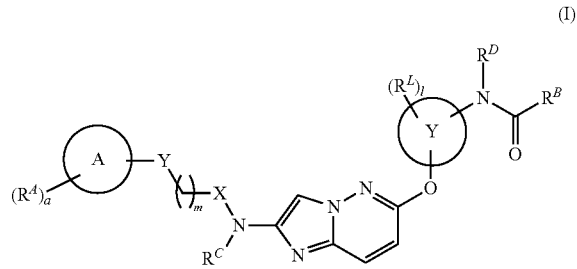

(I)

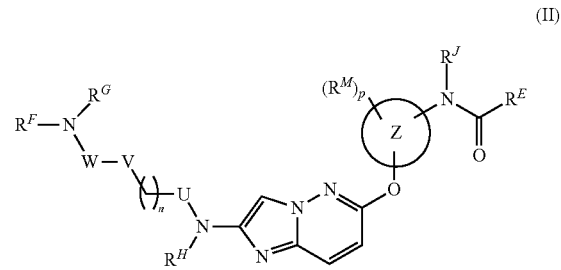

(II)

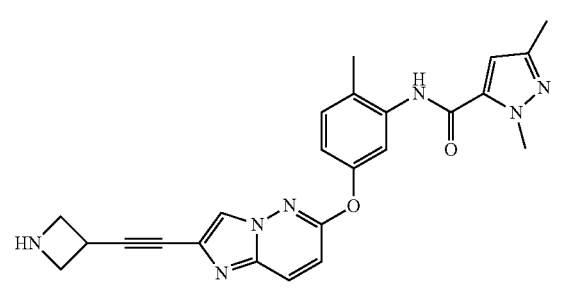

(III)

(Continued)

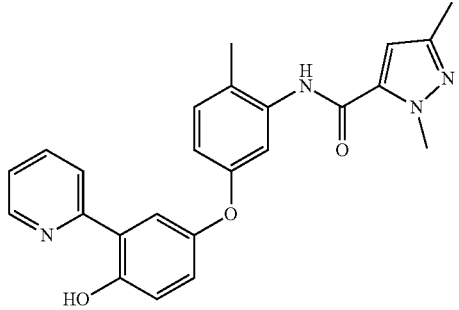

(IV)

46 Claims, No Drawings

Related U.S. Application Data

No. 14/894,214, filed as application No. PCT/US2014/040231 on May 30, 2014, now Pat. No. 9,988,386.

(60) Provisional application No. 61/829,117, filed on May 30, 2013, provisional application No. 61/898,719, filed on Nov. 1, 2013.

(56) References Cited

U.S. PATENT DOCUMENTS

| | | | |
|---|---|---|---|
| 9,988,386 B2 * | 6/2018 | Ong | C07D 487/04 |
| 2009/0137595 A1 | 5/2009 | Sakai et al. | |
| 2010/0029619 A1 | 2/2010 | Uchikawa et al. | |
| 2010/0249119 A1 | 9/2010 | Masaaki et al. | |
| 2010/0311729 A1 | 12/2010 | Capraro et al. | |
| 2013/0316001 A1 | 11/2013 | Popov et al. | |
| 2013/0316006 A1 | 11/2013 | Popov et al. | |

OTHER PUBLICATIONS

U.S. Appl. No. 15/970,740, filed May 3, 2018, Novel Compounds and Uses Thereof.
Miyamoto N et al. "Discovery of N-[5-({2-[(cyclopropylcarbonyl)amino]imidazol[1,2-b]pyridinazin-6-yl}oxy)-2-methylphenyl]-1,3-dimethyl-1H-pyrazole-5-carboxamide (TAK-593), a highly potent VEGFR2 kinase inhibitor", Bioorgan Med Chem 21:2333-2345, 2013.
Okaniwa M et al. "Design and synthesis of novel DFG-out RAF/vascular endothelial growth factor receptor 2 (VEGFR2) inhibitors. 1. Exploration of [5,6]-fused bicyclic scaffolds." J Med Chem 55:3452-3478, 2012.
CAS Registry No. 1005840-87-8 STN entry date Feb. 29, 2008; N-[6-[3-[[(1,3-dimethyl-1H-pyrazol-5-yl)carbonyl]amino]-4-fluorophenoxy]imidazo[1,2-b]pyridazin-2-yl]-4-methyl-1-piperazineacetamide.
CAS Registry No. 1005779-08-7, STN Entry Date: Feb. 29, 2008; N-[6-[3-(acetylamino)phenoxy]imidazo[1,2-b]pyridazin-2-yl-4-(1,1-dimethylethyl)-benzamide.
Fan et al., "Controlling the vasculature: angiogenesis, anti-angiogenesis and vascular targeting of gene therapy." Trends Pharmacol. Sci. 16:57-66, 1995.
Folkman, "Angiogenesis in cancer, vascular, rheumatoid and other disease." Nature Medicine 1:27-31, 1995.
Roskoski R, "Vascular endothelial growth factor (VEGF) signaling in tumor progression." Crit. Rev. Oncol./Hematol. 62:179-213, 2007.
Pinedo HM et al. "Translational Research: The role of VEGF in tumor angiogenesis" The Oncologist 5 (suppl 1):1-2, 2000.
McMahon G "VEGF receptor signaling in tumor angiogenesis" The Oncologist 5 (suppl 1):3-10, 2000.
Ogura Y et al. "Design, synthesis, and evaluation of novel VEGFR2 kinase inhibitors: discovery of [1,2,4]triazolo[1,5-a]pyridine derivatives with slow dissociation kinetics," Bioorg Med Chem 21:4714-4729, 2014.
Oguro Y et al. "Design, synthesis, and evaluation of novel VEGFR2 kinase inhibitors: discovery of [1,2,4]triazolo[1,5-a]pyridine derivatives with slow dissociation kinetics," Bioorg Med Chem 21:4714-4729, 2013.

* cited by examiner

COMPOUNDS AND USES THEREOF

CROSS REFERENCE TO RELATED APPLICATIONS

The present application is a continuation of U.S. patent application Ser. No. 15/970,740, filed May 30, 2018, which is a continuation of U.S. patent application Ser. No. 14/894,214 filed Nov. 25, 2015, which is a National Phase application under section 371 of International Patent Application PCT/US2014/040231 filed May 30, 2014, which claims the benefit of U.S. Provisional Patent Applications 61/829,117 filed May 30, 2013 and 61/898,719 filed Nov. 1, 2013. The entire contents of each of these applications are incorporated herein by reference.

BACKGROUND OF THE INVENTION

Growth factors play an important role in angiogenesis, lymphangiogenesis, and vasculogenesis. Growth factors regulate angiogenesis in a variety of processes including embryonic development, wound healing, and several aspects of female reproductive function. Undesirable or pathological angiogenesis is associated with diseases including diabetic retinopathy, psoriasis, cancer, rheumatoid arthritis, atheroma, Kaposi's sarcoma, and hemangioma (Fan et al., 1995, *Trends Pharmacol. Sci.* 16: 57 66; Folkman, 1995, *Nature Medicine* 1: 27 31). Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively. Efforts have been developed to inhibit angiogenesis in the treatment of these conditions (R. Roskoski Jr., *Critical Reviews in Oncology/Hematology*, 62 (2007), 179-213).

Therefore, there is a need for new therapeutic compounds for the treatment of diseases associated with the aberrant signaling of growth factors and diseases associated with angiogenesis, such as cancer, macular degeneration, and diabetic retinopathy.

SUMMARY OF THE INVENTION

The present invention provides novel compounds of Formulae (I)-(IV), and pharmaceutical compositions thereof, and kits useful in treating and/or preventing diseases associated with abnormal angiogenesis and/or aberrant signaling of a growth factor (e.g., vascular endothelial growth factor (VEGF)). The diseases that may be treated and/or prevented by the inventive compounds, pharmaceutical compositions, kits, uses, and methods include proliferative diseases (e.g., cancers, benign neoplasms, inflammatory diseases, autoimmune diseases) and ocular diseases (e.g., macular degeneration, glaucoma, diabetic retinopathy, retinoblastoma, edema, uveitis, dry eye, blepharitis, and post-surgical inflammation).

In one aspect, the present invention provides compounds of Formula (I):

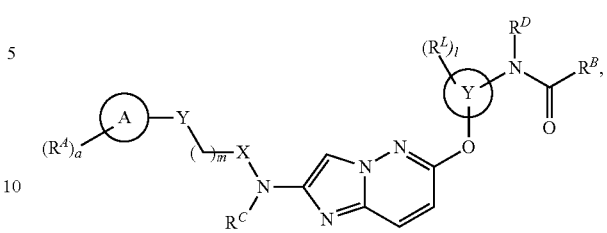

and pharmaceutically acceptable salts, solvates, hydrates, polymorphs, co-crystals, tautomers, stereoisomers, isotopically labeled derivatives, and prodrugs thereof, wherein X, Y, Ring A, Ring Y, $R^A$, $R^B$, $R^C$, $R^D$, $R^L$, a, l, and m are as defined herein.

Exemplary compounds of Formula (I) include, but are not limited to:

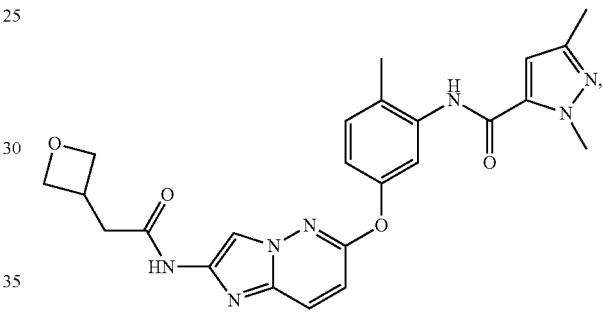

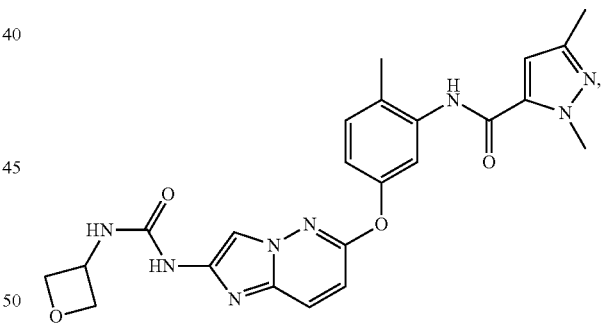

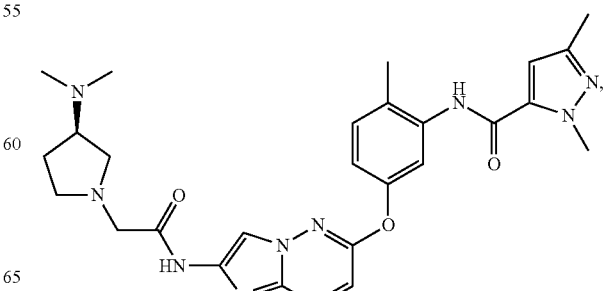

-continued

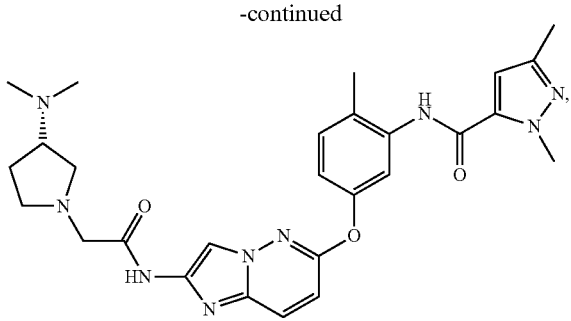

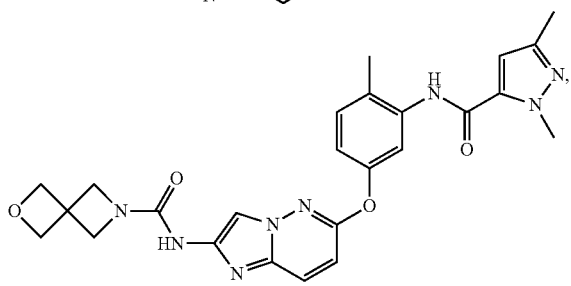

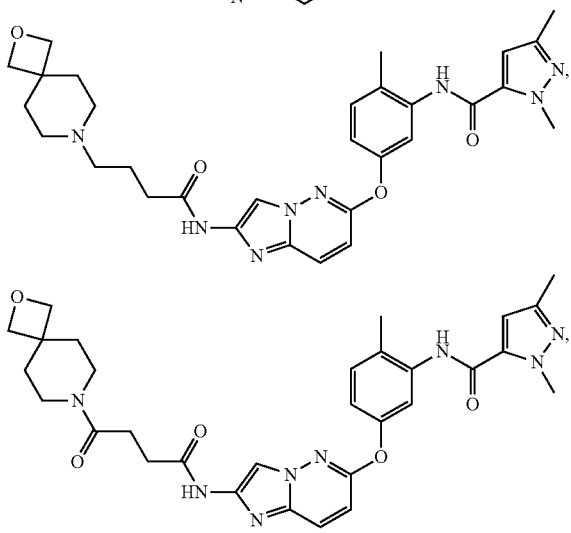

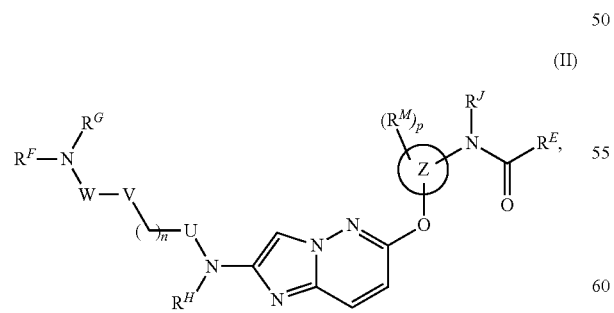

and pharmaceutically acceptable salts, solvates, hydrates, polymorphs, co-crystals, tautomers, stereoisomers, isotopically labeled derivatives, and prodrugs thereof.

In another aspect, the present invention provides compounds of Formula (II):

(II)

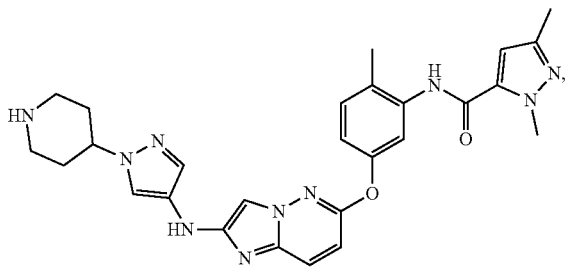 [SMILES: Cc1cc(C(=O)Nc2cc(Oc3ccc4nc(Nc5cnn(C6CCNCC6)c5)cn4n3)ccc2C)n(C)n1]

and pharmaceutically acceptable salts, solvates, hydrates, polymorphs, co-crystals, tautomers, stereoisomers, isotopically labeled derivatives, and prodrugs thereof, wherein U, V, W, Ring Z, $R^E$, $R^F$, $R^G$, $R^H$, $R^J$, $R^M$, p, and n are as defined herein.

An exemplary compound of Formula (II) is:

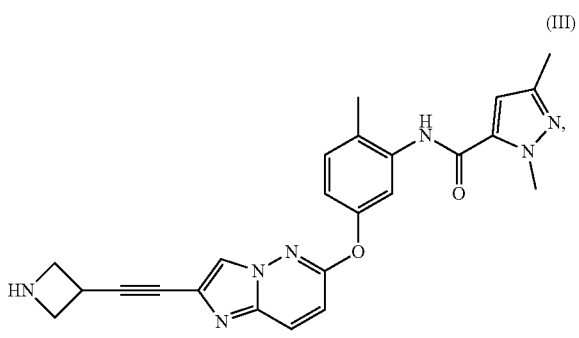 [SMILES: Cc1cc(C(=O)Nc2cc(Oc3ccc4nc(C#CC5CNC5)cn4n3)ccc2C)n(C)n1]

and pharmaceutically acceptable salts, solvates, hydrates, polymorphs, co-crystals, tautomers, stereoisomers, isotopically labeled derivatives, and prodrugs thereof.

In yet another aspect, the present invention provides the compound of Formula (III):

(III)

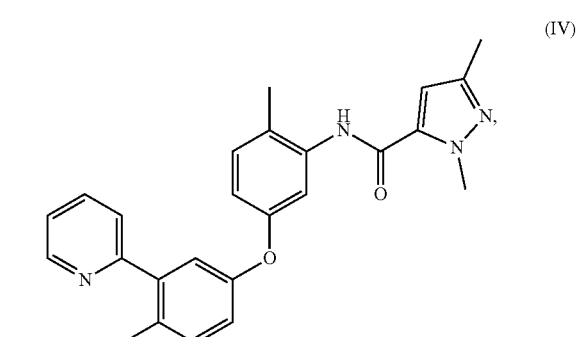

and pharmaceutically acceptable salts, solvates, hydrates, polymorphs, co-crystals, tautomers, stereoisomers, isotopically labeled derivatives, and prodrugs thereof.

In still another aspect, the present invention provides the compound of Formula (IV):

(IV)

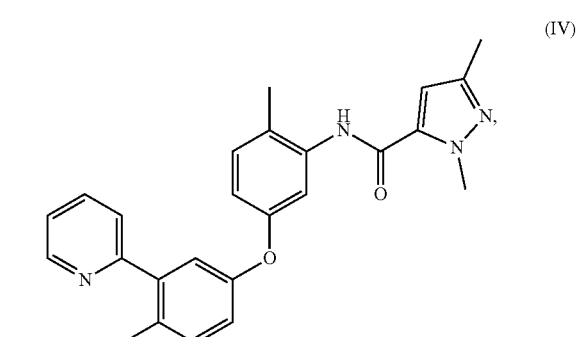

and pharmaceutically acceptable salts, solvates, hydrates, polymorphs, co-crystals, tautomers, stereoisomers, isotopically labeled derivatives, and prodrugs thereof.

In still another aspect, the present invention provides pharmaceutical compositions including a compound of the invention, and optionally a pharmaceutically acceptable excipient. In certain embodiments, the pharmaceutical compositions described herein include an effective amount of a compound of the invention. The pharmaceutical composition may be useful for treating proliferative diseases (e.g., cancers, benign neoplasms, inflammatory diseases, autoimmune diseases) and/or ocular diseases (e.g., macular degeneration, glaucoma, diabetic retinopathy, retinoblastoma, edema, uveitis, dry eye, blepharitis, and post-surgical inflammation) in a subject in need thereof. The pharmaceutical composition may also be useful for inhibiting abnormal angiogenesis and/or aberrant signaling of a growth factor in a subject or cell.

In some embodiments, the compounds described herein may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). For effective drug delivery, compound or particles that are immobilized in the mucus are quickly eliminated by mucus clearance mechanisms: therefore, they are not able to effectively deliver the intended therapeutic effect. In these tissues, for the compound to effective, it must quickly penetrate the mucus and/or avoid mucus clearance mechanisms. Accordingly, modifying mucoadhesive compounds or particles containing compounds with a coating to reduce the mucoadhesiveness, and decreasing the size of the particles of compound may allow for efficient delivery and therapeutic effect.

In one aspect of the invention, the compounds described herein are formulated into mucus penetrating particles or mucus penetrating crystals (collectively, MPPs) suitable for administration (e.g., topical or inhalation) to tissues of the subject having mucus (e.g., eye, respiratory tract, gastrointestinal tract, genito-urinary tract). In certain embodiments, the inventive compounds are crystalline.

In another aspect, the present invention provides particles containing a compound described herein or particles comprising a compound described herein. In certain embodiments, the particles are mucus penetrating. The particles of the invention may include a coating surrounding a core. The core may contain primarily a compound of the invention, or the core may be a polymeric core with the compound encapsulated in the polymer. In certain embodiments, the inventive particles are nanoparticles (e.g., particles having an average diameter of at least about 10 nm and less than about 1 µm). The inventive particles may be useful in delivering the pharmaceutical agent to a subject. In certain embodiments, the particles of the invention are capable of delivering the pharmaceutical agent in or through mucus of a subject.

Another aspect of the invention relates to pharmaceutical compositions comprising an inventive compound and/or a plurality of inventive particles. In certain embodiments, the pharmaceutical compositions are useful in delivering a pharmaceutical agent (e.g., the compound of the invention) to a subject.

In another aspect of the invention, the present invention provides pharmaceutical composition comprising a plurality of particles comprising (i) a core comprising a compound of the invention described herein, or a pharmaceutically acceptable salt thereof, and (ii) a coating of a surface altering agent surrounding the core, wherein the surface altering agent is present on the outer surface of the core at a density of at least 0.01 surface altering agent per $nm^2$, and optionally, at least one pharmaceutically acceptable excipient. In some embodiments, the surface altering agent is a triblock copolymer of the structure (hydrophilic block)-(hydrophobic block)-(hydrophilic block). In some aspects, the triblock copolymer is a Pluronic, poloxamer, poly(vinyl alcohol), or a polysorbate.

In certain embodiments, the compound, particle, or pharmaceutical composition is formulated to be mucus penetrating.

Another aspect of the present invention relates to methods of treating and/or preventing a disease associated with abnormal angiogenesis in a subject in need thereof.

Another aspect of the present invention relates to methods of treating and/or preventing a disease associated with aberrant signaling of a growth factor signaling pathway in a subject in need thereof.

In another aspect, the present invention provides methods of inhibiting angiogenesis in a subject in need thereof.

In another aspect, the present invention provides methods of inhibiting aberrant signaling of a growth factor signaling pathway in a subject or cell. In certain embodiments, the growth factor is associated with angiogenesis. In certain embodiments, the growth factor is VEGF.

The methods of the present invention include administering to the subject an effective amount of a compound or pharmaceutical composition of the invention. In certain embodiments, the effective amount is a therapeutically effective amount. In certain embodiments, the effective amount is a prophylactically effective amount.

Another aspect of the invention relates to methods of screening a library of compounds to identify one or more compounds that are useful in the methods of the invention (e.g., inhibiting abnormal angiogenesis).

In yet another aspect, the present invention provides compounds and pharmaceutical compositions of the invention for use in the treatment and/or prevention of a disease associated with abnormal angiogenesis and/or associated with aberrant signaling of a growth factor signaling pathway in a subject in need thereof.

Another aspect of the present invention relates to kits comprising a container with a compound or pharmaceutical composition of the invention. The kits of the invention may include a single dose or multiple doses of the inventive compound, or pharmaceutical compositions thereof. The provided kits may be useful in treating and/or preventing a disease associated with abnormal angiogenesis and/or with aberrant signaling of a growth factor in a subject in need thereof. The kits may also be useful for inhibiting abnormal angiogenesis and/or aberrant signaling of a growth factor signaling pathway in a subject in need thereof. In certain embodiments, the kit further includes instructions for administering the compound, or pharmaceutical composition, to the subject.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry,* University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a nonaromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_{8l}$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or Spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$—OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl; 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$) N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{dd}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, onitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (ROM), siloxymethyl, 2-methoxyethoxymethyl (MEM), 2,2,2-trichloroethoxymethyl, bis(2-chloroethoxy)methyl, 2-(tri methylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenyl methyl p-methoxyphenyidiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylyisilyl, triphenylsilyl, di phenyl methylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —C(=O)R$^{aa}$, —CO$_2$R$^{aa}$, —C(=O)N(R$^{bb}$)$_2$, —C(=NR$^{bb}$) R$^{aa}$, —C(=NR$^{bb}$)OR$^{aa}$, —C(=NR$^{bb}$)N(R$^{bb}$)$_2$, —S(=O) R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis,* T. W. Greene and P. G. M. Wuts, 3$^{rd}$ edition, John Wiley & Sons, 1999, incorporated herein by reference.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)4$^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other nonhuman animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish. A "patient" refers to a human subject in need of treatment of a disease.

The terms "administer," "administering," or "administration," as used herein, refers to implanting, absorbing, ingesting, injecting, inhaling, or otherwise introducing an inventive compound, or a pharmaceutical composition thereof, in or on a subject.

As used herein, the terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a "therapeutically effective amount" of a compound or composition is the amount needed to inhibit angiogenesis in a subject.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

As used herein, the term "growth factor" refers to a naturally occurring substance (e.g., a protein or a steroid hormone) capable of stimulating cellular growth, proliferation, and cellular differentiation. Growth factors may act as signaling molecules between cells and/or promote cell differentiation and maturation.

As used herein, the term "vascular endothelial growth factor" or "VEGF" refers to a signal protein produced by cells that stimulate vasculogenesis and angiogenesis. VEGFs are a sub-family of growth factors, i.e., the platelet-derived growth factor family of cystine-knot growth factors. VEGFs are important signaling proteins involved in both vasculogenesis and angiogenesis. VEGFs' normal function is to create new blood vessels during embryonic development, new blood vessels after injury, muscle following exercise, and new vessels (collateral circulation) to bypass blocked vessels. When VEGF is overexpressed, it can contribute to a range of diseases, such as proliferative diseases (e.g., cancer) and vascular diseases in the retina of the eye and other parts of the body. VEGFs include a number of proteins from two families that result from alternate splicing of mRNA from a single, 8-exon, VEGF gene. Examples of VEGFs include, but are not limited to, VEGF-related proteins such as placental growth factor (PGF), VEGF-A, VEGF-B, VEGF-C, VEGF-D, VEGF-E, and VEGF-F. The term "VEGF" also encompasses VEGF receptors (VEGFRs), such as VEGFR-1, VEGFR-2 and VEGFR-3. A VEGFR may be membrane-bound (mbVEGFR) or soluble (sVEGFR).

A "proliferative disease" refers to a disease that occurs due to abnormal growth or extension by the multiplication of cells (Walker, *Cambridge Dictionary of Biology;* Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

As used herein, the term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a, Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

As used herein, the term "inflammatory disease" or "inflammation" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fascilitis, and necrotizing enterocolitis. Ocular inflammatory diseases include, but are not limited to, allergy of the eye, uveitis (e.g., anterior uveitis, intermediate uveitis, and posterior uveitis), conjunctivitis, panuveitis, cyclitis, scleritis, episcleritis, optic neuritis, retrobulbar optic neuritis, keratitis (e.g., immune keratitis and infectious keratitis), blepharitis, corneal ulcer, conjunctival ulcer and symptoms caused by them, ocular inflammatory diseases caused by ocular disorders, ocular inflammatory diseases caused by a physical injury, post-surgical inflammation, and dry eye (e.g., dry eye syndrome).

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "ocular disease" or "ocular disorder" refers to any eye disease and/or disorder. For example, ocular diseases can be disorders of the eyelid, lacrimal system and orbit, disorders of conjunctiva, disorders of sclera, cornea, iris and ciliary body, disorders of choroid and retina, glaucoma, disorders of optic nerve and visual pathways, occulary inflammatory diseases, or disorders of ocular muscles.

Additionally, ocular disease can also refer to discomfort following injury, surgery, or laser treatment. Diseases and disorders of the eye include, but are not limited to, macular degeneration, dry eye syndrome, uveitis, allergic conjunctivitis, glaucoma, and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals The term "age-related macular degeneration" or "AMD" is an ocular disease which usually affects older adults and results in a loss of vision in the center of the visual field (the macula) because of damage to the retina. It occurs in "dry" and "wet" forms. It is a major cause of blindness and visual impairment in older adults (>50 years). Macular degeneration can make it difficult or impossible to read or recognize faces, although enough peripheral vision remains to allow other activities of daily life. The macula is the central area of the retina, which provides the most detailed central vision. In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached. It can be treated with laser coagulation, and with medication that stops and sometimes reverses the growth of blood vessels. Although some macular dystrophies affecting younger subjects are sometimes referred to as macular degeneration, the term generally refers to age-related macular degeneration (AMD or ARMD). AMD begins with characteristic yellow deposits (drusen) in the macula, between the retinal pigment epithelium and the underlying choroid. Most patients with these early changes (referred to as age-related maculopathy) have good vision. Patients with drusen can go on to develop advanced AMD. The risk is considerably higher when the drusen are large and numerous and associated with disturbance in the pigmented cell layer under the macula. Recent research suggests that large and soft drusen are related to elevated cholesterol deposits and may respond to cholesterol-lowering agents.

The term "macular edema" refers to ocular disease cystoid macular edema (CME) or diabetic macular edema (DME). CME is an ocular disease which affects the central retina or macula of the eye. When this condition is present, multiple cyst-like (cystoid) areas of fluid appear in the macula and cause retinal swelling or edema. CME may accompany a variety of diseases such as retinal vein occlusion, uveitis, and/or diabetes. CME commonly occurs after cataract surgery. DME occurs when blood vessels in the retina of patients with diabetes begin to leak into the macula, the part of the eye responsible for detailed central vision. These leaks cause the macula to thicken and swell, progressively distorting acute vision. While the swelling may not lead to blindness, the effect can cause a severe loss in central vision.

The term "glaucoma" refers to an ocular disease in which the optic nerve is damaged in a characteristic pattern. This can permanently damage vision in the affected eye and lead to blindness if left untreated. It is normally associated with increased fluid pressure in the eye (aqueous humor). The term ocular hypertension is used for patients with consistently raised intraocular pressure (IOP) without any associated optic nerve damage. Conversely, the term normal tension or low tension glaucoma is used for those with optic nerve damage and associated visual field loss but normal or low IOP. The nerve damage involves loss of retinal ganglion cells in a characteristic pattern. There are many different subtypes of glaucoma, but they can all be considered to be a type of optic neuropathy. Raised intraocular pressure (e.g., above 21 mmHg or 2.8 kPa) is the most important and only modifiable risk factor for glaucoma. However, some may have high eye pressure for years and never develop damage, while others can develop nerve damage at a relatively low pressure. Untreated glaucoma can lead to permanent damage of the optic nerve and resultant visual field loss, which over time can progress to blindness.

The term "uveitis" refers to an inflammatory disease of the uvea, the vascular layer of the eye sandwiched between the retina and the white of the eye (sclera). The uvea extends toward the front of the eye and consists of the iris, choroid layer and ciliary body. Uveitis includes anterior uveitis, intermediate uveitis, and posterior uveitis. A common type of uveitis is an inflammation of the iris called iritis (anterior uveitis). Uveitis may also occur at the posterior segment of the eye (e.g., at the choroid). Inflammation of the uvea can be recurring and can cause serious problems such as blindness if left untreated (accounts for 10% of blindness globally). Early diagnosis and treatment are important to prevent the complications of uveitis.

The term "dry eye" or "dry eyes" refers to an ocular disease in which there are insufficient tears to lubricate and nourish the eye. Tears are necessary for maintaining the health of the front surface of the eye and for providing clear vision. Patients with dry eyes either do not produce enough tears or have a poor quality of tears. Dry eye is a common and often chronic problem, particularly in older adults. With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose. Tears are produced by several glands (e.g., lacrimal gland) in and around the eyelids. Tear production tends to diminish with age, with various medical conditions, or as a side effect of certain medicines. Environmental conditions such as wind and dry climates can also affect tear volume by increasing tear evaporation. When the normal amount of tear production decreases or tears evaporate too quickly from the eyes, symptoms of dry eye can develop. The most common form of dry eyes is due to an inadequate amount of the water layer of tears. This condition, called keratoconjunctivitis sicca (KCS), is also referred to as "dry eye syndrome." A non-limiting example of dry eye syndrome is Sjogren's syndrome.

The term "diabetic retinopathy" refers to retinopathy (i.e., a disease of the retina) caused by complications of diabetes, which can eventually lead to blindness. Diabetic retinopathy may cause no symptoms, mild vision problems, or even blindness. Diabetic retinopathy is the result of microvascular retinal changes. Hyperglycemia-induced intramural pericyte death and thickening of the basement membrane lead to incompetence of the vascular walls. These damages change the formation of the blood-retinal barrier and also make the retinal blood vessels become more permeable. The pericyte death is caused when "hyperglycemia persistently activates protein kinase C-δ (PKC-δ, encoded by Prkcd) and p38 mitogen-activated protein kinase (MAPK) to increase the expression of a previously unknown target of PKC-δ signaling, Src homology-2 domain-containing phosphatase-1 (SHP-1), a protein tyrosine phosphatase. This signaling cascade leads to PDGF receptor-dephosphorylation and a reduction in downstream signaling from this receptor, resulting in pericyte apoptosis. Small blood vessels, such as those in the eye, are especially vulnerable to poor control over blood sugar. An overaccumulation of glucose and/or fructose damages the tiny blood vessels in the retina. During the initial stage, called "nonproliferative diabetic retinopathy" (NPDR), most patients do not notice any change in their vision. Early changes that are reversible and do not threaten central vision are sometimes termed simplex retinopathy or background retinopathy. As the disease progresses, severe nonproliferative diabetic retinopathy enters an advanced, "proliferative diabetic retinopathy" (PDR) stage when blood vessels proliferate. The lack of oxygen in the retina causes fragile, new, blood vessels to grow along the retina and in the clear, gel-like vitreous humor that fills the inside of the eye, which may result in bleeding, cloud vision, retina damage, or tractional retinal detachment.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals (e.g., crystalline forms of compounds or active pharmaceutical agent), aggregates, composites, pulverized, milled, or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle. A crystalline nanoparticle is referred to as a "nanocrystal."

The term "microparticle" refers to a particle having a characteristic dimension of less than about 1 millimeter and at least about 1 micrometer, where the characteristic dimension of the particle is the smallest cross-sectional dimension of the particle.

The term "nanostructure" refers to a structure having at least one region or characteristic dimension with a dimension of less than about 1000 nm, e.g., less than about 300 nm, less than about 200 nm, less than about 100 nm, or less than about 50 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g. heterostructures). Nanostructures can be, e.g., substantially crystalline, substantially monocrystalline, polycrystalline, amorphous, or a combination thereof. In one aspect, each of the three dimensions of the nanostructure has a dimension of less than about 1000 nm, e.g., or even less than about 300 nm, less than about 200 nm, less than about 100 nm, or less than about 50 nm. Nanostructures can comprise one or more surface ligands (e.g., surfactants).

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" to materials that are composed of substantially a single crystallite of substantially the same size and orientation.

"Nanocrystal" is a nanostructure that is substantially monocrystalline. A nanocrystal thus has at least one region or characteristic dimension with a dimension of less than about 1000 nm, e.g. less than about 300 nm less than about 200 nm, less than about 100 nm, or less than about 50 nm. Typically, the region or characteristic dimension will be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, and the like. Nanostructures can be substantially homogeneous in material properties, or in certain embodiments can be heterogeneous (e.g. heterostructures). Optionally, a nanocrystal can comprise one or more surface ligands (e.g., surfactants). The nanocrystal is optionally substantially single crystal in structure (a "single crystal nanostructure" or a "monocrystalline nanostructure"). While nanostructures for use in the present invention can be fabricated from essentially any convenient material or material, preferably the nanostructure is prepared from an inorganic material, e.g., an inorganic conductive or semiconductive material. A conductive or semi-conductive nanostructure often displays 1-dimensional quantum confinement, e.g., an electron can often travel along only one dimension of the structure. Nanocrystals can be substantially homogeneous in material properties, or in certain embodiments can be heterogeneous (e.g. heterostructures). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals can be fabricated from essentially any convenient material or materials.

The term "polycrystalline" refers to materials that are composed of many crystallites of varying size and orientation. When used with respect to nanostructures, the term "polycrystalline" refers to a crystalline nanostructure that is not monocrystalline.

A "biocompatible" material refers to a material that does not typically induce an adverse response when inserted or injected into a subject. The adverse response includes significant inflammation and/or acute rejection of the material by the immune system of the subject, for instance, via a T-cell-mediated response. It is recognized that "biocompatibility" is a relative term and that some degree of immune response is to be expected even for materials that are highly compatible with living tissues of the subject. However, as used herein, "biocompatibility" refers to the acute rejection of a material by at least a portion of the immune system, i.e., a material that lacks biocompatibility (i.e. being non-biocompatible) in a subject provokes an immune response in the subject that is severe enough such that the rejection of the material by the immune system cannot be adequately controlled and often is of a degree such that the material must be removed from the subject in order for the subject to be as well as it was before the non-biocompatible material was introduced into the subject. One test to determine biocompatibility of a material is to expose the material to cells (e.g., fibroblasts or epithelial cells) in vitro; the material is considered biocompatible if it does not result in significant cell death at moderate concentrations, e.g., at concentrations of about 50 micrograms/$10^6$ cells. In certain embodiments, there is no significant cell death if less than about 20% of the cells are dead, even if phagocytosed or otherwise uptaken by the cells. In some embodiments, a material is biocompatible if contacting it with cells in vitro results in less than 20% cell death and if the administration of the material in vivo does not induce unwanted inflammation or other adverse responses. In certain embodiments, a biocompatible material is biodegradable. A non-limiting example of biocompatible materials is biocompatible polymers (including biocompatible copolymers).

A "biodegradable" material refers to a material that is able to degrade chemically and/or biologically (e.g., by hydrolysis or enzymatic activity), within a physiological environment, such as within the body or when introduced to cells. For instance, the material may be one that hydrolyzes spontaneously upon exposure to water (e.g., within a subject) and/or may degrade upon exposure to heat (e.g., at temperatures of about 37° C.). Degradation of a material may occur at varying rates, depending on the material used. For example, the half-life of the material (the time at which 50% of the material is degraded into smaller components) may be on the order of days, weeks, months, or years. The material may be biologically degraded, e.g., by enzymatic activity or cellular machinery, for example, through exposure to a lysozyme. In some embodiments, the material may be broken down into smaller components that cells can either reuse or dispose of without significant toxic effect on the cells (e.g., fewer than about 20% of the cells are killed when the components are added to cells in vitro). Non-limiting examples of biodegradable materials are biodegradable polymers (including biodegradable copolymers). Examples of biodegradable polymers include, but are not limited to, poly(ethylene poly(propylene oxide)-poly(ethylene glycol) triblock copolymers, poly(vinyl alcohol) (PVA), poly(lactide) (or poly(lactic acid)), poly(glycolide) (or poly (glycolic acid)), poly(orthoesters), poly(caprolactones), polylysine, poly(ethylene imine), poly(acrylic acid), poly (urethanes), poly(anhydrides), poly(esters), poly(trimethylene carbonate), poly(ethyleneimine), poly(acrylic acid), poly(urethane), poly(beta amino esters), and copolymers thereof (e.g., poly(lactide-co-glycolide) (PLGA)).

As used herein, the terms "pharmaceutical composition" and "formulation" are used interchangeably.

As used herein, the terms "pharmaceutical agent" and "drug" are used interchangeably.

DETAILED DESCRIPTION OF CERTAIN EMBODIMENTS OF THE INVENTION

The present invention provides novel compounds of Formulae (I)-(IV). The invention also provides pharmaceutical compositions including the inventive compounds and kits including the inventive compounds or compositions thereof useful in treating and/or preventing diseases associated with abnormal angiogenesis and/or aberrant signaling of a growth factor pathway (e.g., vascular endothelial growth factor (VEGF)). The diseases that may be treated and/or prevented using the inventive compounds, pharmaceutical compositions, kits, uses, and methods include proliferative diseases (e.g., cancers, benign neoplasms, inflammatory diseases, autoimmune diseases) and ocular diseases (e.g., macular degeneration, glaucoma, diabetic retinopathy, retinoblastoma, edema, uveitis, dry eye, blepharitis, and post-surgical inflammation).

Compounds

The present invention provides compounds of Formula (I):

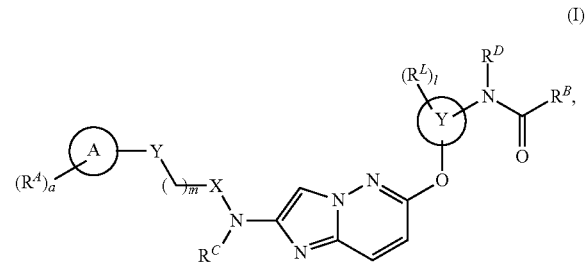

and pharmaceutically acceptable salts, solvates, hydrates, polymorphs, co-crystals, tautomers, stereoisomers, isotopically labeled derivatives, and prodrugs thereof;
wherein:
X is a bond, —C(═O)—, —S(═O)—, or —S(═O)$_2$—;
Y is a bond, —C(═O)—, —S(═O)—, or —S(═O)$_2$—;
Ring A is substituted or unsubstituted, 4- to 7-membered, monocyclic heterocyclyl, or substituted or unsubstituted, 7- to 10-membered, spiro bicyclic heterocyclyl, wherein one or two atoms in the heterocyclic ring are independently selected from the group consisting of oxygen and nitrogen;

Ring Y is substituted or unsubstituted carbocyclyl, substituted or unsubstituted heterocyclyl, substituted or unsubstituted aryl, or substituted or unsubstituted heteroaryl;

each instance of $R^A$ is independently hydrogen, halogen, substituted or unsubstituted alkyl, —$OR^{A1}$, —$N(R^{A1})_2$, oxo, or a nitrogen protecting group when attached to a nitrogen atom;

each instance of $R^{A1}$ is independently hydrogen, substituted or unsubstituted alkyl, a nitrogen protecting group when attached to a nitrogen atom, or an oxygen protecting group when attached to an oxygen atom, or two instances of $R^{A1}$ are joined to form substituted or unsubstituted heterocyclyl;

a is 0, 1, 2, or 3;

$R^B$ is substituted or unsubstituted alkyl or of the formula:

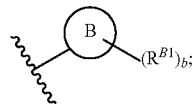

Ring B is substituted or unsubstituted carbocyclyl, substituted or unsubstituted heterocyclyl, substituted or unsubstituted aryl, or substituted or unsubstituted heteroaryl;

each instance of $R^{B1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1a}$, —$N(R^{B1a})_2$, —$SR^{B1a}$, —CN, —SCN, —$C(=NR^{B1a})R^{B1a}$, —$C(=NR^{B1a})OR^{B1a}$, —$C(=NR^{B1a})N(R^{B1a})_2$, —$C(\alpha O)R^{B1a}$, —$C(=O)OR^{B1a}$, —$C(=O)N(R^{B1a})_2$, —$NO_2$, —$NR^{B1a}C(=O)R^{B1a}$, —$NR^{B1a}C(=O)OR^{B1a}$, —$NR^{B1a}C(=O)N(R^{B1a})_2$, —$OC(=O)R^{B1a}$, —$OC(=O)OR^{B1a}$, —$OC(=O)N(R^{B1a})_2$, or a nitrogen protecting group when attached to a nitrogen atom, or two instances of $R^{B1}$ are joined to form substituted or unsubstituted carbocyclyl, substituted or unsubstituted heterocyclyl, substituted or unsubstituted aryl, or substituted or unsubstituted heteroaryl;

each instance of $R^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{B1a}$ are joined to form substituted or unsubstituted heterocyclyl;

b is 0, 1, 2, 3, 4, or 5;

$R^C$ is hydrogen, substituted or unsubstituted $C_{1-6}$ alkyl, or a nitrogen protecting group;

$R^D$ is hydrogen, substituted or unsubstituted $C_{1-6}$ alkyl, or a nitrogen protecting group;

each instance of $R^L$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{L1}$, —$N(R^{L1})_2$, —$SR^{L1}$, —CN, —SCN, —$C(=NR^{L1})R^{L1}$, —$C(=NR^{L1})OR^{L1}$, —$C(=NR^{L1})N(R^{L1})_2$, —$C(=O)R^{L1}$, —$C(=O)OR^{L1}$, —$C(=O)N(R^{L1})_2$, —$NO_2$, —$NR^{L1}C(=O)R^{L1}$, —$NR^{L1}C(=O)OR^{L1}$, —$NR^{L1}C(=O)N(R^{L1})_2$, —$OC(=O)R^{L1}$, —$OC(=O)OR^{L1}$, or —$OC(=O)N(R^{L1})_2$, or two instances of $R^L$ are joined to form substituted or unsubstituted carbocyclyl, substituted or unsubstituted heterocyclyl, substituted or unsubstituted aryl, or substituted or unsubstituted heteroaryl;

each instance of $R^{L1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{L1}$ are joined to form substituted or unsubstituted heterocyclyl;

l is 0, 1, 2, 3, or 4; and m is 0, 1, 2, 3, 4, or 5.

Compounds of Formula (I) include moiety X. In certain embodiments, X is a bond. In certain embodiments, X is a single bond. In certain embodiments, X is —C(=O)—. In certain embodiments, X is —S(=O)—. In certain embodiments, X is —S(=O)$_2$—.

Compounds of Formula (I) include moiety Y. In certain embodiments, Y is a bond. In certain embodiments, Y is a single bond. In certain embodiments, Y is —C(=O)—. In certain embodiments, Y is —S(=O)—. In certain embodiments, Y is —S(=O)$_2$—.

In certain embodiments, each one of X and Y is a bond. In certain embodiments, X is a bond; and Y is —C(=O)—, —S(=O)—, or —S(=O)$_2$—. In certain embodiments, X is —C(=O)—, —S(=O)—, or —S(=O)$_2$—; and Y is a bond. In certain embodiments, each one of X and Y is independently —C(=O)—, —S(=O)—, or —S(=O)$_2$—. In certain embodiments, X is a bond; and Y is —C(=O)—. In certain embodiments, X is —C(=O)—; and Y is a bond. In certain embodiments, each one of X and Y is —C(=O)—.

Compounds of Formula (I) include Ring A that is attached to Y. In certain embodiments, Ring A is substituted or unsubstituted, 4- to 7-membered, monocyclic heterocyclyl, wherein one or two atoms in the heterocyclic ring are independently oxygen or nitrogen. In certain embodiments, Ring A is substituted or unsubstituted, 4- to 6-membered, monocyclic heterocyclyl, wherein one atom in the heterocyclic ring is oxygen. In certain embodiments, Ring A is substituted oxetanyl. In certain embodiments, Ring A is of the formula:

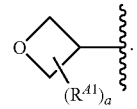

In certain embodiments, Ring A is unsubstituted oxetanyl. In certain embodiments, Ring A is of the formula:

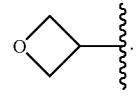

In certain embodiments, Ring A is of the formula:

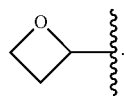

In certain embodiments, Ring A is of the formula:

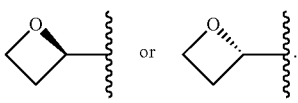

In certain embodiments, Ring A is substituted tetrahydrofuranyl. In certain embodiments, Ring A is unsubstituted tetrahydrofuranyl. In certain embodiments, Ring A is substituted tetrahydropyranyl. In certain embodiments, Ring A is unsubstituted tetrahydropyranyl. In certain embodiments, Ring A is substituted or unsubstituted, 4- to 7-membered, monocyclic heterocyclyl, wherein one atom in the heterocyclic ring is nitrogen. In certain embodiments, Ring A is substituted pyrrolidinyl. In certain embodiments, Ring A is of the formula:

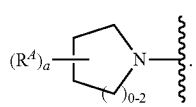

In certain embodiments, Ring A is of the formula:

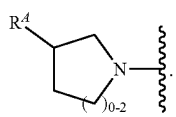

In certain embodiments, Ring A is of the formula:

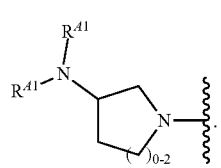

In certain embodiments, Ring A is of the formula:

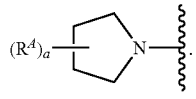

In certain embodiments, Ring A is of the formula:

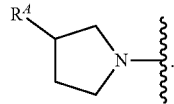

In certain embodiments, Ring A is of the formula:

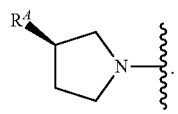

In certain embodiments, Ring A is of the formula:

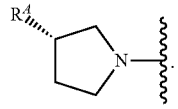

In certain embodiments, Ring A is of the formula:

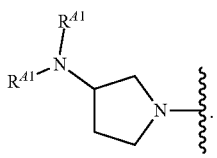

In certain embodiments, Ring A is of the formula:

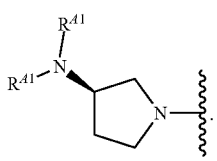

In certain embodiments, Ring A is of the formula:

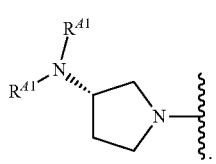

In certain embodiments, Ring A is of the formula:

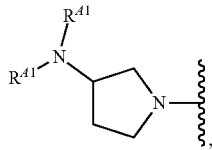

wherein at least one $R^{A1}$ is substituted alkyl. In certain embodiments, Ring A is of the formula:

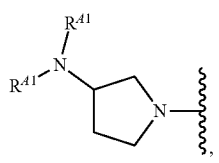

wherein at least one $R^{41}$ is unsubstituted alkyl. In certain embodiments, Ring A is of the formula:

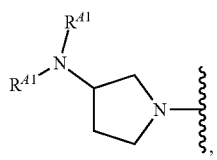

wherein at least one $R^{41}$ is unsubstituted $C_{1-6}$ alkyl. In certain embodiments, Ring A is unsubstituted pyrrolidinyl. In certain embodiments, Ring A is of the formula:

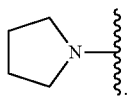

In certain embodiments, Ring A is substituted piperidinyl. In certain embodiments, Ring A is of the formula:

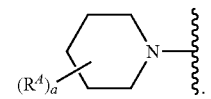

In certain embodiments, Ring A is of the formula:

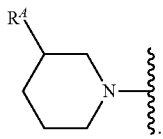

In certain embodiments, Ring A is of the formula:

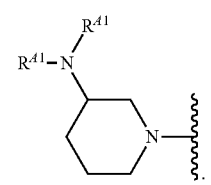

In certain embodiments, Ring A is of the formula:

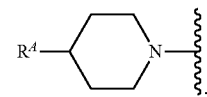

In certain embodiments, Ring A is of the formula:

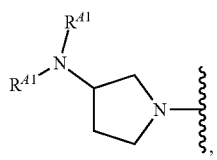

In certain embodiments, Ring A is unsubstituted piperidinyl. In certain embodiments, Ring A is of the formula:

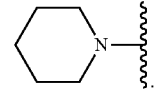

In certain embodiments, Ring A is substituted or unsubstituted, 7- to 10-membered, spiro bicyclic heterocyclyl, wherein two atoms in the heterocyclic ring are independently selected from the group consisting of oxygen and nitrogen. In certain embodiments, Ring A is of the formula:

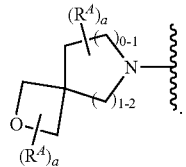

In certain embodiments, Ring A is of the formula:

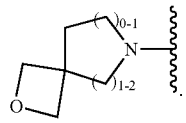

In certain embodiments, Ring A is of the formula:

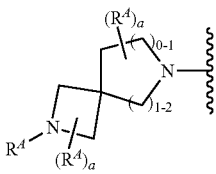

In certain embodiments, Ring A is of the formula:

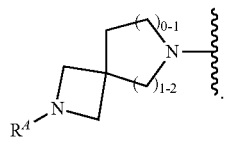

In certain embodiments, Ring A is of the formula:

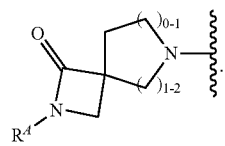

In certain embodiments, Ring A is of the formula:

In certain embodiments, Ring A is of the formula:

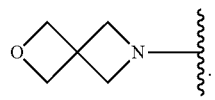

In certain embodiments, Ring A is of the formula:

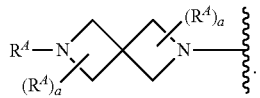

In certain embodiments, Ring A is of the formula:

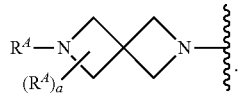

In certain embodiments, Ring A is of the formula:

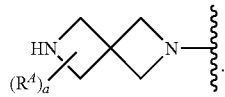

In certain embodiments, Ring A is of the formula:

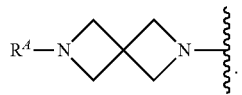

In certain embodiments, Ring A is of the formula:

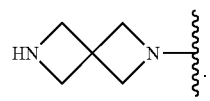

In certain embodiments, Ring A is of the formula:

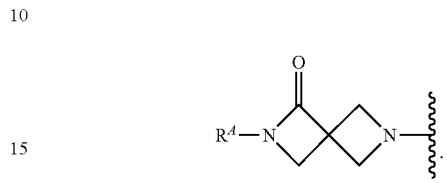

In certain embodiments, Ring A is of the formula:

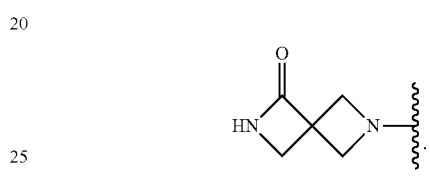

In certain embodiments, Ring A is of the formula:

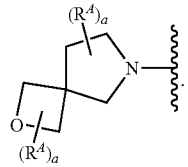

In certain embodiments, Ring A is of the formula:

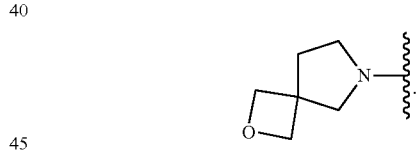

In certain embodiments, Ring A is of the formula:

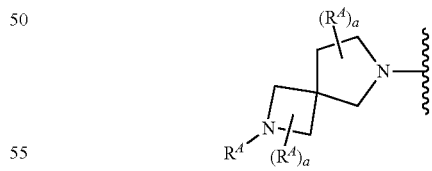

In certain embodiments, Ring A is of the formula:

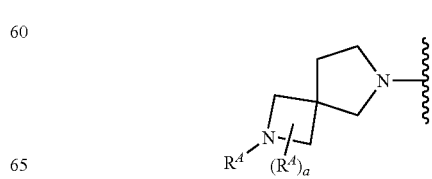

In certain embodiments, Ring A is of the formula:

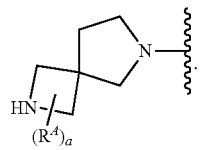

In certain embodiments, Ring A is of the formula:

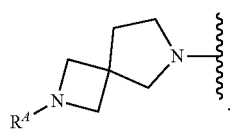

In certain embodiments, Ring A is of the formula:

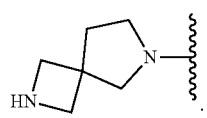

In certain embodiments, Ring A is of the formula:

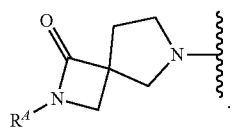

In certain embodiments, Ring A is of the formula:

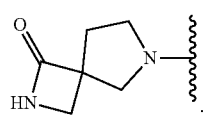

In certain embodiments, Ring A is of the formula:

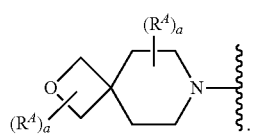

In certain embodiments, Ring A is of the formula:

In certain embodiments, Ring A is of the formula:

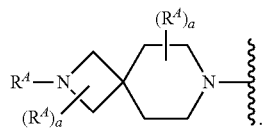

In certain embodiments, Ring A is of the formula:

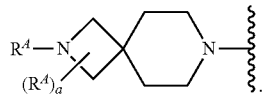

In certain embodiments, Ring A is of the formula:

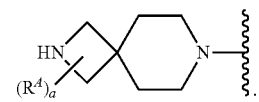

In certain embodiments, Ring A is of the formula:

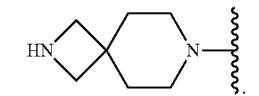

In certain embodiments, Ring A is of the formula:

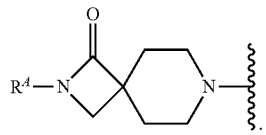

In certain embodiments, Ring A is of the formula:

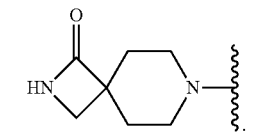

Compounds of Formula (I) may include one or more substituents $R^A$ on Ring A. In certain embodiments, at least one instance of $R^A$ is H. In certain embodiments, at least one instance of $R^A$ is halogen. In certain embodiments, at least one instance of $R^A$ is F. In certain embodiments, at least one instance of $R^A$ is Cl. In certain embodiments, at least one instance of $R^A$ is Br. In certain embodiments, at least one instance of $R^A$ is I (iodine). In certain embodiments, at least one instance of $R^A$ is substituted alkyl. In certain embodiments, at least one instance of $R^A$ is unsubstituted alkyl. In certain embodiments, at least one instance of $R^A$ is $C_{1-12}$ alkyl. In certain embodiments, at least one instance of $R^A$ is $C_{1-6}$ alkyl. In certain embodiments, at least one instance of $R^A$ is unsubstituted methyl. In certain embodiments, at least one instance of $R^A$ is substituted methyl. In certain embodiments, at least one instance of $R^A$ is —CH$_2$F. In certain embodiments, at least one instance of $R^A$ is —CHF$_2$. In certain embodiments, at least one instance of $R^A$ is —CF$_3$. In certain embodiments, at least one instance of $R^A$ is Bn. In certain embodiments, at least one instance of $R^A$ is unsubstituted ethyl. In certain embodiments, at least one instance of $R^A$ is substituted ethyl. In certain embodiments, at least one instance of $R^A$ is —(CH$_2$)$_2$Ph. In certain embodiments, at least one instance of $R^A$ is substituted or unsubstituted propyl. In certain embodiments, at least one instance of $R^A$ is substituted or unsubstituted butyl. In certain embodiments, at least one instance of $R^A$ is substituted or unsubstituted pentyl. In certain embodiments, at least one instance of $R^A$ is substituted or unsubstituted hexyl. In certain embodiments, at least one instance of $R^A$ is halogen or unsubstituted $C_{1-6}$ alkyl. In certain embodiments, at least one instance of $R^A$ is —OR$^{A1}$. In certain embodiments, at least one instance of $R^A$ is —OR$^{A1}$, wherein $R^{A1}$ is substituted alkyl. In certain embodiments, at least one instance of $R^A$ is —OR$^{A1}$, wherein $R^{A1}$ is unsubstituted alkyl. In certain embodiments, at least one instance of $R^A$ is —OR$^{A1}$, wherein $R^{A1}$ is substituted $C_{1-6}$ alkyl. In certain embodiments, at least one instance of $R^A$ is —OR$^{A1}$, wherein $R^{A1}$ is unsubstituted $C_{1-6}$ alkyl. In certain embodiments, at least one instance of $R^A$ is —OPh. In certain embodiments, at least one instance of $R^A$ is —OBn. In certain embodiments, at least one instance of $R^A$ is —O(CH$_2$)$_2$Ph. In certain embodiments, at least one instance of $R^A$ is —OH. In certain embodiments, at least one instance of $R^A$ is —N(R$^{A1}$)$_2$. In certain embodiments, at least one instance of $R^A$ is —N(R$^{A1}$)$_2$, wherein at least one instance of $R^{A1}$ is substituted alkyl. In certain embodiments, at least one instance of $R^A$ is —N(R$^{A1}$)$_2$, wherein at least one instance of $R^{A1}$ is unsubstituted alkyl. In certain embodiments, at least one instance of $R^A$ is —N(R$^{A1}$)$_2$, wherein at least one instance of $R^{A1}$ is substituted $C_{1-6}$ alkyl. In certain embodiments, at least one instance of $R^A$ is —N(R$^{A1}$)$_2$, wherein at least one instance of $R^{A1}$ is unsubstituted $C_{1-6}$ alkyl. In certain embodiments, at least one instance of $R^A$ is —NH$_2$. In certain embodiments, at least one instance of $R^A$ is oxo (=O). In certain embodiments, at least one instance of $R^A$ is a nitrogen protecting group when attached to a nitrogen atom. In certain embodiments, at least one instance of $R^A$ is Bn, Boc, Cbz, Fmoc, trifluoroacetyl, triphenylmethyl, acetyl, or Ts when attached to a nitrogen atom.

In certain embodiments, at least one instance of $R^{A1}$ is H. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is substituted $C_{1-6}$ alkyl. In certain embodiments, at least one instance of $R^{A1}$ is unsubstituted $C_{1-6}$ alkyl. In certain embodiments, at least one instance of $R^{A1}$ is unsubstituted methyl. In certain embodiments, at least one instance of $R^{A1}$ is substituted methyl. In certain embodiments, at least one instance of $R^{A1}$ is —CH$_2$F. In certain embodiments, at least one instance of $R^{A1}$ is —CHF$_2$. In certain embodiments, at least one instance of $R^{A1}$ is —CF$_3$. In certain embodiments, at least one instance of $R^{A1}$ is Bn. In certain embodiments, at least one instance of $R^{A1}$ is unsubstituted ethyl. In certain embodiments, at least one instance of $R^{A1}$ is substituted ethyl. In certain embodiments, at least one instance of $R^{A1}$ is —(CH$_2$)$_2$Ph. In certain embodiments, at least one instance of $R^{A1}$ is propyl. In certain embodiments, at least one instance of $R^{A1}$ is butyl. In certain embodiments, at least one instance of $R^{A1}$ is pentyl. In certain embodiments, at least one instance of $R^{A1}$ is hexyl. In certain embodiments, at least one instance of $R^{A1}$ is a nitrogen protecting group when attached to a nitrogen atom. In certain embodiments, at least one instance of $R^{A1}$ is Bn, Boc, Cbz, Fmoc, trifluoroacetyl, triphenylmethyl, acetyl, or Ts when attached to a nitrogen atom. In certain embodiments, at least one instance of $R^{A1}$ is an oxygen protecting group when attached to an oxygen atom. In certain embodiments, at least one instance of $R^{A1}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, two instances of $R^{A1}$ are joined to form substituted or unsubstituted heterocyclyl. In certain embodiments, two instances of $R^{A1}$ are joined to form saturated or unsaturated heterocyclyl. In certain embodiments, two instances of $R^{A1}$ are joined to form heterocyclyl including one, two, or three double bonds in the ring of the heterocyclyl. In certain embodiments, two instances of $R^{A1}$ are joined to form heterocyclyl, wherein one, two, or three atoms in the ring of the heterocyclyl are independently selected from the group consisting of nitrogen, oxygen, and sulfur. In certain embodiments, two instances of $R^{A1}$ are joined to form 3- to 7-membered, monocyclic heterocyclyl. In certain embodiments, two instances of $R^{A1}$ are joined to form 5- to 13-membered, bicyclic heterocyclyl.

In certain embodiments, a is 0. In certain embodiments, a is 1. In certain embodiments, a is 2. In certain embodiments, a is 3.

In certain embodiments, $R^A$ is —N(R$^{A1}$)$_2$; and a is 1. In certain embodiments, $R^A$ is —N(unsubstituted $C_{1-6}$ alkyl)$_2$; and a is 1. In certain embodiments, $R^A$ is oxo (=O); and a is 1.

Compounds of Formula (I) include Ring Y. In certain embodiments, Ring Y is substituted carbocyclyl. In certain embodiments, Ring Y is unsubstituted carbocyclyl. In certain embodiments, Ring Y is saturated carbocyclyl. In certain embodiments, Ring Y is unsaturated carbocyclyl. In certain embodiments, Ring Y is carbocyclyl including one, two, or three double bonds in the carbocyclic ring. In certain embodiments, Ring Y is monocyclic carbocyclyl. In certain embodiments, Ring Y is 3- to 7-membered, monocyclic carbocyclyl. In certain embodiments, Ring Y is substituted cyclopropyl. In certain embodiments, Ring Y is unsubstituted cyclopropyl. In certain embodiments, Ring Y is cyclobutyl. In certain embodiments, Ring Y is cyclopentyl. In certain embodiments, Ring Y is cyclohexyl. In certain embodiments, Ring Y is cycloheptyl. In certain embodiments, Ring Y is bicyclic carbocyclyl. In certain embodiments, Ring Y is 5- to 13-membered, bicyclic carbocyclyl.

In certain embodiments, Ring Y is substituted heterocyclyl. In certain embodiments, Ring Y is unsubstituted heterocyclyl. In certain embodiments, Ring Y is saturated heterocyclyl. In certain embodiments, Ring Y is unsaturated heterocyclyl. In certain embodiments, Ring Y is heterocyclyl including one, two, or three double bonds in the heterocyclic ring. In certain embodiments, Ring Y is heterocyclyl, wherein one, two, or three atoms in the heterocyclic ring are independently selected from the group consisting of nitrogen, oxygen, and sulfur. In certain embodiments, Ring Y is monocyclic heterocyclyl. In certain embodiments, Ring Y is 3- to 7-membered, monocyclic heterocyclyl. In certain embodiments, Ring Y is 5-membered, monocyclic heterocyclyl. In certain embodiments, Ring Y is substituted or unsubstituted tetrahydrofuranyl. In certain embodiments, Ring Y is 6-membered, monocyclic heterocyclyl. In certain embodiments, Ring Y is substituted or unsubstituted tetrahydropyranyl. In certain embodiments, Ring Y is bicyclic heterocyclyl. In certain embodiments, Ring Y is 5- to 13-membered, bicyclic heterocyclyl.

In certain embodiments, Ring Y is substituted aryl. In certain embodiments, Ring Y is unsubstituted aryl. In certain embodiments, Ring Y is 6- to 14-membered aryl. In certain embodiments, Ring Y is 6- to 10-membered aryl. In certain embodiments, Ring Y is unsubstituted phenyl. In certain embodiments, Ring Y is substituted phenyl. In certain embodiments, Ring Y is of the formula:

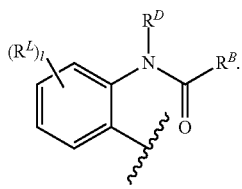

In certain embodiments, Ring Y is of the formula:

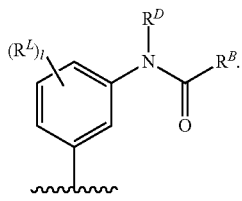

In certain embodiments, Ring Y is of the formula:

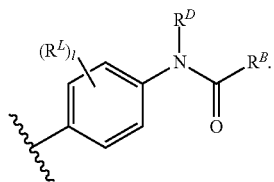

In certain embodiments, Ring Y is substituted heteroaryl. In certain embodiments, Ring Y is unsubstituted heteroaryl. In certain embodiments, Ring Y is 5- to 6-membered, monocyclic heteroaryl, wherein one, two, three, or four atoms in the heteroaryl ring are independently selected from the group consisting of nitrogen, oxygen, and sulfur. In certain embodiments, Ring Y is 5-membered, monocyclic heteroaryl. In certain embodiments, Ring Y is 5-membered, monocyclic heteroaryl, wherein one of the five atoms in the heteroaryl ring is nitrogen, oxygen, or sulfur.

Compounds of Formula (I) include substituent $R^B$. In certain embodiments, $R^B$ is substituted alkyl. In certain embodiments, $R^B$ is unsubstituted alkyl. In certain embodiments, $R^B$ is substituted $C_{1-6}$ alkyl. In certain embodiments, $R^B$ is unsubstituted $C_{1-6}$ alkyl. In certain embodiments, $R^B$ is unsubstituted methyl. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is Bn. In certain embodiments, $R^B$ is unsubstituted ethyl. In certain embodiments, $R^B$ is substituted ethyl. In certain embodiments, $R^B$ is —$(CH_2)_2Ph$. In certain embodiments, $R^B$ is propyl. In certain embodiments, $R^B$ is butyl. In certain embodiments, $R^B$ is unsubstituted t-butyl. In certain embodiments, $R^B$ is pentyl. In certain embodiments, $R^B$ is hexyl.

In certain embodiments, $R^B$ is of the formula:

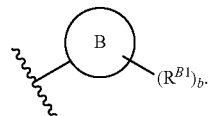

In certain embodiments, Ring B is substituted carbocyclyl. In certain embodiments, Ring B is unsubstituted carbocyclyl. In certain embodiments, Ring B is saturated carbocyclyl. In certain embodiments, Ring B is unsaturated carbocyclyl. In certain embodiments, Ring B is carbocyclyl including one, two, or three double bonds in the carbocyclic ring. In certain embodiments, Ring B is monocyclic carbocyclyl. In certain embodiments, Ring B is 3- to 7-membered, monocyclic carbocyclyl. In certain embodiments, Ring B is substituted cyclopropyl. In certain embodiments, Ring B is unsubstituted cyclopropyl. In certain embodiments, Ring B is cyclobutyl. In certain embodiments, Ring B is cyclopentyl. In certain embodiments, Ring B is cyclohexyl. In certain embodiments, Ring B is cycloheptyl. In certain embodiments, Ring B is bicyclic carbocyclyl. In certain embodiments, Ring B is 5- to 13-membered, bicyclic carbocyclyl.

In certain embodiments, Ring B is substituted heterocyclyl. In certain embodiments, Ring B is unsubstituted heterocyclyl. In certain embodiments, Ring B is saturated heterocyclyl. In certain embodiments, Ring B is unsaturated heterocyclyl. In certain embodiments, Ring B is heterocyclyl including one, two, or three double bonds in the heterocyclic ring. In certain embodiments, Ring B is heterocyclyl, wherein one, two, or three atoms in the heterocyclic ring are independently selected from the group consisting of nitrogen, oxygen, and sulfur. In certain embodiments, Ring B is monocyclic heterocyclyl. In certain embodiments, Ring B is 3- to 7-membered, monocyclic heterocyclyl. In certain embodiments, Ring B is 5-membered, monocyclic heterocyclyl. In certain embodiments, Ring B is substituted or unsubstituted tetrahydrofuranyl. In certain embodiments, Ring B is 6-membered, monocyclic heterocyclyl. In certain embodiments, Ring B is substituted or unsubstituted tetrahydropyranyl. In certain embodiments, Ring B is bicyclic heterocyclyl. In certain embodiments, Ring B is 5- to 13-membered, bicyclic heterocyclyl.

In certain embodiments, Ring B is substituted aryl. In certain embodiments, Ring B is unsubstituted aryl. In certain embodiments, Ring B is 6- to 14-membered aryl. In certain embodiments, Ring B is 6- to 10-membered aryl. In certain embodiments, Ring B is unsubstituted phenyl. In certain embodiments, Ring B is substituted phenyl. In certain embodiments, Ring B is of the formula:

In certain embodiments, Ring B is of the formula:

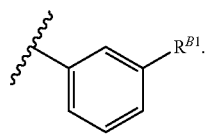

In certain embodiments, Ring B is of the formula:

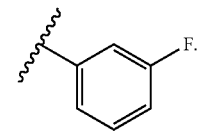 [SMILES: *c1cccc(F)c1]

In certain embodiments, Ring B is of the formula:

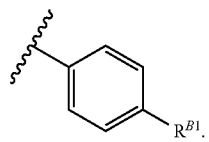

In certain embodiments, Ring B is of the formula:

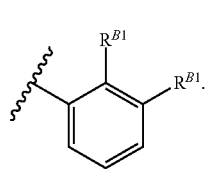

In certain embodiments, Ring B is of the formula:

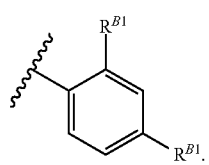

In certain embodiments, Ring B is of the formula:

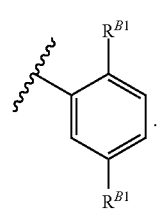

In certain embodiments, Ring B is of the formula:

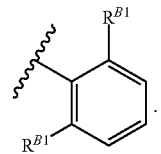

In certain embodiments, Ring B is of the formula:

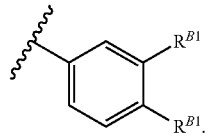

In certain embodiments, Ring B is of the formula:

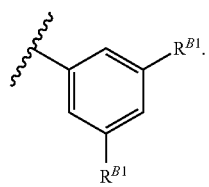

In certain embodiments, Ring B is of the formula:

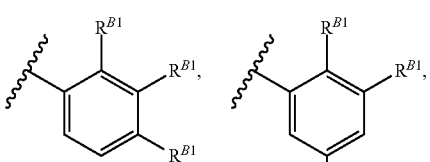
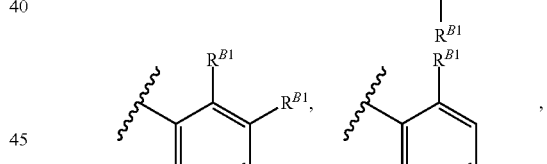
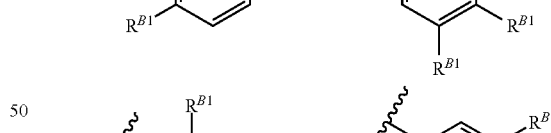
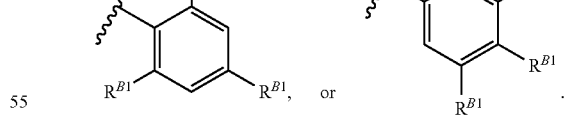

In certain embodiments, Ring B is substituted naphthyl. In certain embodiments, Ring B is unsubstituted naphthyl.

In certain embodiments, Ring B is substituted heteroaryl. In certain embodiments, Ring B is unsubstituted heteroaryl. In certain embodiments, Ring B is 5- to 6-membered, monocyclic heteroaryl, wherein one, two, three, or four atoms in the heteroaryl ring are independently selected from the group consisting of nitrogen, oxygen, and sulfur. In certain embodiments, Ring B is 5-membered, monocyclic heteroaryl. In certain embodiments, Ring B is 5-membered, monocyclic heteroaryl, wherein one of the five atoms in the heteroaryl ring is nitrogen, oxygen, or sulfur. In certain embodiments, Ring B is of the formula:

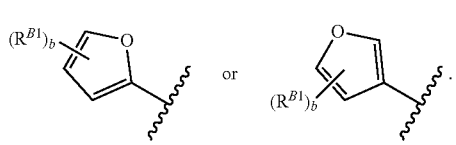

In certain embodiments, Ring B is of the formula:

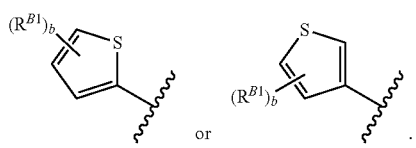

In certain embodiments, Ring B is of the formula:

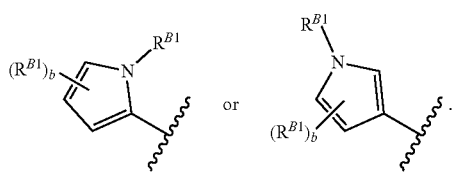

In certain embodiments, Ring B is 5-membered, monocyclic heteroaryl, wherein two of the five atoms in the heteroaryl ring are independently nitrogen, oxygen, or sulfur. In certain embodiments, Ring B is of the formula:

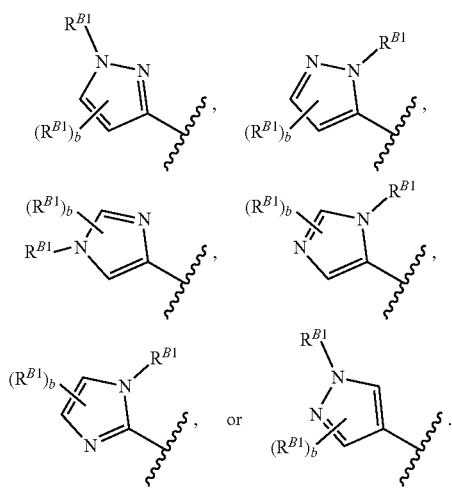

In certain embodiments, Ring B is of the formula:

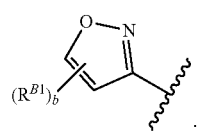

In certain embodiments, Ring B is of the formula:

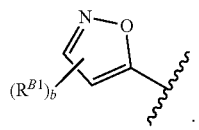

In certain embodiments, Ring B is of the formula:

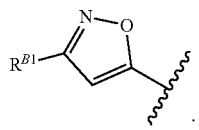

In certain embodiments, Ring B is of the formula:

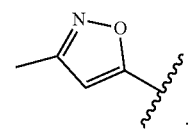

In certain embodiments, Ring B is of the formula:

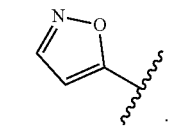

In certain embodiments, Ring B is of the formula:

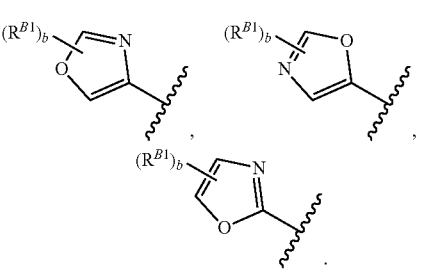

In certain embodiments, Ring B is of the formula:

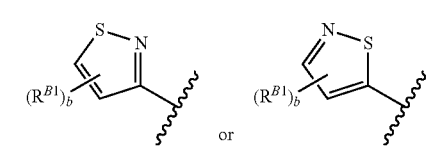

In certain embodiments, Ring B is of the formula:

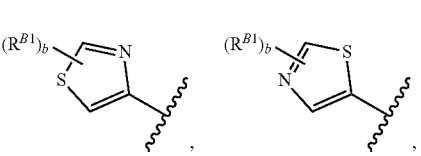

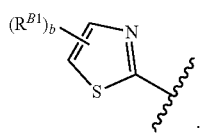

In certain embodiments, Ring B is 5-membered, monocyclic heteroaryl, wherein only three of the five atoms in the heteroaryl ring are independently nitrogen, oxygen, or sulfur. In certain embodiments, Ring B is of the formula:

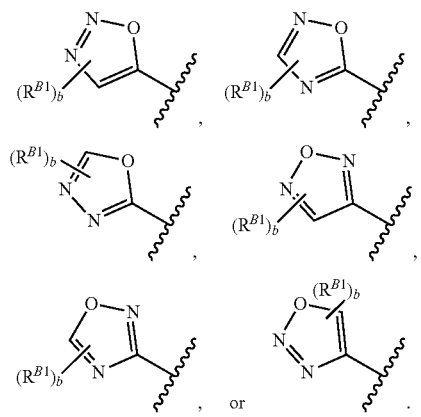

In certain embodiments, Ring B is of the formula:

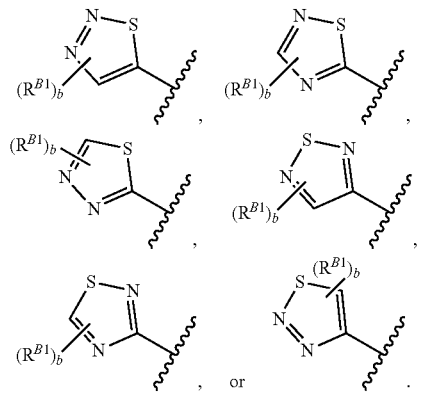

In certain embodiments, Ring B is of the formula:

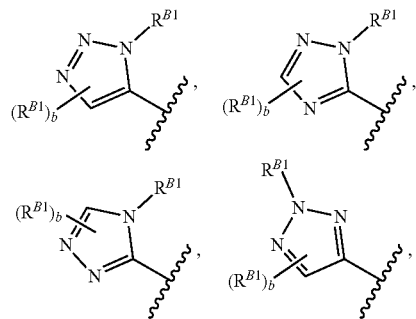

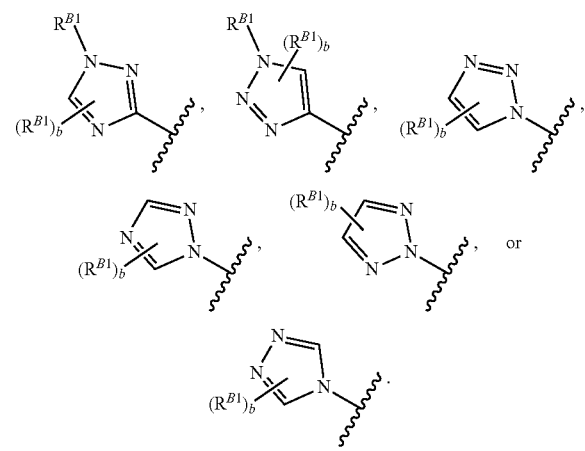

In certain embodiments, Ring B is 5-membered, monocyclic heteroaryl, wherein four of the five atoms in the heteroaryl ring are nitrogen, oxygen, or sulfur. In certain embodiments, Ring B is of the formula:

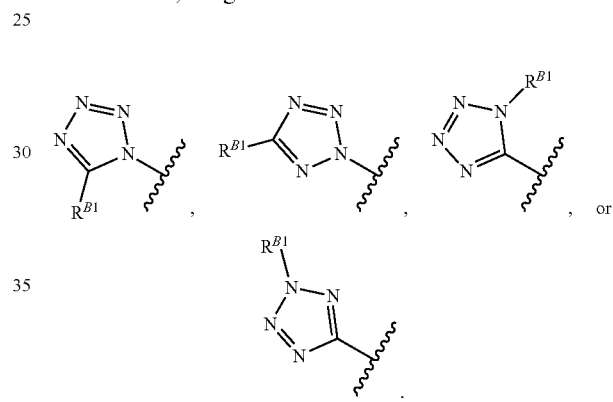

In certain embodiments, Ring B is 6-membered, monocyclic heteroaryl, wherein one, two, or three atoms in the heteroaryl ring are nitrogen. In certain embodiments, Ring B is of the formula:

In certain embodiments, Ring B is of the formula:

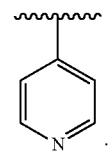

In certain embodiments, Ring B is of the formula:

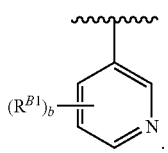

In certain embodiments, Ring B is of the formula:

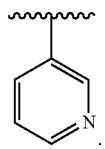

In certain embodiments, Ring B is of the formula:

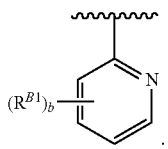

In certain embodiments, Ring B is of the formula:

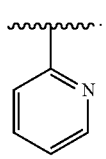 [SMILES: *c1ccccn1]

In certain embodiments, Ring B is of the formula:

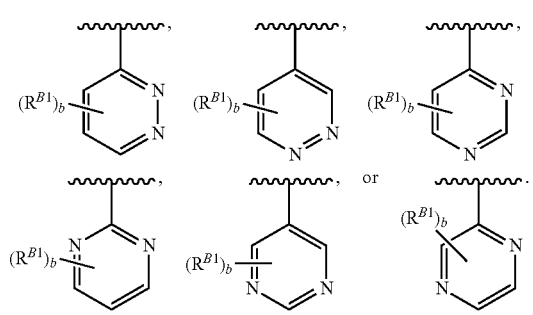

In certain embodiments, Ring B is of the formula:

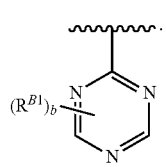

In certain embodiments, Ring B is a bicyclic heteroaryl moiety, wherein the point of attachment may be on any atom of the bicyclic heteroaryl ring system, as valency permits. In certain embodiments, Ring B is substituted bicyclic heteroaryl. In certain embodiments, Ring B is unsubstituted bicyclic heteroaryl. In certain embodiments, Ring B is 9- or 10-membered, bicyclic heteroaryl, wherein one, two, three, or four atoms in the bicyclic ring of the heteroaryl moiety are independently selected from the group consisting of nitrogen, oxygen, and sulfur. In certain embodiments, Ring B is 8- to 10-membered, bicyclic heteroaryl, wherein one atom in the bicyclic ring of the heteroaryl moiety is nitrogen, oxygen, or sulfur. In certain embodiments, Ring B is 8- to 10-membered, bicyclic heteroaryl, wherein two atoms in the bicyclic ring of the heteroaryl moiety are independently selected from the group consisting of nitrogen, oxygen, and sulfur. In certain embodiments, Ring B is 8- to 10-membered, bicyclic heteroaryl, wherein three atoms in the bicyclic ring of the heteroaryl moiety are independently selected from the group consisting of nitrogen, oxygen, and sulfur. In certain embodiments, Ring B is 8- to 10-membered, bicyclic heteroaryl, wherein four atoms in the bicyclic ring of the heteroaryl moiety are independently selected from the group consisting of nitrogen, oxygen, and sulfur.

In certain embodiments, $R^B$ is t-butyl. In certain embodiments, $R^B$ is cyclopropyl. In certain embodiments, $R^B$ is of the formula:

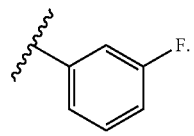

In certain embodiments, $R^B$ is of the formula:

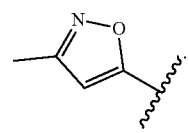 [SMILES: *c1cc(C)no1]

In certain embodiments, $R^B$ is of the formula:

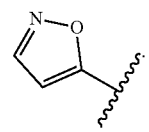

In certain embodiments, $R^B$ is of the formula:

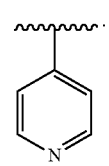

In certain embodiments, $R^B$ is of the formula:
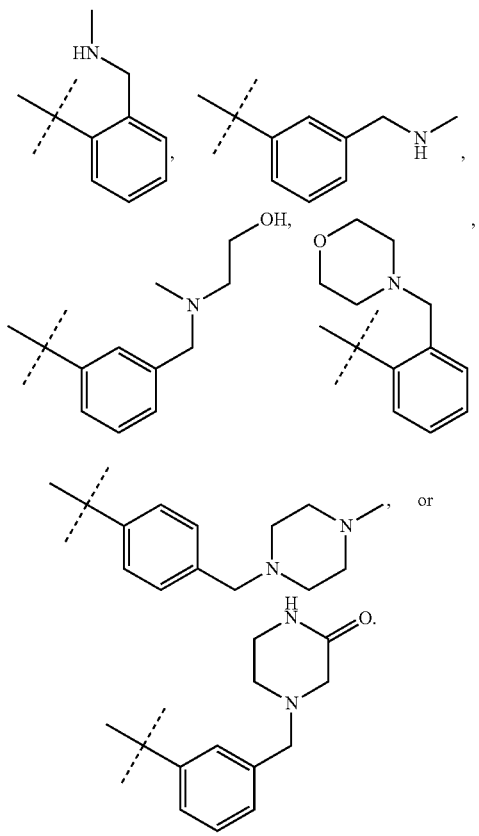
In certain embodiments, $R^B$ is of the formula:
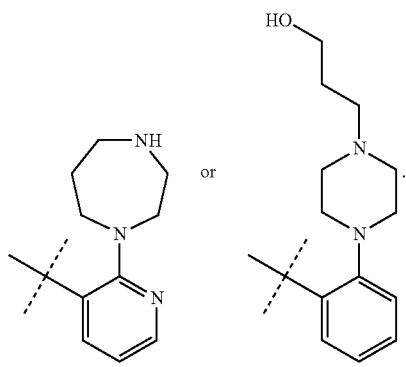
In certain embodiments, $R^B$ is of the formula:
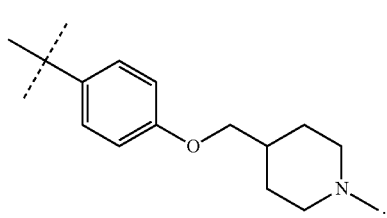
In certain embodiments, $R^B$ is of the formula:
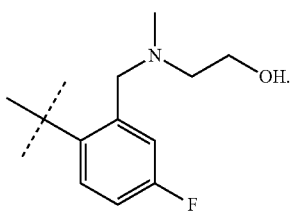
In certain embodiments, $R^B$ is of the formula:
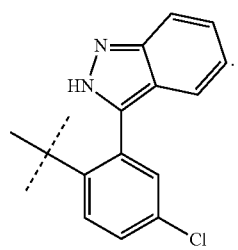
In certain embodiments, $R^B$ is of the formula:
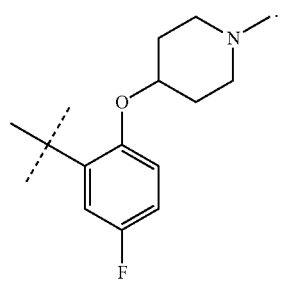
In certain embodiments, $R^B$ is of the formula:
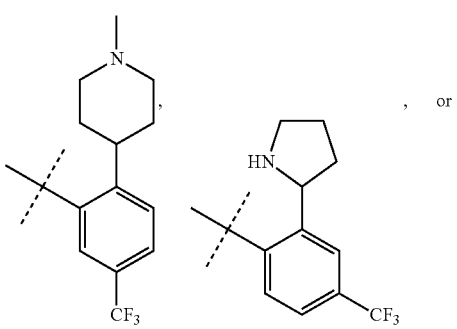
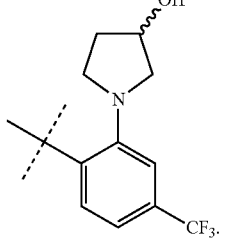

In certain embodiments, $R^B$ is of the formula:

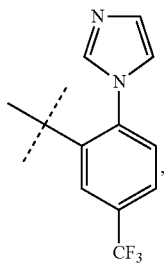

In certain embodiments, $R^B$ is of the formula:

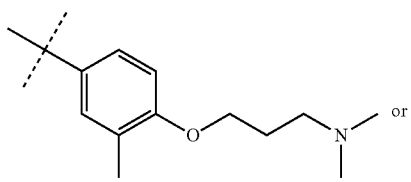

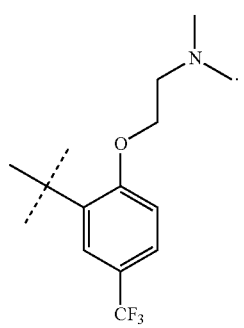

In certain embodiments, $R^B$ is of the formula:

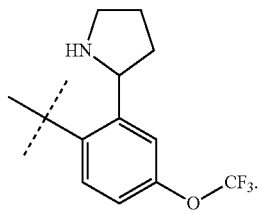

In certain embodiments, $R^B$ is of the formula:

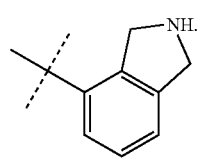

In certain embodiments, $R^B$ is of the formula:

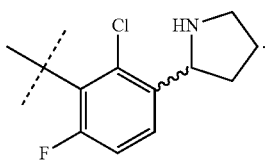

In certain embodiments, $R^B$ is of the formula:

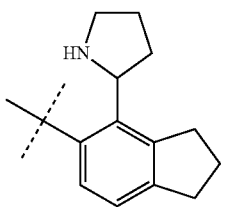

In certain embodiments, $R^B$ is of the formula:

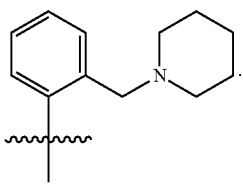 [SMILES: *c1ccccc1CN1CCCCC1]

In certain embodiments, $R^B$ is of the formula:

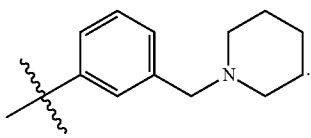 [SMILES: *c1cccc(CN2CCCCC2)c1]

In certain embodiments, $R^B$ is of the formula:

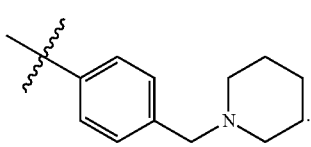 [SMILES: *c1ccc(CN2CCCCC2)cc1]

In certain embodiments, $R^B$ is of the formula:

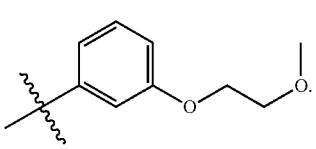 [SMILES: *c1cccc(OCCOC)c1]

In certain embodiments, $R^B$ is of the formula:

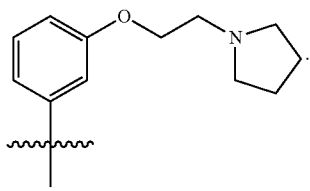 [SMILES: *c1cccc(OCCN2CCCC2)c1]

When $R^B$ is of the formula:

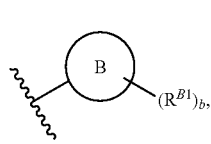

compounds of Formula (I) may include one or more substituents $R^{B1}$. In certain embodiments, at least one instance of $R^{B1}$ is H. In certain embodiments, at least one instance of $R^{B1}$ is halogen. In certain embodiments, at least one instance of $R^{B1}$ is F. In certain embodiments, at least one instance of $R^{B1}$ is Cl. In certain embodiments, at least one instance of $R^{B1}$ is Br. In certain embodiments, at least one instance of $R^{B1}$ is I (iodine). In certain embodiments, at least one instance of $R^{B1}$ is substituted acyl. In certain embodiments, at least one instance of $R^{B1}$ is unsubstituted acyl. In certain embodiments, at least one instance of $R^{B1}$ is substituted alkyl. In certain embodiments, at least one instance of $R^{B1}$ is unsubstituted alkyl. In certain embodiments, at least one instance of $R^{B1}$ is $C_{1-12}$ alkyl. In certain embodiments, at least one instance of $R^{B1}$ is $C_{1-6}$ alkyl. In certain embodiments, at least one instance of $R^{B1}$ is unsubstituted methyl. In certain embodiments, at least one instance of $R^{B1}$ is substituted methyl. In certain embodiments, at least one instance of $R^{B1}$ is —CH$_2$F. In certain embodiments, at least one instance of $R^{B1}$ is —CHF$_2$. In certain embodiments, at least one instance of $R^{B1}$ is —CF$_3$. In certain embodiments, at least one instance of $R^{B1}$ is —CH$_2$—N(R$^{B1a}$)$_2$. In certain embodiments, at least one instance of $R^{B1}$ is —CH$_2$—N (unsubstituted C$_{1-6}$ alkyl)-(CH$_2$)$_{2-4}$—OH. In certain embodiments, at least one instance of $R^{B1}$ is —CH$_2$—N(CH$_3$)—(CH$_2$)$_2$—OH. In certain embodiments, at least one instance of $R^{B1}$ is of the formula:

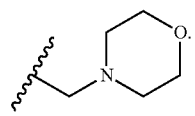

In certain embodiments, at least one instance of $R^{B1}$ is of the formula:

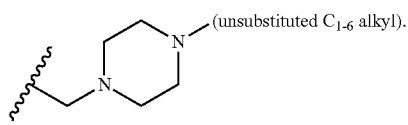

In certain embodiments, at least one instance of $R^{B1}$ is of the formula:

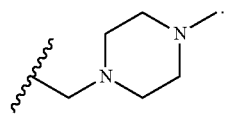 [SMILES: *CN1CCN(C)CC1]

In certain embodiments, at least one instance of $R^{B1}$ is

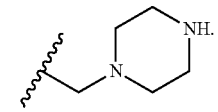

In certain embodiments, at least one instance of $R^{B1}$ is of the formula:

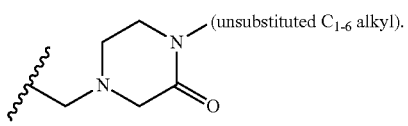

In certain embodiments, at least one instance of $R^{B1}$ is of the formula:

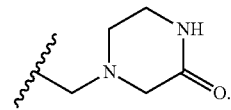 [SMILES: *CN1CCNC(=O)C1]

In certain embodiments, at least one instance of $R^{B1}$ is —CH$_2$—NH(R$^{B1a}$). In certain embodiments, at least one instance of $R^{B1}$ is —CH$_2$—NH (unsubstituted C$_{1-6}$ alkyl). In certain embodiments, at least one instance of $R^{B1}$ is —CH$_2$—NH(CH$_3$). In certain embodiments, at least one instance of $R^{B1}$ is Bn. In certain embodiments, at least one instance of $R^{B1}$ is unsubstituted ethyl. In certain embodiments, at least one instance of $R^{B1}$ is substituted ethyl. In certain embodiments, at least one instance of $R^{B1}$ is —(CH$_2$)$_2$Ph. In certain embodiments, at least one instance of $R^{B1}$ is propyl. In certain embodiments, at least one instance of $R^{B1}$ is butyl. In certain embodiments, at least one instance of $R^{B1}$ is pentyl. In certain embodiments, at least one instance of $R^{B1}$ is hexyl. In certain embodiments, at least one instance of $R^{B1}$ is halogen or substituted or unsubstituted $C_{1-6}$ alkyl. In certain embodiments, at least one instance of $R^{B1}$ is substituted alkenyl. In certain embodiments, at least one instance of $R^{B1}$ is unsubstituted alkenyl. In certain embodiments, at least one instance of $R^{B1}$ is vinyl. In certain embodiments, at least one instance of $R^{B1}$ is substituted alkynyl. In certain embodiments, at least one instance of $R^{B1}$ is unsubstituted alkynyl. In certain embodiments, at least one instance of $R^{B1}$ is ethynyl. In certain embodiments, at least one instance of $R^{B1}$ is substituted carbocyclyl. In certain embodiments, at least one instance of $R^{B1}$ is unsubstituted carbocyclyl. In certain embodiments, at least one instance of $R^{B1}$ is saturated carbocyclyl. In certain embodiments, at least one instance of $R^{B1}$ is unsaturated carbocyclyl. In certain embodiments, at least one instance of $R^{B1}$ is carbocyclyl including one, two, or three double bonds in the carbocyclic ring. In certain embodiments, at least one instance of $R^{B1}$ is monocyclic carbocyclyl. In certain embodiments, at least one instance of $R^{B1}$ is 3- to 7-membered, monocyclic carbocyclyl. In certain embodiments, at least one instance of $R^{B1}$ is cyclopropyl. In certain embodiments, at least one instance of $R^{B1}$ is cyclobutyl. In certain embodiments, at least one instance of $R^{B1}$ is cyclopentyl. In certain embodiments, at least one instance of $R^{B1}$ is cyclohexyl. In certain embodiments, at least one instance of $R^{B1}$ is cycloheptyl. In certain embodiments, at least one instance of $R^{B1}$ is bicyclic carbocyclyl. In certain embodiments, at least one instance of $R^{B1}$ is 5- to 13-membered, bicyclic carbocyclyl. In certain embodiments, at least one instance of $R^{B1}$ is substituted heterocyclyl. In certain embodiments, at least one instance of $R^{B1}$ is unsubstituted heterocyclyl. In certain embodiments, at least one instance of $R^{B1}$ is saturated heterocyclyl. In certain embodiments, at least one instance of $R^{B1}$ is unsaturated heterocyclyl. In certain embodiments, at least one instance of $R^{B1}$ is heterocyclyl including one, two, or three double bonds in the heterocyclic ring. In certain embodiments, at least one instance of $R^{B1}$ is heterocyclyl, wherein one, two, or three atoms in the heterocyclic ring are independently selected from the group consisting of nitrogen, oxygen, and sulfur. In certain embodiments, at least one instance of $R^{B1}$ is monocyclic heterocyclyl. In certain embodiments, at least one instance of $R^{B1}$ is 3- to 7-membered, monocyclic heterocyclyl. In certain embodiments, at least one instance of $R^{B1}$ is of the formula:

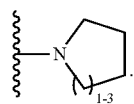

In certain embodiments, at least one instance of $R^{B1}$ is of the formula:

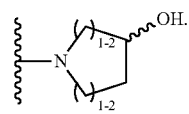

In certain embodiments, at least one instance of $R^{B1}$ is of the formula:

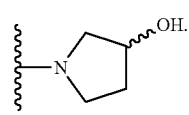 [SMILES: *N1CCC(O)C1]

In certain embodiments, at least one instance of $R^{B1}$ is of the formula:

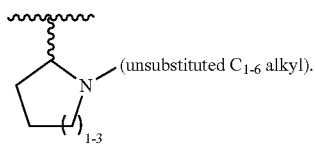

In certain embodiments, at least one instance of $R^{B1}$ is of the formula:

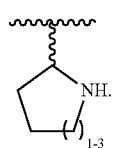

In certain embodiments, at least one instance of $R^{B1}$ is of the formula:

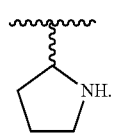

In certain embodiments, at least one instance of $R^{B1}$ is of the formula:

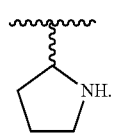

In certain embodiments, at least one instance of $R^{B1}$ is of the formula:

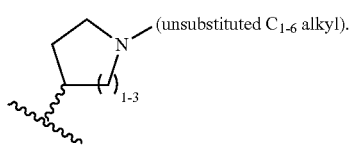

In certain embodiments, at least one instance of $R^{B1}$ is of the formula:

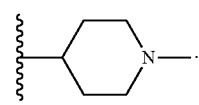

In certain embodiments, at least one instance of $R^{B1}$ is of the formula:

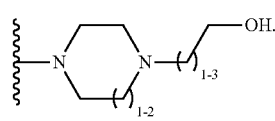

In certain embodiments, at least one instance of $R^{B1}$ is of the formula:

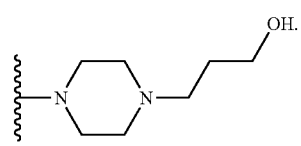 [SMILES: *N1CCN(CCCO)CC1]

In certain embodiments, at least one instance of $R^{B1}$ is of the formula:

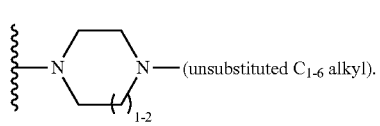

In certain embodiments, at least one instance of $R^{B1}$ is of the formula:

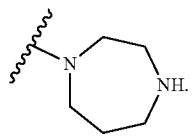

In certain embodiments, at least one instance of $R^{B1}$ is of the formula:

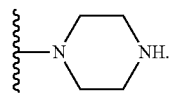

In certain embodiments, at least one instance of $R^{B1}$ is bicyclic heterocyclyl. In certain embodiments, at least one instance of $R^{B1}$ is 5- to 13-membered, bicyclic heterocyclyl. In certain embodiments, at least one instance of $R^{B1}$ is substituted aryl. In certain embodiments, at least one instance of $R^{B1}$ is unsubstituted aryl. In certain embodiments, at least one instance of $R^{B1}$ is 6- to 14-membered aryl. In certain embodiments, at least one instance of $R^{B1}$ is 6- to 10-membered aryl. In certain embodiments, at least one instance of $R^{B1}$ is substituted phenyl. In certain embodiments, at least one instance of $R^{B1}$ is unsubstituted phenyl. In certain embodiments, at least one instance of $R^{B1}$ is substituted naphthyl. In certain embodiments, at least one instance of $R^{B1}$ is unsubstituted naphthyl. In certain embodiments, at least one instance of $R^{B1}$ is substituted heteroaryl. In certain embodiments, at least one instance of $R^{B1}$ is unsubstituted heteroaryl. In certain embodiments, at least one instance of $R^{B1}$ is heteroaryl, wherein one, two, three, or four atoms in the heteroaryl ring are independently selected from the group consisting of nitrogen, oxygen, and sulfur. In certain embodiments, at least one instance of $R^{B1}$ is monocyclic heteroaryl. In certain embodiments, at least one instance of $R^{B1}$ is 5-membered, monocyclic heteroaryl. In certain embodiments, at least one instance of $R^{B1}$ is of the formula:

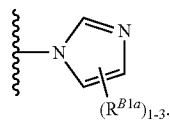

In certain embodiments, at least one instance of $R^{B1}$ is of the formula:

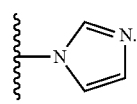

In certain embodiments, at least one instance of $R^{B1}$ is 6-membered, monocyclic heteroaryl. In certain embodiments, at least one instance of $R^{B1}$ is pyridyl. In certain embodiments, at least one instance of $R^{B1}$ is bicyclic heteroaryl, wherein the point of attachment may be on any atom of the bicyclic heteroaryl ring system, as valency permits. In certain embodiments, at least one instance of $R^{B1}$ is 9-membered, bicyclic heteroaryl. In certain embodiments, at least one instance of $R^{B1}$ is of the formula:

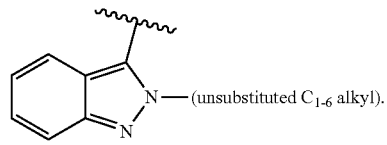

In certain embodiments, at least one instance of $R^{B1}$ is of the formula:

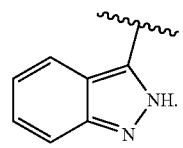 [SMILES: *c1[nH]nc2ccccc12]

In certain embodiments, at least one instance of $R^{B1}$ is 10-membered, bicyclic heteroaryl. In certain embodiments, at least one instance of $R^{B1}$ is —$OR^{B1a}$. In certain embodiments, at least one instance of $R^{B1}$ is —OMe. In certain embodiments, at least one instance of $R^{B1}$ is —OEt. In certain embodiments, at least one instance of $R^{B1}$ is —OPr. In certain embodiments, at least one instance of $R^{B1}$ is —OBu. In certain embodiments, at least one instance of $R^{B1}$ is —O(pentyl). In certain embodiments, at least one instance of $R^{B1}$ is —O(hexyl). In certain embodiments, at least one instance of $R^{B1}$ is —OPh. In certain embodiments, at least one instance of $R^{B1}$ is —OBn. In certain embodiments, at least one instance of $R^{B1}$ is —O(CH$_2$)$_2$Ph. In certain embodiments, at least one instance of $R^{B1}$ is —OH. In certain embodiments, at least one instance of $R^{B1}$ is —O—CF$_3$. In certain embodiments, at least one instance of $R^{B1}$ is —O—(CH$_2$)$_{2-4}$—N($R^{B1a}$)$_2$. In certain embodiments, at least one instance of $R^{B1}$ is —O—(CH$_2$)$_{2-4}$—N(unsubstituted C$_{1-6}$ alkyl)$_2$. In certain embodiments, at least one instance of $R^{B1}$ is —O—(CH$_2$)$_2$—N(CH$_3$)$_2$. In certain embodiments, at least one instance of $R^{B1}$ is —O—(CH$_2$)$_3$—N(CH$_3$)$_2$. In certain embodiments, at least one instance of $R^{B1}$ is of the formula:

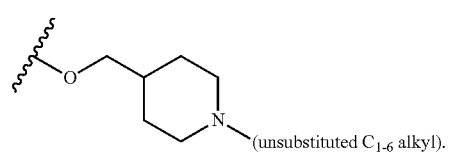

In certain embodiments, at least one instance of $R^{B1}$ is of the formula:

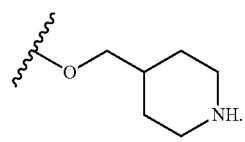 [SMILES: *OCC1CCNCC1]

In certain embodiments, at least one instance of $R^{B1}$ is of the formula:

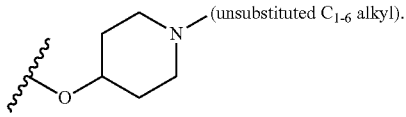

In certain embodiments, at least one instance of $R^{B1}$ is of the formula:

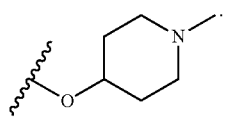 [SMILES: *OC1CCN(C)CC1]

In certain embodiments, at least one instance of $R^{B1}$ is of the formula:

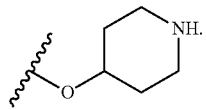

In certain embodiments, at least one instance of $R^{B1}$ is —$SR^{B1a}$. In certain embodiments, at least one instance of $R^{B1}$ is —SH. In certain embodiments, at least one instance of $R^{B1}$ is —$N(R^{B1a})_2$. In certain embodiments, at least one instance of $R^{B1}$ is —$NH_2$. In certain embodiments, at least one instance of $R^{B1}$ is —CN. In certain embodiments, at least one instance of $R^{B1}$ is —SCN. In certain embodiments, at least one instance of $R^{B1}$ is —$C(=NR^{B1a})R^{B1a}$, —$C(=NR^{B1a})OR^{B1a}$, or —$C(=NR^{B1a})N(R^{B1a})_2$. In certain embodiments, at least one instance of $R^{B1}$ is —$C(=O)R^{B1a}$, —$C(=O)OR^{B1a}$, or —$C(=O)N(R^{B1a})_2$. In certain embodiments, at least one instance of $R^{B1}$ is —$NO_2$. In certain embodiments, at least one instance of $R^{B1}$ is —$NR^{B1a}C(=O)R^{B1a}$, —$NR^{B1a}C(=O)OR^{B1a}$, or —$NR^{B1a}C(=O)N(R^{B1a})_2$. In certain embodiments, at least one instance of $R^{B1}$ is —$OC(=O)R^{B1a}$, —$OC(=O)OR^{B1a}$, or —$OC(=O)N(R^{B1a})_2$. In certain embodiments, at least one instance of $R^{B1}$ is a nitrogen protecting group when attached to a nitrogen atom. In certain embodiments, at least one instance of $R^{B1}$ is Bn, Boc, Cbz, Fmoc, trifluoroacetyl, triphenylmethyl, acetyl, or Ts when attached to a nitrogen atom.

In certain embodiments, at least one instance of $R^{B1}$ is hydrogen, halogen, substituted or unsubstituted alkyl, substituted or unsubstituted heterocyclyl, substituted or unsubstituted heteroaryl, —$OR^{B1a}$, or —$N(R^{B1a})_2$, or two instances of $R^{B1}$ are joined to form substituted or unsubstituted heterocyclyl. In certain embodiments, at least one instance of $R^{B1}$ is hydrogen, halogen, or unsubstituted alkyl. In certain embodiments, at least one instance of $R^{B1}$ is hydrogen, halogen, or unsubstituted $C_{1-6}$ alkyl. In certain embodiments, at least one instance of $R^{B1}$ is halogen or unsubstituted alkyl. In certain embodiments, at least one instance of $R^{B1}$ is halogen or unsubstituted $C_{1-6}$ alkyl.

In compounds of Formula (I), two $R^{B1}$ groups may be joined to form substituted or unsubstituted carbocyclyl. In certain embodiments, two instances of $R^{B1}$ are joined to form saturated or unsaturated carbocyclyl. In certain embodiments, two instances of $R^{B1}$ are joined to form carbocyclyl including one, two, or three double bonds in the carbocyclic ring. In certain embodiments, two instances of $R^{B1}$ are joined to form 3- to 7-membered, monocyclic carbocyclyl. In certain embodiments, two instances of $R^{B1}$ are joined to form 3-membered carbocyclyl. In certain embodiments, two instances of $R^{B1}$ are joined to form 4-membered carbocyclyl. In certain embodiments, two instances of $R^{B1}$ are joined to form 5-membered carbocyclyl. In certain embodiments, two instances of $R^{B1}$ are joined to form 6-membered carbocyclyl. In certain embodiments, two instances of $R^{B1}$ are joined to form 7-membered carbocyclyl. In certain embodiments, two instances of $R^{B1}$ are joined to form 5- to 13-membered, bicyclic carbocyclyl.

In certain embodiments, two instances of $R^{B1}$ are joined to form substituted or unsubstituted heterocyclyl. In certain embodiments, two instances of $R^{B1}$ are joined to form saturated or unsaturated heterocyclyl. In certain embodiments, two instances of $R^{B1}$ are joined to form heterocyclyl including one, two, or three double bonds in the heterocyclic ring. In certain embodiments, two instances of $R^{B1}$ are joined to form heterocyclyl, wherein one, two, or three atoms in the heterocyclic ring are independently selected from the group consisting of nitrogen, oxygen, and sulfur. In certain embodiments, two instances of $R^{B1}$ are joined to form 3- to 7-membered, monocyclic heterocyclyl. In certain embodiments, two instances of $R^{B1}$ are joined to form

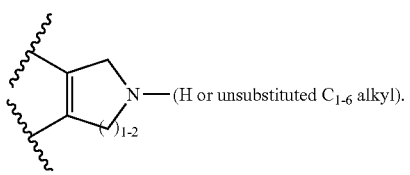

In certain embodiments, two instances of $R^{B1}$ are joined to form

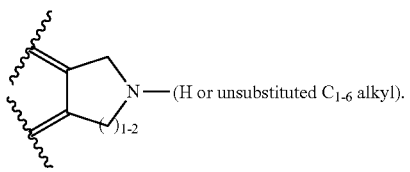

In certain embodiments, two instances of $R^{B1}$ are joined to form

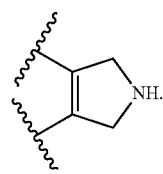 [SMILES: *C1=C(*)CNC1]

In certain embodiments, two instances of $R^{B1}$ are joined to form

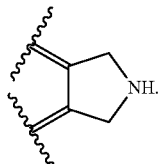 [SMILES: *=C1CNCC1=*]

In certain embodiments, two instances of $R^{B1}$ are joined to form 5- to 13-membered, bicyclic heterocyclyl.

In certain embodiments, two instances of $R^{B1}$ are joined to form substituted or unsubstituted aryl. In certain embodiments, two instances of $R^{B1}$ are joined to form 6- to 14-membered aryl. In certain embodiments, two instances of $R^{B1}$ are joined to form 6- to 10-membered aryl. In certain embodiments, two instances of $R^{B1}$ are joined to form monocyclic aryl. In certain embodiments, two instances of $R^{B1}$ are joined to form phenyl. In certain embodiments, two instances of $R^{B1}$ are joined to form bicyclic aryl. In certain embodiments, two instances of $R^{B1}$ are joined to form naphthyl.

In certain embodiments, two instances of $R^{B1}$ are joined to form substituted or unsubstituted heteroaryl. In certain embodiments, two instances of $R^{B1}$ are joined to form monocyclic heteroaryl, wherein one, two, or three atoms in the heteroaryl ring are independently selected from the group consisting of nitrogen, oxygen, and sulfur. In certain embodiments, two instances of $R^{B1}$ are joined to form 5-membered, monocyclic heteroaryl. In certain embodiments, two instances of $R^{B1}$ are joined to form pyrrolyl. In certain embodiments, two instances of $R^{B1}$ are joined to form 6-membered, monocyclic heteroaryl. In certain embodiments, two instances of $R^{B1}$ are joined to form pyridyl. In certain embodiments, two instances of $R^{B1}$ are joined to form bicyclic heteroaryl, wherein one, two, three, or four atoms in the heteroaryl ring are independently selected from the group consisting of nitrogen, oxygen, and sulfur. In certain embodiments, two instances of $R^{B1}$ are joined to form 9-membered, bicyclic heterocyclyl. In certain embodiments, two instances of $R^{B1}$ are joined to form 10-membered, bicyclic heteroaryl.

In certain embodiments, at least one instance of $R^{B1a}$ is H. In certain embodiments, at least one instance of $R^{B1a}$ is substituted acyl. In certain embodiments, at least one instance of $R^{B1a}$ is unsubstituted acyl. In certain embodiments, at least one instance of $R^{B1a}$ is acetyl. In certain embodiments, at least one instance of $R^{B1a}$ is substituted alkyl. In certain embodiments, at least one instance of $R^{B1a}$ is unsubstituted alkyl. In certain embodiments, at least one instance of $R^{B1a}$ is $C_{1-12}$ alkyl. In certain embodiments, at least one instance of $R^{B1a}$ is $C_{1-6}$ alkyl. In certain embodiments, at least one instance of $R^{B1a}$ is methyl. In certain embodiments, at least one instance of $R^{B1a}$ is ethyl. In certain embodiments, at least one instance of $R^{B1a}$ is propyl. In certain embodiments, at least one instance of $R^{B1a}$ is butyl. In certain embodiments, at least one instance of $R^{B1a}$ is pentyl. In certain embodiments, at least one instance of $R^{B1a}$ is hexyl. In certain embodiments, at least one instance of $R^{B1a}$ is substituted alkenyl. In certain embodiments, at least one instance of $R^{B1a}$ is unsubstituted alkenyl. In certain embodiments, at least one instance of $R^{B1a}$ is vinyl. In certain embodiments, at least one instance of $R^{B1a}$ is substituted alkynyl. In certain embodiments, at least one instance of $R^{B1a}$ is unsubstituted alkynyl. In certain embodiments, at least one instance of $R^{B1a}$ is ethynyl. In certain embodiments, at least one instance of $R^{B1a}$ is substituted carbocyclyl. In certain embodiments, at least one instance of $R^{B1a}$ is unsubstituted carbocyclyl. In certain embodiments, at least one instance of $R^{B1a}$ is saturated carbocyclyl. In certain embodiments, at least one instance of $R^{B1a}$ is unsaturated carbocyclyl. In certain embodiments, at least one instance of $R^{B1a}$ is carbocyclyl including one, two, or three double bonds in the carbocyclic ring. In certain embodiments, at least one instance of $R^{B1a}$ is 3- to 7-membered, monocyclic carbocyclyl. In certain embodiments, at least one instance of $R^{B1a}$ is cyclopropyl. In certain embodiments, at least one instance of $R^{B1a}$ is cyclobutyl. In certain embodiments, at least one instance of $R^{B1a}$ is cyclopentyl. In certain embodiments, at least one instance of $R^{B1a}$ is cyclohexyl. In certain embodiments, at least one instance of $R^{B1a}$ is cycloheptyl. In certain embodiments, at least one instance of $R^{B1a}$ is 5- to 13-membered, bicyclic carbocyclyl. In certain embodiments, at least one instance of $R^{B1a}$ is substituted heterocyclyl. In certain embodiments, at least one instance of $R^{B1a}$ is unsubstituted heterocyclyl. In certain embodiments, at least one instance of $R^{B1a}$ is saturated heterocyclyl. In certain embodiments, at least one instance of $R^{B1a}$ is unsaturated heterocyclyl. In certain embodiments, at least one instance of $R^{B1a}$ is heterocyclyl including one, two, or three double bonds in the heterocyclic ring. In certain embodiments, at least one instance of $R^{B1a}$ is heterocyclyl, wherein one, two, or three atoms in the heterocyclic ring are independently selected from the group consisting of nitrogen, oxygen, and sulfur. In certain embodiments, at least one instance of $R^{B1a}$ is 3- to 7-membered, monocyclic heterocyclyl. In certain embodiments, at least one instance of $R^{B1a}$ is 5- to 13-membered, bicyclic heterocyclyl. In certain embodiments, at least one instance of $R^{B1a}$ is substituted or unsubstituted aryl. In certain embodiments, at least one instance of $R^{B1a}$ is 6- to 14-membered aryl. In certain embodiments, at least one instance of $R^{B1a}$ is 6- to 10-membered aryl. In certain embodiments, at least one instance of $R^{B1a}$ is monocyclic aryl. In certain embodiments, at least one instance of $R^{B1a}$ is phenyl. In certain embodiments, at least one instance of $R^{B1a}$ is bicyclic aryl. In certain embodiments, at least one instance of $R^{B1a}$ is naphthyl. In certain embodiments, at least one instance of $R^{B1a}$ is substituted or unsubstituted heteroaryl. In certain embodiments, at least one instance of $R^{B1a}$ is heteroaryl, wherein one, two, three, or four atoms in the heteroaryl ring are independently selected from the group consisting of nitrogen, oxygen, and sulfur. In certain embodiments, at least one instance of $R^{B1a}$ is monocyclic heteroaryl. In certain embodiments, at least one instance of $R^{B1a}$ is 5-membered, monocyclic heteroaryl. In certain embodiments, at least one instance of $R^{B1a}$ is 6-membered, monocyclic heteroaryl. In certain embodiments, at least one instance of $R^{B1a}$ is pyridyl. In certain embodiments, at least one instance of $R^{B1a}$ is bicyclic heteroaryl, wherein the point of attachment may be on any atom of the bicyclic heteroaryl ring system, as valency permits. In certain embodiments, at least one instance of $R^{B1a}$ is 9-membered, bicyclic heteroaryl. In certain embodiments, at least one instance of $R^{B1a}$ is 10-membered, bicyclic heteroaryl. In certain embodiments, at least one instance of $R^{B1a}$ is a nitrogen protecting group when attached to a nitrogen atom. In certain embodiments, at least one instance of $R^{B1a}$ is Bn, Boc, Cbz, Fmoc, trifluoroacetyl, triphenylmethyl, acetyl, or Ts when attached to a nitrogen atom. In certain embodiments, $R^{B1a}$ is an oxygen protecting group when attached to an oxygen atom. In certain embodiments, $R^{B1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1a}$ is a sulfur protecting group when attached to a sulfur atom. In certain embodiments, $R^{B1a}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{B1}$ are joined to form substituted or unsubstituted heterocyclyl. In certain embodiments, two instances of $R^{B1a}$ are joined to form saturated or unsaturated heterocyclyl. In certain embodiments, two instances of $R^{B1a}$ are joined to form heterocyclyl including one, two, or three double bonds in the heterocyclic ring. In certain embodiments, two instances of $R^{B1a}$ are joined to form heterocyclyl, wherein one, two, or three atoms in the heterocyclic ring are independently selected from the group consisting of nitrogen, oxygen, and sulfur. In certain embodiments, two instances of $R^{B1a}$ are joined to form 3- to 7-membered, monocyclic heterocyclyl. In certain embodiments, two instances of $R^{B1a}$ are joined to form 5- to 13-membered, bicyclic heterocyclyl.

In certain embodiments, b is 0. In certain embodiments, b is 1. In certain embodiments, b is 2. In certain embodiments, b is 3. In certain embodiments, b is 4. In certain embodiments, b is 5.

In certain embodiments, at least one instance of $R^{B1}$ is halogen or substituted alkyl; and b is 1. In certain embodiments, at least one instance of $R^{B1}$ is halogen or unsubstituted alkyl; and b is 1. In certain embodiments, at least one instance of $R^{B1}$ is halogen or unsubstituted $C_{1-6}$ alkyl; and b is 1.

Compounds of Formula (I) include substituent In certain embodiments, $R^C$ is H. In certain embodiments, $R^C$ is substituted $C_{1-6}$ alkyl. In certain embodiments, $R^C$ is unsubstituted $C_{1-6}$ alkyl. In certain embodiments, $R^C$ is unsubstituted methyl. In certain embodiments, $R^C$ is substituted methyl. In certain embodiments, $R^C$ is —$CH_2F$. In certain embodiments, $R^C$ is —$CHF_2$. In certain embodiments, $R^C$ is —$CF_3$. In certain embodiments, $R^C$ is Bn. In certain embodiments, $R^C$ is unsubstituted ethyl. In certain embodiments, $R^C$ is substituted ethyl. In certain embodiments, $R^C$ is —$(CH_2)_2Ph$. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is a nitrogen protecting group. In certain embodiments, $R^C$ is Bn, Boc, Cbz, Fmoc, trifluoroacetyl, triphenylmethyl, acetyl, or Ts. In certain embodiments, $R^C$ is acetyl.

Compounds of Formula (I) include substituent $R^D$. In certain embodiments, $R^D$ is H. In certain embodiments, $R^D$ is substituted $C_{1-6}$ alkyl. In certain embodiments, $R^D$ is unsubstituted $C_{1-6}$ alkyl. In certain embodiments, $R^D$ is unsubstituted methyl. In certain embodiments, $R^D$ is substituted methyl. In certain embodiments, $R^D$ is —$CH_2F$. In certain embodiments, $R^D$ is —$CHF_2$. In certain embodiments, $R^D$ is —$CF_3$. In certain embodiments, $R^D$ is Bn. In certain embodiments, $R^D$ is unsubstituted ethyl. In certain embodiments, $R^D$ is substituted ethyl. In certain embodiments, $R^D$ is —$(CH_2)_2Ph$. In certain embodiments, $R^C$ is propyl. In certain embodiments, $R^D$ is butyl. In certain embodiments, $R^D$ is pentyl. In certain embodiments, $R^D$ is hexyl. In certain embodiments, $R^D$ is a nitrogen protecting group. In certain embodiments, $R^D$ is Bn, Boc, Cbz, Fmoc, trifluoroacetyl, triphenylmethyl, acetyl, or Ts.

In certain embodiments, each one of $R^C$ and $R^D$ is hydrogen.

Compounds of Formula (I) may include one or more $R^L$ groups. In certain embodiments, at least one instance of $R^L$ is H. In certain embodiments, at least one instance of $R^L$ is halogen. In certain embodiments, at least one instance of $R^L$ is F. In certain embodiments, at least one instance of $R^L$ is Cl. In certain embodiments, at least one instance of $R^L$ is Br. In certain embodiments, at least one instance of $R^L$ is I (iodine). In certain embodiments, at least one instance of $R^L$ is substituted acyl. In certain embodiments, at least one instance of $R^L$ is unsubstituted acyl. In certain embodiments, at least one instance of $R^L$ is substituted alkyl. In certain embodiments, at least one instance of $R^L$ is unsubstituted alkyl. In certain embodiments, at least one instance of $R^L$ is $C_{1-12}$ alkyl. In certain embodiments, at least one instance of $R^L$ is $C_{1-6}$ alkyl. In certain embodiments, at least one instance of $R^L$ is unsubstituted methyl. In certain embodiments, at least one instance of $R^L$ is substituted methyl. In certain embodiments, at least one instance of $R^L$ is —$CH_2F$. In certain embodiments, at least one instance of $R^L$ is —$CHF_2$. In certain embodiments, at least one instance of $R^L$ is —$CF_3$. In certain embodiments, at least one instance of $R^L$ is Bn. In certain embodiments, at least one instance of $R^L$ is unsubstituted ethyl. In certain embodiments, at least one instance of $R^L$ is substituted ethyl. In certain embodiments, at least one instance of $R^L$ is —$(CH_2)_2Ph$. In certain embodiments, at least one instance of $R^L$ is propyl. In certain embodiments, at least one instance of $R^L$ is butyl. In certain embodiments, at least one instance of $R^L$ is pentyl. In certain embodiments, at least one instance of $R^L$ is hexyl. In certain embodiments, at least one instance of $R^L$ is halogen or substituted or unsubstituted $C_{1-6}$ alkyl. In certain embodiments, at least one instance of $R^L$ is substituted alkenyl. In certain embodiments, at least one instance of $R^L$ is unsubstituted alkenyl. In certain embodiments, at least one instance of $R^L$ is vinyl. In certain embodiments, at least one instance of $R^L$ is substituted alkynyl. In certain embodiments, at least one instance of $R^L$ is unsubstituted alkynyl. In certain embodiments, at least one instance of $R^L$ is ethynyl. In certain embodiments, at least one instance of $R^L$ is substituted carbocyclyl. In certain embodiments, at least one instance of $R^L$ is unsubstituted carbocyclyl. In certain embodiments, at least one instance of $R^L$ is saturated carbocyclyl. In certain embodiments, at least one instance of $R^L$ is unsaturated carbocyclyl. In certain embodiments, at least one instance of $R^L$ is carbocyclyl including one, two, or three double bonds in the carbocyclic ring. In certain embodiments, at least one instance of $R^L$ is monocyclic carbocyclyl. In certain embodiments, at least one instance of $R^L$ is 3- to 7-membered, monocyclic carbocyclyl. In certain embodiments, at least one instance of $R^L$ is cyclopropyl. In certain embodiments, at least one instance of $R^L$ is cyclobutyl. In certain embodiments, at least one instance of $R^L$ is cyclopentyl. In certain embodiments, at least one instance of $R^L$ is cyclohexyl. In certain embodiments, at least one instance of $R^L$ is cycloheptyl. In certain embodiments, at least one instance of $R^L$ is bicyclic carbocyclyl. In certain embodiments, at least one instance of $R^L$ is 5- to 13-membered, bicyclic carbocyclyl. In certain embodiments, at least one instance of $R^L$ is substituted heterocyclyl. In certain embodiments, at least one instance of $R^L$ is unsubstituted heterocyclyl. In certain embodiments, at least one instance of $R^L$ is saturated heterocyclyl. In certain embodiments, at least one instance of $R^L$ is unsaturated heterocyclyl. In certain embodiments, at least one instance of $R^L$ is heterocyclyl including one, two, or three double bonds in the heterocyclic ring. In certain embodiments, at least one instance of $R^L$ is heterocyclyl, wherein one, two, or three atoms in the heterocyclic ring are independently selected from the group consisting of nitrogen, oxygen, and sulfur. In certain embodiments, at least one instance of $R^L$ is monocyclic heterocyclyl. In certain embodiments, at least one instance of $R^L$ is 3- to 7-membered, monocyclic heterocyclyl. In certain embodiments, at least one instance of $R^L$ is bicyclic heterocyclyl. In certain embodiments, at least one instance of $R^L$ is 5- to 13-membered, bicyclic heterocyclyl. In certain embodiments, at least one instance of $R^L$ is substituted aryl. In certain embodiments, at least one instance of $R^L$ is unsubstituted aryl. In certain embodiments, at least one instance of $R^L$ is 6- to 14-membered aryl. In certain embodiments, at least one instance of $R^L$ is 6- to 10-membered aryl. In certain embodiments, at least one instance of $R^L$ is substituted phenyl. In certain embodiments, at least one instance of $R^L$ is unsubstituted phenyl. In certain embodiments, at least one instance of $R^L$ is substituted naphthyl. In certain embodiments, at least one instance of $R^L$ is unsubstituted naphthyl. In certain embodiments, at least one instance of $R^L$ is substituted heteroaryl. In certain embodiments, at least one instance of $R^L$ is unsubstituted heteroaryl. In certain embodiments, at least one instance of $R^L$ is heteroaryl, wherein one, two, three, or four atoms in the heteroaryl ring are independently selected from the group consisting of nitrogen, oxygen, and sulfur. In certain embodiments, at least one instance of $R^L$ is monocyclic heteroaryl. In certain embodiments, at least one instance of $R^L$ is 5-membered, monocyclic heteroaryl. In certain embodiments, at least one instance of $R^L$ is 6-membered, monocyclic heteroaryl. In certain embodiments, at least one instance of $R^L$ is pyridyl. In certain embodiments, at least one instance of $R^L$ is bicyclic heteroaryl, wherein the point of attachment may be on any atom of the bicyclic heteroaryl ring system, as valency permits. In certain embodiments, at least one instance of $R^L$ is 9-membered, bicyclic heteroaryl. In certain embodiments, at least one instance of $R^L$ is 10-membered, bicyclic heteroaryl. In certain embodiments, at least one instance of $R^L$ is —$OR^{L1}$. In certain embodiments, at least one instance of $R^L$ is —OMe. In certain embodiments, at least one instance of $R^L$ is —OEt. In certain embodiments, at least one instance of $R^L$ is —OPr. In certain embodiments, at least one instance of $R^L$ is —OBu. In certain embodiments, at least one instance of $R^L$ is —O(pentyl). In certain embodiments, at least one instance of $R^L$ is —O(hexyl). In certain embodiments, at least one instance of $R^L$ is —OPh. In certain embodiments, at least one instance of $R^L$ is —OBn. In certain embodiments, at least one instance of $R^L$ is —O(CH$_2$)$_2$Ph. In certain embodiments, at least one instance of $R^L$ is —OH. In certain embodiments, at least one instance of $R^L$ is —$SR^{L1}$. In certain embodiments, at least one instance of $R^L$ is —SH. In certain embodiments, at least one instance of $R^L$ is —N($R^{L1}$)$_2$. In certain embodiments, at least one instance of $R^L$ is —NH$_2$. In certain embodiments, at least one instance of $R^L$ is —CN. In certain embodiments, at least one instance of $R^L$ is —SCN. In certain embodiments, at least one instance of $R^L$ is —C(=$NR^{L1}$)$R^{L1}$, —C(=$NR^{L1}$)$OR^{L1}$, or —C(=$NR^{L1}$)N($R^{L1}$)$_2$. In certain embodiments, at least one instance of $R^L$ is —C(=O)$R^{L1}$, —C(=O)$OR^{L1}$, or —C(=O)N($R^{L1}$)$_2$. In certain embodiments, at least one instance of $R^L$ is —NO$_2$. In certain embodiments, at least one instance of $R^L$ is —$NR^{L1}$C(=O)$R^{L1}$, —$NR^{L1}$C(=O)$OR^{L1}$, or —$NR^{L1}$C(=O)N($R^{L1}$)$_2$. In certain embodiments, at least one instance of $R^L$ is —OC(=O)$R^{L1}$, —OC(=O)$OR^{L1}$, or —OC(=O)N($R^{L1}$)$_2$.

In certain embodiments, at least one instance of $R^L$ is hydrogen, halogen, or unsubstituted alkyl. In certain embodiments, at least one instance of $R^L$ is hydrogen, halogen, or unsubstituted $C_{1-6}$ alkyl. In certain embodiments, at least one instance of $R^L$ is halogen or unsubstituted alkyl. In certain embodiments, at least one instance of $R^L$ is halogen or unsubstituted $C_{1-6}$ alkyl. In certain embodiments, $R^L$ is halogen; and l is 1. In certain embodiments, $R^L$ is unsubstituted $C_{1-6}$ alkyl; and l is 1. In certain embodiments, each instance of $R^L$ is independently halogen or unsubstituted $C_{1-6}$ alkyl; and l is 2.

In compounds of Formula (I), two $R^L$ groups may be joined to form substituted or unsubstituted carbocyclyl. In certain embodiments, two instances of $R^L$ are joined to form saturated or unsaturated carbocyclyl. In certain embodiments, two instances of $R^L$ are joined to form carbocyclyl including one, two, or three double bonds in the carbocyclic ring. In certain embodiments, two instances of $R^L$ are joined to form 3- to 7-membered, monocyclic carbocyclyl. In certain embodiments, two instances of $R^L$ are joined to form 3-membered carbocyclyl. In certain embodiments, two instances of $R^L$ are joined to form 4-membered carbocyclyl. In certain embodiments, two instances of $R^L$ are joined to form 5-membered carbocyclyl. In certain embodiments, two instances of $R^L$ are joined to form 6-membered carbocyclyl. In certain embodiments, two instances of $R^L$ are joined to form 7-membered carbocyclyl. In certain embodiments, two instances of $R^L$ are joined to form 5- to 13-membered, bicyclic carbocyclyl.

In certain embodiments, two instances of $R^L$ are joined to form substituted or unsubstituted heterocyclyl. In certain embodiments, two instances of $R^L$ are joined to form saturated or unsaturated heterocyclyl. In certain embodiments, two instances of $R^L$ are joined to form heterocyclyl including one, two, or three double bonds in the heterocyclic ring. In certain embodiments, two instances of $R^L$ are joined to form heterocyclyl, wherein one, two, or three atoms in the heterocyclic ring are independently selected from the group consisting of nitrogen, oxygen, and sulfur. In certain embodiments, two instances of $R^L$ are joined to form 3- to 7-membered, monocyclic heterocyclyl. In certain embodiments, two instances of $R^L$ are joined to form 5- to 13-membered, bicyclic heterocyclyl.

In certain embodiments, two instances of $R^L$ are joined to form substituted or unsubstituted aryl. In certain embodiments, two instances of $R^L$ are joined to form 6- to 14-membered aryl. In certain embodiments, two instances of $R^L$ are joined to form 6- to 10-membered aryl. In certain embodiments, two instances of $R^L$ are joined to form monocyclic aryl. In certain embodiments, two instances of $R^L$ are joined to form phenyl. In certain embodiments, two instances of $R^L$ are joined to form bicyclic aryl. In certain embodiments, two instances of $R^L$ are joined to form naphthyl.

In certain embodiments, two instances of $R^L$ are joined to form substituted or unsubstituted heteroaryl. In certain embodiments, two instances of $R^L$ are joined to form monocyclic heteroaryl, wherein one, two, or three atoms in the heteroaryl ring are independently selected from the group consisting of nitrogen, oxygen, and sulfur. In certain embodiments, two instances of $R^L$ are joined to form 5-membered, monocyclic heteroaryl. In certain embodiments, two instances of $R^L$ are joined to form pyrrolyl. In certain embodiments, two instances of $R^L$ are joined to form 6-membered, monocyclic heteroaryl. In certain embodiments, two instances of $R^L$ are joined to form pyridyl. In certain embodiments, two instances of $R^L$ are joined to form bicyclic heteroaryl, wherein one, two, three, or four atoms in the heteroaryl ring are independently selected from the group consisting of nitrogen, oxygen, and sulfur. In certain embodiments, two instances of $R^L$ are joined to form 9-membered, bicyclic heteroaryl. In certain embodiments, two instances of $R^L$ are joined to form 10-membered, bicyclic heteroaryl.

In certain embodiments, at least one instance of $R^{L1}$ is H. In certain embodiments, at least one instance of $R^{L1}$ is substituted acyl. In certain embodiments, at least one instance of $R^{L1}$ is unsubstituted acyl. In certain embodiments, at least one instance of $R^{L1}$ is acetyl. In certain embodiments, at least one instance of $R^{L1}$ is substituted alkyl. In certain embodiments, at least one instance of $R^{L1}$ is unsubstituted alkyl. In certain embodiments, at least one instance of $R^{L1}$ is $C_{1-12}$ alkyl. In certain embodiments, at least one instance of $R^{L1}$ is $C_{1-6}$ alkyl. In certain embodiments, at least one instance of $R^{L1}$ is methyl. In certain embodiments, at least one instance of $R^{L1}$ is ethyl. In certain embodiments, at least one instance of $R^{L1}$ is propyl. In certain embodiments, at least one instance of $R^{L1}$ is butyl. In certain embodiments, at least one instance of $R^{L1}$ is pentyl. In certain embodiments, at least one instance of $R^{L1}$ is hexyl. In certain embodiments, at least one instance of $R^{L1}$ is substituted alkenyl. In certain embodiments, at least one instance of $R^{L1}$ is unsubstituted alkenyl. In certain embodiments, at least one instance of $R^{L1}$ is vinyl. In certain embodiments, at least one instance of is substituted alkynyl. In certain embodiments, at least one instance of $R^{L1}$ is unsubstituted alkynyl. In certain embodiments, at least one instance of $R^{L1}$ is ethynyl. In certain embodiments, at least one instance of $R^{L1}$ is substituted carbocyclyl. In certain embodiments, at least one instance of $R^{L1}$ is unsubstituted carbocyclyl. In certain embodiments, at least one instance of $R^{L1}$ is saturated carbocyclyl. In certain embodiments, at least one instance of is unsaturated carbocyclyl. In certain embodiments, at least one instance of $R^{L1}$ is carbocyclyl including one, two, or three double bonds in the carbocyclic ring. In certain embodiments, at least one instance of $R^{L1}$ is 3- to 7-membered, monocyclic carbocyclyl. In certain embodiments, at least one instance of $R^{L1}$ is cyclopropyl. In certain embodiments, at least one instance of $R^{L1}$ is cyclobutyl. In certain embodiments, at least one instance of $R^{L1}$ is cyclopentyl. In certain embodiments, at least one instance of $R^{L1}$ is cyclohexyl. In certain embodiments, at least one instance of $R^{L1}$ is cycloheptyl. In certain embodiments, at least one instance of $R^{L1}$ is 5- to 13-membered, bicyclic carbocyclyl. In certain embodiments, at least one instance of $R^{L1}$ is substituted heterocyclyl. In certain embodiments, at least one instance of $R^{L1}$ is unsubstituted heterocyclyl. In certain embodiments, at least one instance of $R^{L1}$ is saturated heterocyclyl. In certain embodiments, at least one instance of $R^{L1}$ is unsaturated heterocyclyl. In certain embodiments, at least one instance of $R^{L1}$ is heterocyclyl including one, two, or three double bonds in the heterocyclic ring. In certain embodiments, at least one instance of $R^{L1}$ is heterocyclyl, wherein one, two, or three atoms in the heterocyclic ring are independently selected from the group consisting of nitrogen, oxygen, and sulfur. In certain embodiments, at least one instance of $R^{L1}$ is 3- to 7-membered, monocyclic heterocyclyl. In certain embodiments, at least one instance of $R^{L1}$ is 5- to 13-membered, bicyclic heterocyclyl. In certain embodiments, at least one instance of $R^{L1}$ is substituted or unsubstituted aryl. In certain embodiments, at least one instance of $R^{L1}$ is 6- to 14-membered aryl. In certain embodiments, at least one instance of $R^{L1}$ is 6- to 10-membered aryl. In certain embodiments, at least one instance of $R^{L1}$ is monocyclic aryl. In certain embodiments, at least one instance of $R^{L1}$ is phenyl. In certain embodiments, at least one instance of $R^{L1}$ is bicyclic aryl. In certain embodiments, at least one instance of $R^{L1}$ is naphthyl. In certain embodiments, at least one instance of $R^{L1}$ is substituted or unsubstituted heteroaryl. In certain embodiments, at least one instance of $R^{L1}$ is heteroaryl, wherein one, two, three, or four atoms in the heteroaryl ring are independently selected from the group consisting of nitrogen, oxygen, and sulfur. In certain embodiments, at least one instance of $R^{L1}$ is monocyclic heteroaryl. In certain embodiments, at least one instance of $R^{L1}$ is 5-membered, monocyclic heteroaryl. In certain embodiments, at least one instance of Fe is 6-membered, monocyclic heteroaryl. In certain embodiments, at least one instance of $R^{L1}$ is pyridyl. In certain embodiments, at least one instance of $R^{L1}$ is bicyclic heteroaryl, wherein the point of attachment may be on any atom of the bicyclic heteroaryl ring system, as valency permits. In certain embodiments, at least one instance of $R^{L1}$ is 9-membered, bicyclic heteroaryl. In certain embodiments, at least one instance of $R^{L1}$ is 10-membered, bicyclic heteroaryl. In certain embodiments, at least one instance of $R^{L1}$ is a nitrogen protecting group when attached to a nitrogen atom. In certain embodiments, at least one instance of $R^{L1}$ is Bn, Boc, Cbz, Fmoc, trifluoroacetyl, triphenylmethyl, acetyl, or Ts when attached to a nitrogen atom. In certain embodiments, $R^{L1}$ is an oxygen protecting group when attached to an oxygen atom. In certain embodiments, $R^{L1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{L1}$ is a sulfur protecting group when attached to a sulfur atom. In certain embodiments, $R^{L1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{L1}$ are joined to form substituted or unsubstituted heterocyclyl. In certain embodiments, two instances of $R^{L1}$ are joined to form saturated or unsaturated heterocyclyl. In certain embodiments, two instances of $R^u$ are joined to form heterocyclyl including one, two, or three double bonds in the heterocyclic ring. In certain embodiments, two instances of $R^{L1}$ are joined to form heterocyclyl, wherein one, two, or three atoms in the heterocyclic ring are independently selected from the group consisting of nitrogen, oxygen, and sulfur. In certain embodiments, two instances of $R^{L1}$ are joined to form 3- to 7-membered, monocyclic heterocyclyl. In certain embodiments, two instances of $R^{L1}$ are joined to form 5- to 13-membered, bicyclic heterocyclyl.

In certain embodiments, l is 0. In certain embodiments, l is 1. In certain embodiments, l is 2. In certain embodiments, l is 3. In certain embodiments, l is 4.

In compounds of Formula (I), the X and Y moieties may be directly connected to each other, or there may be one or more methylene groups between X and Y. In certain embodiments, m is 0. In certain embodiments, m is 1, 2, 3, 4, or 5. In certain embodiments, m is 1. In certain embodiments, m is 2. In certain embodiments, m is 3. In certain embodiments, m is 4. In certain embodiments, m is 5.

In certain embodiments, the compound of Formula (I) is of the formula:

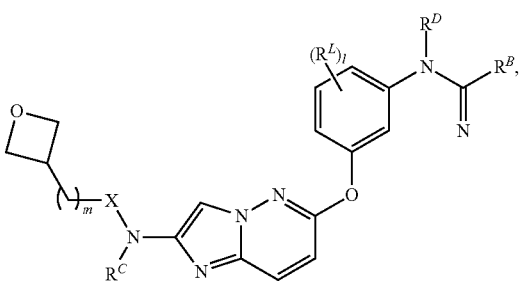

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

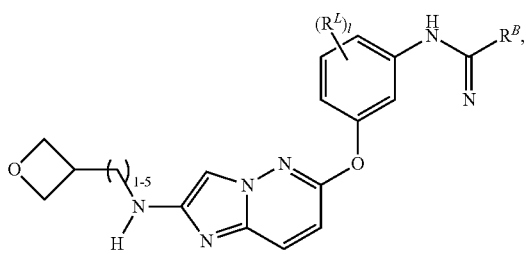

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

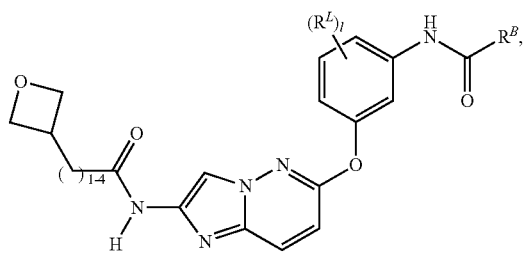

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

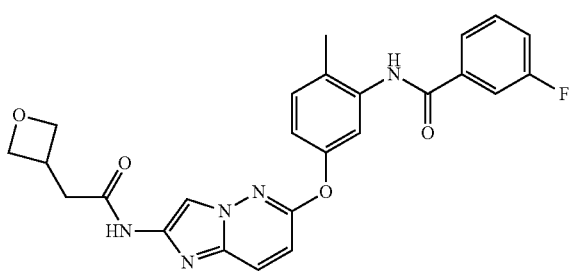 [SMILES: Cc1ccc(Oc2ccc3nc(NC(=O)CC4COC4)cn3n2)cc1NC(=O)c1cccc(F)c1]

or a pharmaceutically acceptable salt, solvate, hydrate, polymorph, co-crystal, tautomer, stereoisomer, isotopically labeled derivative, or prodrug thereof.

In certain embodiments, the compound is of the formula:

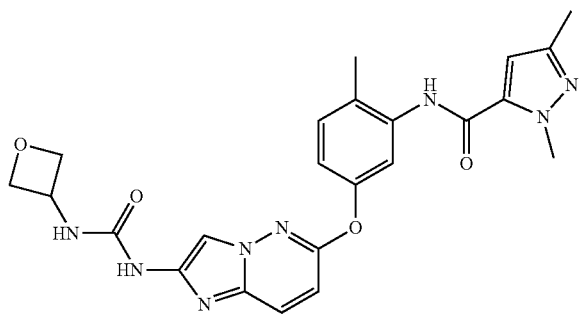 [SMILES: Cc1cc(C(=O)Nc2cc(Oc3ccc4nc(NC(=O)NC5COC5)cn4n3)ccc2C)n(C)n1]

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

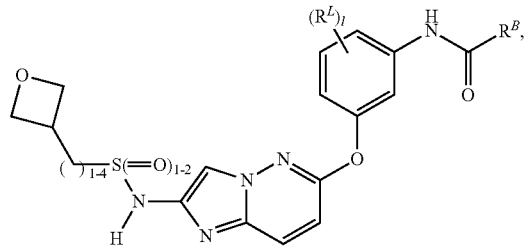

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

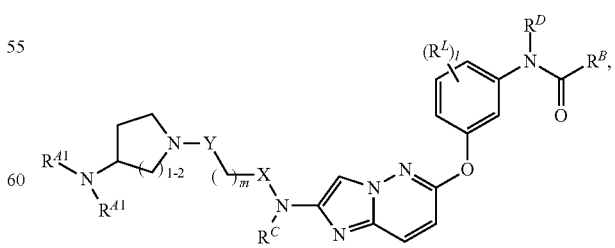

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

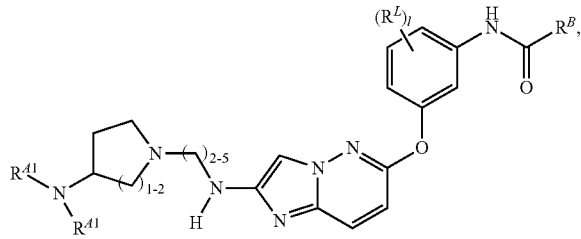

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

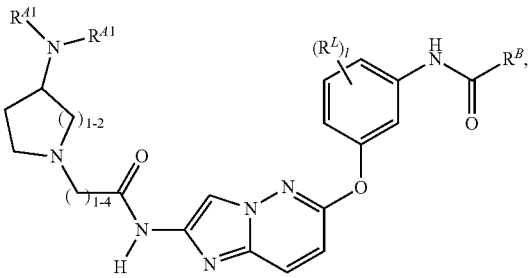

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

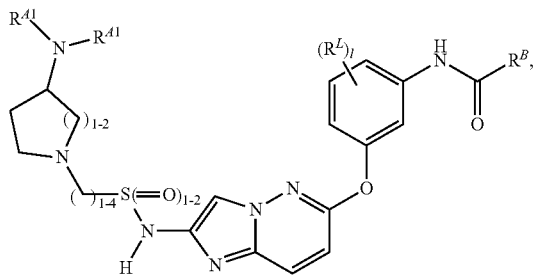

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

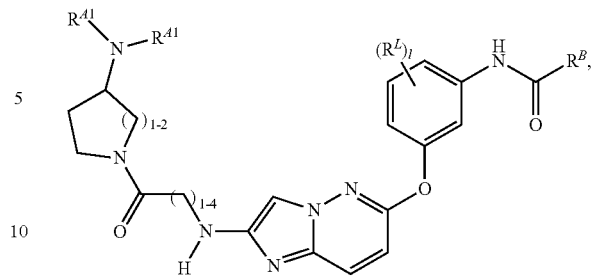

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

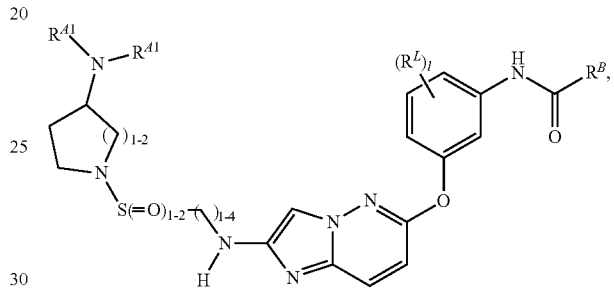

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

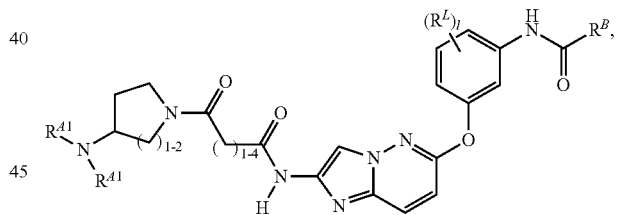

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

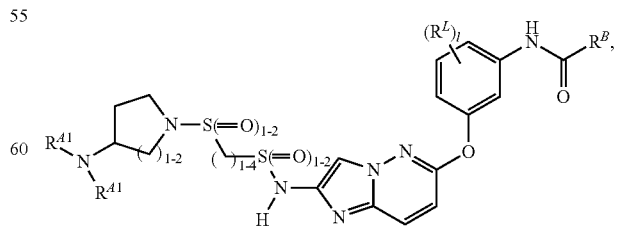

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

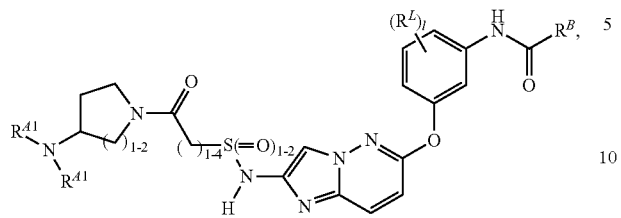

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

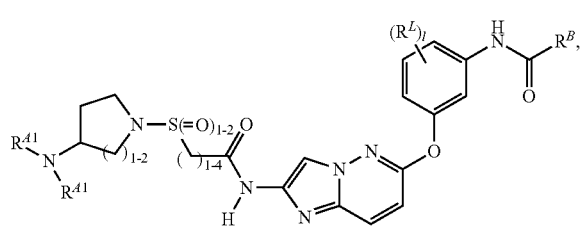

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

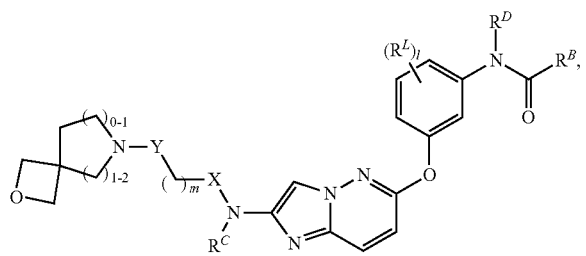

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

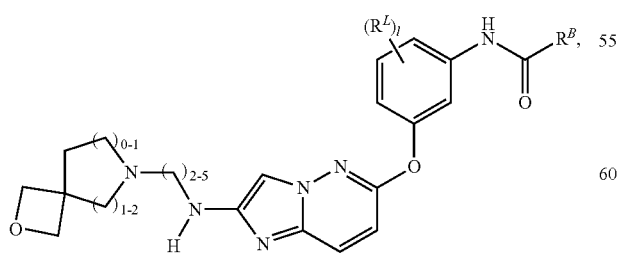

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

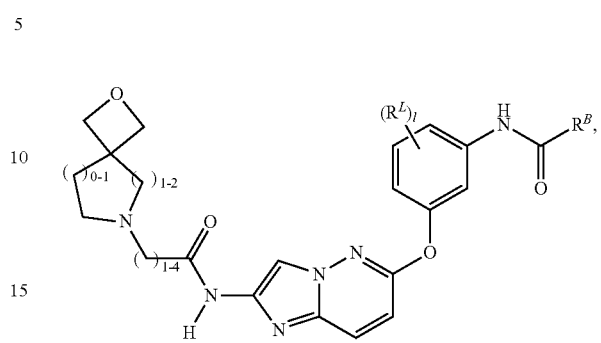

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

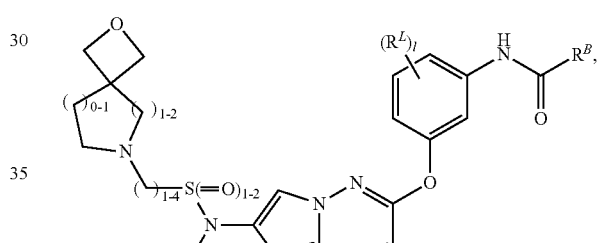

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

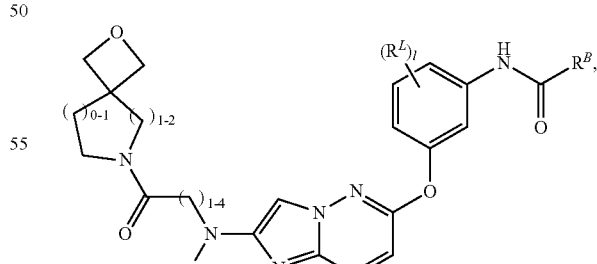

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

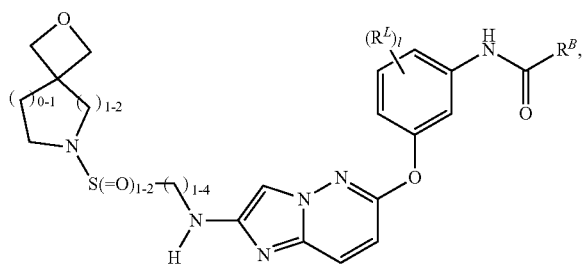

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

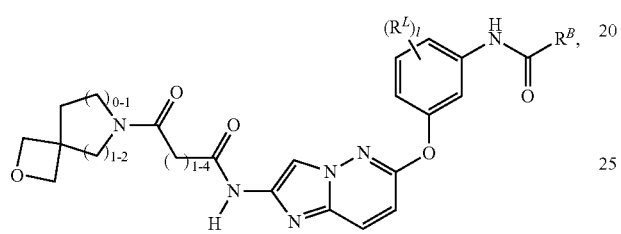

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

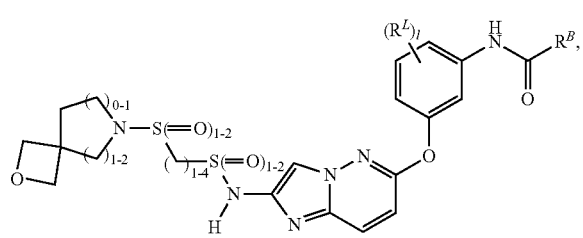

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

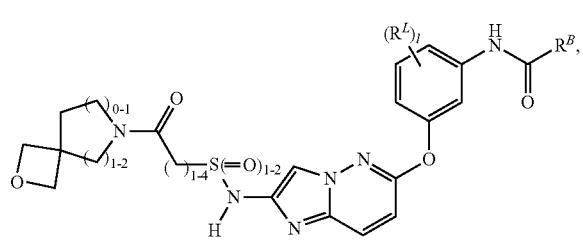

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

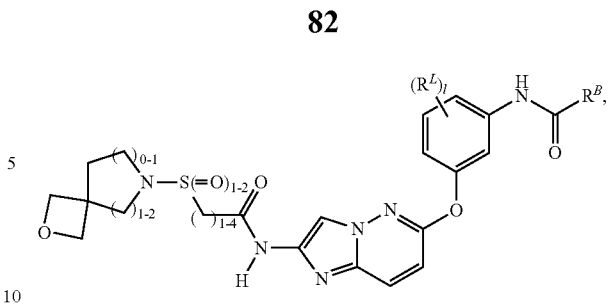

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

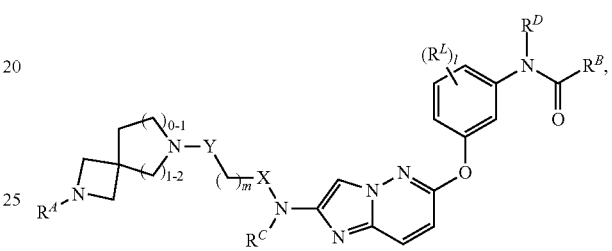

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

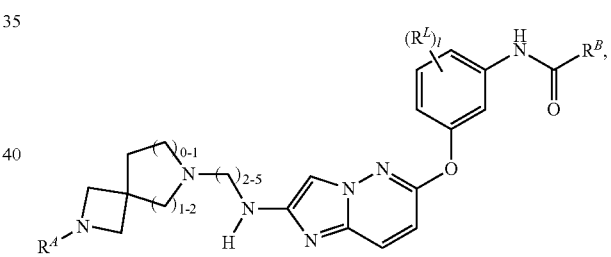

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

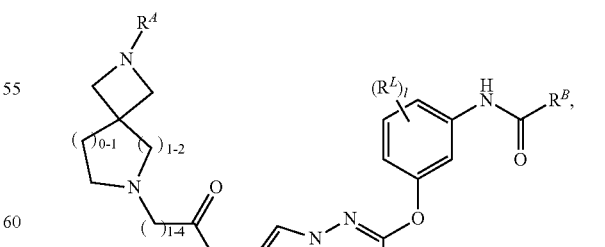

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

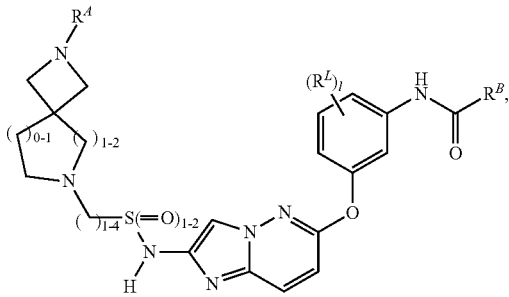

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

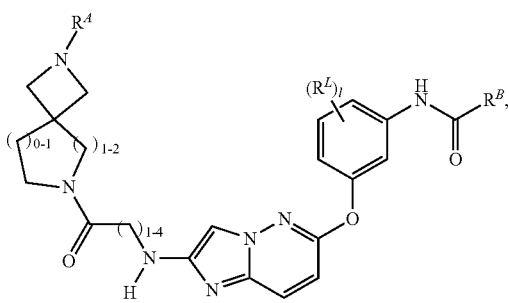

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

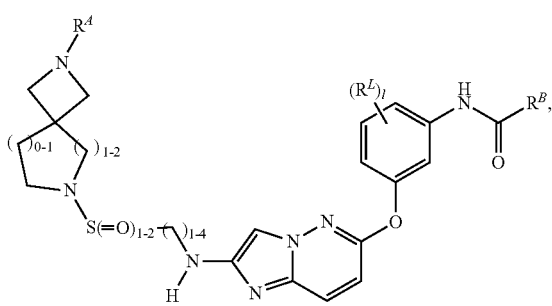

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

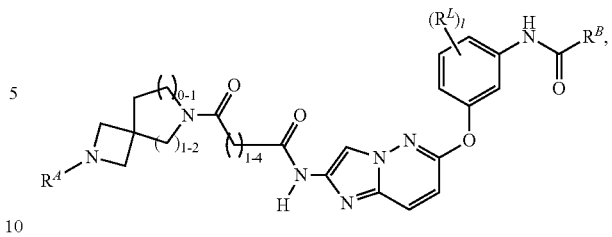

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

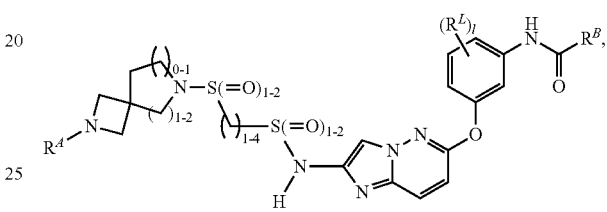

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

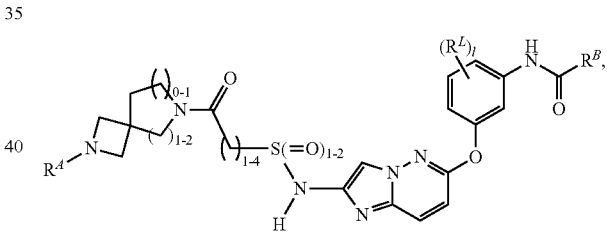

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

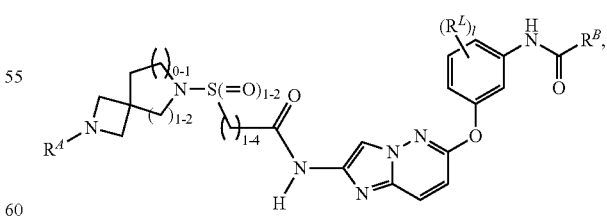

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

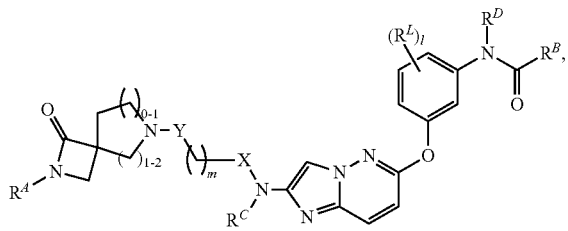

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

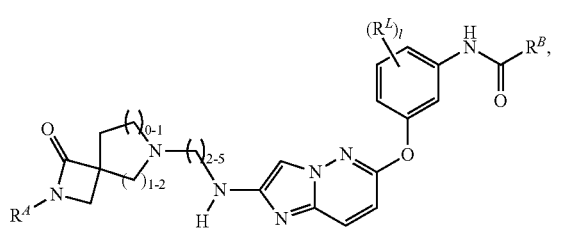

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

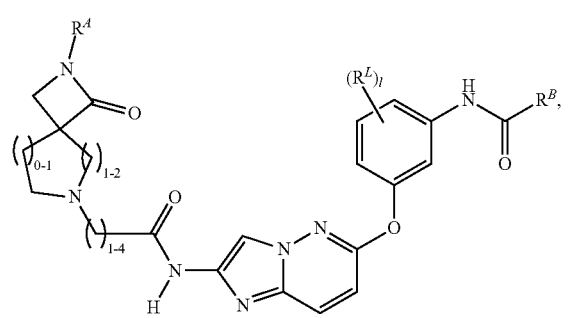

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

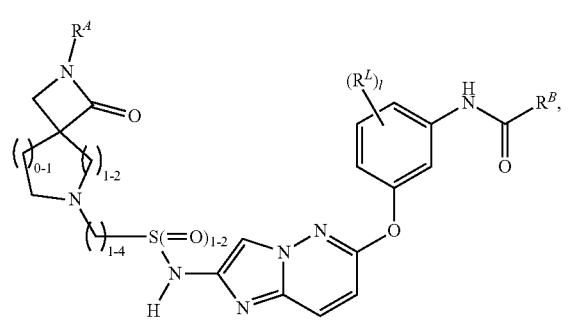

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

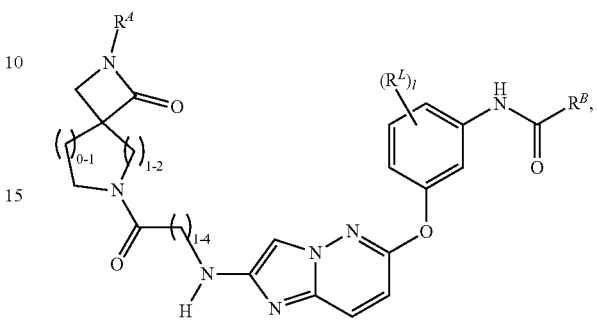

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

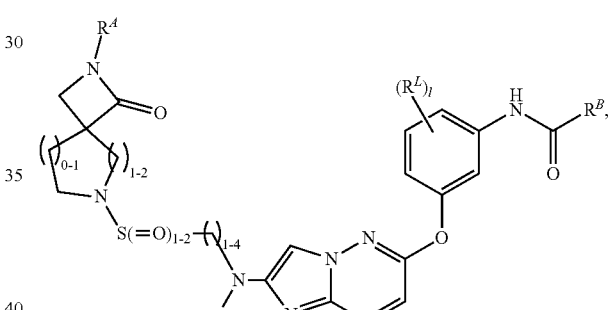

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

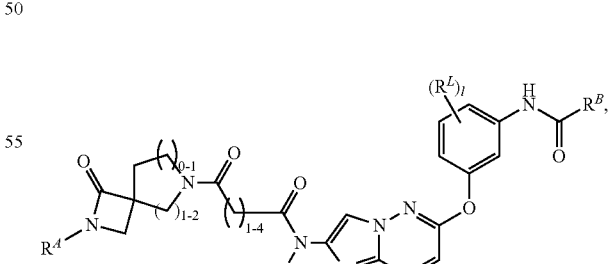

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

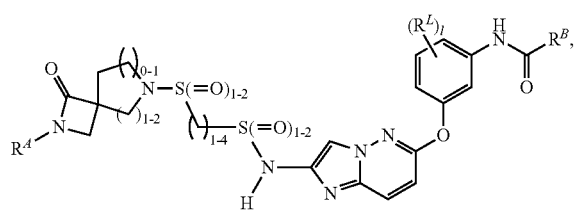

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

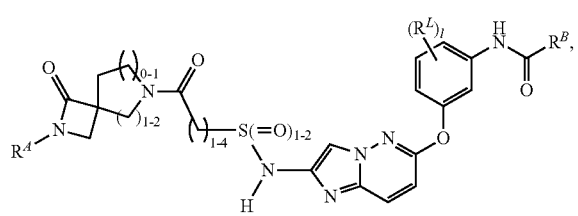

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

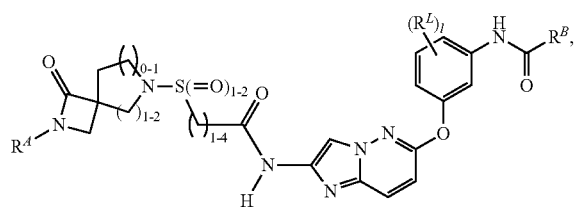

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

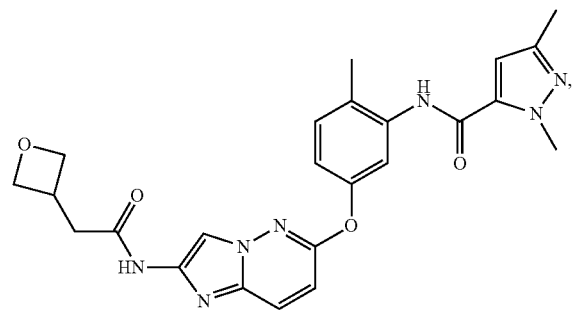

-continued

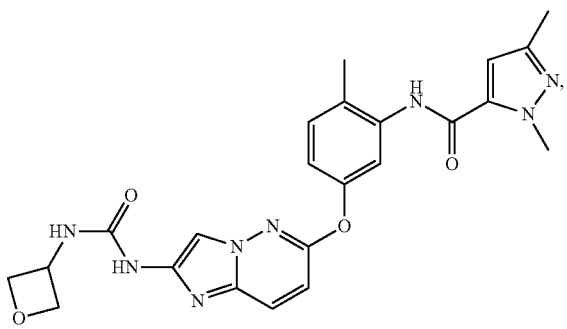

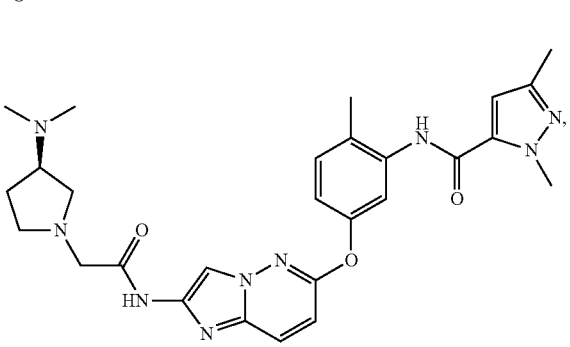

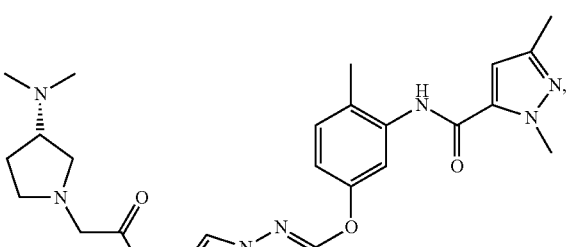

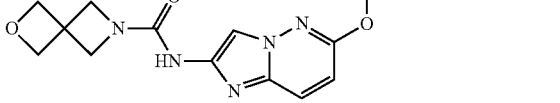

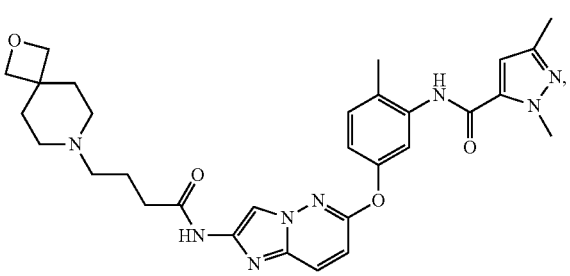

-continued

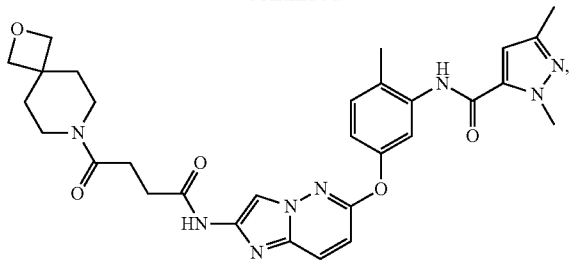 [SMILES: Cc1cc(C(=O)Nc2cc(Oc3ccc4nc(NC(=O)CCC(=O)N5CCC6(CC5)COC6)cn4n3)ccc2C)n(C)n1]

or a pharmaceutically acceptable salt, solvate, hydrate, polymorph, co-crystal, tautomer, stereoisomer, isotopically labeled derivative, or prodrug thereof.

The present invention also provides compounds of Formula (II):

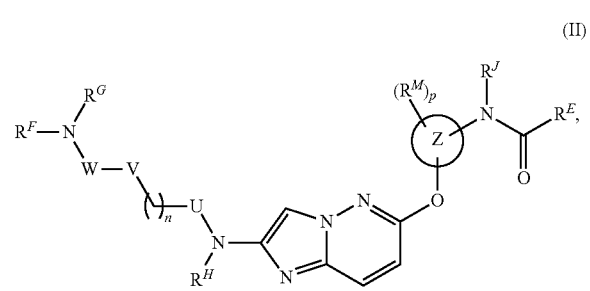

and pharmaceutically acceptable salts, solvates, hydrates, polymorphs, co-crystals, tautomers, stereoisomers, isotopically labeled derivatives, and prodrugs thereof; wherein:

U is a bond, —C(=O)—, —S(=O)—, —S(=O)$_2$—, —N(R$^N$)—S(=O)—, or —N(R$^N$)—S(=O)$_2$—;

V is a bond, CH, CH$_2$, —C(=O)—, —S(=O)—, or —S(=O)$_2$—;

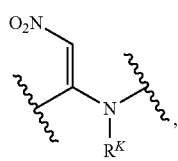

W is a bond, CH, —S(=O)$_2$—, —S(=O)$_2$—N(R$^K$)—, or wherein when V is C and W is CH, V and R$^G$ are joined to form substituted or unsubstituted, 5- to 6-membered, monocyclic heteroaryl;

Ring Z is substituted or unsubstituted carbocyclyl, substituted or unsubstituted heterocyclyl, substituted or unsubstituted aryl, or substituted or unsubstituted heteroaryl;

R$^N$ is hydrogen, substituted or unsubstituted C$_{1-6}$ alkyl, or a nitrogen protecting group;

R$^K$ is hydrogen, substituted or unsubstituted C$_{1-6}$ alkyl, or a nitrogen protecting group;

R$^E$ is substituted or unsubstituted alkyl or of the formula:

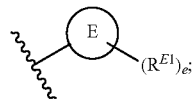

Ring E is substituted or unsubstituted carbocyclyl, substituted or unsubstituted heterocyclyl, substituted or unsubstituted aryl, or substituted or unsubstituted heteroaryl;

each instance of R$^{E1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{E1a}$, —N(R$^{E1a}$)$_2$, —SR$^{E1a}$, —CN, —SCN, —C(=NR$^{E1a}$)R$^{E1a}$, —C(=NR$^{E1a}$)OR$^{E1a}$, —C(=NR$^{E1a}$)N(R$^{E1a}$)$_2$, —C(=O)R$^{E1a}$, —C(=O)OR$^{E1a}$, —C(=O)N(R$^{E1a}$)$_2$, NO$_2$, NR$^{E1a}$C(=O)R$^{E1a}$, —NR$^{E1a}$C(=O)OR$^{E1a}$, —NR$^{E1a}$C(=O)N(R$^{E1a}$)$_2$, —OC(=O)R$^{E1a}$, —OC(=O)OR$^{E1a}$, or —OC(=O)N(R$^{E1a}$)$_2$, or two instances of R$^{E1}$ are joined to form substituted or unsubstituted carbocyclyl, substituted or unsubstituted heterocyclyl, substituted or unsubstituted aryl, or substituted or unsubstituted heteroaryl;

each instance of R$^{E1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{E1a}$ are joined to form substituted or unsubstituted heterocyclyl;

e is 0, 1, 2, 3, 4, or 5;

R$^F$ is hydrogen, substituted or unsubstituted alkyl, substituted or unsubstituted heterocyclyl, or a nitrogen protecting group, or R$^F$ and R$^G$ are joined to form a substituted or unsubstituted heterocyclic ring of the formula:

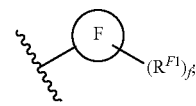

Ring F is substituted or unsubstituted, 4- to 7-membered, monocyclic heterocyclyl, or substituted or unsubstituted, 7- to 10-membered, Spiro bicyclic heterocyclyl, wherein one or two atoms in the heterocyclic ring are independently selected from the group consisting of oxygen and nitrogen;

each instance of R$^{F1}$ is independently hydrogen, halogen, substituted or unsubstituted alkyl, —OR$^{F1a}$, N(R$^{F1a}$)$_2$, oxo, or a nitrogen protecting group when attached to a nitrogen atom;

each instance of R$^{F1a}$ is independently hydrogen, substituted or unsubstituted alkyl, or a nitrogen protecting group when attached to a nitrogen atom, or an oxygen protecting group when attached to an oxygen atom, or two instances of R$^{F1a}$ are joined to form substituted or unsubstituted heterocyclyl;

f is 0, 1, 2, or 3;

R$^G$ is hydrogen, substituted or unsubstituted C$_{1-6}$ alkyl, or a nitrogen protecting group, or R$^G$ and R$^F$ are joined to form substituted or unsubstituted heterocyclyl;

R$^H$ is hydrogen, substituted or unsubstituted C$_{1-6}$ alkyl, or a nitrogen protecting group;

R$^J$ is hydrogen, substituted or unsubstituted C$_{1-6}$ alkyl, or a nitrogen protecting group;

each instance of R$^M$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{M1}$, $N(R^{M1})_2$, —$SR^{M1}$, —CN, —SCN, —C(=$NR^{M1}$)$R^{M1}$, —C(=$NR^{M1}$)$OR^{M1}$, —C(=$NR^{M1}$)$N(R^{M1})_2$, —C(=O)$R^{M1}$, —C(=O)$OR^{M1}$, —C(=O)$N(R^{M1})_2$, —$NO_2$, —$NR^{M1}$C(=O)$R^{M1}$, —$NR^{M1}$C(=O)$OR^{M1}$, —$NR^{M1}$C(=O)$N(R^{M1})_2$, —OC(=O)$R^{M1}$, —OC(=O)$OR^{M1}$, or OC(=O)$N(R^{M1})_2$, or two instances of $R^M$ are joined to form substituted or unsubstituted carbocyclyl, substituted or unsubstituted heterocyclyl, substituted or unsubstituted aryl, or substituted or unsubstituted heteroaryl;

each instance of $R^{M1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{M1}$ are joined to form substituted or unsubstituted heterocyclyl;

p is 0, 1, 2, 3, or 4; and n is 0, 1, 2, 3, 4, or 5.

Compounds of Formula (II) include moiety U. In certain embodiments, U is a bond. In certain embodiments, U is a single bond. In certain embodiments, U is —C(=O)—. In certain embodiments, U is —S(=O)—. In certain embodiments, U is —S(=O)$_2$—. In certain embodiments, U is —N($R^N$)—S(=O)—. In certain embodiments, U is —NH—S(=O)—. In certain embodiments, U is —N($R^N$)—S(=O)$_2$—. In certain embodiments, U is —NH—S(=O)$_2$—.

Compounds of Formula (II) include moiety V. In certain embodiments, V is a bond. In certain embodiments, V is a single bond. In certain embodiments, V is CH. In certain embodiments, V is $CH_2$. In certain embodiments, V is —C(=O). In certain embodiments, V is —S(=O)—. In certain embodiments, V is —S(=O)$_2$—.

In certain embodiments, each one of U and V is a bond. In certain embodiments, U is a bond; and V is —C(=O)—, —S(=O)—, or —S(=O)$_2$—. In certain embodiments, U is —C(=O)—, —S(=O)—, or —S(=O)$_2$—; and V is a bond. In certain embodiments, each one of U and V is independently —C(=O)—, —S(=O)—, or —S(=O)$_2$—. In certain embodiments, U is a bond; and V is —C(=O)—. In certain embodiments, U is —C(=O)—; and V is a bond. In certain embodiments, each one of U and V is —C(=O)—.

Compounds of Formula (II) include moiety W. In certain embodiments, W is a bond. In certain embodiments, W is a single bond. In certain embodiments, W is $CH_2$. In certain embodiments, W is =CH—. In certain embodiments, W is —CH=. In certain embodiments, W is —S(=O)$_2$—. In certain embodiments, W is —S(=O)$_2$—N($R^K$)—. In certain embodiments, W is —S(=O)$_2$—NH. In certain embodiments, W is of the formula:

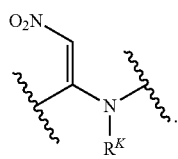

In certain embodiments, W is of the formula:

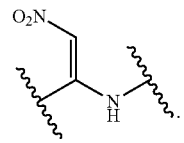 [SMILES: *N/C(*)=C/[N+](=O)[O-] ; "."]

In certain embodiments, V is CH; W is $CH_2$; and V and $R^G$ are joined to form substituted or unsubstituted, 5- to 6-membered, monocyclic heteroaryl. In certain embodiments, V is C; W is CH; and V and $R^G$ are joined to form substituted or unsubstituted, 5- to 6-membered, monocyclic heteroaryl, wherein one, two, three, or four atoms in the heteroaryl ring are independently selected from the group consisting of nitrogen, oxygen, and sulfur. In certain embodiments, V is C; W is CH; and V and $R^G$ are joined to form substituted pyrazolyl. In certain embodiments, V is C; W is CH; and V and $R^G$ are joined to form unsubstituted pyrazolyl. In certain embodiments, V is C; W is CH; V and $R^G$ are joined to form substituted or unsubstituted, 5- to 6-membered, monocyclic heteroaryl; U is a bond; and n is 0. In certain embodiments, V is CH; W is $CH_2$; V and $R^G$ are joined to form substituted or unsubstituted pyrazolyl; U is a bond; and n is 0.

In certain embodiments, $R^N$ is H. In certain embodiments, $R^N$ is substituted $C_{1-6}$ alkyl. In certain embodiments, $R^N$ is unsubstituted $C_{1-6}$ alkyl. In certain embodiments, $R^N$ is unsubstituted methyl. In certain embodiments, $R^N$ is substituted methyl. In certain embodiments, $R^N$ is —$CH_2F$. In certain embodiments, $R^N$ is —$CHF_2$. In certain embodiments, $R^N$ is —$CF_3$. In certain embodiments, $R^N$ is Bn. In certain embodiments, $R^N$ is unsubstituted ethyl. In certain embodiments, $R^N$ is substituted ethyl. In certain embodiments, $R^N$ is —$(CH_2)_2$Ph. In certain embodiments, $R^N$ is propyl. In certain embodiments, $R^N$ is butyl. In certain embodiments, $R^N$ is pentyl. In certain embodiments, $R^N$ is hexyl. In certain embodiments, $R^N$ is a nitrogen protecting group. In certain embodiments, $R^N$ is Bn, Boc, Cbz, Fmoc, trifluoroacetyl, triphenylmethyl, acetyl, or Ts.

In certain embodiments, $R^K$ is H. In certain embodiments, $R^K$ is substituted $C_{1-6}$ alkyl. In certain embodiments, $R^K$ is unsubstituted $C_{1-6}$ alkyl. In certain embodiments, $R^K$ is unsubstituted methyl. In certain embodiments, $R^K$ is substituted methyl. In certain embodiments, $R^K$ is —$CH_2F$. In certain embodiments, $R^K$ is —$CHF_2$. In certain embodiments, $R^K$ is —$CF_3$. In certain embodiments, $R^K$ is Bn. In certain embodiments, $R^K$ is unsubstituted ethyl. In certain embodiments, $R^K$ is substituted ethyl. In certain embodiments, $R^K$ is —$(CH_2)_2$Ph. In certain embodiments, $R^K$ is propyl. In certain embodiments, $R^K$ is butyl. In certain embodiments, $R^K$ is pentyl. In certain embodiments, $R^K$ is hexyl. In certain embodiments, $R^K$ is a nitrogen protecting group. In certain embodiments, $R^K$ is Bn, Boc, Cbz, Fmoc, trifluoroacetyl, triphenylmethyl, acetyl, or Ts.

Compounds of Formula (II) include Ring Z. In certain embodiments, Ring Z is substituted carbocyclyl. In certain embodiments, Ring Z is unsubstituted carbocyclyl. In certain embodiments, Ring Z is saturated carbocyclyl. In certain embodiments, Ring Z is unsaturated carbocyclyl. In certain embodiments, Ring Z is carbocyclyl including one, two, or three double bonds in the carbocyclic ring. In certain embodiments, Ring Z is monocyclic carbocyclyl. In certain embodiments, Ring Z is 3- to 7-membered, monocyclic carbocyclyl. In certain embodiments, Ring Z is substituted cyclopropyl. In certain embodiments, Ring Z is unsubstituted cyclopropyl. In certain embodiments, Ring Z is cyclobutyl. In certain embodiments, Ring Z is cyclopentyl. In certain embodiments, Ring Z is cyclohexyl. In certain embodiments, Ring Z is cycloheptyl. In certain embodiments, Ring Z is bicyclic carbocyclyl. In certain embodiments, Ring Z is 5- to 13-membered, bicyclic carbocyclyl.

In certain embodiments, Ring Z is substituted heterocyclyl. In certain embodiments, Ring Z is unsubstituted heterocyclyl. In certain embodiments, Ring Z is saturated heterocyclyl. In certain embodiments, Ring Z is unsaturated heterocyclyl. In certain embodiments, Ring Z is heterocyclyl including one, two, or three double bonds in the heterocyclic ring. In certain embodiments, Ring Z is heterocyclyl, wherein one, two, or three atoms in the heterocyclic ring are independently selected from the group consisting of nitrogen, oxygen, and sulfur. In certain embodiments, Ring Z is monocyclic heterocyclyl. In certain embodiments, Ring Z is 3- to 7-membered, monocyclic heterocyclyl. In certain embodiments, Ring Z is 5-membered, monocyclic heterocyclyl. In certain embodiments, Ring Z is substituted or unsubstituted tetrahydrofuranyl. In certain embodiments, Ring Z is 6-membered, monocyclic heterocyclyl. In certain embodiments, Ring Z is substituted or unsubstituted tetrahydropyranyl. In certain embodiments, Ring Z is bicyclic heterocyclyl. In certain embodiments, Ring Z is 5- to 13-membered, bicyclic heterocyclyl.

In certain embodiments, Ring Z is substituted aryl. In certain embodiments, Ring Z is unsubstituted aryl. In certain embodiments, Ring Z is 6- to 14-membered aryl. In certain embodiments, Ring Z is 6- to 10-membered aryl. In certain embodiments, Ring Z is unsubstituted phenyl. In certain embodiments, Ring Z is substituted phenyl. In certain embodiments, Ring Z is of the formula:

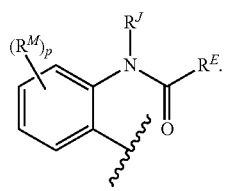

In certain embodiments, Ring Z is of the formula:

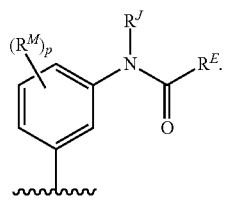

In certain embodiments, Ring Z is of the formula:

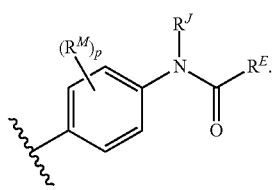

In certain embodiments, Ring Z is substituted heteroaryl. In certain embodiments, Ring Z is unsubstituted heteroaryl. In certain embodiments, Ring Z is 5- to 6-membered, monocyclic heteroaryl, wherein one, two, three, or four atoms in the heteroaryl ring are independently selected from the group consisting of nitrogen, oxygen, and sulfur. In certain embodiments, Ring Z is 5-membered, monocyclic heteroaryl. In certain embodiments, Ring Z is 5-membered, monocyclic heteroaryl, wherein one of the five atoms in the heteroaryl ring is nitrogen, oxygen, or sulfur.

Compounds of Formula (II) include substituent $R^E$. In certain embodiments, $R^E$ is substituted alkyl. In certain embodiments, $R^E$ is unsubstituted alkyl. In certain embodiments, $R^E$ is substituted $C_{1-6}$ alkyl. In certain embodiments, $R^E$ is unsubstituted $C_{1-6}$ alkyl. In certain embodiments, $R^E$ is unsubstituted methyl. In certain embodiments, $R^E$ is substituted methyl. In certain embodiments, $R^E$ is —CH$_2$F. In certain embodiments, $R^E$ is —CHF$_2$. In certain embodiments, $R^E$ is —CF$_3$. In certain embodiments, $R^E$ is Bn. In certain embodiments, $R^E$ is unsubstituted ethyl. In certain embodiments, $R^E$ is substituted ethyl. In certain embodiments, $R^E$ is —(CH$_2$)$_2$Ph. In certain embodiments, $R^E$ is propyl. In certain embodiments, $R^E$ is butyl. In certain embodiments, $R^E$ is unsubstituted t-butyl. In certain embodiments, $R^E$ is pentyl. In certain embodiments, $R^E$ is hexyl.

In certain embodiments, $R^E$ is of the formula:

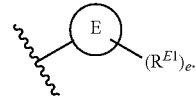

In certain embodiments, Ring E is substituted carbocyclyl. In certain embodiments, Ring E is unsubstituted carbocyclyl. In certain embodiments, Ring E is saturated carbocyclyl. In certain embodiments, Ring E is unsaturated carbocyclyl. In certain embodiments, Ring E is carbocyclyl including one, two, or three double bonds in the carbocyclic ring. In certain embodiments, Ring E is monocyclic carbocyclyl. In certain embodiments, Ring E is 3- to 7-membered, monocyclic carbocyclyl. In certain embodiments, Ring E is substituted cyclopropyl. In certain embodiments, Ring E is unsubstituted cyclopropyl. In certain embodiments, Ring E is cyclobutyl. In certain embodiments, Ring E is cyclopentyl. In certain embodiments, Ring E is cyclohexyl. In certain embodiments, Ring E is cycloheptyl. In certain embodiments, Ring E is bicyclic carbocyclyl. In certain embodiments, Ring E is 5- to 13-membered, bicyclic carbocyclyl.

In certain embodiments, Ring E is substituted heterocyclyl. In certain embodiments, Ring E is unsubstituted heterocyclyl. In certain embodiments, Ring E is saturated heterocyclyl. In certain embodiments, Ring E is unsaturated heterocyclyl. In certain embodiments, Ring E is heterocyclyl including one, two, or three double bonds in the heterocyclic ring. In certain embodiments, Ring E is heterocyclyl, wherein one, two, or three atoms in the heterocyclic ring are independently selected from the group consisting of nitrogen, oxygen, and sulfur. In certain embodiments, Ring E is monocyclic heterocyclyl. In certain embodiments, Ring E is 3- to 7-membered, monocyclic heterocyclyl. In certain embodiments, Ring E is 5-membered, monocyclic heterocyclyl. In certain embodiments, Ring E is substituted or unsubstituted tetrahydrofuranyl. In certain embodiments, Ring E is 6-membered, monocyclic heterocyclyl. In certain embodiments, Ring E is substituted or unsubstituted tetrahydropyranyl. In certain embodiments, Ring E is bicyclic heterocyclyl. In certain embodiments, Ring E is 5- to 13-membered, bicyclic heterocyclyl.

In certain embodiments, Ring E is substituted aryl. In certain embodiments, Ring E is unsubstituted aryl. In certain embodiments, Ring E is 6- to 14-membered aryl. In certain embodiments, Ring E is 6- to 10-membered aryl. In certain embodiments, Ring E is unsubstituted phenyl. In certain embodiments, Ring E is substituted phenyl. In certain embodiments, Ring E is of the formula:

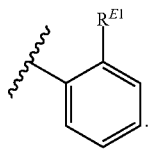

In certain embodiments, Ring E is of the formula:

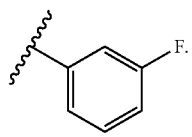 [SMILES: *c1cccc(F)c1]

In certain embodiments, Ring E is of the formula:

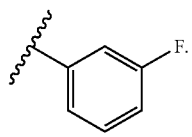 [SMILES: *c1cccc(F)c1]

In certain embodiments, Ring E is of the formula:

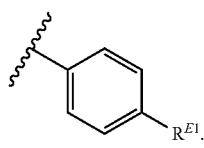

In certain embodiments, Ring E is of the formula:

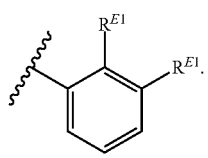

In certain embodiments, Ring E is of the formula:

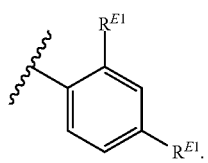

In certain embodiments, Ring E is of the formula:

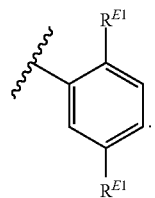

In certain embodiments, Ring E is of the formula:

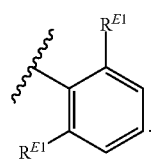

In certain embodiments, Ring E is of the formula:

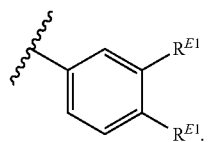

In certain embodiments, Ring E is of the formula:

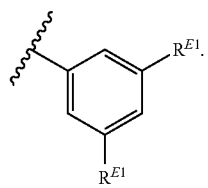

In certain embodiments, Ring E is of the formula:

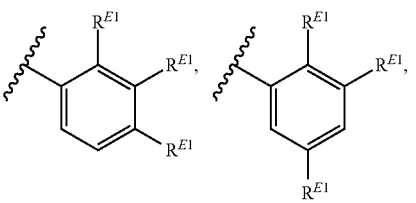

-continued

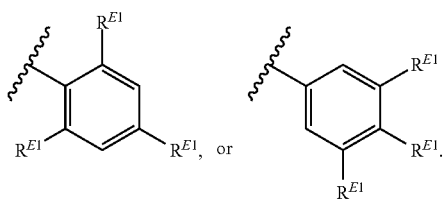

In certain embodiments, Ring E is of the formula:

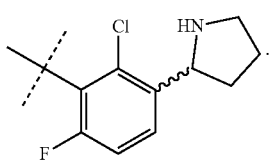

In certain embodiments, Ring E is of the formula:

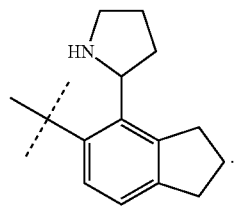

In certain embodiments, Ring E is substituted naphthyl. In certain embodiments, Ring E is unsubstituted naphthyl.

In certain embodiments, Ring E is substituted heteroaryl. In certain embodiments, Ring E is unsubstituted heteroaryl. In certain embodiments, Ring E is 5- to 6-membered, monocyclic heteroaryl, wherein one, two, three, or four atoms in the heteroaryl ring are independently selected from the group consisting of nitrogen, oxygen, and sulfur. In certain embodiments, Ring E is 5-membered, monocyclic heteroaryl. In certain embodiments, Ring E is 5-membered, monocyclic heteroaryl, wherein one of the five atoms in the heteroaryl ring is nitrogen, oxygen, or sulfur. In certain embodiments, Ring E is of the formula:

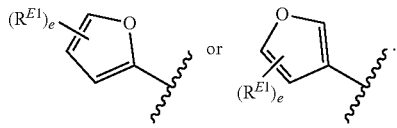

In certain embodiments, Ring E is of the formula:

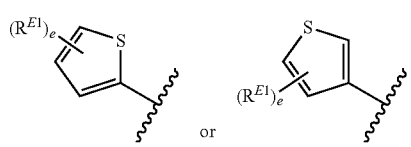

In certain embodiments, Ring E is of the formula:

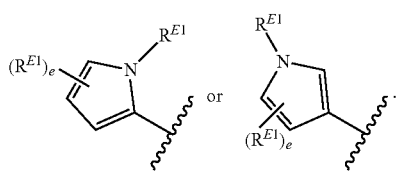

In certain embodiments, Ring E is 5-membered, monocyclic heteroaryl, wherein two of the five atoms in the heteroaryl ring are independently nitrogen, oxygen, or sulfur. In certain embodiments, Ring E is of the formula:

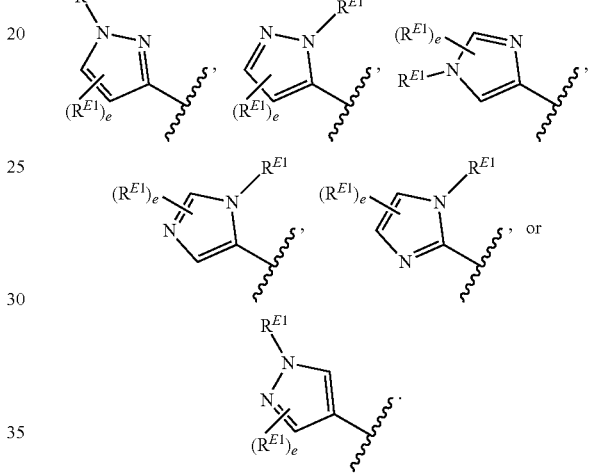

In certain embodiments, Ring E is of the formula:

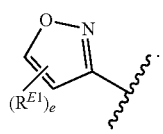

In certain embodiments, Ring E is of the formula:

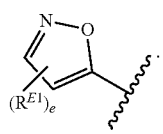

In certain embodiments, Ring E is of the formula:

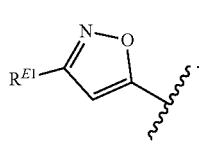

In certain embodiments, Ring E is of the formula:

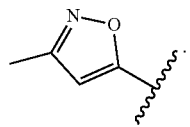 [SMILES: *c1cc(C)no1 ; "."]

In certain embodiments, Ring E is of the formula:

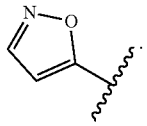 [SMILES: *c1ccno1 ; "."]

In certain embodiments, Ring E is of the formula:

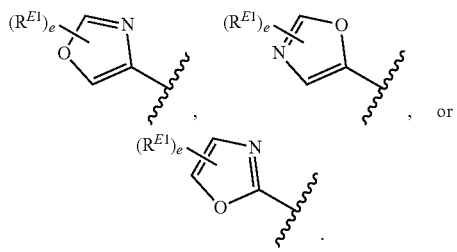

In certain embodiments, Ring E is of the formula:

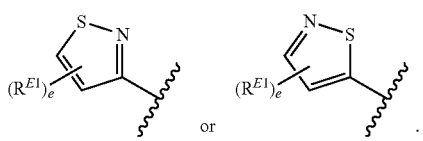

or

In certain embodiments, Ring E is of the formula:

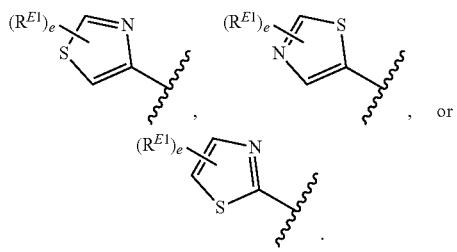

or

In certain embodiments, Ring E is 5-membered, monocyclic heteroaryl, wherein three of the five atoms in the heteroaryl ring are independently nitrogen, oxygen, or sulfur. In certain embodiments, Ring E is of the formula:

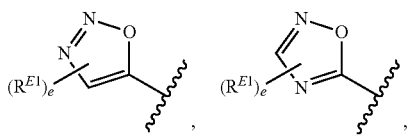

-continued

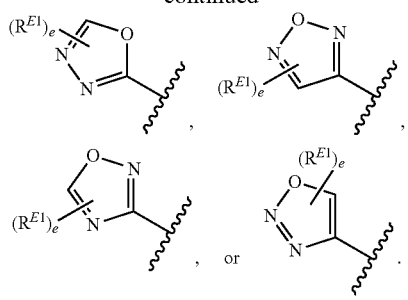

,

In certain embodiments, Ring E is of the formula:

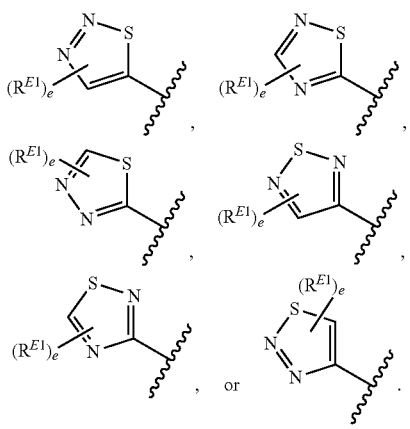

, or

In certain embodiments, Ring E is of the formula:

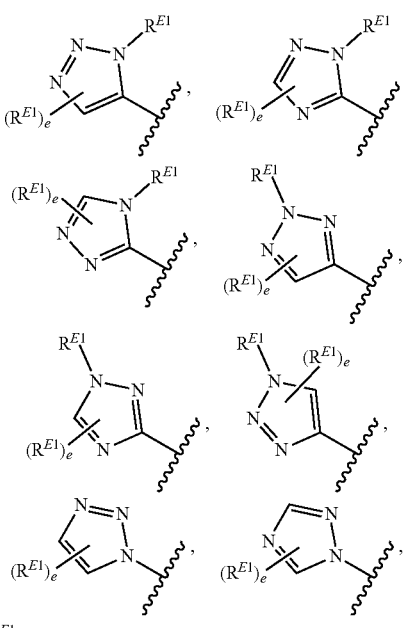

or

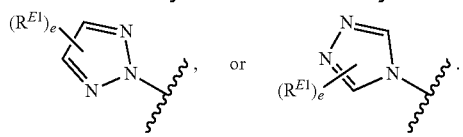

.

In certain embodiments, Ring E is 5-membered, monocyclic heteroaryl, wherein only four of the five atoms in the heteroaryl ring are nitrogen, oxygen, or sulfur. In certain embodiments, Ring E is of the formula:

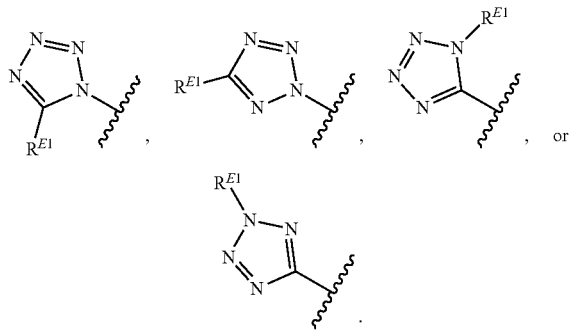

In certain embodiments, Ring E is 6-membered, monocyclic heteroaryl, wherein one, two, or three atoms in the heteroaryl ring is nitrogen. In certain embodiments, Ring E is of the formula:

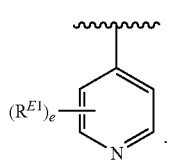

In certain embodiments, Ring E is of the formula:

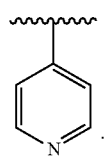

In certain embodiments, Ring E is of the formula:

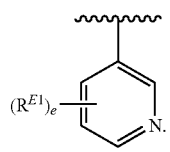

In certain embodiments, Ring E is of the formula:

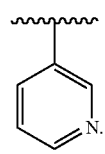

In certain embodiments, Ring E is of the formula:

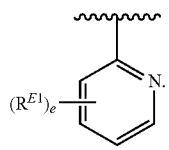

In certain embodiments, Ring E is of the formula:

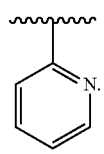

In certain embodiments, Ring E is of the formula:

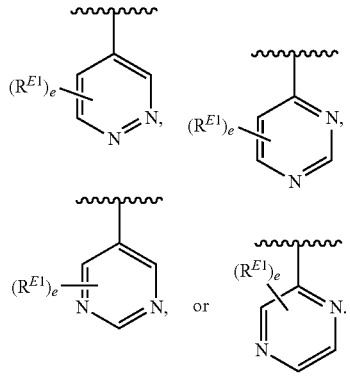

In certain embodiments, Ring E is of the formula:

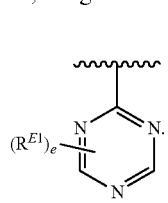

In certain embodiments, Ring E is bicyclic heteroaryl, wherein the point of attachment may be on any atom of the bicyclic heteroaryl ring system, as valency permits. In certain embodiments, Ring E is substituted bicyclic heteroaryl. In certain embodiments, Ring E is unsubstituted bicyclic heteroaryl. In certain embodiments, Ring E is 9- or 10-membered, bicyclic heteroaryl, wherein one, two, three, or four atoms in the bicyclic ring of the heteroaryl are independently selected from the group consisting of nitrogen, oxygen, and sulfur. In certain embodiments, Ring E is 8- to 10-membered, bicyclic heteroaryl, wherein one atom in the bicyclic ring of the heteroaryl is nitrogen, oxygen, or sulfur. In certain embodiments, Ring E is 8- to 10-membered, bicyclic heteroaryl, wherein two atoms in the bicyclic ring of the heteroaryl are independently selected from the group consisting of nitrogen, oxygen, and sulfur. In certain embodiments, Ring E is 8- to 10-membered, bicyclic heteroaryl, wherein three atoms in the bicyclic ring of the heteroaryl are independently selected from the group consisting of nitrogen, oxygen, and sulfur. In certain embodiments, Ring E is 8- to 10-membered, bicyclic heteroaryl, wherein only four atoms in the bicyclic ring of the heteroaryl are independently selected from the group consisting of nitrogen, oxygen, and sulfur.

In certain embodiments, $R^E$ is t-butyl. In certain embodiments, $R^E$ is cyclopropyl. In certain embodiments, $R^E$ is of the formula:

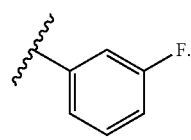 [SMILES: *c1cccc(F)c1]

In certain embodiments, $R^E$ is of the formula:

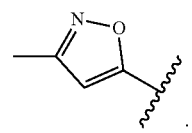

In certain embodiments, $R^E$ is of the formula:

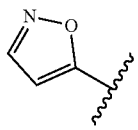

In certain embodiments, $R^E$ is of the formula:

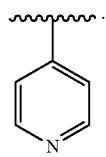

In certain embodiments, $R^E$ is of the formula:

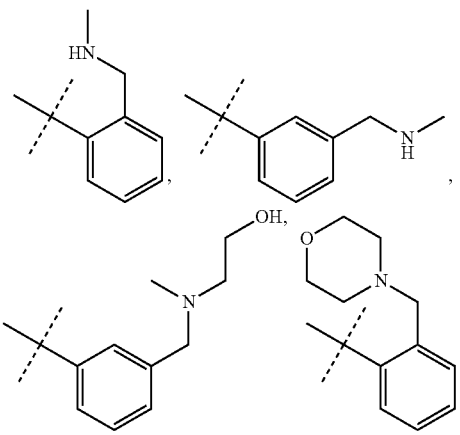

-continued

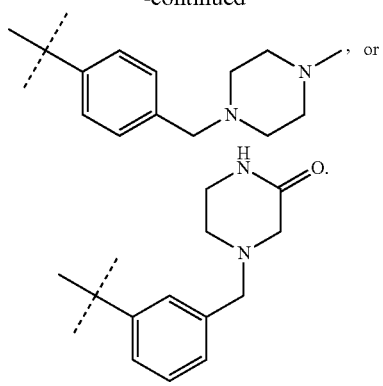

In certain embodiments, $R^E$ is of the formula:

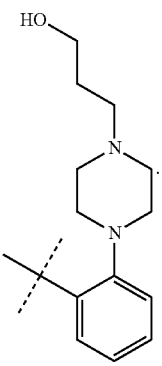

In certain embodiments, $R^E$ is of the formula:

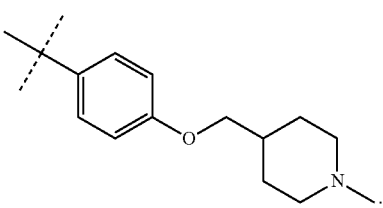

In certain embodiments, $R^E$ is of the formula:

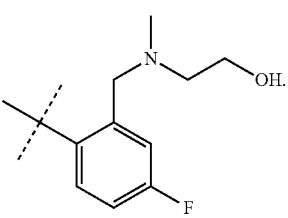

In certain embodiments, $R^E$ is of the formula:

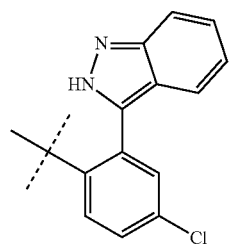

In certain embodiments, $R^E$ is of the formula:

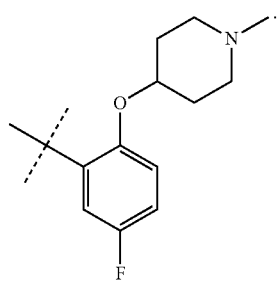

In certain embodiments, $R^E$ is of the formula:

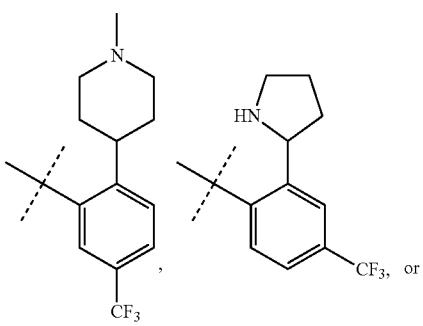

In certain embodiments, $R^E$ is of the formula:

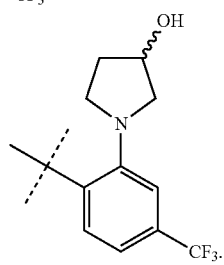

In certain embodiments, $R^E$ is of the formula:

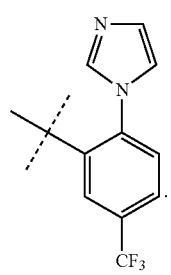

In certain embodiments, $R^E$ is of the formula:

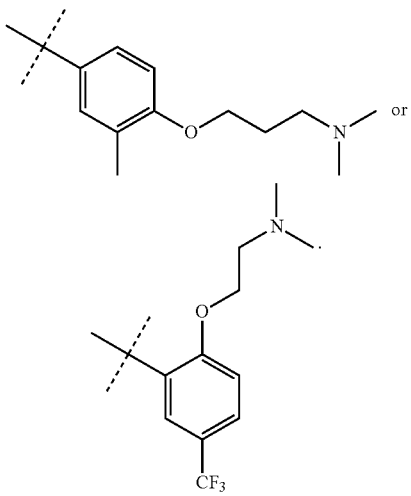

In certain embodiments, $R^E$ is of the formula:

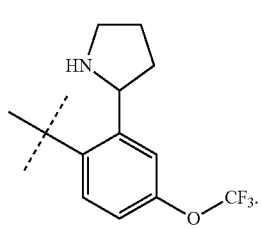

In certain embodiments, $R^E$ is of the formula:

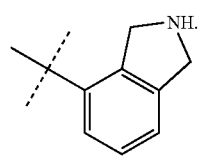

In certain embodiments, $R^E$ is of the formula:

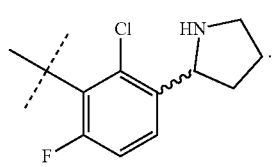

In certain embodiments, $R^E$ is of the formula:

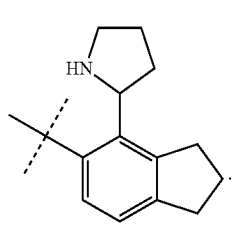

When $R^E$ is of the formula:

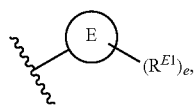

compounds of Formula (II) may include one or more substituents $R^{E1}$. In certain embodiments, at least one instance of $R^{E1}$ is H. In certain embodiments, at least one instance of $R^{E1}$ is halogen. In certain embodiments, at least one instance of $R^{E1}$ is F. In certain embodiments, at least one instance of $R^{E1}$ is Cl. In certain embodiments, at least one instance of $R^{E1}$ is Br. In certain embodiments, at least one instance of $R^{E1}$ is I (iodine). In certain embodiments, at least one instance of $R^{E1}$ is substituted acyl. In certain embodiments, at least one instance of $R^{E1}$ is unsubstituted acyl. In certain embodiments, at least one instance of $R^{E1}$ is substituted alkyl. In certain embodiments, at least one instance of $R^{E1}$ is unsubstituted alkyl. In certain embodiments, at least one instance of $R^{E1}$ is $C_{1-12}$ alkyl. In certain embodiments, at least one instance of $R^{E1}$ is $C_{1-6}$ alkyl. In certain embodiments, at least one instance of $R^{E1}$ is unsubstituted methyl. In certain embodiments, at least one instance of $R^{E1}$ is substituted methyl. In certain embodiments, at least one instance of $R^{E1}$ is —$CH_2F$. In certain embodiments, at least one instance of $R^{E1}$ is —$CHF_2$. In certain embodiments, at least one instance of $R^{E1}$ is —$CF_3$. In certain embodiments, at least one instance of $R^{E1}$ is —$CH_2$—$N(R^{E1a})_2$. In certain embodiments, at least one instance of $R^{E1}$ is —$CH_2$—N(unsubstituted $C_{1-6}$ alkyl)-$(CH_2)_{2-4}$—OH. In certain embodiments, at least one instance of $R^{E1}$ is —$CH_2$—N($CH_3$)—$(CH_2)_2$—OH. In certain embodiments, at least one instance of $R^{E1}$ is of the formula:

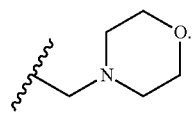

In certain embodiments, at least one instance of $R^{E1}$ is of the formula:

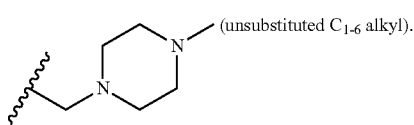

In certain embodiments, at least one instance of $R^{E1}$ is of the formula:

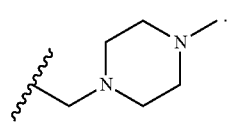 [SMILES: *CN1CCN(C)CC1 ; "."]

In certain embodiments, at least one instance of $R^{E1}$ is

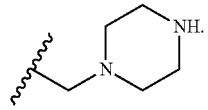

In certain embodiments, at least one instance of $R^{E1}$ is of the formula:

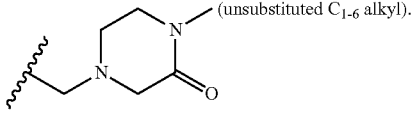

In certain embodiments, at least one instance of $R^{E1}$ is of the formula:

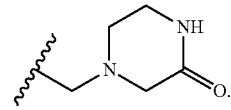 [SMILES: *CN1CCNC(=O)C1]

In certain embodiments, at least one instance of $R^{E1}$ is —$CH_2$—NH($R^{E1a}$). In certain embodiments, at least one instance of $R^{E1}$ is —$CH_2$—NH(unsubstituted $C_{1-6}$ alkyl). In certain embodiments, at least one instance of $R^{E1}$ is —$CH_2$—NH($CH_3$). In certain embodiments, at least one instance of $R^{E1}$ is Bn. In certain embodiments, at least one instance of $R^{E1}$ is unsubstituted ethyl. In certain embodiments, at least one instance of $R^{E1}$ is substituted ethyl. In certain embodiments, at least one instance of $R^{E1}$ is —$(CH_2)_2Ph$. In certain embodiments, at least one instance of $R^{E1}$ is propyl. In certain embodiments, at least one instance of $R^{E1}$ is butyl. In certain embodiments, at least one instance of $R^{E1}$ is pentyl. In certain embodiments, at least one instance of $R^{E1}$ is hexyl. In certain embodiments, at least one instance of $R^{E1}$ is halogen or substituted or unsubstituted $C_{1-6}$ alkyl. In certain embodiments, at least one instance of $R^{E1}$ is substituted alkenyl. In certain embodiments, at least one instance of $R^{E1}$ is unsubstituted alkenyl. In certain embodiments, at least one instance of $R^{E1}$ is vinyl. In certain embodiments, at least one instance of $R^{E1}$ is substituted alkynyl. In certain embodiments, at least one instance of $R^{E1}$ is unsubstituted alkynyl. In certain embodiments, at least one instance of $R^{E1}$ is ethynyl. In certain embodiments, at least one instance of $R^{E1}$ is substituted carbocyclyl. In certain embodiments, at least one instance of $R^{E1}$ is unsubstituted carbocyclyl. In certain embodiments, at least one instance of $R^{E1}$ is saturated carbocyclyl. In certain embodiments, at least one instance of $R^{E1}$ is unsaturated carbocyclyl. In certain embodiments, at least one instance of $R^{E1}$ is carbocyclyl including one, two, or three double bonds in the carbocyclic ring. In certain embodiments, at least one instance of $R^{E1}$ is monocyclic carbocyclyl. In certain embodiments, at least one instance of $R^{E1}$ is 3- to 7-membered, monocyclic carbocyclyl. In certain embodiments, at least one instance of $R^{E1}$ is cyclopropyl. In certain embodiments, at least one instance of $R^{E1}$ is cyclobutyl. In certain embodiments, at least one instance of $R^{E1}$ is cyclopentyl. In certain embodiments, at least one instance of $R^{E1}$ is cyclohexyl. In certain embodiments, at least one instance of $R^{E1}$ is cycloheptyl. In certain embodiments, at least one instance of $R^{E1}$ is bicyclic carbocyclyl. In certain embodiments, at least one instance of $R^{E1}$ is 5- to 13-membered, bicyclic carbocyclyl. In certain embodiments, at least one instance of $R^{E1}$ is substituted heterocyclyl. In certain embodiments, at least one instance of $R^{E1}$ is unsubstituted heterocyclyl. In certain embodiments, at least one instance of $R^{E1}$ is saturated heterocyclyl. In certain embodiments, at least one instance of $R^{E1}$ is unsaturated heterocyclyl. In certain embodiments, at least one instance of $R^{E1}$ is heterocyclyl including one, two, or three double bonds in the heterocyclic ring. In certain embodiments, at least one instance of $R^{E1}$ is heterocyclyl, wherein one, two, or three atoms in the heterocyclic ring are independently selected from the group consisting of nitrogen, oxygen, and sulfur. In certain embodiments, at least one instance of $R^{E1}$ is monocyclic heterocyclyl. In certain embodiments, at least one instance of $R^{E1}$ is 3- to 7-membered, monocyclic heterocyclyl. In certain embodiments, at least one instance of $R^{E1}$ is of the formula:

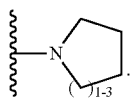

In certain embodiments, at least one instance of $R^{E1}$ is of the formula:

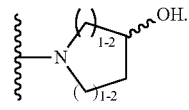

In certain embodiments, at least one instance of $R^{E1}$ is of the formula:

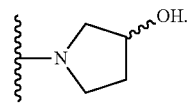

In certain embodiments, at least one instance of $R^{E1}$ is of the formula:

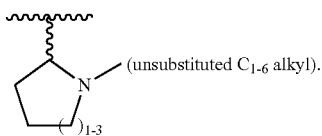

In certain embodiments, at least one instance of $R^{E1}$ is of the formula:

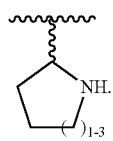

In certain embodiments, at least one instance of $R^{E1}$ is of the formula:

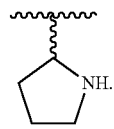

In certain embodiments, at least one instance of $R^{E1}$ is of the formula:

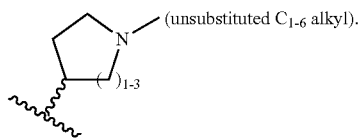

In certain embodiments, at least one instance of $R^{E1}$ is of the formula:

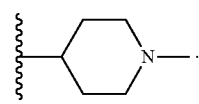

In certain embodiments, at least one instance of $R^{E1}$ is of the formula:

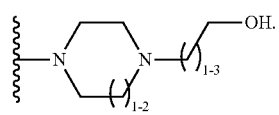

In certain embodiments, at least one instance of $R^{E1}$ is of the formula:

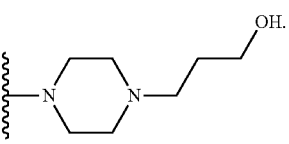 [SMILES: *N1CCN(CCCO)CC1]

In certain embodiments, at least one instance of $R^{E1}$ is of the formula:

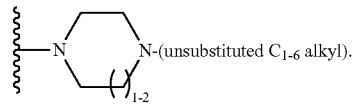

In certain embodiments, at least one instance of $R^{E1}$ is of the formula:

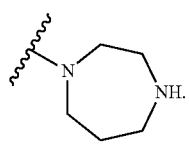 [SMILES: *N1CCCNCC1]

In certain embodiments, at least one instance of $R^{E1}$ is of the formula:

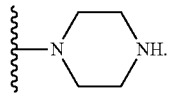

In certain embodiments, at least one instance of $R^{E1}$ is bicyclic heterocyclyl. In certain embodiments, at least one instance of $R^{E1}$ is 5- to 13-membered, bicyclic heterocyclyl. In certain embodiments, at least one instance of $R^{E1}$ is substituted aryl. In certain embodiments, at least one instance of $R^{E1}$ is unsubstituted aryl. In certain embodiments, at least one instance of $R^{E1}$ is 6- to 14-membered aryl. In certain embodiments, at least one instance of $R^{E1}$ is 6- to 10-membered aryl. In certain embodiments, at least one instance of $R^{E1}$ is substituted phenyl. In certain embodiments, at least one instance of $R^{E1}$ is unsubstituted phenyl. In certain embodiments, at least one instance of $R^{E1}$ is substituted naphthyl. In certain embodiments, at least one instance of $R^{E1}$ is unsubstituted naphthyl. In certain embodiments, at least one instance of $R^{E1}$ is substituted heteroaryl. In certain embodiments, at least one instance of $R^{E1}$ is unsubstituted heteroaryl. In certain embodiments, at least one instance of $R^{E1}$ is heteroaryl, wherein one, two, three, or four atoms in the heteroaryl ring are independently selected from the group consisting of nitrogen, oxygen, and sulfur. In certain embodiments, at least one instance of $R^{E1}$ is monocyclic heteroaryl. In certain embodiments, at least one instance of $R^{E1}$ is 5-membered, monocyclic heteroaryl. In certain embodiments, at least one instance of $R^{E1}$ is of the formula:

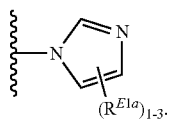

In certain embodiments, at least one instance of $R^{E1}$ is of the formula:

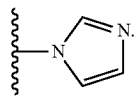

In certain embodiments, at least one instance of $R^{E1}$ is 6-membered, monocyclic heteroaryl. In certain embodiments, at least one instance of $R^{E1}$ is pyridyl. In certain embodiments, at least one instance of $R^{E1}$ is bicyclic heteroaryl, wherein the point of attachment may be on any atom of the bicyclic heteroaryl ring system, as valency permits. In certain embodiments, at least one instance of $R^{E1}$ is 9-membered, bicyclic heteroaryl. In certain embodiments, at least one instance of $R^{E1}$ is of the formula:

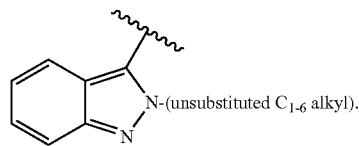

In certain embodiments, at least one instance of $R^{E1}$ is of the formula:

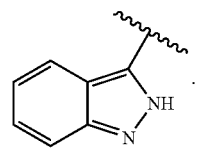 [SMILES: *c1[nH]nc2ccccc12]

In certain embodiments, at least one instance of $R^{E1}$ is 10-membered, bicyclic heteroaryl. In certain embodiments, at least one instance of $R^{E1}$ is —$OR^{E1a}$. In certain embodiments, at least one instance of $R^{E1}$ is —OMe. In certain embodiments, at least one instance of $R^{E1}$ is —OEt. In certain embodiments, at least one instance of $R^{E1}$ is —OPr. In certain embodiments, at least one instance of $R^{E1}$ is —OBu. In certain embodiments, at least one instance of $R^{E1}$ is —O(pentyl). In certain embodiments, at least one instance of $R^{E1}$ is —O(hexyl). In certain embodiments, at least one instance of $R^{E1}$ is —OPh. In certain embodiments, at least one instance of $R^{E1}$ is —OBn. In certain embodiments, at least one instance of $R^{E1}$ is —O(CH$_2$)$_2$Ph. In certain embodiments, at least one instance of $R^{E1}$ is —OH. In certain embodiments, at least one instance of $R^{E1}$ is —O—CF$_3$. In certain embodiments, at least one instance of $R^{E1}$ is —O—(CH$_2$)$_{2-4}$—N($R^{E1a}$)$_2$. In certain embodiments, at least one instance of $R^{E1}$ is —O—(CH$_2$)$_{2-4}$—N(unsubstituted C$_{1-6}$ alkyl)$_2$. In certain embodiments, at least one instance of $R^{E1}$ is —O—(CH$_2$)$_2$—N(CH$_3$)$_2$. In certain embodiments, at least one instance of $R^{E1}$ is —O—(CH$_2$)$_3$—N(CH$_3$)$_2$. In certain embodiments, at least one instance of $R^{E1}$ is of the formula:

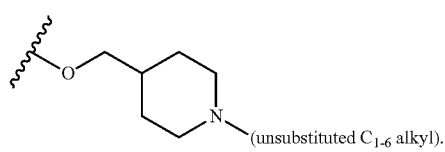

In certain embodiments, at least one instance of $R^{E1}$ is of the formula:

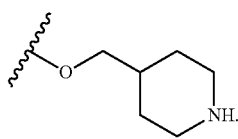 [SMILES: *OCC1CCNCC1]

In certain embodiments, at least one instance of $R^{E1}$ is of the formula:

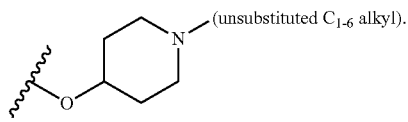

In certain embodiments, at least one instance of $R^{E1}$ is of the formula:

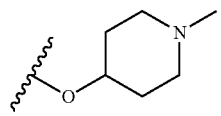

In certain embodiments, at least one instance of $R^{E1}$ is of the formula:

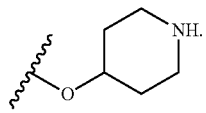 [SMILES: *OC1CCNCC1]

In certain embodiments, at least one instance of $R^{E1}$ is —$SR^{E1a}$. In certain embodiments, at least one instance of $R^{E1}$ is —SH. In certain embodiments, at least one instance of $R^{E1}$ is —$N(R^{E1a})_2$. In certain embodiments, at least one instance of $R^{E1}$ is —$NH_2$. In certain embodiments, at least one instance of $R^{E1}$ is —CN. In certain embodiments, at least one instance of $R^{E1}$ is —SCN. In certain embodiments, at least one instance of $R^{E1}$ is —$C(=NR^{E1a})R^{E1a}$, —$C(=NR^{E1a})OR^{E1a}$, or —$C(=NR^{E1a})N(R^{E1a})_2$. In certain embodiments, at least one instance of $R^{E1}$ is —$C(=O)R^{E1a}$, —$C(=O)OR^{E1a}$, or —$C(=O)N(R^{E1a})_2$. In certain embodiments, at least one instance of $R^{E1}$ is —$NO_2$. In certain embodiments, at least one instance of $R^{E1}$ is —$NR^{E1a}C(=O)R^{E1a}$, —$NR^{E1a}C(=O)OR^{E1a}$, or —$NR^{E1a}C(=O)N(R^{E1a})_2$. In certain embodiments, at least one instance of $R^{E1a}$, is —$OC(=O)R^{E1a}$, —$OC(=O)OR^{E1a}$, or —$OC(=O)N(R^{E1a})_2$.

In certain embodiments, at least one instance of $R^{E1}$ is hydrogen, halogen, or unsubstituted alkyl. In certain embodiments, at least one instance of $R^{E1}$ is hydrogen, halogen, or unsubstituted $C_{1-6}$ alkyl. In certain embodiments, at least one instance of $R^{E1}$ is halogen or unsubstituted alkyl. In certain embodiments, at least one instance of $R^{E1}$ is halogen or unsubstituted $C_{1-6}$ alkyl.

In compounds of Formula (II), two $R^{E1}$ groups may be joined to form substituted or unsubstituted carbocyclyl. In certain embodiments, two instances of $R^{E1}$ are joined to form saturated or unsaturated carbocyclyl. In certain embodiments, two instances of $R^{E1}$ are joined to form carbocyclyl including one, two, or three double bonds in the carbocyclic ring. In certain embodiments, two instances of $R^{E1}$ are joined to form 3- to 7-membered, monocyclic carbocyclyl. In certain embodiments, two instances of $R^{E1}$ are joined to form 3-membered carbocyclyl. In certain embodiments, two instances of $R^{E1}$ are joined to form 4-membered carbocyclyl. In certain embodiments, two instances of $R^{E1}$ are joined to form 5-membered carbocyclyl. In certain embodiments, two instances of $R^{E1}$ are joined to form 6-membered carbocyclyl. In certain embodiments, two instances of $R^{E1}$ are joined to form 7-membered carbocyclyl. In certain embodiments, two instances of $R^{E1}$ are joined to form 5- to 13-membered, bicyclic carbocyclyl.

In certain embodiments, two instances of $R^{E1}$ are joined to form substituted or unsubstituted heterocyclyl. In certain embodiments, two instances of $R^{E1}$ are joined to form saturated or unsaturated heterocyclyl. In certain embodiments, two instances of $R^{E1}$ are joined to form heterocyclyl including one, two, or three double bonds in the heterocyclic ring. In certain embodiments, two instances of $R^{E1}$ are joined to form heterocyclyl, wherein one, two, or three atoms in the heterocyclic ring are independently selected from the group consisting of nitrogen, oxygen, and sulfur. In certain embodiments, two instances of $R^{E1}$ are joined to form 3- to 7-membered, monocyclic heterocyclyl. In certain embodiments, two instances of $R^{E1}$ are joined to form

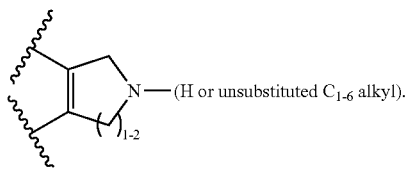

In certain embodiments, two instances of $R^{E1}$ are joined to form

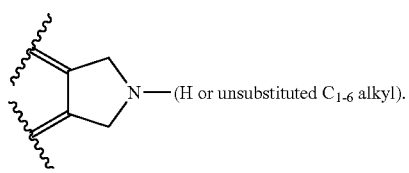

In certain embodiments, two instances of $R^{E1}$ are joined to form

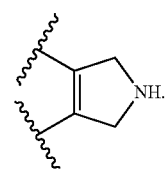 [SMILES: *C1=C(*)CNC1]

In certain embodiments, two instances of $R^{E1}$ are joined to form

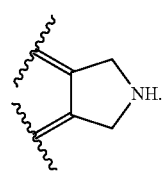 [SMILES: *=C1CNCC1=*]

In certain embodiments, two instances of $R^{E1}$ are joined to form 5- to 13-membered, bicyclic heterocyclyl.

In certain embodiments, two instances of $R^{E1}$ are joined to form substituted or unsubstituted aryl. In certain embodiments, two instances of $R^{E1}$ are joined to form 6- to 14-membered aryl. In certain embodiments, two instances of $R^{E1}$ are joined to form 6- to 10-membered aryl. In certain embodiments, two instances of $R^{E1}$ are joined to form monocyclic aryl. In certain embodiments, two instances of $R^{E1}$ are joined to form phenyl. In certain embodiments, two instances of $R^{E1}$ are joined to form bicyclic aryl. In certain embodiments, two instances of $R^{E1}$ are joined to form naphthyl.

In certain embodiments, two instances of $R^{E1}$ are joined to form substituted or unsubstituted heteroaryl. In certain embodiments, two instances of $R^{E1}$ are joined to form monocyclic heteroaryl, wherein one, two, or three atoms in the heteroaryl ring are independently selected from the group consisting of nitrogen, oxygen, and sulfur. In certain embodiments, two instances of $R^{E1}$ are joined to form 5-membered, monocyclic heteroaryl. In certain embodiments, two instances of $R^{E1}$ are joined to form pyrrolyl. In certain embodiments, two instances of $R^{E1}$ are joined to form 6-membered, monocyclic heteroaryl. In certain embodiments, two instances of $R^{E1}$ are joined to form pyridyl. In certain embodiments, two instances of $R^{E1}$ are joined to form bicyclic heteroaryl, wherein one, two, three, or four atoms in the heteroaryl ring are independently selected from the group consisting of nitrogen, oxygen, and sulfur. In certain embodiments, two instances of $R^{E1}$ are joined to form 9-membered, bicyclic heteroaryl. In certain embodiments, two instances of $R^{E1}$ are joined to form 10-membered, bicyclic heteroaryl.

In certain embodiments, at least one instance of $R^{E1a}$ is H. In certain embodiments, at least one instance of $R^{E1a}$ is substituted acyl. In certain embodiments, at least one instance of $R^{E1a}$ is unsubstituted acyl. In certain embodiments, at least one instance of $R^{E1a}$ is acetyl. In certain embodiments, at least one instance of $R^{E1a}$ is substituted alkyl. In certain embodiments, at least one instance of $R^{E1a}$ is unsubstituted alkyl. In certain embodiments, at least one instance of $R^{E1a}$ is $C_{1-12}$ alkyl. In certain embodiments, at least one instance of $R^{E1a}$ is $C_{1-6}$ alkyl. In certain embodiments, at least one instance of $R^{E1a}$ is methyl. In certain embodiments, at least one instance of $R^{E1a}$ is ethyl. In certain embodiments, at least one instance of $R^{E1a}$ is propyl. In certain embodiments, at least one instance of $R^{E1a}$ is butyl. In certain embodiments, at least one instance of $R^{E1a}$ is pentyl. In certain embodiments, at least one instance of $R^{E1a}$ is hexyl. In certain embodiments, at least one instance of $R^{E1a}$ is substituted alkenyl. In certain embodiments, at least one instance of $R^{E1a}$ is unsubstituted alkenyl. In certain embodiments, at least one instance of $R^{E1a}$ is vinyl. In certain embodiments, at least one instance of $R^{E1a}$ is substituted alkynyl. In certain embodiments, at least one instance of $R^{E1a}$ is unsubstituted alkynyl. In certain embodiments, at least one instance of $R^{E1a}$ is ethynyl. In certain embodiments, at least one instance of $R^{E1a}$ is substituted carbocyclyl. In certain embodiments, at least one instance of $R^{E1a}$ is unsubstituted carbocyclyl. In certain embodiments, at least one instance of $R^{E1a}$ is saturated carbocyclyl. In certain embodiments, at least one instance of $R^{E1a}$ is unsaturated carbocyclyl. In certain embodiments, at least one instance of $R^{E1a}$ is carbocyclyl including one, two, or three double bonds in the carbocyclic ring. In certain embodiments, at least one instance of $R^{E1a}$ is 3- to 7-membered, monocyclic carbocyclyl. In certain embodiments, at least one instance of $R^{E1a}$ is cyclopropyl. In certain embodiments, at least one instance of $R^{E1a}$ is cyclobutyl. In certain embodiments, at least one instance of $R^{E1a}$ is cyclopentyl. In certain embodiments, at least one instance of $R^{E1a}$ is cyclohexyl. In certain embodiments, at least one instance of $R^{E1a}$ is cycloheptyl. In certain embodiments, at least one instance of $R^{E1a}$ is 5- to 13-membered, bicyclic carbocyclyl. In certain embodiments, at least one instance of $R^{E1a}$ is substituted heterocyclyl. In certain embodiments, at least one instance of $R^{E1a}$ is unsubstituted heterocyclyl. In certain embodiments, at least one instance of $R^{E1a}$ is saturated heterocyclyl. In certain embodiments, at least one instance of $R^{E1a}$ is unsaturated heterocyclyl. In certain embodiments, at least one instance of $R^{E1a}$ is heterocyclyl including one, two, or three double bonds in the heterocyclic ring. In certain embodiments, at least one instance of $R^{E1a}$ is heterocyclyl, wherein one, two, or three atoms in the heterocyclic ring are independently selected from the group consisting of nitrogen, oxygen, and sulfur. In certain embodiments, at least one instance of $R^{E1a}$ is 3- to 7-membered, monocyclic heterocyclyl. In certain embodiments, at least one instance of $R^{E1a}$ is 5- to 13-membered, bicyclic heterocyclyl. In certain embodiments, at least one instance of $R^{E1a}$ is substituted or unsubstituted aryl. In certain embodiments, at least one instance of $R^{E1a}$ is 6- to 14-membered aryl. In certain embodiments, at least one instance of $R^{E1a}$ is 6- to 10-membered aryl. In certain embodiments, at least one instance of $R^{E1a}$ is monocyclic aryl. In certain embodiments, at least one instance of $R^{E1a}$ is phenyl. In certain embodiments, at least one instance of $R^{E1a}$ is bicyclic aryl. In certain embodiments, at least one instance of $R^{E1a}$ is naphthyl. In certain embodiments, at least one instance of $R^{E1a}$ is substituted or unsubstituted heteroaryl. In certain embodiments, at least one instance of $R^{E1a}$ is heteroaryl, wherein one, two, three, or four atoms in the heteroaryl ring are independently selected from the group consisting of nitrogen, oxygen, and sulfur. In certain embodiments, at least one instance of $R^{E1a}$ is monocyclic heteroaryl. In certain embodiments, at least one instance of $R^{E1a}$ is 5-membered, monocyclic heteroaryl. In certain embodiments, at least one instance of $R^{E1a}$ is 6-membered, monocyclic heteroaryl. In certain embodiments, at least one instance of $R^{E1a}$ is pyridyl. In certain embodiments, at least one instance of $R^{E1a}$ is bicyclic heteroaryl, wherein the point of attachment may be on any atom of the bicyclic heteroaryl ring system, as valency permits. In certain embodiments, at least one instance of $R^{E1a}$ is 9-membered, bicyclic heteroaryl. In certain embodiments, at least one instance of $R^{E1a}$ is 10-membered, bicyclic heteroaryl. In certain embodiments, at least one instance of $R^{E1a}$ is a nitrogen protecting group when attached to a nitrogen atom. In certain embodiments, at least one instance of $R^{E1a}$ is Bn, Boc, Cbz, Fmoc, trifluoroacetyl, triphenylmethyl, acetyl, or Ts when attached to a nitrogen atom. In certain embodiments, $R^{E1a}$ is an oxygen protecting group when attached to an oxygen atom. In certain embodiments, $R^{E1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E1a}$ is a sulfur protecting group when attached to a sulfur atom. In certain embodiments, $R^{E1a}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{E1a}$ are joined to form substituted or unsubstituted heterocyclyl. In certain embodiments, two instances of $R^{E1a}$ are joined to form saturated or unsaturated heterocyclyl. In certain embodiments, two instances of $R^{E1a}$ are joined to form heterocyclyl including one, two, or three double bonds in the heterocyclic ring. In certain embodiments, two instances of $R^{E1a}$ are joined to form heterocyclyl, wherein one, two, or three atoms in the heterocyclic ring are independently selected from the group consisting of nitrogen, oxygen, and sulfur. In certain embodiments, two instances of $R^{E1a}$ are joined to form 3- to 7-membered, monocyclic heterocyclyl. In certain embodiments, two instances of $R^{E1a}$ are joined to form 5- to 13-membered, bicyclic heterocyclyl.

In certain embodiments, e is 0. In certain embodiments, e is 1. In certain embodiments, e is 2. In certain embodiments, e is 3. In certain embodiments, e is 4. In certain embodiments, e is 5.

In certain embodiments, at least one instance of $R^{E1}$ is halogen or substituted alkyl; and e is 1. In certain embodiments, at least one instance of $R^{E1}$ is halogen or unsubstituted alkyl; and e is 1. In certain embodiments, at least one instance of $R^{E1}$ is halogen or unsubstituted $C_{1-6}$ alkyl; and e is 1.

Compounds of Formula (II) include substituent $R^F$. In certain embodiments, $R^F$ is H. In certain embodiments, $R^F$ is substituted alkyl. In certain embodiments, $R^F$ is unsubstituted alkyl. In certain embodiments, $R^F$ is $C_{1-12}$ alkyl. In certain embodiments, $R^F$ is $C_{1-6}$ alkyl. In certain embodiments, $R^F$ is unsubstituted methyl. In certain embodiments, $R^F$ is substituted methyl. In certain embodiments, $R^F$ is —CH$_2$F. In certain embodiments, $R^F$ is —CHF$_2$. In certain embodiments, $R^F$ is —CF$_3$. In certain embodiments, $R^F$ is Bn. In certain embodiments, $R^F$ is unsubstituted ethyl. In certain embodiments, $R^F$ is substituted ethyl. In certain embodiments, $R^F$ is —(CH$_2$)$_2$Ph. In certain embodiments, $R^F$ is propyl. In certain embodiments, $R^F$ is butyl. In certain embodiments, $R^F$ is pentyl. In certain embodiments, $R^F$ is hexyl. In certain embodiments, $R^F$ is —(CH$_2$)$_{1-5}$—(oxetanyl). In certain embodiments, $R^F$ is of the formula:

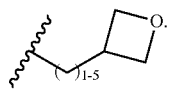

In certain embodiments, $R^F$ is —(CH$_2$)$_{1-5}$—(tetrahydrofuranyl). In certain embodiments, $R^F$ is —(CH$_2$)$_{1-5}$—(tetrahydropyranyl). In certain embodiments, $R^F$ is a nitrogen protecting group. In certain embodiments, $R^F$ is Bn, Boc, Cbz, Fmoc, trifluoroacetyl, triphenylmethyl, acetyl, or Ts.

In certain embodiments, $R^F$ is substituted heterocyclyl. In certain embodiments, $R^F$ is unsubstituted heterocyclyl. In certain embodiments, $R^F$ is saturated heterocyclyl. In certain embodiments, $R^F$ is unsaturated heterocyclyl. In certain embodiments, $R^F$ is heterocyclyl including one, two, or three double bonds in the heterocyclic ring. In certain embodiments, $R^F$ is heterocyclyl, wherein one, two, or three atoms in the heterocyclic ring are independently selected from the group consisting of nitrogen, oxygen, and sulfur. In certain embodiments, $R^F$ is monocyclic heterocyclyl. In certain embodiments, $R^F$ is 3- to 7-membered, monocyclic heterocyclyl. In certain embodiments, $R^F$ is bicyclic heterocyclyl. In certain embodiments, $R^F$ is 5- to 13-membered, bicyclic heterocyclyl. In certain embodiments, $R^F$ is substituted or unsubstituted, 4- to 7-membered, monocyclic heterocyclyl, wherein one or two atoms in the heterocyclic ring are independently oxygen or nitrogen. In certain embodiments, $R^F$ is substituted oxetanyl. In certain embodiments, $R^F$ is unsubstituted oxetanyl. In certain embodiments, $R^F$ is of the formula:

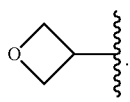

In certain embodiments, $R^E$ is of the formula:

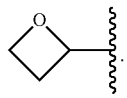

In certain embodiments, $R^F$ is of the formula:

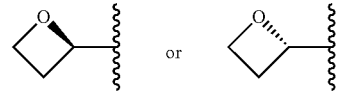

In certain embodiments, $R^F$ and $R^G$ are joined to form a substituted or unsubstituted heterocyclic ring of the formula:

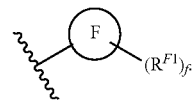

In certain embodiments, Ring F is substituted pyrrolidinyl. In certain embodiments, Ring F is of the formula:

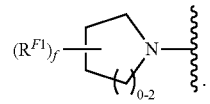

In certain embodiments, Ring A is of the formula:

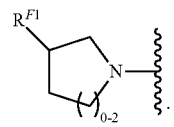

In certain embodiments, Ring F is of the formula:

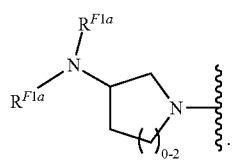

In certain embodiments, Ring F is of the formula:

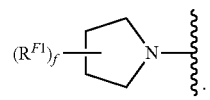

In certain embodiments, Ring F is of the formula:

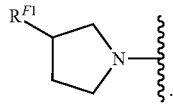

In certain embodiments, Ring F is of the formula:

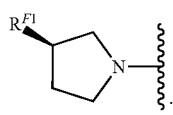

In certain embodiments, Ring F is of the formula:

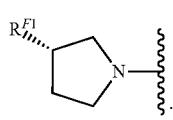

In certain embodiments, Ring F is of the formula:

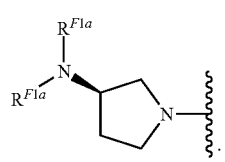

In certain embodiments, Ring F is of the formula:

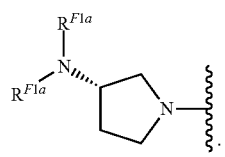

In certain embodiments, Ring F is of the formula:

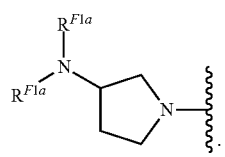

In certain embodiments, Ring F is of the formula:

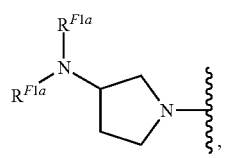

wherein at least one $R^{F1a}$ is substituted alkyl. In certain embodiments, Ring F is of the formula:

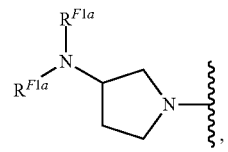

wherein at least one $R^{F1a}$ is unsubstituted alkyl. In certain embodiments, Ring F is of the formula:

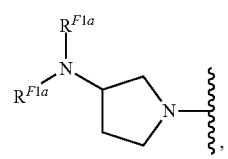

wherein at least one $R^{F1a}$ is unsubstituted $C_{1-6}$ alkyl. In certain embodiments, Ring F is unsubstituted pyrrolidinyl. In certain embodiments, Ring F is of the formula:

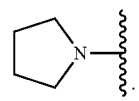

In certain embodiments, Ring F is substituted piperidinyl. In certain embodiments, Ring F is of the formula:

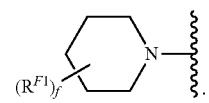

In certain embodiments, Ring F is of the formula:

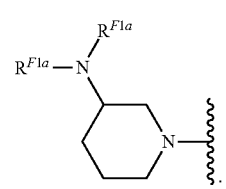

In certain embodiments, Ring F is of the formula:

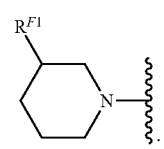

In certain embodiments, Ring F is of the formula:

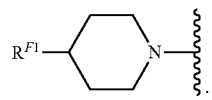

In certain embodiments, Ring F is of the formula:

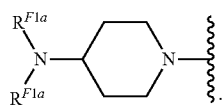

In certain embodiments, Ring F is unsubstituted piperidinyl.
In certain embodiments, Ring F is of the formula:

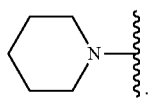

In certain embodiments, Ring F is substituted or unsubstituted, 7- to 10-membered, Spiro bicyclic heterocyclyl, wherein two atoms in the heterocyclic ring are independently selected from the group consisting of oxygen and nitrogen. In certain embodiments, Ring F is of the formula:

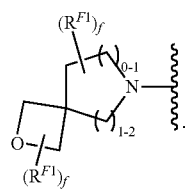

In certain embodiments, Ring F is of the formula:

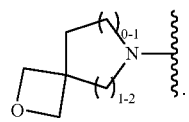

In certain embodiments, Ring F is of the formula:

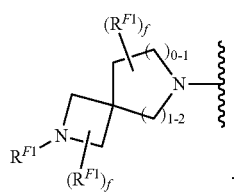

In certain embodiments, Ring F is of the formula:

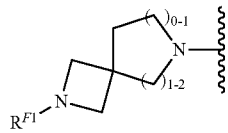

In certain embodiments, Ring F is of the formula:

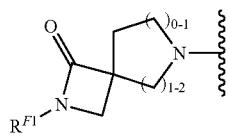

In certain embodiments, Ring F is of the formula:

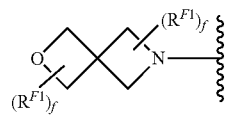

In certain embodiments, Ring F is of the formula:

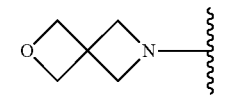

In certain embodiments, Ring F is of the formula:

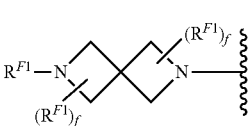

In certain embodiments, Ring F is of the formula:

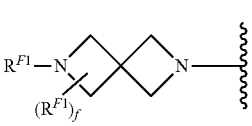

In certain embodiments, Ring F is of the formula:

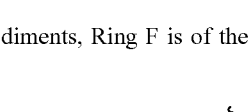

In certain embodiments, Ring F is of the formula:

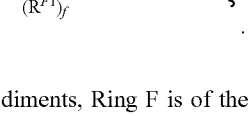

In certain embodiments, Ring F is of the formula:

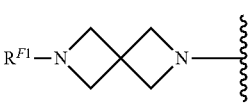

In certain embodiments, Ring F is of the formula:

In certain embodiments, Ring F is of the formula:

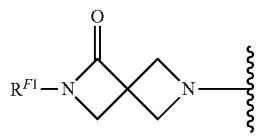

In certain embodiments, Ring F is of the formula:

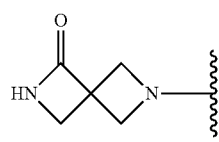

In certain embodiments, Ring F is of the formula:

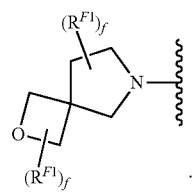

In certain embodiments, Ring F is of the formula:

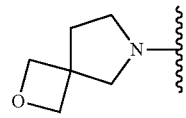

In certain embodiments, Ring F is of the formula:

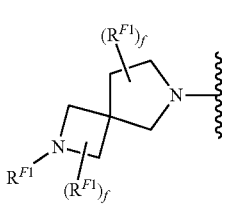

In certain embodiments, Ring F is of the formula:

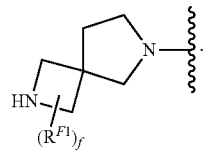

In certain embodiments, Ring F is of the formula:

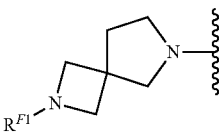

In certain embodiments, Ring F is of the formula:

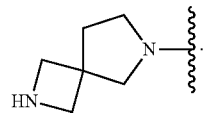

In certain embodiments, Ring F is of the formula:

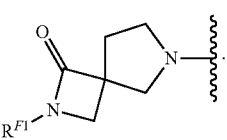

In certain embodiments, Ring F is of the formula:

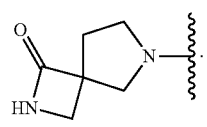

In certain embodiments, Ring F is of the formula:

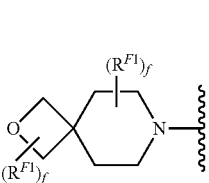

In certain embodiments, Ring F is of the formula:

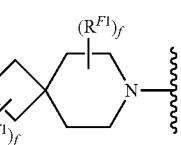

In certain embodiments, Ring F is of the formula:

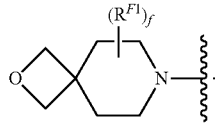

In certain embodiments, Ring F is of the formula:

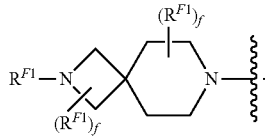

In certain embodiments, Ring F is of the formula:

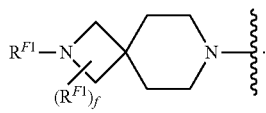

In certain embodiments, Ring F is of the formula:

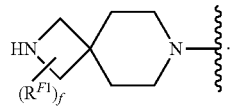

In certain embodiments, Ring F is of the formula:

In certain embodiments, Ring F is of the formula:

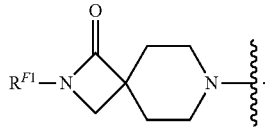

In certain embodiments, Ring F is of the formula:

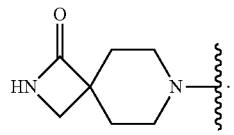

In certain embodiments, $R^F$ is H. In certain embodiments, $R^F$ is methyl. In certain embodiments, $R^F$ is

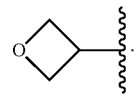

Compounds of Formula (II) may include one or more substituents $R^{F1}$ on Ring F. In certain embodiments, at least one instance of $R^{F1}$ is H. In certain embodiments, at least one instance of $R^{F1}$ is halogen. In certain embodiments, at least one instance of $R^{F1}$ is F. In certain embodiments, at least one instance of $R^{F1}$ is Cl. In certain embodiments, at least one instance of $R^{F1}$ is Br. In certain embodiments, at least one instance of $R^{F1}$ is I (iodine). In certain embodiments, at least one instance of $R^{F1}$ is substituted alkyl. In certain embodiments, at least one instance of $R^{F1}$ is unsubstituted alkyl. In certain embodiments, at least one instance of $R^{F1}$ is $C_{1-12}$ alkyl. In certain embodiments, at least one instance of $R^{F1}$ is $C_{1-6}$ alkyl. In certain embodiments, at least one instance of $R^{F1}$ is unsubstituted methyl. In certain embodiments, at least one instance of $R^{F1}$ is substituted methyl. In certain embodiments, at least one instance of $R^{F1}$ is —CH$_2$F. In certain embodiments, at least one instance of $R^{F1}$ is —CHF$_2$. In certain embodiments, at least one instance of $R^{F1}$ is —CF$_3$. In certain embodiments, at least one instance of $R^{F1}$ is Bn. In certain embodiments, at least one instance of $R^{F1}$ is unsubstituted ethyl. In certain embodiments, at least one instance of $R^{F1}$ is substituted ethyl. In certain embodiments, at least one instance of $R^{F1}$ is —(CH$_2$)$_2$Ph. In certain embodiments, at least one instance of $R^{F1}$ is substituted or unsubstituted propyl. In certain embodiments, at least one instance of $R^{F1}$ is substituted or unsubstituted butyl. In certain embodiments, at least one instance of $R^{F1}$ is substituted or unsubstituted pentyl. In certain embodiments, at least one instance of $R^{F1}$ is substituted or unsubstituted hexyl. In certain embodiments, at least one instance of $R^{F1}$ is halogen or unsubstituted $C_{1-6}$ alkyl. In certain embodiments, at least one instance of $R^{F1}$ is —OR$^{F1a}$. In certain embodiments, at least one instance of $R^{F1}$ is —OR$^{F1a}$, wherein $R^{F1a}$ is substituted alkyl. In certain embodiments, at least one instance of $R^{F1}$ is —OR$^{F1a}$, wherein $R^{F1a}$ is unsubstituted alkyl. In certain embodiments, at least one instance of $R^{F1}$ is —OR$^{F1a}$, wherein $R^{F1}$ is substituted $C_{1-6}$ alkyl. In certain embodiments, at least one instance of $R^{F1}$ is —OR$^{F1a}$, wherein $R^{F1a}$ is unsubstituted $C_{1-6}$ alkyl. In certain embodiments, at least one instance of $R^{F1}$ is —OPh. In certain embodiments, at least one instance of $R^{F1}$ is —OBn. In certain embodiments, at least one instance of $R^{F1}$ is —O(CH$_2$)$_2$Ph. In certain embodiments, at least one instance of $R^{F1}$ is —OH. In certain embodiments, at least one instance of $R^{F1}$ is —N(R$^{F1a}$)$_2$. In certain embodiments, at least one instance of $R^{F1}$ is —N(R$^{F1a}$)$_2$, wherein at least one instance of $R^{F1a}$ is substituted alkyl. In certain embodiments, at least one instance of $R^{F1}$ is —N(R$^{F1a}$)$_2$, wherein at least one instance of $R^{F1a}$ is unsubstituted alkyl. In certain embodiments, at least one instance of $R^{F1}$ is —N(R$^{F1a}$)$_2$, wherein at least one instance of $R^{F1a}$ is substituted $C_{1-6}$ alkyl. In certain embodiments, at least one instance of $R^{F1}$ is —N(R$^{F1a}$)$_2$, wherein at least one instance of $R^{F1a}$ is unsubstituted $C_{1-6}$ alkyl. In certain embodiments, at least one instance of $R^{F1}$ is —NH$_2$. In certain embodiments, at least one instance of $R^{F1}$ is oxo. In certain embodiments, at least one instance of $R^{F1}$ is a nitrogen protecting group when attached to a nitrogen atom. In certain embodiments, at least one instance of $R^{F1}$ is Bn, Boc, Cbz, Fmoc, trifluoroacetyl, triphenylmethyl, acetyl, or Ts when attached to a nitrogen atom.

In certain embodiments, at least one instance of $R^{F1a}$ is H. In certain embodiments, at least one instance of $R^{F1a}$ is substituted alkyl. In certain embodiments, at least one instance of $R^{F1a}$ is unsubstituted alkyl. In certain embodiments, at least one instance of $R^{F1a}$ is substituted $C_{1-6}$ alkyl. In certain embodiments, at least one instance of $R^{F1a}$ is unsubstituted $C_{1-6}$ alkyl. In certain embodiments, at least one instance of $R^{F1a}$ is unsubstituted methyl. In certain embodiments, at least one instance of $R^{F1a}$ is substituted methyl. In certain embodiments, at least one instance of $R^{F1a}$ is —$CH_2F$. In certain embodiments, at least one instance of $R^{F1a}$ is —$CHF_2$. In certain embodiments, at least one instance of $R^{F1a}$ is —$CF_3$. In certain embodiments, at least one instance of $R^{F1a}$ is Bn. In certain embodiments, at least one instance of $R^{F1a}$ is unsubstituted ethyl. In certain embodiments, at least one instance of $R^{F1a}$ is substituted ethyl. In certain embodiments, at least one instance of $R^{F1a}$ is —$(CH_2)_2Ph$. In certain embodiments, at least one instance of $R^{F1a}$ is propyl. In certain embodiments, at least one instance of $R^{F1a}$ is butyl. In certain embodiments, at least one instance of $R^{F1a}$ is pentyl. In certain embodiments, at least one instance of $R^{F1a}$ is hexyl. In certain embodiments, at least one instance of $R^{F1a}$ is a nitrogen protecting group when attached to a nitrogen atom. In certain embodiments, at least one instance of $R^{F1a}$ is Bn, Boc, Cbz, Fmoc, trifluoroacetyl, triphenylmethyl, acetyl, or Ts when attached to a nitrogen atom. In certain embodiments, at least one instance of $R^{F1a}$ is an oxygen protecting group when attached to an oxygen atom. In certain embodiments, at least one instance of $R^{F1a}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, two instances of $R^{F1a}$ are joined to form substituted or unsubstituted heterocyclyl. In certain embodiments, two instances of $R^{F1a}$ are joined to form saturated or unsaturated heterocyclyl. In certain embodiments, two instances of $R^{F1a}$ are joined to form heterocyclyl including one, two, or three double bonds in the ring of the heterocyclyl. In certain embodiments, two instances of $R^{F1a}$ are joined to form heterocyclyl, wherein one, two, or three atoms in the ring of the heterocyclyl are independently selected from the group consisting of nitrogen, oxygen, and sulfur. In certain embodiments, two instances of $R^{F1a}$ are joined to form 3- to 7-membered, monocyclic heterocyclyl. In certain embodiments, two instances of $R^{F1a}$ are joined to form 5- to 13-membered, bicyclic heterocyclyl.

In certain embodiments, f is 0. In certain embodiments, f is 1. In certain embodiments, f is 2. In certain embodiments, f is 3.

In certain embodiments, $R^{F1}$ is —$N(R^{F1a})_2$; and f is 1. In certain embodiments, $R^H$ is —N(unsubstituted $C_{1-6}$ alkyl)$_2$; and f is 1. In certain embodiments, $R^{F1}$ is oxo; and f is 1.

Compounds of Formula (II) include substituent $R^G$. In certain embodiments, $R^G$ is H. In certain embodiments, $R^G$ is substituted $C_{1-6}$ alkyl. In certain embodiments, $R^G$ is unsubstituted $C_{1-6}$ alkyl. In certain embodiments, $R^G$ is unsubstituted methyl. In certain embodiments, $R^G$ is substituted methyl. In certain embodiments, $R^G$ is —$CH_2F$. In certain embodiments, $R^G$ is —$CHF_2$. In certain embodiments, $R^G$ is —$CF_3$. In certain embodiments, $R^G$ is Bn. In certain embodiments, $R^G$ is unsubstituted ethyl. In certain embodiments, $R^G$ is substituted ethyl. In certain embodiments, $R^G$ is —$(CH_2)_2Ph$. In certain embodiments, $R^G$ is propyl. In certain embodiments, $R^G$ is butyl. In certain embodiments, $R^G$ is pentyl. In certain embodiments, $R^G$ is hexyl. In certain embodiments, $R^G$ is a nitrogen protecting group. In certain embodiments, $R^G$ is Bn, Boc, Cbz, Fmoc, trifluoroacetyl, triphenylmethyl, acetyl, or Ts.

Compounds of Formula (II) include substituent $R^H$. In certain embodiments, $R^H$ is H. In certain embodiments, $R^H$ is substituted $C_{1-6}$ alkyl. In certain embodiments, $R^H$ is unsubstituted $C_{1-6}$ alkyl. In certain embodiments, $R^H$ is unsubstituted methyl. In certain embodiments, $R^H$ is substituted methyl. In certain embodiments, $R^H$ is —$CH_2F$. In certain embodiments, $R^H$ is —$CHF_2$. In certain embodiments, $R^H$ is —$CF_3$. In certain embodiments, $R^H$ is Bn. In certain embodiments, $R^H$ is unsubstituted ethyl. In certain embodiments, $R^H$ is substituted ethyl. In certain embodiments, $R^H$ is —$(CH_2)2Ph$. In certain embodiments, $R^H$ is propyl. In certain embodiments, $R^H$ is butyl. In certain embodiments, $R^H$ is pentyl. In certain embodiments, $R^H$ is hexyl. In certain embodiments, $R^H$ is a nitrogen protecting group. In certain embodiments, $R^H$ is Bn, Boc, Cbz, Fmoc, trifluoroacetyl, triphenylmethyl, acetyl, or Ts.

Compounds of Formula (II) include substituent $R^J$. In certain embodiments, $R^J$ is H. In certain embodiments, $R^J$ is substituted $C_{1-6}$ alkyl. In certain embodiments, $R^J$ is unsubstituted $C_{1-6}$ alkyl. In certain embodiments, $R^J$ is unsubstituted methyl. In certain embodiments, $R^J$ is substituted methyl. In certain embodiments, $R^J$ is —$CH_2F$. In certain embodiments, is —$CHF_2$. In certain embodiments, $R^J$ is —$CF_3$. In certain embodiments, $R^J$ is Bn. In certain embodiments, $R^J$ is unsubstituted ethyl. In certain embodiments, $R^J$ is substituted ethyl. In certain embodiments, $R^J$ is —$(CH_2)_2Ph$. In certain embodiments, $R^J$ is propyl. In certain embodiments, $R^J$ is butyl. In certain embodiments, $R^J$ is pentyl. In certain embodiments, $R^J$ is hexyl. In certain embodiments, $R^J$ is a nitrogen protecting group. In certain embodiments, $R^J$ is Bn, Boc, Cbz, Fmoc, trifluoroacetyl, triphenylmethyl, acetyl, or Ts.

In certain embodiments, each one of $R^H$ and $R^J$ is hydrogen. In certain embodiments, each one of $R^G$, $R^H$, and $R^J$ is hydrogen.

Compounds of Formula (II) may include one or more $R^M$ groups. In certain embodiments, at least one instance of $R^M$ is H. In certain embodiments, at least one instance of $R^M$ is halogen. In certain embodiments, at least one instance of $R^M$ is F. In certain embodiments, at least one instance of $R^M$ is Cl. In certain embodiments, at least one instance of $R^M$ is Br. In certain embodiments, at least one instance of $R^M$ is I (iodine). In certain embodiments, at least one instance of $R^M$ is substituted acyl. In certain embodiments, at least one instance of $R^M$ is unsubstituted acyl. In certain embodiments, at least one instance of $R^M$ is substituted alkyl. In certain embodiments, at least one instance of $R^M$ is unsubstituted alkyl. In certain embodiments, at least one instance of $R^M$ is $C_{1-12}$ alkyl. In certain embodiments, at least one instance of $R^M$ is $C_{1-6}$ alkyl. In certain embodiments, at least one instance of $R^M$ is unsubstituted methyl. In certain embodiments, at least one instance of $R^M$ is substituted methyl. In certain embodiments, at least one instance of $R^M$ is —$CH_2F$. In certain embodiments, at least one instance of $R^M$ is —$CHF_2$. In certain embodiments, at least one instance of $R^M$ is —$CF_3$. In certain embodiments, at least one instance of $R^M$ is Bn. In certain embodiments, at least one instance of $R^M$ is unsubstituted ethyl. In certain embodiments, at least one instance of $R^M$ is substituted ethyl. In certain embodiments, at least one instance of $R^M$ is —$(CH_2)_2Ph$. In certain embodiments, at least one instance of $R^M$ is propyl. In certain embodiments, at least one instance of $R^M$ is butyl. In certain embodiments, at least one instance of $R^M$ is pentyl. In certain embodiments, at least one instance of $R^M$ is hexyl. In certain embodiments, at least one instance of $R^M$ is halogen or substituted or unsubstituted $C_{1-6}$ alkyl. In certain embodiments, at least one instance of $R^M$ is substituted alkenyl. In certain embodiments, at least one instance of $R^M$ is unsubstituted alkenyl. In certain embodiments, at least one instance of $R^M$ is vinyl. In certain embodiments, at least one instance of $R^M$ is substituted alkynyl. In certain embodiments, at least one instance of $R^M$ is unsubstituted alkynyl. In certain embodiments, at least one instance of $R^M$ is ethynyl. In certain embodiments, at least one instance of $R^M$ is substituted carbocyclyl. In certain embodiments, at least one instance of $R^M$ is unsubstituted carbocyclyl. In certain embodiments, at least one instance of $R^M$ is saturated carbocyclyl. In certain embodiments, at least one instance of $R^M$ is unsaturated carbocyclyl. In certain embodiments, at least one instance of $R^M$ is carbocyclyl including one, two, or three double bonds in the carbocyclic ring. In certain embodiments, at least one instance of $R^M$ is monocyclic carbocyclyl. In certain embodiments, at least one instance of $R^M$ is 3- to 7-membered, monocyclic carbocyclyl. In certain embodiments, at least one instance of $R^M$ is cyclopropyl. In certain embodiments, at least one instance of $R^M$ is cyclobutyl. In certain embodiments, at least one instance of $R^M$ is cyclopentyl. In certain embodiments, at least one instance of $R^M$ is cyclohexyl. In certain embodiments, at least one instance of $R^M$ is cycloheptyl. In certain embodiments, at least one instance of $R^M$ is bicyclic carbocyclyl. In certain embodiments, at least one instance of $R^M$ is 5- to 13-membered, bicyclic carbocyclyl. In certain embodiments, at least one instance of $R^M$ is substituted heterocyclyl. In certain embodiments, at least one instance of $R^M$ is unsubstituted heterocyclyl. In certain embodiments, at least one instance of $R^M$ is saturated heterocyclyl. In certain embodiments, at least one instance of $R^M$ is unsaturated heterocyclyl. In certain embodiments, at least one instance of $R^M$ is heterocyclyl including one, two, or three double bonds in the heterocyclic ring. In certain embodiments, at least one instance of $R^M$ is heterocyclyl, wherein one, two, or three atoms in the heterocyclic ring are independently selected from the group consisting of nitrogen, oxygen, and sulfur. In certain embodiments, at least one instance of $R^M$ is monocyclic heterocyclyl. In certain embodiments, at least one instance of $R^M$ is 3- to 7-membered, monocyclic heterocyclyl. In certain embodiments, at least one instance of $R^M$ is bicyclic heterocyclyl. In certain embodiments, at least one instance of $R^M$ is 5- to 13-membered, bicyclic heterocyclyl. In certain embodiments, at least one instance of $R^M$ is substituted aryl. In certain embodiments, at least one instance of $R^M$ is unsubstituted aryl. In certain embodiments, at least one instance of $R^M$ is 6- to 14-membered aryl. In certain embodiments, at least one instance of $R^M$ is 6- to 10-membered aryl. In certain embodiments, at least one instance of $R^M$ is substituted phenyl. In certain embodiments, at least one instance of $R^M$ is unsubstituted phenyl. In certain embodiments, at least one instance of $R^M$ is substituted naphthyl. In certain embodiments, at least one instance of $R^M$ is unsubstituted naphthyl. In certain embodiments, at least one instance of $R^M$ is substituted heteroaryl. In certain embodiments, at least one instance of $R^M$ is unsubstituted heteroaryl. In certain embodiments, at least one instance of $R^M$ is heteroaryl, wherein one, two, three, or four atoms in the heteroaryl ring are independently selected from the group consisting of nitrogen, oxygen, and sulfur. In certain embodiments, at least one instance of $R^M$ is monocyclic heteroaryl. In certain embodiments, at least one instance of $R^M$ is 5-membered, monocyclic heteroaryl. In certain embodiments, at least one instance of $R^M$ is 6-membered, monocyclic heteroaryl. In certain embodiments, at least one instance of $R^M$ is pyridyl. In certain embodiments, at least one instance of $R^M$ is bicyclic heteroaryl, wherein the point of attachment may be on any atom of the bicyclic heteroaryl ring system, as valency permits. In certain embodiments, at least one instance of $R^M$ is 9-membered, bicyclic heteroaryl. In certain embodiments, at least one instance of $R^M$ is 10-membered, bicyclic heteroaryl. In certain embodiments, at least one instance of $R^M$ is —$OR^{M1}$. In certain embodiments, at least one instance of $R^M$ is —OMe. In certain embodiments, at least one instance of $R^M$ is —OEt. In certain embodiments, at least one instance of $R^M$ is —OPr. In certain embodiments, at least one instance of $R^M$ is —OBu. In certain embodiments, at least one instance of $R^M$ is —O(pentyl). In certain embodiments, at least one instance of $R^M$ is —O(hexyl). In certain embodiments, at least one instance of $R^M$ is —OPh. In certain embodiments, at least one instance of $R^M$ is —OBn. In certain embodiments, at least one instance of $R^M$ is —O(CH$_2$)$_2$Ph. In certain embodiments, at least one instance of $R^M$ is —OH. In certain embodiments, at least one instance of $R^M$ is —$SR^{M1}$. In certain embodiments, at least one instance of $R^M$ is —SH. In certain embodiments, at least one instance of $R^M$ is —N($R^{M1}$)$_2$. In certain embodiments, at least one instance of $R^M$ is —NH$_2$. In certain embodiments, at least one instance of $R^M$ is —CN. In certain embodiments, at least one instance of $R^M$ is —SCN. In certain embodiments, at least one instance of $R^M$ is —C(=N$R^{M1}$)$R^{M1}$, —C(=N$R^{M1}$)O$R^{M1}$, or —C(=N$R^{M1}$)N($R^{M1}$)$_2$. In certain embodiments, at least one instance of $R^M$ is —C(=O)$R^{M1}$, —C(=O)O$R^{M1}$, or —C(=O)N($R^{M1}$)$_2$. In certain embodiments, at least one instance of $R^M$ is —NO$_2$. In certain embodiments, at least one instance of $R^M$ is —N$R^{M1}$C(=O)$R^{M1}$, —N$R^{M1}$C(=O)O$R^{M1}$, or —N$R^{M1}$C(=O)N($R^{M1}$)$_2$. In certain embodiments, at least one instance of $R^M$ is —OC(=O)$R^{M1}$, —OC(=O)O$R^{M1}$, or —OC(=O)N($R^{M1}$)$_2$.

In certain embodiments, at least one instance of $R^M$ is hydrogen, halogen, or unsubstituted alkyl. In certain embodiments, at least one instance of $R^M$ is hydrogen, halogen, or unsubstituted $C_{1-6}$ alkyl. In certain embodiments, at least one instance of $R^M$ is halogen or unsubstituted alkyl. In certain embodiments, at least one instance of $R^M$ is halogen or unsubstituted $C_{1-6}$ alkyl. In certain embodiments, $R^M$ is halogen; and p is 1. In certain embodiments, $R^M$ is unsubstituted $C_{1-6}$ alkyl; and p is 1. In certain embodiments, each instance of $R^M$ is independently halogen or unsubstituted $C_{1-6}$ alkyl; and p is 2.

In compounds of Formula (I), two $R^M$ groups may be joined to form substituted or unsubstituted carbocyclyl. In certain embodiments, two instances of $R^M$ are joined to form saturated or unsaturated carbocyclyl. In certain embodiments, two instances of $R^M$ are joined to form carbocyclyl including one, two, or three double bonds in the carbocyclic ring. In certain embodiments, two instances of $R^M$ are joined to form 3- to 7-membered, monocyclic carbocyclyl. In certain embodiments, two instances of $R^M$ are joined to form 3-membered carbocyclyl. In certain embodiments, two instances of $R^M$ are joined to form 4-membered carbocyclyl. In certain embodiments, two instances of $R^M$ are joined to form 5-membered carbocyclyl. In certain embodiments, two instances of $R^M$ are joined to form 6-membered carbocyclyl. In certain embodiments, two instances of $R^M$ are joined to form 7-membered carbocyclyl. In certain embodiments, two instances of $R^M$ are joined to form 5- to 13-membered, bicyclic carbocyclyl.

In certain embodiments, two instances of $R^M$ are joined to form substituted or unsubstituted heterocyclyl. In certain embodiments, two instances of $R^M$ are joined to form saturated or unsaturated heterocyclyl. In certain embodiments, two instances of $R^M$ are joined to form heterocyclyl including one, two, or three double bonds in the heterocyclic ring. In certain embodiments, two instances of $R^M$ are joined to form heterocyclyl, wherein one, two, or three atoms in the heterocyclic ring are independently selected from the group consisting of nitrogen, oxygen, and sulfur. In certain embodiments, two instances of $R^M$ are joined to form 3- to 7-membered, monocyclic heterocyclyl. In certain embodiments, two instances of $R^M$ are joined to form 5- to 13-membered, bicyclic heterocyclyl.

In certain embodiments, two instances of $R^M$ are joined to form substituted or unsubstituted aryl. In certain embodiments, two instances of $R^M$ are joined to form 6- to 14-membered aryl. In certain embodiments, two instances of $R^M$ are joined to form 6- to 10-membered aryl. In certain embodiments, two instances of $R^M$ are joined to form monocyclic aryl. In certain embodiments, two instances of $R^M$ are joined to form phenyl. In certain embodiments, two instances of $R^M$ are joined to form bicyclic aryl. In certain embodiments, two instances of $R^M$ are joined to form naphthyl.

In certain embodiments, two instances of $R^M$ are joined to form substituted or unsubstituted heteroaryl. In certain embodiments, two instances of $R^M$ are joined to form monocyclic heteroaryl, wherein one, two, or three atoms in the heteroaryl ring are independently selected from the group consisting of nitrogen, oxygen, and sulfur. In certain embodiments, two instances of $R^M$ are joined to form 5-membered, monocyclic heteroaryl. In certain embodiments, two instances of $R^M$ are joined to form pyrrolyl. In certain embodiments, two instances of Fe are joined to form 6-membered, monocyclic heteroaryl. In certain embodiments, two instances of $R^M$ are joined to form pyridyl. In certain embodiments, two instances of $R^M$ are joined to form bicyclic heteroaryl, wherein one, two, three, or four atoms in the heteroaryl ring are independently selected from the group consisting of nitrogen, oxygen, and sulfur. In certain embodiments, two instances of $R^M$ are joined to form 9-membered, bicyclic heteroaryl. In certain embodiments, two instances of $R^M$ are joined to form 10-membered, bicyclic heteroaryl.

In certain embodiments, at least one instance of $R^{M1}$ is H. In certain embodiments, at least one instance of $R^{M1}$ is substituted acyl. In certain embodiments, at least one instance of $R^{M1}$ is unsubstituted acyl. In certain embodiments, at least one instance of $R^{M1}$ is acetyl. In certain embodiments, at least one instance of $R^{M1}$ is substituted alkyl. In certain embodiments, at least one instance of $R^{M1}$ is unsubstituted alkyl. In certain embodiments, at least one instance of $R^{M1}$ is $C_{1-12}$ alkyl. In certain embodiments, at least one instance of $R^{M1}$ is $C_{1-6}$ alkyl. In certain embodiments, at least one instance of $R^{M1}$ is methyl. In certain embodiments, at least one instance of $R^{M1}$ is ethyl. In certain embodiments, at least one instance of $R^{M1}$ is propyl. In certain embodiments, at least one instance of $R^{M1}$ is butyl. In certain embodiments, at least one instance of $R^{M1}$ is pentyl. In certain embodiments, at least one instance of $R^{M1}$ is hexyl. In certain embodiments, at least one instance of $R^{M1}$ is substituted alkenyl. In certain embodiments, at least one instance of $R^{M1}$ is unsubstituted alkenyl. In certain embodiments, at least one instance of $R^{M1}$ is vinyl. In certain embodiments, at least one instance of $R^{M1}$ is substituted alkynyl. In certain embodiments, at least one instance of $R^{M1}$ is unsubstituted alkynyl. In certain embodiments, at least one instance of $R^{M1}$ is ethynyl. In certain embodiments, at least one instance of $R^{M1}$ is substituted carbocyclyl. In certain embodiments, at least one instance of $R^{M1}$ is unsubstituted carbocyclyl. In certain embodiments, at least one instance of $R^{M1}$ is saturated carbocyclyl. In certain embodiments, at least one instance of $R^{M1}$ is unsaturated carbocyclyl. In certain embodiments, at least one instance of $R^{M1}$ is carbocyclyl including one, two, or three double bonds in the carbocyclic ring. In certain embodiments, at least one instance of $R^{M1}$ is 3- to 7-membered, monocyclic carbocyclyl. In certain embodiments, at least one instance of $R^{M1}$ is cyclopropyl. In certain embodiments, at least one instance of $R^{M1}$ is cyclobutyl. In certain embodiments, at least one instance of $R^{M1}$ is cyclopentyl. In certain embodiments, at least one instance of $R^{M1}$ is cyclohexyl. In certain embodiments, at least one instance of $R^{M1}$ is cycloheptyl. In certain embodiments, at least one instance of $R^{M1}$ is 5- to 13-membered, bicyclic carbocyclyl. In certain embodiments, at least one instance of $R^{M1}$ is substituted heterocyclyl. In certain embodiments, at least one instance of $R^{M1}$ is unsubstituted heterocyclyl. In certain embodiments, at least one instance of $R^{M1}$ is saturated heterocyclyl. In certain embodiments, at least one instance of $R^{M1}$ is unsaturated heterocyclyl. In certain embodiments, at least one instance of $R^{M1}$ is heterocyclyl including one, two, or three double bonds in the heterocyclic ring. In certain embodiments, at least one instance of $R^{M1}$ is heterocyclyl, wherein one, two, or three atoms in the heterocyclic ring are independently selected from the group consisting of nitrogen, oxygen, and sulfur. In certain embodiments, at least one instance of $R^{M1}$ is 3- to 7-membered, monocyclic heterocyclyl. In certain embodiments, at least one instance of $R^{M1}$ is 5- to 13-membered, bicyclic heterocyclyl. In certain embodiments, at least one instance of $R^{M1}$ is substituted or unsubstituted aryl. In certain embodiments, at least one instance of $R^{M1}$ is 6- to 14-membered aryl. In certain embodiments, at least one instance of $R^{M1}$ is 6- to 10-membered aryl. In certain embodiments, at least one instance of $R^{M1}$ is monocyclic aryl. In certain embodiments, at least one instance of $R^{M1}$ is phenyl. In certain embodiments, at least one instance of $R^{M1}$ is bicyclic aryl. In certain embodiments, at least one instance of $R^{M1}$ is naphthyl. In certain embodiments, at least one instance of $R^{M1}$ is substituted or unsubstituted heteroaryl. In certain embodiments, at least one instance of $R^{M1}$ is heteroaryl, wherein one, two, three, or four atoms in the heteroaryl ring are independently selected from the group consisting of nitrogen, oxygen, and sulfur. In certain embodiments, at least one instance of $R^{M1}$ is monocyclic heteroaryl. In certain embodiments, at least one instance of $R^{M1}$ is 5-membered, monocyclic heteroaryl. In certain embodiments, at least one instance of $R^{M1}$ is 6-membered, monocyclic heteroaryl. In certain embodiments, at least one instance of $R^{M1}$ is pyridyl. In certain embodiments, at least one instance of $R^{M1}$ is bicyclic heteroaryl, wherein the point of attachment may be on any atom of the bicyclic heteroaryl ring system, as valency permits. In certain embodiments, at least one instance of $R^{M1}$ is 9-membered, bicyclic heteroaryl. In certain embodiments, at least one instance of $R^{M1}$ is 10-membered, bicyclic heteroaryl. In certain embodiments, at least one instance of $R^{M1}$ is a nitrogen protecting group when attached to a nitrogen atom. In certain embodiments, at least one instance of $R^{M1}$ is Bn, Boc, Cbz, Fmoc, trifluoroacetyl, triphenylmethyl, acetyl, or Ts when attached to a nitrogen atom. In certain embodiments, $R^{M1}$ is an oxygen protecting group when attached to an oxygen atom. In certain embodiments, $R^{M1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{M1}$ is a sulfur protecting group when attached to a sulfur atom. In certain embodiments, $R^{M1}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{M1}$ are joined to form substituted or unsubstituted heterocyclyl. In certain embodiments, two instances of $R^{M1}$ are joined to form saturated or unsaturated heterocyclyl. In certain embodiments, two instances of $R^{M1}$ are joined to form heterocyclyl including one, two, or three double bonds in the heterocyclic ring. In certain embodiments, two instances of $R^{M1}$ are joined to form heterocyclyl, wherein one, two, or three atoms in the heterocyclic ring are independently selected from the group consisting of nitrogen, oxygen, and sulfur. In certain embodiments, two instances of $R^{M1}$ are joined to form 3- to 7-membered, monocyclic heterocyclyl. In certain embodiments, two instances of $R^{M1}$ are joined to form 5- to 13-membered, bicyclic heterocyclyl.

In certain embodiments, p is 0. In certain embodiments, p is 1. In certain embodiments, p is 2. In certain embodiments, p is 3. In certain embodiments, p is 4.

In compounds of Formula (II), the U and V moieties may be directly connected, or there may be one or more methylene groups between U and V. In certain embodiments, n is 0. In certain embodiments, n is 1. In certain embodiments, n is 2. In certain embodiments, n is 3. In certain embodiments, n is 4. In certain embodiments, n is 5.

In certain embodiments, the compound of Formula (II) is of the formula:

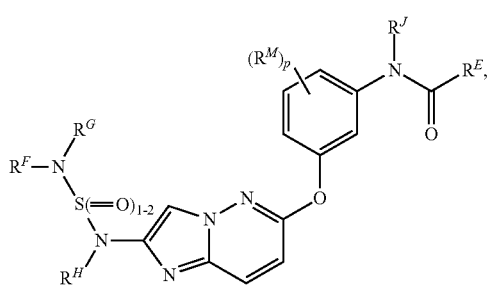

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

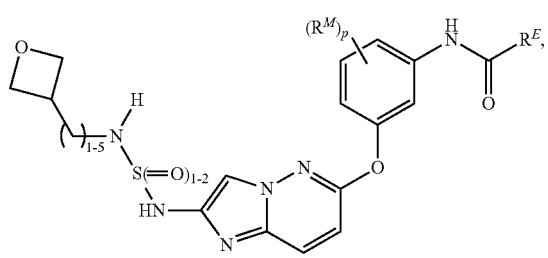

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

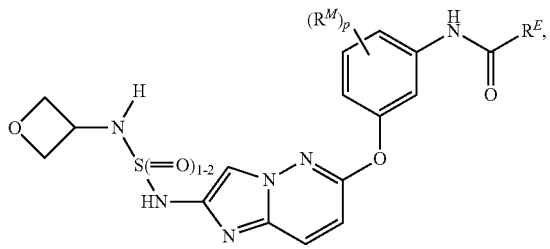

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

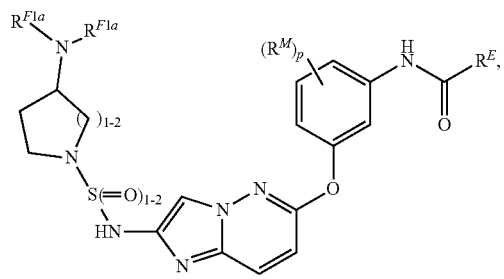

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

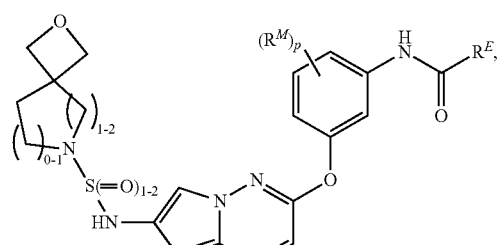

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

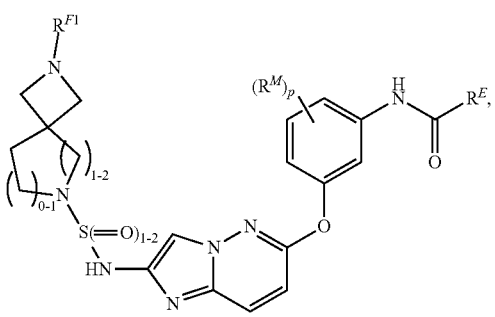

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

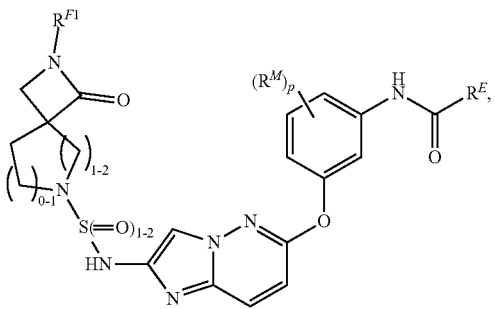

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

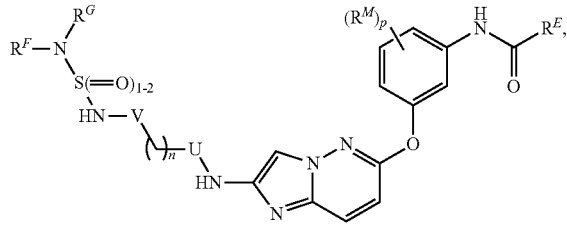

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

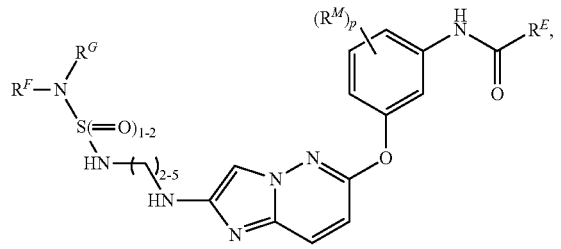

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

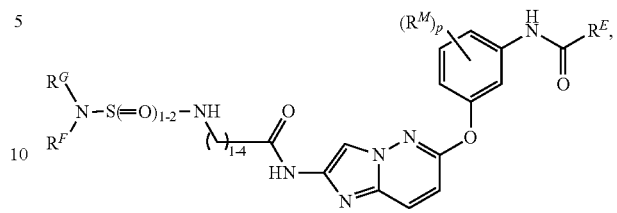

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

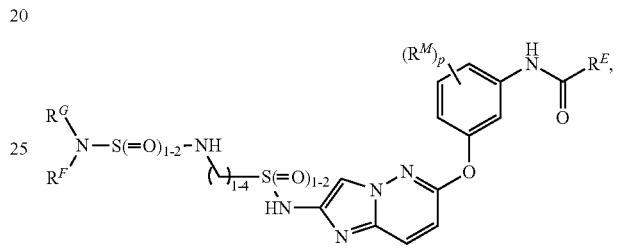

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

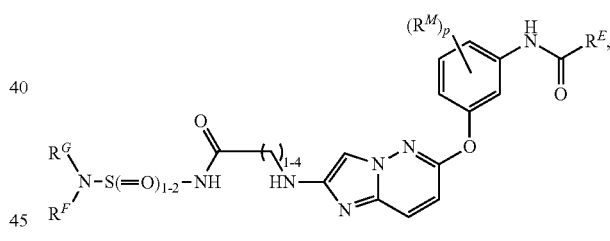

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

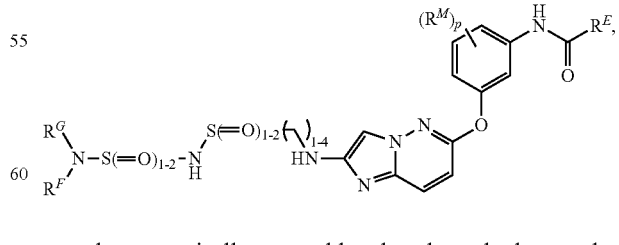

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

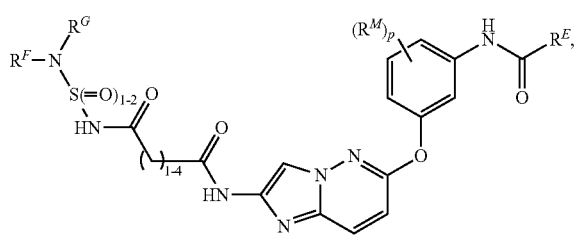

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

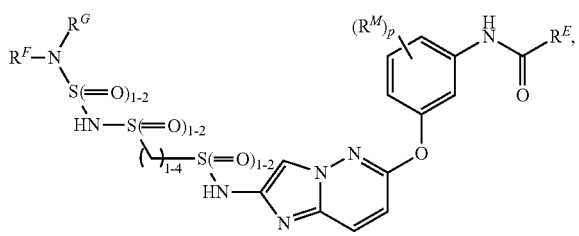

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

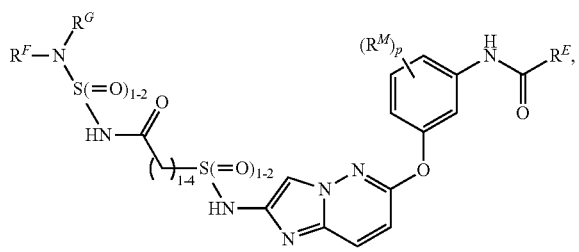

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

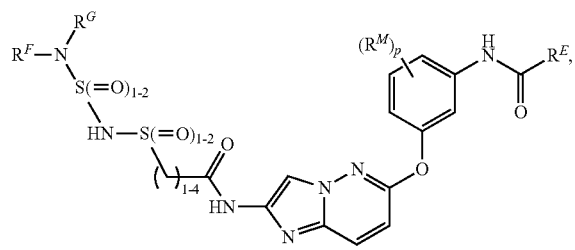

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

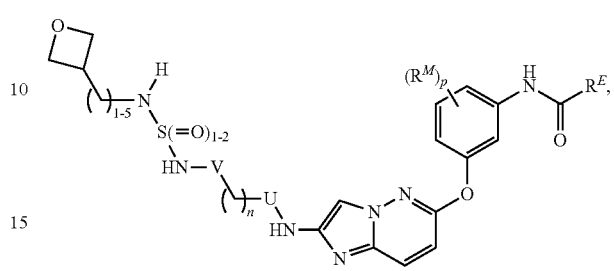

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

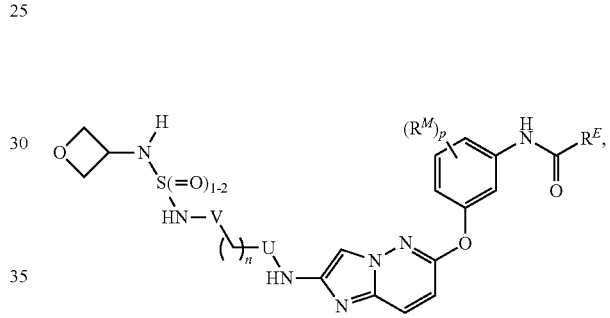

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

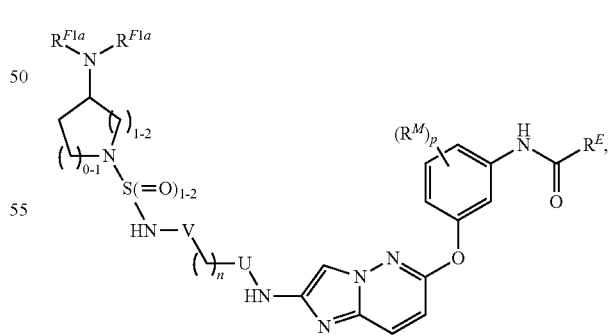

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

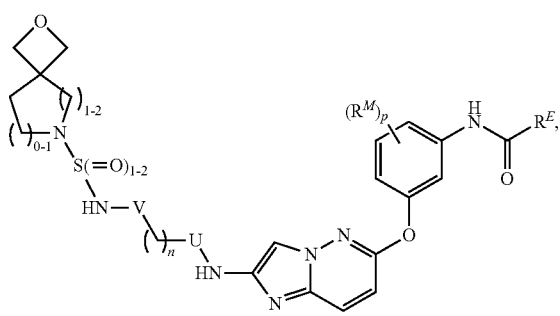

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

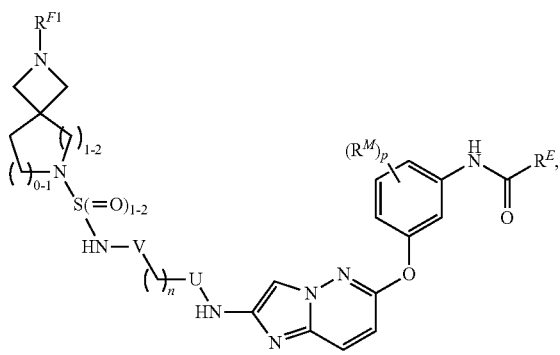

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

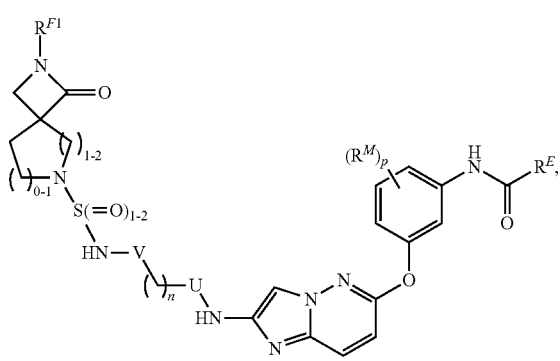

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

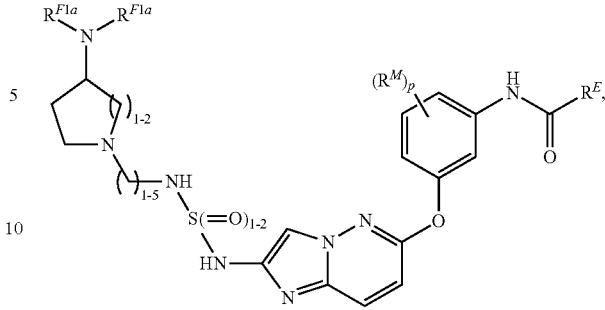

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

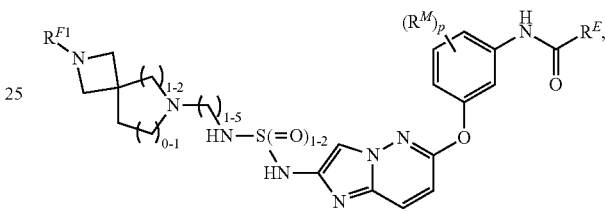

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

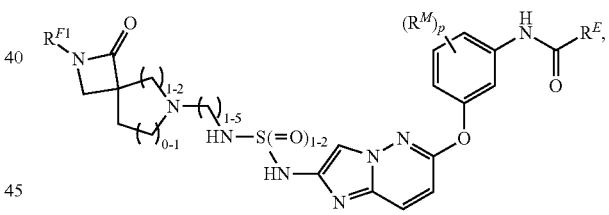

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

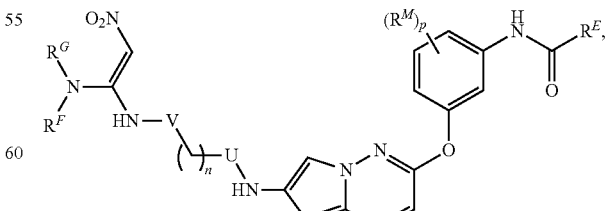

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

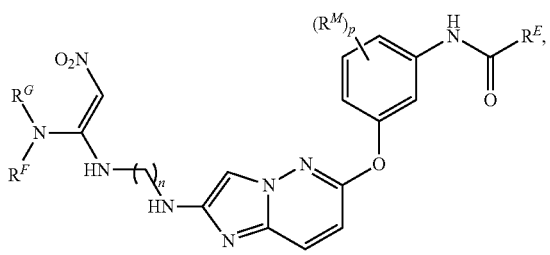

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

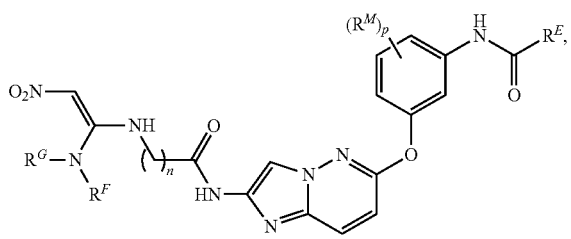

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

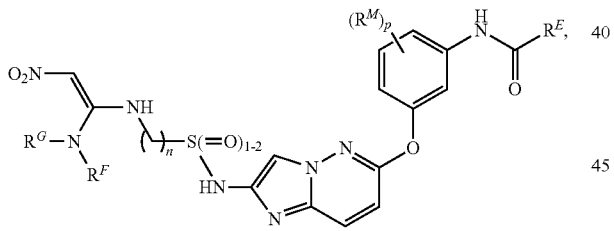

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

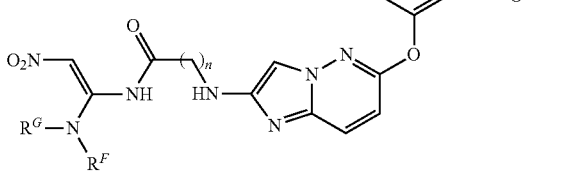

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

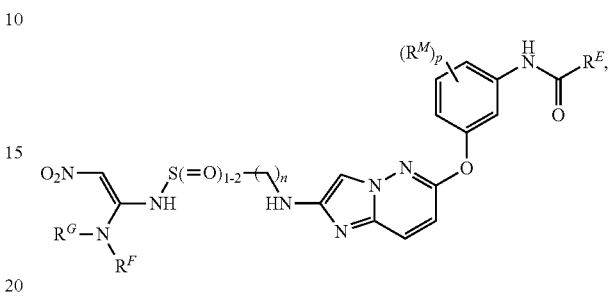

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

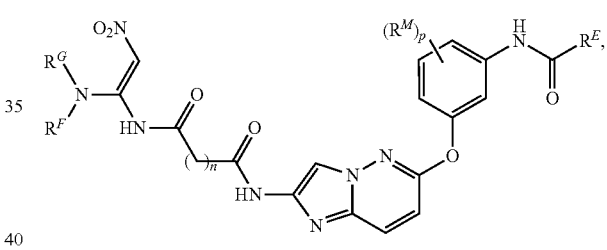

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

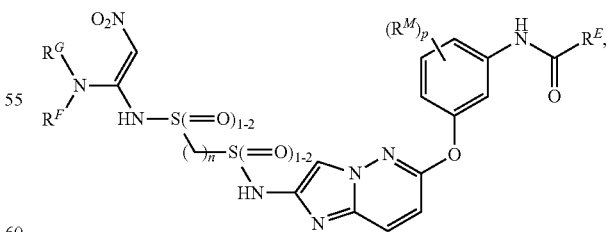

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

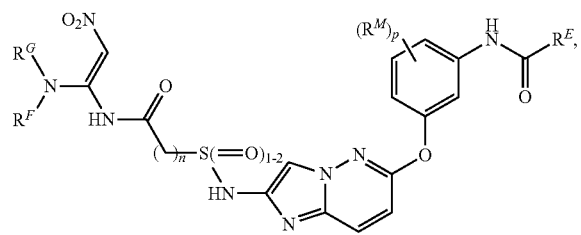

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

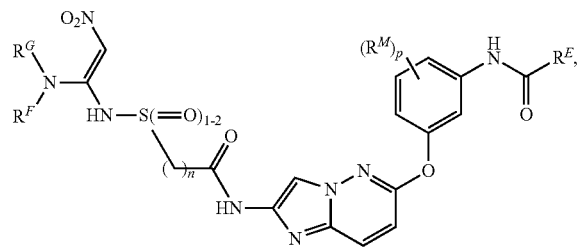

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

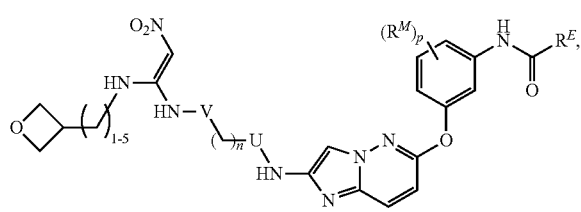

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

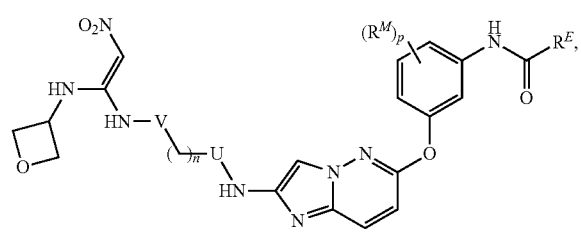

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

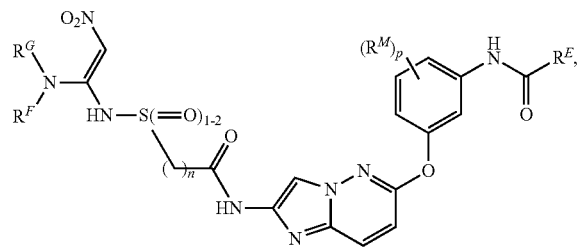

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

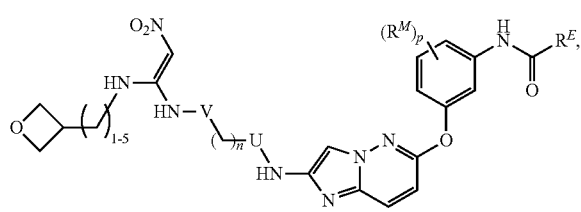

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

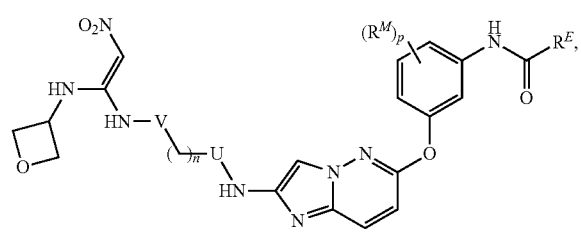

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

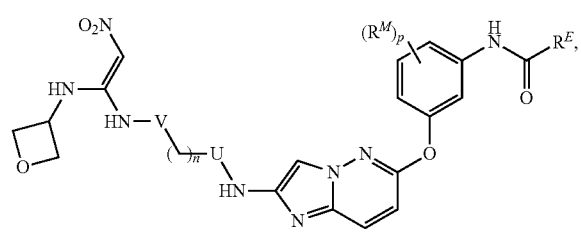

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

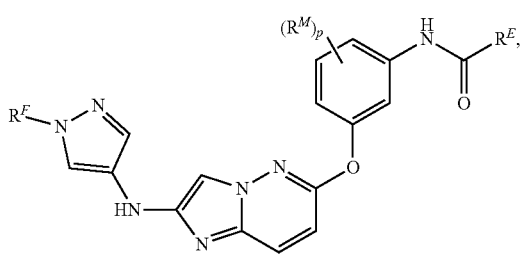

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

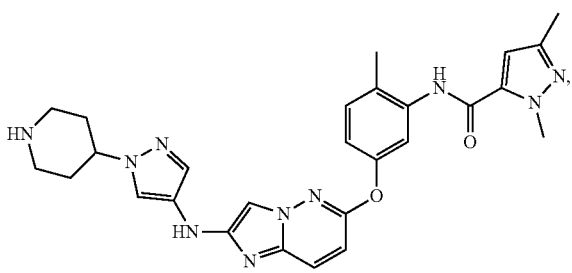 [SMILES: Cc1cc(C(=O)Nc2cc(Oc3ccc4nc(Nc5cnn(C6CCNCC6)c5)cn4n3)ccc2C)n(C)n1]

or a pharmaceutically acceptable salt, solvate, hydrate, polymorph, co-crystal, tautomer, stereoisomer, isotopically labeled derivative, or prodrug thereof.

The present invention also provides the compound of Formula (I (III)

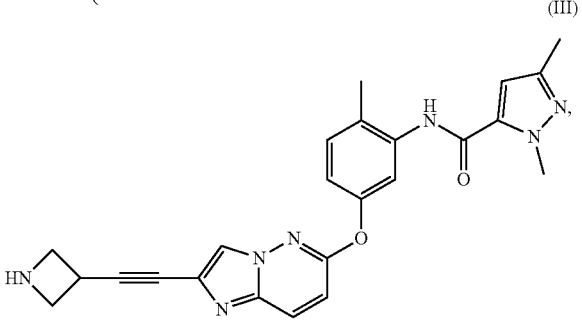 [SMILES: Cc1cc(C(=O)Nc2cc(Oc3ccc4nc(C#CC5CNC5)cn4n3)ccc2C)n(C)n1]

or a pharmaceutically acceptable salt, solvate, hydrate, polymorph, co-crystal, tautomer, stereoisomer, isotopically labeled derivative, or prodrug thereof.

The present invention further provides the compound of Formula (IV):

(IV)

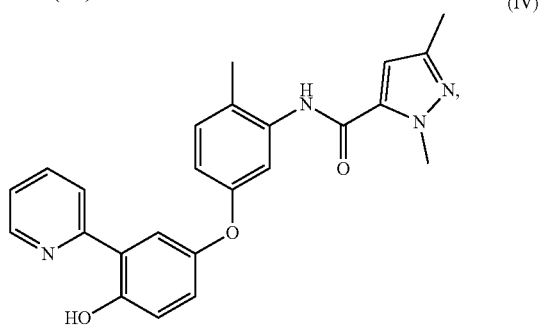

or a pharmaceutically acceptable salt, solvate, hydrate, polymorph, co-crystal, tautomer, stereoisomer, isotopically labeled derivative, or prodrug thereof.

Compounds of the invention may be crystalline. In certain embodiments, the compounds of the invention are monocrystalline. In certain embodiments, the compounds of the invention are polycrystalline.

Compounds of the invention may also have a relatively low aqueous solubility (i.e., a solubility in water, optionally with one or more buffers). For example, compounds of the invention may have an aqueous solubility of less than about or equal to about 3 mg/mL, less than about 1 mg/mL, less than about 0.3 mg/mL, less than about 0.1 mg/mL, less than about 0.03 mg/mL, less than about 0.01 mg/mL, less than about 1 µg/mL, less than about 0.1 µg/mL, less than about 0.01 µg/mL, less than about 1 ng/mL, less than about 0.1 ng/mL, or less than about 0.01 ng/mL at 25° C. In some embodiments, the compounds of the invention have an aqueous solubility of at least about 1 pg/mL, at least about 10 pg/mL, at least about 0.1 ng/mL, at least about 1 ng mL, at least about 10 ng/mL, at least about 0.1 µg/mL, at least about 1 µg/mL, at least about 3 µg/mL, at least about 0.01 mg/mL, at least about 0.03 mg/mL, at least about 0.1 mg/mL, at least about 0.3 mg/mL, at least about 1.0 mg/mL, or at least about 3 mg/mL at 25° C. Combinations of the above-noted ranges are possible (e.g., an aqueous solubility of at least about 10 pg/mL and less than about 1 mg/mL). Other ranges are also possible. The compounds of the invention may have these or other ranges of aqueous solubilities at any point throughout the pH range (e.g., at about pH 7 or from pH 1 to pH 14).

Compounds of the invention may be suitable for being processed into mucus-penetrating pharmaceutical compositions (e.g., particles or crystals). In certain embodiments, the compounds of the invention are suitable for milling (e.g., nano-milling). In certain embodiments, the compounds of the invention are suitable for precipitation (e.g., microprecipitation, nanoprecipitation, crystallization, or controlled crystallization). In certain embodiments, the compounds of the invention are suitable for emulsification. In certain embodiments, the compounds of the invention are suitable for freeze-drying.

The compounds of the invention include the compounds described herein (e.g., compounds of any one of Formulae (I)-(IV)), and pharmaceutically acceptable salts, solvates, hydrates, polymorphs, co-crystals, tautomers, stereoisomers, isotopically labeled derivatives, and prodrugs thereof. In certain embodiments, the compounds of the invention are compounds of Formula (I) and pharmaceutically acceptable salts thereof. In certain embodiments, the compounds of the invention are compounds of Formula (II) and pharmaceutically acceptable salts thereof. In certain embodiments, the compounds of the invention are the compound of Formula (III) and pharmaceutically acceptable salts thereof. In certain embodiments, the compounds of the invention are the compound of Formula (IV) and pharmaceutically acceptable salts thereof. The compounds of the invention may be useful in treating and/or preventing a disease (e.g., a disease associated with abnormal angiogenesis and/or aberrant signaling of a growth factor signaling pathway (e.g., VEGF)) in a subject in need thereof. The compounds of the invention may also be useful in inhibiting abnormal angiogenesis and/or aberrant signaling of a growth factor pathway in a subject and/or cell.

Pharmaceutical Compositions, Kits, and Administration

The present invention provides pharmaceutical compositions comprising a compound of the invention (e.g., a compound of any one of Formulae (I)-(IV), or a pharmaceutically acceptable salt, solvate, hydrate, polymorph, co-crystal, tautomer, stereoisomer, isotopically labeled derivative, or prodrug thereof), and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the pharmaceutical composition of the invention comprises a compound of Formula (II), or a pharmaceutically acceptable salt thereof, and optionally a pharmaceutically acceptable excipient. In certain embodiments, the pharmaceutical composition of the invention comprises the compound of Formula (III), or a pharmaceutically acceptable salt thereof, and optionally a pharmaceutically acceptable excipient. In certain embodiments, the pharmaceutical composition of the invention comprises the compound of Formula (IV), or a pharmaceutically acceptable salt thereof, and optionally a pharmaceutically acceptable excipient.

In certain embodiments, the compound of the invention is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease. In certain embodiments, the effective amount is an amount effective for treating and/or preventing a disease associated with aberrant signaling of a growth factor. In certain embodiments, the effective amount is an amount effective for treating a disease associated with aberrant signaling of a growth factor. In certain embodiments, the effective amount is an amount effective for treating and/or preventing a disease associated with aberrant signaling of vascular endothelial growth factor (VEGF). In certain embodiments, the effective amount is an amount effective for treating a disease associated with aberrant signaling of vascular endothelial growth factor (VEGF). In certain embodiments, the effective amount is an amount effective for treating and/or preventing a disease associated with abnormal angiogenesis, such as cancer, benign neoplasm, atherosclerosis, hypertension, inflammatory disease, rheumatoid arthritis, macular degeneration, choroidal neovascularization, retinal neovascularization, and diabetic retinopathy. In certain embodiments, the effective amount is an amount effective to treat cancer (e.g., an ocular cancer). In certain embodiments, the effective amount is an amount effective to treat macular degeneration.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An effective amount of a compound of the invention may inhibit abnormal angiogenesis and/or aberrant signaling of a growth factor by at least about 10%, at least about 20%, at least about 30%, at least about 40%, at least about 50%, at least about 60%, at least about 70%, at least about 80%, or at least about 90%. An effective amount of a compound of the invention may inhibit abnormal angiogenesis and/or aberrant signaling of a growth factor by less than about 90%, less than about 80%, less than about 70%, less than about 60%, less than about 50%, less than about 40%, less than about 30%, less than about 20%, or less than about 10%. Combinations of the ranges described herein (e.g., at least 20% and less than 50%) are also within the scope of the invention. In certain embodiments, an effective amount of a compound of the invention inhibits abnormal angiogenesis and/or aberrant signaling of a growth factor by a percentage or a range of percentage described herein, compared to normal angiogenesis and/or signaling.

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), polyvinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The formulation can also be prepared under aseptic conditions or sterilized with heat or irradiation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound of this invention may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 0.001% to about 50% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration. Such a formulation may comprise dry particles which comprise the active ingredient and which have a diameter in the range from about 0.5 to about 7 microns, or from about 1 to about 6 microns. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 20 microns. Alternatively, at least 95% of the particles by weight have a diameter greater than 1 nanometer and at least 90% of the particles by number have a diameter less than 15 microns. In some embodiments the majority of the particles have a diameter in the range of 1-10 microns. In some embodiments, the majority of the particles have a diameter in the range of 1-5 microns. Dry powder compositions may include a solid fine powder diluent such as sugar and are conveniently provided in a unit dose form.

Low boiling propellants generally include liquid propellants having a boiling point of below 65 T at atmospheric pressure. Generally the propellant may constitute 50 to 99.9% (w/w) of the composition, and the active ingredient may constitute 0.001 to 20% (w/vv) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.01 to about 200 microns.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.001% (w/w) to as much as 100% (wA,v) of the active ingredient, and may comprise one or more of the additional ingredients described herein. A pharmaceutical composition of the invention can be prepared, packaged, and/or sold in a formulation for oral administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for pulmonary administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.01 to about 200 microns, and may further comprise one or more of the additional ingredients described herein.

Formulations described herein may also be delivered via buccal administration. Such formulations may, for example, be in the form of tablets and/or lozenges made using conventional methods, and may contain, for example, 0.001 to 50% (w/w) active ingredient, the balance comprising an orally dissolvable and/or degradable composition and, optionally, one or more of the additional ingredients described herein.

A pharmaceutical composition of the invention can be prepared, packaged, and/or sold in a formulation for ophthalmic administration. Such formulations may, for example, be in the form of eye drops including, for example, a 0.001-10.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

A pharmaceutical composition of the invention may also be formulated for ophthalmic administration; by injection in any acceptable form (e.g., intravenous, intraperitoneal, intramuscular, subcutaneous, parenteral, epidural, intravitreal or perocular); and by implant or the use of reservoirs (e.g., subcutaneous pump, intrathecal pump, suppository, biodegradable delivery system, non-biodegradable delivery system and other implanted extended or slow release device or formulation). A pharmaceutical composition of the invention may also be formulated for administration by the ophthalmic mucous membrane route, such as, for example, eye drops or eye ointments. These formulations may be prepared by conventional means, and, if desired, the subject compositions may be mixed with any conventional additive, such as a buffering or pH-adjusting agent, tonicity adjusting agents, viscosity modifiers, suspension stabilizers, preservatives, and other pharmaceutical excipients. In addition, in certain embodiments, subject compositions described herein may be lyophilized or subjected to another appropriate drying technique such as spray drying.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, injections, including intravenous administration (e.g., systemic intravenous injection), regional administration via blood and/or lymph supply, and/or direct administration to an affected site, including topical administration. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition of the invention is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 1000 mg/kg, from about 0.01 mg/kg to about 500 mg/kg, preferably from about 0.1 mg/kg to about 400 mg/kg, preferably from about 0.5 mg/kg to about 300 mg/kg, from about 0.01 mg/kg to about 100 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity in preventing and/or treating a disease associated with aberrant signaling of a growth factor (e.g., VEGF) or with abnormal angiogenesis in a subject, in inhibiting aberrant signaling of a growth factor (e.g., VEGF) in a subject or cell, or in inhibiting abnormal angiogenesis in a subject), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents (e.g., anti-cancer agents), anti-angiogenesis agents, anti-inflammatory agents, immunosuppressants, anti-bacterial agents, anti-viral agents, anti-diabetic agents, anti-allergic agents, and pain-relieving agents. In certain embodiments, the additional pharmaceutical agent is a growth factor inhibitor. In certain embodiments, the additional pharmaceutical agent is a VEGF inhibitor. In certain embodiments, the additional pharmaceutical agent is an angiogenesis inhibitor. In certain embodiments, the additional pharmaceutical agent is an endogenous angiogenesis inhibitor (e.g., vascular endothelial growth factor receptor 1 (VEGFR-1, e.g., pazopanib (Votrient®), cediranib (Recentin®), tivozanib (AV-951), axitinib (Inlyta®), semaxanib), HER2 (lapatinib (Tykerb®, Tyverb®), linifanib (ABT-869), MGCD-265, and KRN-633), VEGFR-2 (e.g., regorafenib (BAY 73-4506), telatinib (BAY 57-9352), vatalanib (PTK787, PTK/ZK), MGCD-265, OSI-930, and KRN-633), NRP-1, angiopoietin 2, TSP-1, TSP-2, angiostatin, endostatin, vasostatin, calreticulin, platelet factor-4, TIMP, CDAI, Meth-1, Meth-2, IFN-α, IFN-β, IFN-γ, CXCL10, IL-4, 1L-12, IL-18, prothrombin (kringle domain-2), antithrombin III fragment, prolactin, VEGI, SPARC, osteopontin, maspin, canstatin, a proliferin-related protein, sorafenib (Nexavar®), and restin). In certain embodiments, the additional pharmaceutical agent is an exogenous angiogenesis inhibitor (e.g., bevacizumab, itraconazole, carboxyamidotriazole, TNP-470, CM101, IFN-α, IL-12, platelet factor-4, suramin, SU5416, thrombospondin, a VEGFR antagonist, an angiostatic steroid, an angiostatic steroid+heparin, a cartilage-derived angiogenesis inhibitory factor, a matrix metalloproteinase inhibitor, angiostatin, endostatin, 2-methoxyestradiol, tecogalan, tetrathiomolybdate, thalidomide, thrombospondin, prolactin, a $\alpha_\nu\beta_3$ inhibitor, linomide, and tasquinimod). In certain embodiments, the additional pharmaceutical agent is a corticosteroid, a receptor tyrosine kinase (RTK) inhibitor, a cyclooxygenase (COX) inhibitor, a prostaglandin analog, a non-steroidal anti-inflammatory drug (NSAID), a beta blocker, or a carbonic anhydrase inhibitor. In certain embodiments, the additional pharmaceutical agent is a pharmaceutical agent useful for treating and/or preventing AMD, such as verteporfin (e.g., Chlorin®, Visudyne®), thalidomide (e.g., Ambiodry®, Synovir®, Thalomid®), talaporfin sodium (e.g., Aptocine®, Laserphyrin®, Litx®), ranibizumab (e.g., Lucentis®), pegaptanib octasodium (e.g., Macugen®, Macuverse®), isopropyl unoprostone (e.g., Ocuseva®, Rescula®), interferon beta (e.g., Feron®), fluocinolone acetonide (e.g., Envision TD®, Retisert®), everolimus (e.g., Afinitor®, Certican®, Votubia®, Zortress®), eculizumab (e.g., Solaris®, Soliris®), dexamethasone (e.g., Osurdex®, Ozurdex®, Posurdex®, Surodex®), canakinumab (e.g., Ilaris®), bromfenac (Bromday®), ophthalmic (e.g., Bronac®, Bronuck®, Xibrom®, Yellox®), brimonidine (e.g., Alphagan®, Bromoxidine®, Enidin®), anecortave acetate (e.g., Retaane®, Edex®, Prostavasin®, Rigidur®, Vasoprost®, Viridal®), aflibercept ophthalmic solution (e.g., Eyelea®, Eylea®, VEGF-Trap-Eye®), ocriplasmin (e.g., Iluvien®, Medidur®, Medidur FA®), sirolimus (e.g., Perceiva®), NT-501, KH-902, fosbretabulin tromethamine (e.g., Zybrestat®), AL-8309, aganirsen (e.g., Norvess®), volociximab (e.g., Opthotec®), triamcinolone (e.g., Icon Bioscience), TRC-105, Burixafor (e.g., TG-0054), TB-403 (e.g., R-7334), squalamine (e.g., Evizon®), SB-623, S-646240, RTP-801i-14 (e.g., PF-4523655), RG-7417 (e.g., FCFD-4514S), AL-78898A (e.g., POT-4), PG-11047 (e.g., CGC-11047), pazopanib hydrochloride, sonepcizumab (e.g., Asonep®, Sphingomalo®), padeliporfin (e.g., Stakel®), OT-551, ontecizumab, NOX-A12, hCNS-SC, Neu-2000, NAFB001, MA09-hRPE, LFG-316, iCo-007 (e.g., ISIS-13650), hI-con1, GSK-933776A, GS-6624 (e.g., AB-0024), ESBA-1008, epitalon, E-10030 (e.g., ARC-127), dalantercept, MP-0112, CNTO-2476, CERE-120, AAV-NTN, CCX-168, Brimonidine-DDS, bevasiranib sodium (e.g., Cand5), bertilimumab, AVA-101, ALG-1001, AL-39324, AGN-150998, ACU-4429, A6 (e.g., Paralit®), TT-30, sFLT-01 gene therapy, RetinoStat®, PRS-050 (e.g., Angiocal®), PF-4382923, Palomid-529, MC-1101, GW-824575, Dz13 (e.g., TRC-093), D93, CDX-1135 (e.g., TP10), ATL-1103, ARC-1905, XV-615, wet-AMD antibodies (e.g., pSivida), VEGF/rGel, VAR-10200, VAL-566-620-MULTI, TKI, TK-001, STP-601, dry AMD stem cell therapy (e.g., Eye-Cyte), OpRegen, SMT-D004, SAR-397769, RTU-007, RST-001, RGNX-004, RFE-007-CAI, retinal degeneration programme (e.g., Orphagen), retinal cells (e.g., ISCO), ReN003, PRM-167, ProDex, Photoswitches (e.g., Photoswitch Biosciences), Parkinson's therapy, OMS-721, OC-10X, NV. AT.08, NT-503, NAFB002, NADPH oxidase inhibitors (e.g., Alimera Sciences), MC-2002, lycium anti-angiogenic proteoglycan, IXSVEGF, integrin inhibitors, GW-771806, GBS-007, Eos-013, EC-400, dry-AMD therapy (e.g., Neuron Systems), CGEN-25017, CERE-140, AP-202, AMD therapy (e.g., Valens Therapeutics), AMD therapy (e.g., Amarna Therapeutics), AMD RNAi therapy (e.g., RXi), ALK-001, AMD therapy (e.g., Aciont), AC-301, 4-IPP, zinc-monocysteine complexes (e.g., Adeona), vatalanib, TG-100-344, prinomastat, PMX-53, Neovastat, mecamylamine, JSM-6427, JPE-1375, CereCRIB, BA-285, ATX-S10, AG-13958, verteporfin/alphavβ3 conjugate, VEGF/rGel, VEGF-saporin, VEGF-R2 antagonist (e.g., Allostera), VEGF inhibitors (e.g., Santen), VEGF antagonists (e.g., Ark), Vangiolux®, Triphenylmethanes (e.g., Alimera), TG-100-801, TG-100-572, TA-106, T2-TrpRS, SU-0879, stem cell therapy (e.g., Pfizer and UCL), SOD mimetics (e.g., Inotek), SHEF-1, rostaporfin (e.g., Photrex®, Purlytin®, SnET2), RNA interference (e.g., Idera and Merck), rhCFHp (e.g., Optherion), retino-NPY, retinitis pigmentosa therapy (e.g., Mimetogen), AMD gene therapy (e.g., Novartis), retinal gene therapy (e.g., Genzyme), AMD gene therapy (e.g., Copernicus), retinal dystrophy ther (e.g., Fovea and Genzyme), Ramot project No. K-734B, PRS-055, porcine RPE cells (e.g., GenVec), PMI-002, PLG-101 (e.g., BiCentis®), PJ-34, PI3K conjugates (e.g., Semafore), PhotoPoint, Pharmaprojects No, 6526, pegaptanib sodium (e.g., SurModics®), PEDF ZFP TF, PEDF gene therapy (e.g., GenVec), PDS-1.0, PAN-90806, Opt-21, OPK-HVB-010, OPK-HVB-004, Ophthalmologicals (e.g., Cell NetwoRx), ophthalmic compounds (e.g., AstraZenca and Alcon), OcuXan, NTC-200, NT-502, NOVA-21012, Neurosolve®, neuroprotective (e.g., BDSI), MEDI-548, MCT-355, McEye®, LentiVue®, LYN-002, LX-213, lutetium texaphyrin (e.g., Antrin®), LG-339 inhibitors (e.g., Lexicon), KDR kinase inhibitors (e.g., Merck), ISV-616, INDUS-815C, ICAM-1 aptamer (e.g., Eyetech), hedgehog antagonists (e.g., Opthalmo), GTx-822, GS-102, Granzyme B/VEGF®, gene therapy (e.g., EyeGate), GCS-100 analogue programme, FOV-RD-27, fibroblast growth factor (e.g., Ramot), fenretinide, F-200 (e.g., Eos-200-F), Panzem SR®, ETX-6991, ETX-6201, EG-3306, Dz-13, disulfiram (e.g., ORA-102), Diclofenac (e.g., Ophthalmopharma), ACU-02, CLT-010, CLT-009, CLT-008, CLT-007, CLT-006, CLT-005, CLT-004, CLT-003 (e.g., Chirovis®), CLT-001, Cethrin® (e.g., BA-210), celecoxib, CD91 antagonist (e.g., Ophthalmophar), CB-42, BNC-4, bestrophin, batimastat, BA-1049, AVT-2, AVT-1, atu012, Ape1 programme (e.g., ApeX-2), anti-VEGF (e.g., Gryphon), AMD ZFPs (e.g., ToolGen), AMD therapy (e.g., Optherion), AMD therapy (e.g., ItherX), dry AMD therapy (e.g., Opko), AMD therapy (e.g., CSL), AMD therapies (e.g., Pharmacopeia and Allergan), AMD therapeutic protein (e.g., ItherX), AMD RNAi therapy (e.g., BioMolecular Therapeutics), AM-1101, ALN-VEG01, AK-1003, AGN-211745, ACU-XSP-001 (e.g., Excellair®), ACU-HTR-028, ACU-HHY-011, ACT-MD (e.g., NewNeural), ABCA4 modulators (e.g., Active Pass), A36 (e.g., Angstrom), 267268 (e.g., SB-267268), bevacizumab (e.g., Avastin®), aflibercept (e.g., Eylea®), 131-I-TM-601, vandetanib (e.g., Caprelsa®, Zactima®, Zictifa®), sunitinib malate (e.g., Sutene®, Sutent®), sorafenib (e.g., Nexavar®), pazopanib (e.g., Armala®, Patorma®, Votrient®), axitinib (e.g., Inlyta®), tivozanib, XL-647. RAF-265, pegdinetanib (e.g., Angiocept®), pazopanib, MGCD-265, icrucumab, foretinib, ENMD-2076. BMS-690514, regorafenib, ramucirumab, plitidepsin (e.g., Aplidin®), orantinib, nintedanib (e.g., Vargatef®), motesanib, midostaurin, linifanib, telatinib, lenvatinib, elpamotide, dovitinib, cediranib (e.g., Recentin®), JI-101, cabozantinib, brivanib, apatinib, Angiozyme®, X-82, SSR-106462, rebastinib, PF-337210, IMC-3C5, CYC116, AL-3818, VEGFR-2 inhibitor (e.g., AB Science), VEGF/rGel (e.g., Clayton Biotechnologies), TLK-60596, TLK-60404, R84 antibody (e.g., Peregrine), MG-516, FLT4 kinase inhibitors (e.g., Sareum), flt-4 kinase inhibitors, Sareum, DCC-2618, CH-330331, XL-999, XL-820, vatalanib, SU-14813, semaxanib, KRN-633, CEP-7055, CEP-5214, ZK-CDK, ZK-261991, YM-359445, YM-231146, VEGFR-2 kinase inhibitors (e.g., Takeda), VEGFR-2 kinase inhibitors (e.g., Hanmi), VEGFR-2 antagonist (e.g., Affymax), VEGF/rGel (e.g., Targa), VEGF-TK inhibitors (e.g., AstraZeneca), tyrosine kinase inhibitors (e.g., Abbott), tyrosine kinase inhibitors (e.g., Abbott), Tie-2 kinase inhibitors (e.g., GSK), SU-0879, SP-5.2, sorafenib bead (e.g., Nexavar® bead), SAR-131675, Ro-4383596, R-1530, Pharmaprojects No. 6059, OSI-930, OSI-817, OSI-632, MED-A300, L-000021649, KM-2550, kinase inhibitors (e.g., MethylGene), kinase inhibitors (e.g., Amgen), Ki-8751, KDR kinase inhibitors (e.g., Celltech), KDR kinase inhibitors (e.g., Merck), KDR kinase inhibitors (e.g., Amgen), KDR inhibitors (e.g., Abbott), KDR inhibitor (e.g., LGLS), JNJ-17029259, IMC-1C11, Flt ¾ anticancer (e.g., Sentinel), EG-3306, DP-2514, DCC-2157, CDP-791, CB-173, c-kit inhibitors (e.g., Deciphera), BIW-8556, anticancers (e.g., Bracco and Dyax), anti-Flt-1 MAbs (e.g., ImClone), AGN-211745, AEE-788, or AB-434. In certain embodiments, the additional pharmaceutical agent is a pharmaceutical agent useful for treating and/or preventing dry eye, such as cyclosporine (Restasis®). In certain embodiments, the additional pharmaceutical agent is a pharmaceutical agent useful for treating and/or preventing cystoid macular edema (CME), such as an NSAID (e.g., bromfenac (Bromday®)). In certain embodiments, the additional pharmaceutical agent is a pharmaceutical agent useful for treating and/or preventing diabetic macular edema (DME), such as ranibizumab (Lucentis®). In certain embodiments, the additional pharmaceutical agent is a pharmaceutical agent useful for treating and/or preventing uveitis, such as Tobra-Dex® (0.1% dexamethasone/0.3% tobramycin), Zylet® (0.5% loteprednol etabonate/0.3% tobramycin)), triamcinolone acetonide (Trivaris® and Triesence®), fluocinolone acetonide (Retisert®), and dexamethasone (Ozurdex®). In certain embodiments, the additional pharmaceutical agent is a pharmaceutical agent useful for treating and/or preventing glaucoma, such as latanoprost (Xalatan®), bimatoprost (Lumigan®), travoprost (Travatan Z®), timolol (Timoptic®), brimonidine tartrate (Alphagan®), dorzolamide (Trusopt®), and pilocarpine (Isopto®). In certain embodiments, the additional pharmaceutical agent is a pharmaceutical agent useful for treating and/or preventing an ocular inflammatory disease (e.g., post-surgical inflammation), such as steroids (e.g., loteprednol etabonate (Lotemax®), difluprednate (Durezol®), prednisolone acetate (Pred Mild® and Omnipred®) and NSAIDs (e.g., bromfenac (Bromday®), nepafenac (Nevanac®), ketorolac tromethamine (Acular LS®, Acuvail®, Toradol®, and Sprix®), diclofenac (Voltaren®, Aclonac®, and Cataflam®).

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits described herein are useful for preventing and/or treating a disease described herein. In certain embodiments, the kits described herein are useful for preventing and/or treating a disease associated with aberrant signaling of a growth factor (e.g., VEGF) in a subject in need thereof. In certain embodiments, the kits described herein are useful for preventing and/or treating a disease associated with abnormal angiogenesis in a subject in need thereof. In certain embodiments, the kits described herein are useful for preventing and/or treating proliferative diseases (e.g., cancers, benign neoplasms, inflammatory diseases, autoimmune diseases) and/or ocular diseases (e.g., macular degeneration, glaucoma, diabetic retinopathy, retinoblastoma, edema, uveitis, dry eye, blepharitis, or post-surgical inflammation). In certain embodiments, the kits described herein are useful for inhibiting aberrant signaling of a growth factor (e.g., VEGF) in a subject or cell in need thereof. In certain embodiments, the kits described herein are useful for inhibiting abnormal angiogenesis in a subject in need thereof. In certain embodiments, the kits further include instructions for administering the compound, or the pharmaceutically acceptable salt, solvate, hydrate, polymorph, co-crystal, tautomer, stereoisomer, isotopically labeled derivative, or prodrug, or the pharmaceutical composition thereof. The kits may also include information as required by a regulatory agency such as the U.S. Food and Drug Administration (FDA). In certain embodiments, the information included in the kits is prescribing information. In certain embodiments, the kits and instructions provide for treating and/or preventing a disease described herein. In certain embodiments, the kits and instructions provide for preventing and/or treating a disease associated with aberrant signaling of a growth factor (e.g., VEGF) in a subject in need thereof. In certain embodiments, the kits and instructions provide for preventing and/or treating a disease associated with abnormal angiogenesis in a subject in need thereof. In certain embodiments, the kits and instructions provide for inhibiting aberrant signaling of a growth factor (e.g., VEGF) in a subject or cell in need thereof. In certain embodiments, the kits and instructions provide for inhibiting abnormal angiogenesis in a subject in need thereof. The kit of the invention may include one or more additional pharmaceutical agents described herein as a separate composition.

Also provided by the present invention are particles that may penetrate mucus, pharmaceutical compositions thereof, kits, and methods of using and preparing the particles, and pharmaceutical compositions thereof. The pharmaceutical compositions, kits, and methods may involve modifying the surface coatings of particles, such as particles of pharmaceutical agents that have a low aqueous solubility. Such pharmaceutical compositions, kits, and methods can be used to achieve efficient transport of particles comprising the inventive compounds through mucus barriers in a subject.

In certain embodiments, the compounds, particles, pharmaceutical compositions, kits, and methods of the invention are useful for applications in the eye, such as treating and/or preventing an ocular disease (e.g., macular degeneration, dry eye syndrome, uveitis, allergic conjunctivitis, glaucoma, and rosacea).

The particles (e.g., nanoparticles and microparticles) of the invention comprise a compound of the invention. The particles of the invention also include a surface-altering agent that modifies the surface of the particles to reduce the adhesion of the particles to mucus and/or to facilitate penetration of the particles through mucus.

The present invention also provides pharmaceutical compositions comprising the inventive particles. In certain embodiments, the pharmaceutical compositions of the invention can be topically administered to the eye of a subject. Topical pharmaceutical compositions are advantageous over pharmaceutical compositions that are administered by injection or orally.

Particles

The present invention also provides pharmaceutical compositions comprising a plurality of particles of the invention, which may be mucus-penetrating and may include a pharmaceutical agent (e.g., a compound of the invention). The inventive pharmaceutical compositions may be useful to deliver the pharmaceutical agent to the eye of a subject and to treat and/or prevent an ocular disease of the subject.

Without wishing to be bound by theory, it is believed that conventional particles (CPs, e.g., non-MPPs) are trapped in the mucus layer (e.g., eye mucin) and are readily cleared from the subject. Thus, the conventional particles may be cleared before the drugs contained in the particles can be transported to target tissue or site (e.g., by diffusion or other mechanisms). In contrast, the particles of the invention (e.g., MPPs) may avoid adhesion to secreted mucins, thereby prolonging particle retention and sustaining drug release.

In some embodiments, once a particle is successfully transported across a mucosal barrier (e.g., mucus or a mucosal membrane) in a subject, further interactions between the particle in the subject may take place. Interactions may take place, in some instances, through the coating and/or the core, and may involve, for example, the exchange of materials (e.g., pharmaceutical agents, therapeutic agents, proteins, peptides, polypeptides, nucleic acids, nutrients, e.g.) from the one or more components of the subject to the particle and/or from the particle to the one or more components of the subject. For example, in some embodiments in which the core is formed of or comprises a pharmaceutical agent, the breakdown, release and/or transport of the pharmaceutical agent from the particle can lead to certain beneficial and/or therapeutic effects in the subject. As such, the particles described herein can be used for the diagnosis, prevention, treatment or management of certain diseases or bodily conditions.

In some embodiments, the particles of the invention have a core-shell type configuration. The core may comprise any suitable material such as a solid pharmaceutical agent or a salt thereof having a relatively low aqueous solubility, a polymeric carrier, a lipid, and/or a protein. The core may also comprise a gel or a liquid. The core may be coated with a coating or shell comprising a surface-altering agent that facilitates mobility of the particle in mucus. As described in more detail below, the surface-altering agent may comprise a polymer (e.g., a synthetic or a natural polymer) having pendant hydroxyl groups on the backbone of the polymer. The molecular weight and/or degree of hydrolysis of the polymer may be chosen to impart certain transport characteristics to the particles, such as increased transport through mucus. In certain embodiments, the surface-altering agent may comprise a triblock copolymer comprising a (hydrophilic block)-(hydrophobic block)-(hydrophilic block) configuration. The molecular weights of each one of the blocks may be chosen to impart certain transport characteristics to the particles, such as increased transport through mucus. In some embodiments, at least one particle of the invention includes a core and a coating surrounding the core. A particle including a core and a coating on the core is referred to as a "coated particle." In certain embodiments, at least one particle of the invention includes a core but not a coating on the core. A particle including a core but not a coating on the core is referred to as an "uncoated particle."

In some embodiments, the compositions and methods involve the use of poloxamers that aid particle transport in mucus. Poloxamers are typically nonionic triblock copolymers comprising a central hydrophobic block (e.g., a poly(propylene oxide) block) flanked by two hydrophilic blocks (e.g., poly(ethylene oxide) blocks). Poloxamers have the trade name Pluronic®, examples of which are provided below In certain embodiments, the compositions and methods involve the use of polysorbates that aid particle transport in mucus. Polysorbates are typically derived from PEGylated sorbitan (a derivative of sorbitol) esterified with fatty acids. Common brand names for polysorbates include Tween®, Alkest®, Canarcel®. Examples of polysorbates include polyoxyethylene sorbitan monooleate (e.g., Tween 80®), polyoxyethylene sorbitan monostearate (e.g., Tween 60®), polyoxyethylene sorbitan monopalmitate (e.g., Tween 40®), and polyoxyethylene sorbitan monolaurate (e.g., Tween 20®).

In some embodiments, a substantial portion of the core is formed of one or more solid pharmaceutical agents (e.g., a compound of the invention) that can lead to certain beneficial and/or therapeutic effects. The core may be, for example, a nanocrystal (i.e., a nanocrystalline particle) of a pharmaceutical agent. In certain embodiments, the core includes a polymeric carrier, optionally with one or more pharmaceutical agents encapsulated or otherwise associated with the core. In certain embodiments, the core includes a lipid, protein, gel, liquid, and/or another suitable material to be delivered to a subject. The core includes a surface to which one or more surface-altering agents can be attached. In some embodiments, the core is surrounded by coating, which includes an inner surface and an outer surface. The coating may be formed, at least in part, of one or more surface-altering agents, such as a polymer (e.g., a block copolymer and/or a polymer having pendant hydroxyl groups), which may associate with the surface of the core. The surface-altering agent may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof. In some embodiments, the surface-altering agents, or portions thereof, are chosen to facilitate transport of the particle through or into a mucosal barrier (e.g., mucus or a mucosal membrane). In certain embodiments described herein, one or more surface-altering agents are oriented in a particular configuration in the coating. In some embodiments, in which a surface-altering agent is a triblock copolymer, such as a triblock copolymer having a (hydrophilic block)-(hydrophobic block)-(hydrophilic block) configuration, a hydrophobic block may be oriented towards the surface of the core, and hydrophilic blocks may be oriented away from the core surface (e.g., towards the exterior of the particle). The hydrophilic blocks may have characteristics that facilitate transport of the particle through a mucosal barrier, as described in more detail below.

In some embodiments the core may be formed of solid materials having various aqueous solubilities (i.e., a solubility in water, optionally with one or more buffers), and/or various solubilities in the solution in which the solid material is being coated with a surface-altering agent. For example, the solid material may have an aqueous solubility (or a solubility in a coating solution) of less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the solid material may have an aqueous solubility (or a solubility in a coating solution) of at least about 1 pg/mL, at least about 10 pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility or a solubility in a coating solution of at least about 10 pg/mL and less than or equal to about 1 mg/mL). Other ranges are also possible. The solid material may have these or other ranges of aqueous solubilities at any point throughout the pH range (e.g., from pH 1 to pH 14).

In embodiments in which the core comprises an inorganic material (e.g., for use as imaging agents), the inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt %. In one embodiment, the core is formed of 100 wt % inorganic material. In some cases, the inorganic material may be present in the core at less than or equal to about 100 wt %, less than or equal to about 90 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 2 wt %, or less than or equal to about 1 wt %. Combinations of the above-referenced ranges are also possible (e.g., present in an amount of at least about 1 wt % and less than or equal to about 20 wt %). Other ranges are also possible.

The core of a particle described herein may include a mixture of more than one polymer. In some embodiments, the core, or at least a portion of the core, includes a mixture of a first polymer and a second polymer. In certain embodiments, the first polymer is a polymer described herein. In certain embodiments, the first polymer is a relatively hydrophobic polymer (e.g., a polymer having a higher hydrophobicity than the second polymer). In certain embodiments, the first polymer is not a polyalkyl ether. In certain embodiments, the first polymer is polylactide (PLA), e.g., 100DL7A MW108K In certain embodiments, the first polymer is polylactide-co-glycolide (PLGA), e.g., PLGA1A MW4K. In other embodiments, however, the first polymer may be a relatively hydrophilic polymer (e.g., a polymer having a higher hydrophilicity than the second polymer).

In certain embodiments, the second polymer is a block copolymer described herein (e.g., a diblock copolymer or a triblock copolymer). In certain embodiments, the second polymer is a diblock copolymer including a relatively hydrophilic block (e.g., a polyalkyl ether block) and a relatively hydrophobic block (e.g., a non-(polyalkyl ether) block). In certain embodiments, the polyalkyl ether block of the second polymer is PEG (e.g., PEG2K or PEG5K). In certain embodiments, the non-(polyalkyl ether) block of the second polymer is PLA (e.g., 100DL9K, 100DL30, or 100DL95). In certain embodiments, the non-(polyalkyl ether) block of the second polymer is PLGA (e.g., 8515PLGA54K, 7525PLGA15K, or 5050PLGA18K). In certain embodiments, the second polymer is 100DL9K-co-PEG2K. In certain embodiments, the second polymer is 8515PLGA54K-co-PEG2K.

It should be appreciated that while "first" and "second" polymers are described, in some embodiments, a particle or core described herein may include only one such polymer. Additionally, while specific examples of first and second polymers are provided, it should be appreciated that other polymers, such as the polymers listed herein, can be used as first or second polymers.

The first polymer and the relatively hydrophobic block of the second polymer may be the same or different polymer. In some cases, the relatively hydrophilic block of the second polymer is present primarily at or on the surface of the core that includes the first and second polymers. For instance, the relatively hydrophilic block of the second polymer may act as a surface-altering agent as described herein. In some cases, the relatively hydrophobic block of the second polymer and the first polymer are present primarily inside the surface of the core that includes the first and second polymers.

The relatively hydrophilic block (e.g., a polyalkyl ether block, such as PEG block) of the second polymer may have any suitable molecular weight. In certain embodiments, the molecular weight of the relatively hydrophilic block of the second polymer is at least about 0.1 kDa, at least about 0.2 kDa, at least about 0.5 kDa, at least about 1 kDa, at least about 1.5 kDa, at least about 2 kDa, at least about 2.5 kDa, at least about 3 kDa, at least about 4 kDa, at least about 5 kDa, at least about 6 kDa, at least about 8 kDa, at least about 10 kDa, at least about 20 kDa, at least about 50 kDa, at least about 100 kDa, or at least about 300 kDa. In certain embodiments, the molecular weight of the relatively hydrophilic block of the second polymer is less than or equal to about 300 kDa, less than or equal to about 100 kDa, less than or equal to about 50 kDa, less than or equal to about 20 kDa, less than or equal to about 10 kDa, less than or equal to about 8 kDa, less than or equal to about 6 kDa, at least about 5 kDa, less than or equal to about 4 kDa, less than or equal to about 3 kDa, less than or equal to about 2.5 kDa, less than or equal to about 2 kDa, less than or equal to about 1.5 kDa, less than or equal to about 1 kDa, less than or equal to about 0.5 kDa, less than or equal to about 0.2 kDa, or less than or equal to about 0.1 kDa. Combinations of the above-mentioned ranges are also possible (e.g., at least about 0.5 kDa and less than or equal to about 10 kDa). Other ranges are also possible. In certain embodiments, the molecular weight of the relatively hydrophilic block of the second polymer is about 2 kDa. In certain embodiments, the molecular weight of the relatively hydrophilic block of the second polymer is about 5 kDa.

The relatively hydrophobic block (e.g., a non-(polyalkyl ether) block, such as PLGA or PLA block) of the second polymer may have any suitable molecular weight. In certain embodiments, the relatively hydrophobic block of the second polymer is relatively short in length and/or low in molecular weight. In certain embodiments, the molecular weight of the relatively hydrophobic block of the second polymer is less than or equal to about 300 kDa, less than or equal to about 100 kDa, less than or equal to about 80 kDa, less than or equal to about 60 kDa, less than or equal to about 54 kDa, less than or equal to about 50 kDa, less than or equal to about 40 kDa, less than or equal to about 30 kDa, less than or equal to about 20 kDa, less than or equal to about 15 kDa less than or equal to about 10 kDa, less than or equal to about 5 kDa, less than or equal to about 2 kDa, or less than or equal to about 1 kDa. In certain embodiments, the molecular weight of the PLGA or PLA block of the second polymer is at least about 0.1 kDa, at least about 0.3 kDa, at least about 1 kDa, at least about 2 kDa, at least about 4 kDa, at least about 6 kDa, at least about 7 kDa, at least about 8 kDa, at least about 9 kDa, at least about 10 kDa, at least about 12 kDa, at least about 15 kDa, at least about 20 kDa, at least about 30 kDa, at least about 50 kDa, or at least about 100 kDa. Combinations of the above-mentioned ranges are also possible (e.g., less than or equal to about 20 kDa and at least about 1 kDa). Other ranges are also possible. In certain embodiments, the molecular weight of the relatively hydrophobic block of the second polymer is about 9 kDa.

The relatively hydrophilic block (e.g., a polyalkyl ether block, such as PEG block) of the second polymer may be present in any suitable amount or density at or on the surface of a core described herein. In certain embodiments, the PEG block of the second polymer is present at or on the surface of the core at at least about 0.001, at least about 0.003, at least about 0.03, at least about 0.1 at least about 0.15, at least about 0.18, at least about 0.2, at least about 0.3, at least about 0.5, at least about 1, at least about 3, at least about 30, or at least about 100 PEG chains per $nm^2$ of the surface area of the core. In certain embodiments, the PEG block of the second polymer is present at or on the surface of the core at less than or equal to about 100, less than or equal to about 30, less than or equal to about 10, less than or equal to about 3, less than or equal to about 1, less than or equal to about 0.5, less than or equal to about 0.3, less than or equal to about 0.2, less than or equal to about 0.18, less than or equal to about 0.15, less than or equal to about 0.1, less than or equal to about 0.03, less than or equal to about 0.01, less than or equal to about 0.003, or less than or equal to about 0.001 PEG chains per $nm^2$ of the surface area of the core. Combinations of the above-mentioned ranges are also possible (e.g., at least about 0.03 and less than or equal to about 1 PEG chains per $nm^2$ of the surface area of the core). Other ranges are also possible. In certain embodiments, the PEG block of the second polymer is present at or on the surface of the core at at least about 0.18 PEG chains per $nm^2$ of the surface area of the core.

The relatively hydrophilic block (e.g., a polyalkyl ether block, such as PEG block) of the second polymer may be present in any suitable amount in a particle or core described herein. In certain embodiments, the relatively hydrophilic block of the second polymer is present in the core at less than or equal to about less than or equal to about 90 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 4 wt %, less than or equal to about 3 wt %, less than or equal to about 2 wt %, less than or equal to about 1 wt %, less than or equal to about 0.5 wt %, less than or equal to about 0.2 wt %, less than or equal to about 0.1 wt %, less than or equal to about 0.05 wt %, less than or equal to about 0.02 wt %, or less than or equal to about 0.01 wt % of the particle or core. In certain embodiments, the relatively hydrophilic block of the second polymer is present in the core at at least about 0.01 wt %, at least about 0.02 wt %, at least about 0.05 wt %, at least about 0.1 wt %, at least about 0.2 wt %, at least about 0.5 wt %, at least about 1 wt %, at least about 2 wt %, at least about 3 wt %, at least about 4 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the particle or core. Combinations of the above-mentioned ranges are also possible (e.g., less than or equal to about 10 wt % and at least about 0.5 wt % of the particle or core). Other ranges are also possible. In certain embodiments, the relatively hydrophilic block of the second polymer is present at less than or equal to about 3 wt % of the particle or core.

The relatively hydrophilic block (e.g., a polyalkyl ether block, such as PEG block) and the relatively hydrophobic block (e.g., a non-(polyalkyl ether) block, such as PLGA or PLA block) of the second polymer may be present in the core in any suitable ratio. In certain embodiments, the ratio of the relatively hydrophilic block to relatively hydrophobic block of the second polymers is at least about 1:99, at least about 10:90, at least about 20:80, at least about 30:70, at least about 40:60, at least about 50:50, at least about 60:40, at least about 70:30, at least about 80:20, at least about 90:10, or at least about 99:1 w/w. In certain embodiments, the ratio of the relatively hydrophilic block to relatively hydrophobic block is less than or equal to about 99:1, less than or equal to about 90:10, less than or equal to about 80:20, less than or equal to about 70:30, less than or equal to about 60:40, less than or equal to about 50:50, less than or equal to about 40:60, less than or equal to about 30:70, less than or equal to about 20:80, less than or equal to about 10:90, or less than or equal to about 1:99 w/w, Combinations of the above-mentioned ranges are also possible (e.g., greater than about 70:30 and less than or equal to about 90:10 w/w). Other ranges are also possible. In certain embodiments, the ratio of the relatively hydrophilic block to relatively hydrophobic block is about 20:80 w/w.

The first polymer (e.g., PLA or PLGA) and the second polymer (e.g., PLA-co-PEG or PLGA-co-PEG) may be present in the particle or core in any suitable ratio. In certain embodiments, the ratio of the first polymer to second polymer in the particle or core is at least about 1:99, at least about 10:90, at least about 20:80, at least about 30:70, at least about 40:60, at least about 50:50, at least about 60:40, at least about 65:35, at least about 70:30, at least about 75:25, at least about 80:20, at least about 85:15, at least about 90:10, at least about 95:5, or at least about 99:1 w/w. In certain embodiments, the ratio of the first polymer to second polymer in the particle or core is less than or equal to about 99:1, less than or equal to about 95:5, less than or equal to about 90:10, less than or equal to about 85:15, less than or equal to about 80:20, less than or equal to about 75:25, less than or equal to about 70:30, less than or equal to about 65:35, less than or equal to about 60:40, less than or equal to about 50:50, less than or equal to about 40:60, less than or equal to about 30:70, less than or equal to about 20:80, less than or equal to about 10:90, or less than or equal to about 1:99 w/w. Combinations of the above-mentioned ranges are also possible (e.g., greater than about 70:30 and less than or equal to about 90:10 w/w). Other ranges are also possible. In certain embodiments, the ratio of the first polymer to second polymer in the particle or core is about 70:30 w/w. In certain embodiments, the ratio of the first polymer to second polymer in the particle or core is about 80:20 w/w.

The particle or core comprising a mixture of the first polymer and the second polymer described herein may further include a coating described herein. The coating may be at or on the surface of the particle (e.g., the surface of the first polymer and/or the second polymer). In some embodiments, the coating includes a hydrophilic material. The coating may include one or more surface-altering agents described herein, such as a polymer and/or a surfactant (e.g., a PVA, a poloxamer, a polysorbate (e.g., Tween 80®)).

It should be understood that components and configurations other than those described herein may be suitable for certain particles and pharmaceutical compositions, and that not all of the components described are necessarily present in some embodiments.

In some embodiments, particles of the invention, when introduced into a subject, may interact with one or more components in the subject such as mucus, cells, tissues, organs, particles, fluids (e.g., blood), microorganisms, and portions or combinations thereof. In some embodiments, the coating of the inventive particle can be designed to include surface-altering agents or other components with properties that allow favorable interactions (e.g., transport, binding, and adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One example is choosing a hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported into and/or across a mucosal barrier (e.g., mucus or a mucosal membrane) in a subject, further interactions between the particle and the subject may take place. In some embodiments, in which the core comprises a pharmaceutical agent or compound of the invention, the conversion, breakdown, release, and/or transport of the pharmaceutical agent from the particle can lead to certain beneficial and/or therapeutic effects in the subject. Therefore, the particles of the invention can be used for the treatment and/or prevention of certain diseases.

Examples for the use of the particles of the invention are provided below in the context of being suitable for administration to a mucosal barrier (e.g., mucus or a mucosal membrane) in a subject. It should be appreciated that while many of the embodiments herein are described in this context, and in the context of providing a benefit for diseases that involve transport of materials across a mucosal barrier, the invention is not limited as such, and the particles, pharmaceutical compositions, and kits of the invention may be used to treat and/or prevent other diseases.

In some embodiments, the pharmaceutical compositions of the invention comprise MPPs that include a compound of the invention and optionally at least one additional pharmaceutical agent, each of which is associated with polymer carriers via encapsulation or other processes. In other embodiments, the pharmaceutical compositions of the invention comprise MPPs without any polymeric carriers or with minimal use of polymeric carriers. Polymer-based MPPs may have one or more inherent limitations in some embodiments. In particular, in light of drug delivery applications, these limitations may include one or more of the following. A) Low drug encapsulation efficiency and low drug loading: encapsulation of drugs into polymeric particles is often inefficient, as generally less than 10% of the total amount of drug used gets encapsulated into particles during manufacturing; additionally, drug loadings above 50% are rarely achieved. B) Convenience of usage: pharmaceutical compositions based on drug-loaded polymeric particles, in general, typically need to be stored as dry powder to avoid premature drug release and thus require either point-of-use re-constitution or a sophisticated dosing device. C) Biocompatibility: accumulation of slowly degrading polymer carriers following repeated dosing and their toxicity over the long term present a major concern for polymeric drug carriers. D) Chemical and physical stability: polymer degradation may compromise stability of encapsulated drugs. In many encapsulation processes, the drug undergoes a transition from a solution phase to a solid phase, which is not well-controlled in terms of physical form of the emerging solid phase (i.e., amorphous vs. crystalline vs.

crystalline polymorphs); this is a concern for multiple aspects of pharmaceutical composition performance, including physical and chemical stability and release kinetics. E) Manufacturing complexity: manufacturing, especially scalability, of drug-loaded polymeric MPPs is a fairly complex process that may involve multiple steps and a considerable amount of toxic organic solvents. Therefore, by avoiding or minimizing the need to encapsulate pharmaceutical agents into polymeric carriers, certain limitations of polymeric MPPs with respect to drug loading, convenience of usage, biocompatibility, stability, and/or complexity of manufacturing, may be addressed.

It should be appreciated, however, that in other embodiments, pharmaceutical agents may be associated with polymer carriers via encapsulation or other processes. Thus, the description provided herein is not limited in this respect. For instance, despite the above-mentioned drawbacks of certain mucus-penetrating particles including a polymeric carrier, in certain embodiments such particles may be preferred. For example, it may be preferable to use polymer carriers for controlled release purposes and/or for encapsulating certain pharmaceutical agents that are difficult to formulate into particles. As such, in some embodiments described herein, particles that include a polymer carrier are described.

In some embodiments, the pharmaceutical compositions of the invention involve the use of poly(vinyl alcohols) (PVAs) to aid particle transport in mucus. The pharmaceutical compositions may involve making MPPs or MPCs by, for example, an emulsification process in the presence of specific PVAs. In certain embodiments, the pharmaceutical compositions and methods involve making MPPs or MPCs from pre-fabricated particles by non-covalent coating with specific PVAs. In some embodiments, the pharmaceutical compositions and methods involve making MPPs in the presence of specific PVAs without any polymeric carriers or with minimal use of polymeric carriers. It should be appreciated, however, that in other embodiments, polymeric carriers can be used.

PVA is a water-soluble non-ionic synthetic polymer. Due to its surface active properties, PVA is widely used in the food and drug industries as a stabilizing agent for emulsions and, in particular, to enable encapsulation of a wide variety of compounds by emulsification techniques. PVA has the "generally recognized as safe" (GRAS) status with the Food and Drug Administration (FDA), and has been used in auricular, intramuscular, intraocular, intravitreal, iontophoretic, ophthalmic, oral, topical, and transdermal drug products and/or drug delivery systems.

In certain previous studies, many have described PVA as a mucoadhesive polymer, suggesting that incorporating PVA in the particle formulation process leads to particles that are strongly mucoadhesive. Surprisingly, and contrary to the established opinion that PVA is a mucoadhesive polymer, it is discovered that pharmaceutical compositions of the invention utilizing specific PVA grades in fact aid particle transport in mucus and are not mucoadhesive in certain applications of the invention. Specifically, MPPs can be prepared by tailoring the degree of hydrolysis and/or molecular weight of the PVA, which was previously unknown. This discovery significantly broadens the arsenal of techniques and ingredients applicable for manufacturing MPPs.

In other embodiments, the pharmaceutical compositions of the invention and the methods of making the particles and pharmaceutical compositions of the invention involve PVAs in conjunction with other polymers or do not involve PVAs at all. For example, PEG and/or Pluronics® (poloxamers) may be included in the pharmaceutical compositions of the invention and methods of making the particles and pharmaceutical compositions of the invention, in addition to or in replace of PVAs. Other polymers, such as those described herein, may also be used.

Core of the Particles

A particle of the invention includes a core. The core of the inventive particles may be formed of any suitable material, such as an organic material, inorganic material, polymer, lipid, protein, or combinations thereof. In some embodiments, the core is a solid. The solid may be, for example, a crystalline, semi-crystalline, or amorphous solid, such as a crystalline, semi-crystalline, or amorphous solid pharmaceutical agent (e.g., a compound of the invention), or a salt thereof. In certain embodiments, the core is a gel or liquid (e.g., an oil-in-water or water-in-oil emulsion).

One or more pharmaceutical agents may be present in the core. The pharmaceutical agent may be present in the core in any suitable amount, e.g., at least about 80 wt % and less than about 100 wt % of the core). Other ranges are also possible.

Particles that are formed by encapsulating pharmaceutical agents into polymeric carriers typically have a low loading of the pharmaceutical agent (e.g., less than about 50 wt % of the core of the particles). In contrast, in certain embodiments, the loading of the pharmaceutical agent in the core of the inventive particles is high (e.g., at least about 50 wt % of the core). A high drug loading is an advantage for drug delivery, since a high drug loading often means that fewer numbers of particles may be needed to achieve a desired effect. As described herein, in other embodiments in which a relatively high amount of a polymer or other material forms the core, the loading of the pharmaceutical agent in the core is low (e.g., less than about 50 wt % of the core).

The core may comprise a solid material having various aqueous solubilities and/or various solubilities in a coating solution (a solution in which the solid material is being coated with a surface-altering agent). For example, the solid material may have an aqueous solubility (or a solubility in a coating solution) of at least about 10 pg/mL and less than about or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

In certain embodiments, the core of the particles of the invention is hydrophobic. In certain embodiments, the core is substantially hydrophobic. In certain embodiments, the core is hydrophilic. In certain embodiments, the core is substantially hydrophilic.

In some embodiments, the core includes one or more organic materials, such as a synthetic polymer and/or natural polymer. Examples of synthetic polymers include non-degradable polymers (e.g., polymethacrylate) and degradable polymers (e.g., polylactic acid and polyglycolic acid), and copolymers thereof. Examples of natural polymers include hyaluronic acid, chitosan, and collagen. Other examples of polymers that may be suitable for portions of the core include those suitable for forming coatings on particles, as described herein. In some cases, the one or more polymers present in the core may be used to encapsulate or adsorb one or more pharmaceutical agents.

When a polymer is present in the core, the polymer may be present in the core in any suitable amount, e.g., less than about 100 wt %, less than about 80 wt %, less than about 60 wt %, less than about 50 wt %, less than about 40 wt %, less than about 30 wt %, less than about 20 wt %, less than about 10 wt %, less than about 5 wt %, or less than about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than about 20 wt %). Other ranges are also possible. In some embodiments, the core is substantially free of a polymeric component.

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than about 10 µm, less than about 3 µm, less than about 1 µm, less than about 500 nm, less than 400 nm, less than 300 nm, less than about 200 nm, less than about 100 nm, less than about 30 nm, or less than about 10 nm. In some cases, the core may have a largest or smallest cross-sectional dimension of, for example, at least about 10 nm, at least about 30 nm, at least about 100 nm, at least about 200 nm, at least about 300 nm, at least about 400 nm, at least about 500 nm, at least about 1 µm, or at least about 3 µm. Combinations of the above-referenced ranges are also possible (e.g., a largest or smallest cross-sectional dimension of at least about 30 nm and less than about 500 nm). Other ranges are also possible. In some embodiments, the sizes of the cores formed by a process described herein have a Gaussian-type distribution. Unless indicated otherwise, the measurements of the particle sizes or core sizes refer to the smallest cross-sectional dimension.

Techniques to determine sizes (e.g., smallest or largest cross-sectional dimensions) of particles are known in the art. Examples of suitable techniques include dynamic light scattering (DLS), transmission electron microscopy, scanning electron microscopy, electroresistance counting and laser diffraction. Although many methods for determining sizes of particles are known, the sizes described herein (e.g., average particle sizes and thicknesses) refer to ones measured by DLS.

Coating of the Particles

A particle of the invention may include a coating. An inventive particle including a coating may be referred to as a coated particle of the invention. An inventive particle not including a coating may be referred to as an uncoated particle of the invention. In some embodiments, the coating is formed of one or more surface-altering agents or other molecules disposed on the surface of the core. The particular chemical makeup and/or components of the coating and surface-altering agent(s) can be chosen so as to impart certain functionality to the particles, such as enhanced transport through mucosal barriers.

It should be understood that a coating which surrounds a core need not completely surround the core, although such embodiments may be possible. For example, the coating may surround at least about 10%, at least about 30%, at least about 50%, at least about 70%, at least about 90%, or at least about 99% of the surface area of a core. In some cases, the coating substantially surrounds a core. In other cases, the coating completely surrounds a core. In other embodiments, a coating surrounds less than about 100%, less than about 90%, less than about 70%, or less than about 50% of the surface area of a core. Combinations of the above-referenced ranges are also possible (e.g., surrounding at least 70% and less than 100% of the surface area of a core).

The material of the coating may be distributed evenly across a surface of the core in some cases, and unevenly in other cases. For example, the coating may include portions (e.g., holes) that do not include any material. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material (i.e., a monolayer) or multilayers of materials. A single type or multiple types of surface-altering agent may be present.

The coating of particles of the invention can have any suitable thickness. For example, the coating may have an average thickness of at least about 1 nm, at least about 3 nm, at least about 10 nm, at least about 30 nm, at least about 100 nm, at least about 300 nm, at least about 1 µm, or at least about 3 µm. In some cases, the average thickness of the coating is less than about 3 µm, less than about 1 µm, less than about 300 nm, less than about 100 nm, less than about 30 nm, less than about 10 nm, or less than about 3 nm. Combinations of the above-referenced ranges are also possible (e.g., an average thickness of at least about 1 nm and less than about 100 nm). Other ranges are also possible. For particles having multiple coatings, each coating may have one of the thicknesses described herein.

The pharmaceutical compositions of the invention may allow for the coating of the particles of the invention with hydrophilic surface-altering moieties without requiring covalent association of the surface-altering moieties to the surface of the core. In some embodiments, the core having a hydrophobic surface is coated with a polymer described herein, thereby causing a plurality of surface-altering moieties to be on the surface of the core without substantially altering the characteristics of the core itself. For example, the surface altering agent may be present on (e.g., adsorbed to) the outer surface of the core. In other embodiments, a surface-altering agent is covalently linked to the core.

In certain embodiments in which the surface-altering agent is adsorbed onto a surface of the core, the surface-altering agent may be in equilibrium with other molecules of the surface-altering agent in solution, optionally with other components (e.g., in a pharmaceutical composition). In some cases, the adsorbed surface-altering agent may be present on the surface of the core at a density described herein. The density may be an average density as the surface altering agent is in equilibrium with other components in solution.

The coating and/or surface-altering agent of the particles of the invention may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, or rubber). In certain embodiments, the polymer is a surface active polymer. In certain embodiments, the polymer is a non-ionic polymer. In certain embodiments, the polymer is a linear synthetic non-ionic polymer. In certain embodiments, the polymer is a non-ionic block copolymer. The polymer may be a copolymer. In certain embodiments, one repeat unit of the copolymer is relatively hydrophobic and another repeat unit of the copolymer is relatively hydrophilic. The copolymer may be, for example, a diblock, triblock, alternating, or random copolymer. The polymer may be charged or uncharged.

In some embodiments, the coating of the particles of the invention comprises a synthetic polymer having pendant hydroxyl groups on the backbone of the polymer. Examples of the synthetic polymer are as described herein. Without wishing to be bound by theory, a particle including a coating comprising a synthetic polymer having pendant hydroxyl groups on the backbone of the polymer may have reduced mucoadhesion as compared to a control particle due to, at least in part, the display of a plurality of hydroxyl groups on the particle surface. One possible mechanism for the reduced mucoadhesion is that the hydroxyl groups alter the microenvironment of the particle, for example, by ordering water and other molecules in the particle/mucus environment. An additional or alternative possible mechanism is that the hydroxyl groups shield the adhesive domains of the mucin fibers, thereby reducing particle adhesion and speeding up particle transport.

Moreover, the ability of a particle coated with a synthetic polymer having pendant hydroxyl groups on the backbone of the polymer to be mucus penetrating may also depend, at least in part, on the degree of hydrolysis of the polymer. In some embodiments, the hydrophobic portions of the polymer (e.g., portions of the polymer that are not hydrolyzed) allow the polymer to be adhered to the surface of the core (e.g., in the case that the surface of the core is hydrophobic), thus allowing for a strong association between the core and polymer. Surprisingly, it has been found that, in some embodiments involving PVA as the surface-altering agent, too high of a degree of hydrolysis does not allow for sufficient adhesion between the PVA and the core (e.g., in the case of the core being hydrophobic), and thus, the particles coated with such a polymer generally do not exhibit sufficient reduced mucoadhesion. In some embodiments, too low of a degree of hydrolysis does not enhance particle transport in mucus, perhaps due to the lower amounts of hydroxyl groups available for altering the microenvironment of the particle and/or shielding the adhesive domains of the mucin fibers.

A synthetic polymer having pendant hydroxyl groups on the backbone of the polymer may have any suitable degree of hydrolysis (and, therefore, varying amounts of hydroxyl groups). The appropriate level of hydrolysis may depend on additional factors, such as the molecular weight of the polymer, the pharmaceutical composition of the core, and the hydrophobicity of the core. In some embodiments, the synthetic polymer is at least about 30% hydrolyzed, at least about 40% hydrolyzed, at least about 50% hydrolyzed, at least about 60% hydrolyzed, at least about 70% hydrolyzed, at least about 80% hydrolyzed, at least about 90% hydrolyzed, or at least about 95% hydrolyzed. In some embodiments, the synthetic polymer is less than about 100% hydrolyzed, less than about 95% hydrolyzed, less than about 90% hydrolyzed, less than about 80% hydrolyzed, less than about 70% hydrolyzed, or less than about 60% hydrolyzed. Combinations of the above-mentioned ranges are also possible (e.g., a synthetic polymer that is at least about 80% and less than about 95% hydrolyzed). Other ranges are also possible.

The molecular weight of the synthetic polymer described herein (e.g., one having pendant hydroxyl groups on the backbone of the polymer) may be selected so as to reduce the mucoadhesion of a core and to ensure sufficient association of the polymer with the core. In certain embodiments, the molecular weight of the synthetic polymer is at least about 1 kDa, at least about 2 kDa, at least about 5 kDa, at least about 8 kDa, at least about 9 kDa, at least about 10 kDa, at least about 12 kDa, at least about 15 kDa at least about 20 kDa, at least about 25 kDa, at least about 30 kDa, at least about 40 kDa, at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of the synthetic polymer is less than about 1000 kDa, less than about 500 kDa, less than about 200 kDa, less than about, less than about 150 kDa, less than about 130 kDa, less than about 120 kDa, less than about 100 kDa, less than about 85 kDa, less than about 70 kDa, less than about 65 kDa, less than about 60 kDa, less than about 50 kDa, or less than about 40 kDa, less than about 30 kDa, less than about 20 kDa, less than about 15 kDa, or less than about 10 kDa. Combinations of the above-mentioned ranges are also possible (e.g., a molecular weight of at least about 10 kDa and less than about 30 kDa). The above-mentioned molecular weight ranges can also be combined with the above-mentioned hydrolysis ranges to form suitable polymers.

In some embodiments, the synthetic polymer described herein is or comprises PVA. In some embodiments, the synthetic polymer described herein is or comprises partially hydrolyzed PVA. Partially hydrolyzed PVA includes two types of repeating units: vinyl alcohol units and residual vinyl acetate units. The vinyl alcohol units are relatively hydrophilic, and the vinyl acetate units are relatively hydrophobic. In some instances, the sequence distribution of vinyl alcohol units and vinyl acetate units is blocky. For example, a series of vinyl alcohol units may be followed by a series of vinyl acetate units, and followed by more vinyl alcohol units to form a polymer having a mixed block-copolymer type arrangement, with units distributed in a blocky manner. In certain embodiments, the repeat units form a copolymer, e.g., a diblock, triblock, alternating, or random copolymer. Polymers other than PVA may also have these configurations of hydrophilic units and hydrophobic units.

In some embodiments, the hydrophilic units of the synthetic polymer described herein are substantially present at the outer surface of the particles of the invention. For example, the hydrophilic units may form a majority of the outer surface of the coating and may help stabilize the particles in an aqueous solution containing the particles. The hydrophobic units may be substantially present in the interior of the coating and/or at the surface of the core, e.g., to facilitate attachment of the coating to the core.

The molar fraction of the relatively hydrophilic units and the relatively hydrophobic units of the synthetic polymer described herein may be selected so as to reduce the mucoadhesion of a core and to ensure sufficient association of the polymer with the core, respectively. As described herein, the molar fraction of the hydrophobic units of the polymer may be chosen such that adequate association of the polymer with the core occurs, thereby increasing the likelihood that the polymer remains adhered to the core. The molar fraction of the relatively hydrophilic units to the relatively hydrophobic units of the synthetic polymer may be, for example, at least 0.5:1, at least 1:1, at least 2:1, at least 3:1, at least 5:1, at least 10:1, at least 20:1, at least 30:1, at least 50:1, or at least 100:1. In some embodiments, the molar fraction of the relatively hydrophilic units to the relatively hydrophobic units of the synthetic polymer may be, for example, less than 100:1, less than 50:1, less than 30:1, less than 20:1, less than 10:1, less than 5:1, less than 3:1, less than 2:1, or less than 1:1. Combinations of the above-referenced ranges are also possible (e.g., a ratio of at least 1:1 and less than 50:1). Other ranges are also possible.

The molecular weight of the PVA polymer may also be tailored to increase the effectiveness of the polymer to render particles mucus penetrating. Examples of PVA polymers having various molecular weights and degree of hydrolysis are shown in Table 1.

TABLE 1

Molecular weight (MW) and degree of hydrolysis of various poly(vinyl alcohols) (PVAs).[a]

| PVA | MW (kDa) | Hydrolysis degree (%) |
|---|---|---|
| 2K75 | 2 | 75-79 |
| 9K80 | 9-10 | 80 |
| 13K87 | 13-23 | 87-89 |
| 13K98 | 13-23 | 98 |
| 31K87 | 31-50 | 87-89 |
| 31K98 | 31-50 | 98-99 |
| 57K86 | 57-60 | 86-89 |
| 85K87 | 85-124 | 87-89 |
| 85K99 | 85-124 | 99+ |
| 95K95 | 95 | 95 |
| 105K80 | 104 | 80 |
| 130K87 | 130 | 87-89 |

[a]The values of the molecular weight and hydrolysis degree of the PVAs were provided by the manufacturers of the PVAs.

In certain embodiments, the synthetic polymer is represented by the formula:

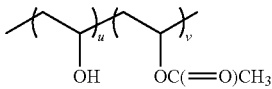

wherein:

u is an integer between 0 and 22730, inclusive; and v is an integer between 0 and 11630, inclusive. In certain embodiments, u is an integer between 25 and 20600, inclusive. In some embodiments, v is an integer between 5 and 1100, inclusive. In certain embodiments, v is an integer between 0 and 400 inclusive or between 1 and 400 inclusive. It is noted that u and v represent the total content of the vinyl alcohol and vinyl acetate repeat units in the polymer, respectively, rather than the block lengths.

The value of u may vary. In certain embodiments, n is at least 5, at least 10, at least 20, at least 30, at least 50, at least 100, at least 200, at least 300, at least 500, at least 800, at least 1000, at least 1200, at least 1500, at least 1800, at least 2000, at least 2200, at least 2400, at least 2600, at least 3000, at least 5000, at least 10000, at least 15000, at least 20000, or at least 25000. In some cases, n is less than or equal to 30000, less than or equal to 25000, less than or equal to 20000, less than or equal to 25000, less than or equal to 20000, less than or equal to 15000, less than or equal to 10000, less than or equal to 5000, less than or equal to 3000, less than or equal to 2800, less than or equal to 2400, less than or equal to 2000, less than or equal to 1800, less than or equal to 1500, less than or equal to 1200, less than or equal to 1000, less than or equal to 800, less than or equal to 500, less than or equal to 300, less than or equal to 200, less than or equal to 100, or less than or equal to 50. Combinations of the above-referenced ranges are also possible (e.g., n being at least 50 and less than or equal to 2000). Other ranges are also possible.

Similarly, the value of v may vary. For instance, in certain embodiments, m is at least 5, at least 10, at least 20, at least 30, at least 50, at least 70, at least 100, at least 150, at least 200, at least 250, at least 300, at least 350, at least 400, at least 500, at least 800, at least 1000, at least 1200, at least 1500, at least 1800, at least 2000, at least 2200, at least 2400, at least 2600, at least 3000, at least 5000, at least 10000, or at least 15000. In some cases, m is less than or equal to 15000, less than or equal to 10000, less than or equal to 5000, less than or equal to 3000, less than or equal to 2800, less than or equal to 2400, less than or equal to 2000, less than or equal to 1800, less than or equal to 1500, less than or equal to 1200, less than or equal to 1000, less than or equal to 800, less than or equal to 500, less than or equal to 400, less than or equal to 350, less than or equal to 300, less than or equal to 250, less than or equal to 200, less than or equal to 150, less than or equal to 100, less than or equal to 70, less than or equal to 50, less than or equal to 30, less than or equal to 20, or less than or equal to 10. Combinations of the above-referenced ranges are also possible (e.g., m being at least 5 and less than or equal to 200). Other ranges are also possible.

In some embodiments, the particles of the invention include a coating comprising a block copolymer having a relatively hydrophilic block and a relatively hydrophobic block. In some cases, the hydrophilic blocks may be substantially present at the outer surface of the particle. For example, the hydrophilic blocks may form a majority of the outer surface of the coating and may help stabilize the particle in an aqueous solution containing the particle. The hydrophobic block may be substantially present in the interior of the coating and/or at the surface of the core, e.g., to facilitate attachment of the coating to the core. In some embodiments, the coating comprises a surface-altering agent including a triblock copolymer, wherein the triblock copolymer comprises a (hydrophilic block)-(hydrophobic block)-(hydrophilic block) configuration. Diblock copolymers having a (hydrophilic block)-(hydrophobic block) configuration are also possible. Combinations of block copolymers with other polymers suitable for use as coatings are also possible. Non-linear block configurations are also possible such as in comb, brush, or star copolymers. In some embodiments, the relatively hydrophilic block includes a synthetic polymer having pendant hydroxyl groups on the backbone of the polymer (e.g., PVA).

The molecular weight of the hydrophilic blocks and the hydrophobic blocks of the block copolymers described herein may be selected so as to reduce the mucoadhesion of a core and to ensure sufficient association of the block copolymer with the core, respectively. The molecular weight of the hydrophobic block of the block copolymer may be chosen such that adequate association of the block copolymer with the core occurs, thereby increasing the likelihood that the block copolymer remains adhered to the core.

In certain embodiments, the molecular weight of each block of or combined blocks of the (one or more) relatively hydrophobic blocks of a block copolymer is at least about 0.5 kDa, at least about 1 kDa, at least about 1.8 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of each block of or combined blocks of the (one or more) relatively hydrophobic blocks is less than about 1000 kDa, less than about 500 kDa, less than about 200 kDa, less than about 150 kDa, less than about 140 kDa, less than about 130 kDa, less than about 120 kDa, less than about 110 kDa, less than about 100 kDa, less than about 90 kDa, less than about 80 kDa, less than about 50 kDa, less than about 20 kDa, less than about 15 kDa, less than about 13 kDa, less than about 12 kDa, less than about 10 kDa, less than about 8 kDa, or less than about 6 kDa. Combinations of the above-mentioned ranges are also possible (e.g., at least about 3 kDa and less than about 15 kDa). Other ranges are also possible.

In some embodiments, the combined relatively hydrophilic blocks (e.g., two hydrophilic blocks of a triblock copolymer) of a block copolymer (e.g., a triblock copolymer) constitute at least about 10 wt %, at least about 20 wt %, at least about 30 wt %, at least about 40 wt %, at least about 50 wt %, at least about 60 wt %, or at least about 70 wt % of the block copolymer. In some embodiments, the combined (one or more) relatively hydrophilic blocks of a block copolymer constitute less than about 90 wt %, less than about 80 wt %, less than about 60 wt %, less than about 50 wt %, or less than about 40 wt % of the block copolymer. Combinations of the above-referenced ranges are also possible (e.g., at least about 30 wt % and less than about 70 wt %). Other ranges are also possible.

In some embodiments, the molecular weight of each block of or combined blocks of the (one or more) relatively hydrophilic blocks of the block copolymer may be at least about 0.5 kDa, at least about 1 kDa, at least about 1.8 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In certain embodiments, the molecular weight of each block of or combined blocks of the (one or more) relatively hydrophilic blocks is less than about 1000 kDa, less than about 500 kDa, less than about 200 kDa, less than about 150 kDa, less than about 140 kDa, less than about 130 kDa, less than about 120 kDa, less than about 110 kDa, less than about 100 kDa, less than about 90 kDa, less than about 80 kDa, less than about 50 kDa, less than about 20 kDa, less than about 15 kDa, less than about 13 kDa, less than about 12 kDa, less than about 10 kDa, less than about 8 kDa, less than about 6 kDa, less than about 5 kDa, less than about 3 kDa, less than about 2 kDa, or less than about 1 kDa. Combinations of the above-mentioned ranges are also possible (e.g., at least about 0.5 kDa and less than about 3 kDa). Other ranges are also possible. In embodiments in which two hydrophilic blocks flank a hydrophobic block, the molecular weights of the two hydrophilic blocks may be substantially the same or different.

In certain embodiments, the polymer of the surface-altering agent includes a polyether portion. In certain embodiments, the polymer includes a polyalkylether portion. In certain embodiments, the polymer includes polyethylene glycol (PEG) tails. In certain embodiments, the polymer includes a polypropylene glycol as the central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a triblock copolymer of one of the polymers described herein. In some embodiments, a diblock or triblock copolymer comprises a synthetic polymer having pendant hydroxyl groups on the backbone of the polymer (e.g., PVA) as one or more of the blocks (with varying degrees of hydrolysis and varying molecular weights as described herein). The synthetic polymer blocks may form the central portion or end portions of the block copolymer.

In certain embodiments, the polymer is a triblock copolymer of a polyalkyl ether (e.g., polyethylene glycol, polypropylene glycol) and another polymer (e.g., a synthetic polymer having pendant hydroxyl groups on the backbone of the polymer (e.g., PVA). In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ethers. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In some embodiments, the hydrophilic units include a synthetic polymer having pendant hydroxyl groups on the backbone of the polymer (e.g., PVA). In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. The molecular weights of the two blocks flanking the central block may be substantially the same or different.

In certain embodiments, the polymer is of the formula:

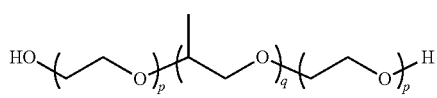

wherein each instance of p is independently an integer between 2 and 1140, inclusive; and q is an integer between 2 and 1730, inclusive. In certain embodiments, each instance of p is independently an integer between 10 and 170, inclusive. In certain embodiments, q is an integer between 5 and 70 inclusive. In certain embodiments, each instance of p is independently at least 2 times of q, 3 times of q, or 4 times of q.

In certain embodiments, the surface-altering agent comprises a (poly(ethylene glycol))-(poly(propylene oxide))-

(poly(ethylene glycol)) triblock copolymer (PEG-PPO-PEG triblock copolymer), present in the coating alone or in combination with another polymer such as a synthetic polymer having pendant hydroxyl groups on the backbone of the polymer (e.g., PVA). The molecular weights of the PEG and PPO segments of the PEG-PPO-PEG triblock copolymer may be selected so as to reduce the mucoadhesion of the particles, as described herein. Without wishing to be bound by any theory, the particles of the invention having a coating comprising a PEG-PPO-PEG triblock copolymer may have reduced mucoadhesion as compared to control particles due to, at least in part, the PEG segments on the surface of the particles of the invention. The PPO segment may be adhered to the surface of the core (e.g., in the case of the surface of the core being hydrophobic), thus allowing for a strong association between the core and the triblock copolymer. In some embodiments, the PEG-PPO-PEG triblock copolymer is associated with the core through non-covalent interactions. For purposes of comparison, the control particle may be, for example, a carboxylate-modified polystyrene particle of similar size as the particle of the invention.

In certain embodiments, the surface-altering agent includes a polymer comprising a poloxamer, having the trade name Pluronic®. Pluronic® polymers that may be useful in the embodiments described herein include, but are not limited to, F127, F38, F108, F68, F77, F87, F88, F98, L101, L121, L31, L35, L43, L44, L61, L62, L64, L81, L92, N3, P103, P104, P105, P123, P65, P84, and P85. Examples of molecular weights of certain Pluronic® polymers are shown in Table 2.

TABLE 2

Molecular weight (MW) of Pluronic ® polymers

| Pluronic ® | Average MW (Da) | MW of the PPO portion (Da) | PEG wt % | MW of the PEG portion (Da) |
|---|---|---|---|---|
| F127 | 12000 | 3600 | 70 | 8400 |
| L44 | 2000 | 1200 | 40 | 800 |
| L81 | 2667 | 2400 | 10 | 267 |
| L101 | 3333 | 3000 | 10 | 333 |
| P65 | 3600 | 1800 | 50 | 1800 |
| L121 | 4000 | 3600 | 10 | 400 |
| P103 | 4286 | 3000 | 30 | 1286 |
| F38 | 4500 | 900 | 80 | 3600 |
| P123 | 5143 | 3600 | 30 | 1543 |
| P105 | 6000 | 3000 | 50 | 3000 |
| F87 | 8000 | 2400 | 70 | 5600 |
| F68 | 9000 | 1800 | 80 | 7200 |
| P123 | 5750 | 4030 | 30 | 1730 |

Although other ranges may be possible, in some embodiments, the hydrophobic block of the PEG-PPO-PEG triblock copolymer has one of the molecular weights described above (e.g., at least about 3 kDa and less than about 15 kDa), and the combined hydrophilic blocks have a weight percentage with respect to the polymer in one of the ranges described above (e.g., at least about 15 wt %, at least about 20 wt %, at least about 25 wt %, or at least about 30 wt %, and less than about 80 wt %). Certain Pluronic® polymers that fall within these criteria include, for example, F127 (poloxamer 407), F108 (poloxamer 338), P105, and P103. In certain embodiments, the particles of the invention including Pluronic® polymers that fall within these criteria are more mucus penetrating than particles including Pluronic® polymers that did not fall within these criteria. Materials that do not render the particles mucus penetrating also include certain polymers such as polyvinylpyrrolidones (PVP/Kollidon), polyvinyl alcohol-polyethylene glycol graft-copolymer (Kollicoat IR), and hydroxypropyl methylcellulose (Methocel); oligomers such as solutol HS 15, Triton X100, tyloxapol, and cremophor RH 40; and small molecules such as Span 20, Span 80, octyl glucoside, cetytrimethylammonium bromide (CTAB), and sodium dodecyl sulfate (SDS).

Although much of the description herein may involve coatings comprising a (hydrophilic block)-(hydrophobic block)-(hydrophilic block) configuration (e.g., a PEG-PPO-PEG triblock copolymer) or coatings comprising a synthetic polymer having pendant hydroxyl groups, it should be appreciated that the coatings are not limited to these configurations and materials and that other configurations and materials are possible.

Furthermore, although many of the embodiments described herein involve a single coating, in other embodiments, a particle may include more than one coating (e.g., at least two, three, four, five, or more coatings), and each coating need not be formed of or comprise a mucus penetrating material. In some embodiments, an intermediate coating (i.e., a coating between the core surface and an outer coating) may include a polymer that facilitates attachment of an outer coating to the core surface. In some embodiments, an outer coating of a particle includes a polymer comprising a material that facilitates the transport of the particle through mucus.

The coating (e.g., an inner coating, intermediate coating, and/or outer coating) of the particles of the invention may include any suitable polymer. In some embodiments, the polymer of the coating is biocompatible and/or biodegradable. In some embodiments, the polymer of the coating comprises more than one type of polymer (e.g., at least two, three, four, five, or more types of polymers). In some embodiments, the polymer of the coating is a random copolymer or a block copolymer (e.g., a diblock or triblock copolymer) as described herein.

Non-limiting examples of suitable polymers of the coating may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly (D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate.

The molecular weight of the polymer of the coating may vary. In some embodiments, the molecular weight of the polymer of the coating is at least about 0.5 kDa, at least about 1 kDa, at least about 1.8 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight of the polymer of the coating is less than about 50 kDa, less than about 40 kDa, less than about 30 kDa, less than about 20 kDa, less than about 12 kDa, less than about 10 kDa, less than about 8 kDa, less than about 6 kDa, less than about 5 kDa, or less than about 4 kDa. Combinations of the above-referenced ranges are possible (e.g., a molecular weight of at least about 2 kDa and less than about 15 kDa). Other ranges are also possible. The molecular weight of the polymer of the coating may be determined using any known technique such as light-scattering and gel permeation chromatography. Other methods are known in the art.

In certain embodiments, the molecular weight of the hydrophobic block of the triblock copolymer of the (hydrophilic block)-(hydrophobic block)-(hydrophilic block) configuration is at least about 2 kDa, and the two hydrophilic blocks constitute at least about 15 wt % of the triblock copolymer.

In certain embodiments, a biocompatible polymer may be biodegradable, i.e., the polymer is able to degrade, chemically and/or biologically (e.g., by the cellular machinery or by hydrolysis), within a physiological environment, such as within the body or when introduced to cells. For instance, the polymer may be one that hydrolyzes spontaneously upon exposure to water (e.g., within a subject), and/or the polymer may degrade upon exposure to heat (e.g., at temperatures of about 37° C). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymer may be biologically degraded, e.g., by enzymatic activity or cellular machinery, in some cases, for example, through exposure to a lysozyme (e.g., having relatively low pH). In some cases, the polymer may be broken down into monomers and/or other nonpolymeric moieties that cells can either reuse or dispose of without significant toxic effect on the cells (i.e., fewer than about 20% of the cells are killed when the components are added to cells in vitro). For example, polylactide may be hydrolyzed to form lactic acid, polyglycolide may be hydrolyzed to form glycolic acid, etc.).

Examples of biodegradable polymers include, but are not limited to, poly(ethylene glycol)-poly(propylene oxide)-poly(ethylene glycol) triblock copolymers, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In certain embodiments, a polymer may biodegrade within a period that is acceptable in the desired application. In certain embodiments, such as in vivo therapy, such degradation occurs in a period usually less than about five years, one year, six months, three months, one month, fifteen days, five days, three days, or even one day or less (e.g., 1-4 hours, 4-8 hours, 4-24 hours, 1-24 hours) on exposure to a physiological solution with a pH between 6 and 8 having a temperature of between 25 and 37° C. In other embodiments, the polymer degrades in a period of between about one hour and several weeks, depending on the desired application.

Although the particles of the invention, and the coating thereof, may each include polymers, in some embodiments, the particles of the invention comprise a hydrophobic material that is not a polymer or pharmaceutical agent. Non-limiting examples of non-polymeric hydrophobic materials include, for example, metals, waxes, and organic materials (e.g., organic silanes and perfluorinated or fluorinated organic materials).

Particles with Reduced Mucoadhesion

Particles of the invention may have reduced mucoadhesiveness. A material in need of increased diffusivity through mucus may be hydrophobic, may include many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles of the invention as having reduced mucoadhesion may alternatively be characterized as having increased transport through mucus, being mobile in mucus, or mucus-penetrating (i.e., mucus-penetrating particles), meaning that the particles are transported through mucus faster than a negative control particle. The negative control particle may be a particle that is known to be mucoadhesive, e.g., an unmodified particle or core that is not coated with a coating described herein, such as a 200 nm carboxylated polystyrene particle.

Particles of the invention may be adapted for delivery (e.g., ocular delivery) to mucus or a mucosal surface of a subject. The particles with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion.

Furthermore, in some embodiments, the particles of the invention having reduced mucoadhesion facilitate better distribution of the particles at the surface of a tissue of a subject and/or have a prolonged presence at the surface of the tissue, compared to particles that are more mucoadhesive. For example, a luminal space such as the gastrointestinal tract is surrounded by a mucus-coated surface. Mucoadhesive particles delivered to such a space are typically removed from the luminal space and from the mucus-coated surface by the subject's natural clearance mechanisms. The particles of the invention with reduced mucoadhesion may remain in the luminal space for relatively longer periods compared to the mucoadhesive particles. This prolonged presence may prevent or reduce clearance of the particles and/or may allow for better distribution of the particles on the surface of the tissue. The prolonged presence may also affect the particle transport through the luminal space, e.g., the particles may distribute into the mucus layer and may reach the underlying epithelium.

In certain embodiments, the core of the particles of the invention coated with the polymer of the coating may pass through mucus or a mucosal barrier in a subject, exhibit prolonged retention, and/or increase uniform distribution of the particles at mucosal surfaces e.g., such substances are cleared more slowly (e.g., at least about 2 times, about 5 times, about 10 times, or even at least about 20 times more slowly) from a subject's body as compared to a negative control particle of the invention.

The mobility of the particles of the invention in mucus may be characterized in, e.g., the relative velocity and/or diffusivity of the particles. In certain embodiments, the particles of the invention have certain relative velocity, $<V_{mean}>_{rel}$, which is defined as follows:

$$<V_{mean}>_{rel} = \frac{<V_{mean}>_{Sample} - <V_{mean}>_{Negative\ control}}{<V_{mean}>_{Positive\ control} - <V_{mean}>_{Negative\ control}} \quad \text{(Equation 1)}$$

wherein:

$<V_{mean}>$ is the ensemble average trajectory-mean velocity;

$V_{mean}$ is the velocity of an individual particle averaged over its trajectory;

the sample is the particle of interest;

the negative control is a 200 nm carboxylated polystyrene particle; and the positive control is a 200 nm polystyrene particle densely PEGylated with 2-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative control, and positive control may be fluorescent particles to observe tracking. Alternatively non-fluorescent particles may be coated with a fluorescent molecule, a fluorescently tagged surface agent, or a fluorescently tagged polymer. An advanced image processing software (e.g., Image Pro or MetaMorph) can be used to measure individual trajectories of multiple particles over a time-scale of at least 3.335 s (50 frames).

In some embodiments, a particle described herein has a relative velocity of greater than or equal to about 0.3, greater than or equal to about 0.4, greater than or equal to about 0.5, greater than or equal to about 0.6, greater than or equal to about 0.7, greater than or equal to about 0.8, greater than or equal to about 0.9, greater than or equal to about 1.0, greater than or equal to about 1.1, greater than or equal to about 1.2, greater than or equal to about 1.3, greater than or equal to about 1.4, greater than or equal to about 1.5, greater than or equal to about 1.6, greater than or equal to about 1.7, greater than or equal to about 1.8, greater than or equal to about 1.9 or greater than or equal to about 2.0 in mucus. In some embodiments, a particle described herein has a relative velocity of less than or equal to about 10.0, less than or equal to about 8.0, less than or equal to about 6.0, less than or equal to about 4.0, less than or equal to about 3.0, less than or equal to about 2.0, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.1, less than or equal to about 1.0, less than or equal to about 0.9, less than or equal to about 0.8, or less than or equal to about 1.7 in mucus. Combinations of the above-noted ranges are possible (e.g., a relative velocity of greater than or equal to about 0.5 and less than or equal to about 6.0). Other ranges are also possible. The mucus may be, for example, human cervicovaginal mucus.

In certain embodiments, a particle described herein can diffuse through mucus or a mucosal barrier at a greater rate or diffusivity than a control particle or a corresponding particle (e.g., a corresponding particle that is unmodified and/or is not coated with a coating described herein). In some cases, a particle described herein may pass through mucus or a mucosal barrier at a rate of diffusivity that is at least about 10 times, 20 times, 30 times, 50 times, 100 times, 200 times, 500 times, 1000 times, 2000 times, 5000 times, 10000 times, or more, higher than a control particle or a corresponding particle. In some cases, a particle described herein may pass through mucus or a mucosal barrier at a rate of diffusivity that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

For the purposes of the comparisons described herein, the corresponding particles may be approximately the same size, shape, and/or density as the particles of the invention but lack the coating that makes the particles of the invention mobile in mucus. In some embodiments, the measurement of the geometric mean square displacement and rate of diffusivity of the particles (e.g., the corresponding particles and particles of the invention) is based on a time scale of about 1 second, about 3 seconds, or about 10 seconds. Methods for determining the geometric mean square displacement and rate of diffusivity are known in the art. The particles of the invention may pass through mucus or a mucosal barrier with a geometric mean squared displacement that is at least about 10 times, about 30 times, about 100 times, about 300 times, about 1000 times, about 3000 times, about 10000 times higher than corresponding particles or negative control particles. In some embodiments, the particles of the invention pass through mucus or a mucosal barrier with a geometric mean squared displacement that is less than about 10000 times higher, less than about 3000 times higher, less than about 1000 times higher, less than about 300 times higher, less than about 100 times higher, less than about 30 times higher, or less than about 10 times higher than negative control particles or corresponding particles. Combinations of the above-referenced ranges are also possible (e.g., at least about 10 times and less than about 1000 times higher than negative control particles or corresponding particles). Other ranges are also possible.

In some embodiments, particles of the invention diffuse through a mucosal barrier at a rate approaching the rate or diffusivity at which the particles can diffuse through water. In some embodiments, the particles of the invention pass through a mucosal barrier at a rate or diffusivity that is less than about 1/100, less than about 1/300, less than about 1/1000, less than about 1/3000, less than about 1/10,000 of the diffusivity that the particles diffuse through water under similar conditions. In some embodiments, particles of the invention pass through a mucosal barrier at a rate or diffusivity that is greater than or equal to about 1/10,000, greater than or equal to about 1/3000, greater than or equal to about 1/1000, greater than or equal to about 1/300, or greater than or equal to about 1/100 of the diffusivity that the particles diffuse through water under similar conditions. Combinations of the above-referenced ranges are also possible (e.g., greater than or equal to about 1/3000 and less than 1/300 the diffusivity that the particles diffuse through water under similar conditions). Other ranges are also possible. The measurement of diffusivity may be based on a time scale of about 1 second, or about 0.5 second, or about 2 seconds, or about 5 seconds, or about 10 seconds.

In some embodiments, the particles of the invention diffuse through human cervicovaginal mucus at a diffusivity that is less than about 1/500 of the diffusivity that the particles diffuse through water. In some embodiments, the measurement of diffusivity is based on a time scale of about 1 second, or about 0.5 second, or about 2 seconds, or about 5 seconds, or about 10 seconds.

In certain embodiments, the present invention provides particles that travel through mucus, such as human cervicovaginal mucus, at certain absolute diffusivities. For example, the particles of described herein may travel at diffusivities of at least about $1\times10^{-4}$ μm/s, $2\times10^{-4}$ μm/s, $5\times10^{-4}$ μm/s, $1\times10^{-3}$ μm/s, $2\times10^{-3}$ μm/s, $5\times10^{-3}$ μm/s, $1\times10^{-2}$ μm/s, $2\times10^{-2}$ μm/s, $4\times10^{-2}$ μm/s, $5\times10^{-2}$ μm/s, $6\times10^{-2}$ μm/s, $8\times10^{-2}$ μm/s, $1\times10^{-1}$ μm/s, $2\times10^{-1}$ μm/s, $5\times10^{-1}$ μm/s, 1 μm/s, or 2 μm/s. In some cases, the particles may travel at diffusivities of less than or equal to about 2 μm/s, less than or equal to about 1 μm/s, less than or equal to about $5\times10^{-1}$ μm/s, less than or equal to about $2\times10^{-1}$ μm/s, less than or equal to about $1\times10^{-1}$ μm/s, less than or equal to about $8\times10^{-2}$ μm/s, less than or equal to about $6\times10^{-2}$ μm/s, less than or equal to about $5\times10^{-2}$ μm/s, less than or equal to about $4\times10^{-2}$ μm/s, less than or equal to about $2\times10^{-2}$ μm/s, less than or equal to about $1\times10^{-2}$ μm/s, less than or equal to about $5\times10^{-3}$ μm/s, less than or equal to about $2\times10^{-3}$ μm/s, less than or equal to about $1\times10^{-3}$ μm/s, less than or equal to about $5\times10^{-4}$ μm/s, less than or equal to about $2\times10^{-4}$ μm/s, or less than or equal to about $1\times10^{-4}$ μm/s. Combinations of the above-referenced ranges are also possible (e.g., greater than or equal to about $2\times10^{-4}$ μm/s and less than or equal to about $1\times10^{-1}$ μm/s). Other ranges are also possible. In some cases, the measurement is based on a time scale of about 1 second, or about 0.5 second, or about 2 seconds, or about 5 seconds, or about 10 seconds.

It should be appreciated that while the mobility (e.g., relative velocity and diffusivity) of the particles of the invention may be measured in human cervicovaginal mucus, the mobility may be measured in other types of mucus as well.

In certain embodiments, a particle described herein comprises surface-altering moieties at a given density. The surface-altering moieties may be the portions of a surface-altering agent that are, for example, exposed to the solvent containing the particle. As an example, the hydrolyzed units/blocks of PVA may be surface-altering moieties of the surface-altering agent PVA. In another example, the PEG segments may be surface-altering moieties of the surface-altering agent PEG-PPO-PEG. In some cases, the surface-altering moieties and/or surface-altering agents are present at a density of at least about 0.001 units or molecules per $nm^2$, at least about 0.002, at least about 0.005, at least about 0.01, at least about 0.02, at least about 0.05, at least about 0.1, at least about 0.2, at least about 0.5, at least about 1, at least about 2, at least about 5, at least about 10, at least about 20, at least about 50, at least about 100 units or molecules per $nm^2$, or more units or molecules per $nm^2$. In some cases, the surface-altering moieties and/or surface-altering agents are present at a density of less than or equal to about 100 units or molecules per $nm^2$, less than or equal to about 50, less than or equal to about 20, less than or equal to about 10, less than or equal to about 5, less than or equal to about 2, less than or equal to about 1, less than or equal to about 0.5, less than or equal to about 0.2, less than or equal to about 0.1, less than or equal to about 0.05, less than or equal to about 0.02, or less than or equal to about 0.01 units or molecules per $nm^2$. Combinations of the above-referenced ranges are possible (e.g., a density of at least about 0.01 and less than or equal to about 1 units or molecules per $nm^2$). Other ranges are also possible. In some embodiments, the density values described above may be an average density as the surface altering agent is in equilibrium with other components in solution.

Those skilled in the art would be aware of methods to estimate the average density of surface-altering moieties (see, for example, Budijono et al., *Colloids and Surfaces A: Physicochem. Eng. Aspects* 2010, 360, 105-110; Joshi et al., *Anal. Chirp. Acta* 1979, 104, 153-160). For example, as described herein, the average density of surface-altering moieties can be determined using HPLC quantitation and DLS analysis. A suspension of particles for which surface density determination is of interest is first sized using DLS: a small volume is diluted to an appropriate concentration (e.g., about 100 μg/mL), and the z-average diameter is taken as a representative measurement of particle size. The remaining suspension is then divided into two aliquots. Using HPLC, the first aliquot is assayed for the total concentration of core material and for the total concentration of the surface-altering moiety. Again using HPLC, the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

In certain embodiments, the particles of the invention comprise surface-altering moieties and/or agents that affect the zeta-potential of the particle. The zeta potential of the particle may be, for example, at least about −100 mV, at least about −30 mV, at least about −10 mV, at least about −3 mV, at least about 3 mV, at least about 10 my, at least about 30 mV, or at least about 100 mV. The zeta potential of the particle may also be, for example, less than about 100 mV, less than about 30 mV, less than about 10 mV, less than about 3 mV, less than about −3 mV, less than about −10 mV, less than about −30 mV, or less than about −100 mV. Combinations of the above-referenced ranges are possible (e.g., a zeta-potential of at least about −30 mV and less than about 30 mV). Other ranges are also possible.

The coated particles described herein may have any suitable shape and/or size. In some embodiments, a coated particle has a shape substantially similar to the shape of the core. In some cases, a coated particle described herein may be a nanoparticle, i.e., the particle has a characteristic dimension of less than about 1 micrometer, where the characteristic dimension of the particle is the diameter of a perfect sphere having the same volume as the particle. In other embodiments, larger sizes are possible (e.g., about 1-10 microns). A plurality of particles, in some embodiments, may also be characterized by an average size (e.g., an average largest cross-sectional dimension, or an average smallest cross-sectional dimension for the plurality of particles). A plurality of particles may have an average size of, for example, less than or equal to about 10 µm, less than or equal to about 5 µm, less than or equal to about 1 µm, less than or equal to about 800 nm, less than or equal to about 700 nm, less than or equal to about 500 nm, less than or equal to 400 nm, less than or equal to 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, a plurality of particles may have an average size of, for example, at least about 5 nm, at least about 20 nm, at least about 50 nm, at least about 100 nm, at least about 200 nm, at least about 300 nm, at least about 400 nm, at least about 500 nm, at least about 1 µm, at least or at least about 5 µm. Combinations of the above-referenced ranges are also possible (e.g., an average size of at least about 50 nm and less than or equal to about 500 nm). Other ranges are also possible. In some embodiments, the sizes of the cores formed by a process described herein have a Gaussian-type distribution.

Pharmaceutical Agents

A particle or pharmaceutical composition of the invention may comprise at least one pharmaceutical agent. In certain embodiments, the pharmaceutical agent described herein is a pharmaceutically acceptable salt, solvate, hydrate, polymorph, tautomer, stereoisomer, isotopically labeled derivative, or prodrug of another pharmaceutical agent. In certain embodiments, the pharmaceutical agent is a co-crystal with another substance (e.g., a solvent, protein, or another pharmaceutical agent). The pharmaceutical agent may be present in the core and/or one or more coatings of the particle (e.g., dispersed throughout the core and/or coating). In some embodiments, the pharmaceutical agent may be disposed on the surface of the particle (e.g., on the outer or inner surface of the one or more coatings or on the surface of the core). The pharmaceutical agent may be contained within the particle and/or disposed in a portion of the particle using commonly known techniques (e.g., coating, adsorption, covalent linkage, and encapsulation). In some embodiments, the pharmaceutical agent is present during the formation of the core. In other embodiments, the pharmaceutical agent is not present during the formation of the core. In certain embodiments, the pharmaceutical agent is present during the coating of the core.

In some embodiments, the pharmaceutical agent contained in a particle or pharmaceutical composition of the invention has a therapeutic and/or prophylactic effect in a mucosal tissue to be targeted. Non-limiting examples of mucosal tissues include ophthalmic, respiratory (e.g., including nasal, pharyngeal, tracheal, and bronchial membranes), oral (e.g., including the buccal and esophagal membranes and tonsil surface), gastrointestinal (e.g., including stomach, small intestine, large intestine, colon, rectum), nasal, and genital (e.g., including vaginal, cervical and urethral membranes) tissues.

Any suitable number of pharmaceutical agents may be present in a particle or pharmaceutical composition of the invention. For example, at least 1, at least 2, at least 3, at least 4, at least 5, or more pharmaceutical agents may be present in the particle or pharmaceutical composition of the invention. In certain embodiments, less than 10 pharmaceutical agents are present in the particle or pharmaceutical composition of the invention.

In certain embodiments, the pharmaceutical agent in the particles or pharmaceutical compositions of the invention is a compound of the invention. The pharmaceutical agent described herein (e.g., a compound of the invention) may be encapsulated in a polymer, a lipid, a protein, or a combination thereof.

Pharmaceutical Compositions

In another aspect, the present invention provides pharmaceutical compositions comprising at least one particle of the invention. Pharmaceutical compositions described herein and for use in accordance with the articles and methods described herein may include a pharmaceutically acceptable excipient or carrier. A pharmaceutically acceptable excipient or pharmaceutically acceptable carrier may include a non-toxic, inert solid, semi-solid or liquid filler, diluent, encapsulating material or formulation auxiliary of any suitable type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on the route of administration as described below, the pharmaceutical agent being delivered, time course of delivery of the agent, etc.

Pharmaceutical compositions containing the particles described herein may be administered to a subject via any route known in the art. These include, but are not limited to, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), buccal and inhalational administration. In some embodiments, compositions described herein may be administered parenterally as injections (intravenous, intramuscular, or subcutaneous), drop infusion preparations, or suppositories. As would be appreciated by one of skill in this art, the route of administration and the effective dosage to achieve the desired biological effect may be determined by the agent being administered, the target organ, the preparation being administered, time course of administration, disease being treated, intended use, etc.

In certain embodiments, the pharmaceutical compositions are useful for the delivery of a pharmaceutical agent described herein (e.g., a compound of the invention) through or to mucus or a mucosal surface in a subject. The pharmaceutical compositions may be delivered to the mucosal surface in the subject and may pass through a mucosal barrier in the subject (e.g., mucus), and/or may show prolonged retention and/or increased uniform distribution of the particles of the invention at the mucosal surface, e.g., due to reduced mucoadhesion. In certain embodiments, the pharmaceutical compositions are useful in increasing the bioavailability of the pharmaceutical agent in the subject. In certain embodiments, the pharmaceutical compositions are useful in increasing the concentration of the pharmaceutical agent in the subject. In certain embodiments, the pharmaceutical compositions are useful in increasing the exposure of the pharmaceutical agent in the subject. Moreover, the pharmaceutical compositions may be useful in treating and/or preventing a disease (e.g., ocular disease) in a subject.

Moreover, the pharmaceutical compositions may be administered parenterally as injections (intravenous, intramuscular, or subcutaneous), drop infusion preparations, or suppositories. For ophthalmic applications, the pharmaceutical compositions may be administered by injection (e.g., intraocular, intrastromal, intravitreal, or intracameral), or by the ophthalmic mucous membrane route, the pharmaceutical compositions may be administered topically, such as suspensions (e.g.,eye drops) or ointments.

In some embodiments, particles described herein that may be administered in inhalant or aerosol formulations comprise one or more pharmaceutical agents, such as adjuvants, diagnostic agents, imaging agents, or therapeutic agents useful in inhalation therapy. The particle size of the particulate medicament should be such as to permit inhalation of substantially all of the medicament into the lungs upon administration of the aerosol formulation and may be, for example, less than about 20 microns, e.g., in the range of about 1 to about 10 microns, e.g., about 1 to about 5 microns, although other ranges are also possible. The particle size of the medicament may be reduced by conventional means, for example by milling or micronization. Alternatively, the particulate medicament can be administered to the lungs via nebulization of a suspension. The final aerosol formulation may contain, for example, between 0.005-90% w/w, between 0.005-50%, between 0.005-10%, between about 0.005-5% w/w, or between 0.01-1.0% w/w, of medicament relative to the total weight of the formulation. Other ranges are also possible.

It is desirable, but by no means required, that the formulations described herein contain no components which may provoke the degradation of stratospheric ozone. In particular, in some embodiments, propellants are selected that do not contain or do not consist essentially of chlorofluorocarbons such as $CCl_3F$, $CCl_2F_2$, and $CF_3CCl_3$.

The aerosol may comprise propellant. The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol, and propylene glycol, preferably ethanol. In general, only small quantities of polar adjuvants (e.g., 0.05-3.0% w/w) may be required to improve the stability of the dispersion-the use of quantities in excess of 5% wlw may tend to dissolve the medicament. Formulations in accordance with the embodiments described herein may contain less than 1% w/w, e.g., about 0.1% w/w, of polar adjuvant. However, the formulations described herein may be substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example, up to 30% w/w of a volatile saturated $C_1$-$C_6$ hydrocarbon. Optionally, the aerosol formulations according to the invention may further comprise one or more surfactants. The surfactants can be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

The formulations described herein may be prepared by dispersal of the particles in the selected propellant and/or co-propellant in an appropriate container, e.g., with the aid of sonication. The particles may be suspended in co-propellant and filled into a suitable container. The valve of the container is then sealed into place and the propellant introduced by pressure filling through the valve in the conventional manner. The particles may be thus suspended or dissolved in a liquefied propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the particles (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the particles. Ordinarily, an aqueous aerosol is made by formulating an aqueous solution or suspension of the particles together with conventional pharmaceutically acceptable carriers and stabilizers. The carriers and stabilizers vary with the requirements of the particular composition, but typically include non-ionic surfactants (Tweens, Pluronic®, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

The compositions and/or formulations described herein may have any suitable osmolarity. In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, or at least about 310 mOsm/L. In certain embodiments, a composition and/or formulation described herein may have an osmolarity of less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible. The osmolarity of the composition and/or formulation can be varied by changing, for example, the concentration of salts present in the solvent of the composition and/or formulation.

The pharmaceutical composition of the invention may include one or more pharmaceutical agents described herein, such as a compound of the invention. In certain embodiments, the pharmaceutical composition includes a plurality of particles of the invention that comprise one or more pharmaceutical agents in the core and/or coating of the particles. In some embodiments, the ratio of surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible. In some embodiments, the pharmaceutical composition of the invention includes the above-noted ranges for the ratio of the weight of each one of the pharmaceutical agents to the weight of each one of the one or more surface-altering agents during a formation process and/or a dilution process described herein. In certain embodiments, the pharmaceutical composition includes the above-noted ranges for the ratio of the weight of each one of the pharmaceutical agents to the weight of each one of the one or more surface-altering agents immediately prior to the pharmaceutical composition being administered to a subject or contacted with a biological sample. The pharmaceutical agent may be present in the pharmaceutical composition of the invention in any suitable amount, e.g., at least about 0.01 wt %, at least about 0.1 wt %, at least about 1 wt %, at least about 5 wt %, at least about 10 wt %, at least about 30 wt % of the pharmaceutical composition. In some cases, the pharmaceutical agent may be present in the pharmaceutical composition at less than about 30 wt %, less than about 10 wt %, less than about 5 wt %, less than about 2 wt %, or less than about 1 wt % of the pharmaceutical composition. Combinations of the above-referenced ranges are also possible (e.g., present in an amount of at least about 0.1 wt % and less than about 10 wt % of the pharmaceutical composition). Other ranges are also possible. In certain embodiments, the pharmaceutical agent is about 0.1-2 wt % of the pharmaceutical composition. In certain embodiments, the pharmaceutical agent is about 2-20 wt % of the pharmaceutical composition. In certain embodiments, the pharmaceutical agent is about 0.2 wt %, about 0.4 wt %, about 1 wt %, about 2 wt %, about 5 wt %, or about 10 wt % of the pharmaceutical composition.

In one set of embodiments, a composition and/or formulation includes one or more chelating agents. A chelating agent used herein refers to a chemical compound that has the ability to react with a metal ion to form a complex through one or more bonds. The one or more bonds are typically ionic or coordination bonds. The chelating agent can be an inorganic or an organic compound. A metal ion capable of catalyzing certain chemical reactions (e.g., oxidation reactions) may lose its catalytic activity when the metal ion is bound to a chelating agent to form a complex. Therefore, a chelating agent may show preservative properties when it binds to a metal ion. Any suitable chelating agent that has preservative properties can be used, such as phosphonic acids, aminocarboxylic acids, hydroxycarboxylic acids, polyamines, aminoalcohols, and polymeric chelating agents. Specific examples of chelating agents include, but are not limited to, ethylenediaminetetraacetic acid (EDTA), nitrilotriacetic acid (NTA), diethylenetriaminepentacetic acid (DTPA), N-hydroxyethylethylene diaminetriacetic acid (HEDTA), tetraborates, triethylamine diamine, and salts and derivatives thereof. In certain embodiments, the chelating agent is EDTA. In certain embodiments, the chelating agent is a salt of EDTA. In certain embodiments, the chelating agent is disodium EDTA.

In certain embodiments, the pharmaceutical composition includes a plurality of particles of the invention that comprise the chelating agent in the formulation containing the particles. In certain embodiments, the concentration of the chelating agent is greater than or equal to about 0 wt %, greater than or equal to about 0.0001 wt %, greater than or equal to about 0.003 wt %, greater than or equal to about 0.01 wt %, greater than or equal to about 0.03 wt %, greater than or equal to about 0.05 wt %, greater than or equal to about 0.1 wt %, greater than or equal to about 0.3 wt %, greater than or equal to about 1 wt %, or greater than or equal to about 3 wt %. In certain embodiments, the concentration of the chelating agent is less than or equal to about 3 wt %, less than or equal to about 1 wt %, less than or equal to about 0.3 wt %, less than or equal to about 0.1 wt %, less than or equal to about 0.05 wt %, less than or equal to about 0.03 wt %, less than or equal to about 0.01 wt %, less than or equal to about 0.003 wt %, less than or equal to about 0.001 wt %, or less than or equal to about 0.0003 wt %. Combinations of the above-noted ranges are possible (e.g., a concentration of greater than or equal to about 0.01 wt % and less than or equal to about 0.3 wt %). Other ranges are also possible. In certain embodiments, the concentration of the chelating agent is about 0.001-0.1 wt %. In certain embodiments, the concentration of the chelating agent is about 0.005 wt %. In certain embodiments, the concentration of the chelating agent is about 0.01 wt %. In certain embodiments, the concentration of the chelating agent is about 0.05%1%. In certain embodiments, the concentration of the chelating agent is about 0.1 wt %.

In some embodiments, an antimicrobial agent may be included in a composition and/or formulation including the coated particles described herein. An antimicrobial agent used herein refers to a bioactive agent effective in the inhibition of, prevention of, or protection against microorganisms such as bacteria, microbes, fungi, viruses, spores, yeasts, molds, and others generally associated with infections. Examples of antimicrobial agents include cephaloporins, clindamycin, chlorampheanicol, carbapenems, minocyclines, rifampin, penicillins, monobactams, quinolones, tetracycline, macrolides, sulfa antibiotics, trimethoprim, fusidic acid, aminoglycosides, amphotericin B, azoles, flucytosine, cilofungin, bactericidal nitrofuran compounds, nanoparticles of metallic silver or an alloy of silver containing about 2.5 wt % copper, silver citrate, silver acetate, silver benzoate, bismuth pyrithione, zinc pyrithione, zinc percarbonates, zinc perborates, bismuth salts, parabens (e.g., methyl-, ethyl-, propyl-, butyl-, and octyl-benzoic acid esters), citric acid, benzalkonium chloride (BAC), rifamycin, and sodium percarbonate.

In certain embodiments, the pharmaceutical composition includes a plurality of particles of the invention that comprise the antimicrobial agent in the formulation containing the particles. In certain embodiments, the concentration of the antimicrobial agent may be greater than or equal to about 0 wt %, greater than or equal to about 0.0001 wt %, greater than or equal to about 0.003 wt %, greater than or equal to about 0.01%1%, greater than or equal to about 0.03 wt %, greater than or equal to about 0.1 wt %, greater than or equal to about 0.3 wt %, greater than or equal to about 1 wt %, or greater than or equal to about 3N,vt %. In certain embodiments, the concentration of the antimicrobial agent may be less than or equal to about 3 wt %, less than or equal to about 1 wt %, less than or equal to about 0.3 wt %, less than or equal to about 0.1 wt %, less than or equal to about 0.03 wt %, less than or equal to about 0.01 wt %, less than or equal to about 0.003 wt %, less than or equal to about 0.001 wt %, or less than or equal to about 0.0003 wt %. Combinations of the above-noted ranges are possible (e.g., a concentration of greater than or equal to about 0.001 wt % and less than or equal to about 0.1 wt %). Other ranges are also possible. In certain embodiments, the concentration of the antimicrobial agent is about 0.001-0.05 wt %. In certain embodiments, the concentration of the antimicrobial agent is about 0.002 wt %. In certain embodiments, the concentration of the antimicrobial agent is about 0.005 wt %. In certain embodiments, the concentration of the antimicrobial agent is about 0.01 wt %. In certain embodiments, the concentration of the antimicrobial agent is about 0.02 wt %. In certain embodiments, the concentration of the antimicrobial agent is about 0.05 wt %.

In some embodiments, a tonicity agent may be included in a composition and/or formulation including the coated particles described herein. A tonicity agent used herein refers to a compound or substance that can be used to adjust the composition of a formulation to the desired osmolarity range. In certain embodiments, the desired osmolarity range is an isotonic range compatible with blood. In certain embodiments, the desired osmolarity range is hypotonic. In certain embodiments, the desired osmolarity range is hypertonic. Examples of tonicity agents include glycerin, lactose, mannitol, dextrose, sodium chloride, sodium sulfate, sorbitol, saline-sodium citrate (SSC), and the like. In certain embodiments, a combination of one or more tonicity agents may be used. In certain embodiments, the tonicity agent is glycerin. In certain embodiments, the tonicity agent is sodium chloride.

A tonicity agent (such as one described herein) may be present at a suitable concentration in a composition and/or formulation including the coated particles described herein. In certain embodiments, the concentration of the tonicity agent is greater than or equal to about 0 wt %, greater than or equal to about 0.001 wt %, greater than or equal to about 0.03 wt %, greater than or equal to about 0.1 wt %, greater than or equal to about 0.3 wt %, greater than or equal to about 1 wt %, greater than or equal to about 3 wt %, greater than or equal to about 10 wt %, greater than or equal to about 20 wt %, or greater than or equal to about 30 wt %. In certain embodiments, the concentration of the tonicity agent is less than or equal to about 30 wt %, less than or equal to about 10 wt %, less than or equal to about 3 wt %, less than or equal to about 1 wt %, less than or equal to about 0.3 wt %, less than or equal to about 0.1 wt %, less than or equal to about 0.03 wt %, less than or equal to about 0.01 wt %, or less than or equal to about 0.003 wt %, Combinations of the above-noted ranges are possible (e.g., a concentration of greater than or equal to about 0.1 wt % and less than or equal to about l0 wt %). Other ranges are also possible. In certain embodiments, the concentration of the tonicity agent is about 0.1-1%. In certain embodiments, the concentration of the tonicity agent is about 0.5-3%. In certain embodiments, the concentration of the tonicity agent is about 0.25 wt %. In certain embodiments, the concentration of the tonicity agent is about 0.45 wt %. In certain embodiments, the concentration of the tonicity agent is about 0.9 wt %. In certain embodiments, the concentration of the tonicity agent is about 1.2 wt %. In certain embodiments, the concentration of the tonicity agent is about 2.4 wt %. In certain embodiments, the concentration of the tonicity agent is about 5 wt %.

In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, at least about 310 mOsm/L, or at least about 450 mOsm/L. In certain embodiments, a composition and/or formulation described herein may have an osmolarity of less than or equal to about 450 mOsm/L, less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible.

It is appreciated in the art that the ionic strength of an inventive pharmaceutical composition that comprises a plurality of particles of the invention may affect the polydispersity of the plurality of the particles. The ionic strength may also affect the colloidal stability of the plurality of the particles. For example, a relatively high ionic strength of the pharmaceutical composition may cause the plurality of particles to coagulate and therefore may destabilize the pharmaceutical composition. In some embodiments, the pharmaceutical composition is stabilized by repulsive inter-particle forces. For example, the plurality of particles may be electrically or electrostatically charged. Two charged particles may repel each other, preventing collision and aggregation. When the repulsive inter-particle forces weaken or become attractive, the plurality of particles may start to aggregate. For instance, when the ionic strength of the pharmaceutical composition is increased to a certain level, the charges (e.g., negative charges) of the plurality of particles may be neutralized by the oppositely charged ions present in the pharmaceutical composition (e.g., Na$^+$ ions in solution). As a result, the plurality of particles may collide and bond to each other to form aggregates (e.g., clusters or flocs) of larger sizes. The formed aggregates of particles may also differ in size, and thus the polydispersity of the pharmaceutical composition may also increase. For example, an inventive pharmaceutical composition comprising similarly-sized particles may become a pharmaceutical composition comprising particles having various sizes (e.g., due to aggregation) when the ionic strength of the pharmaceutical composition is increased beyond a certain level. In the course of aggregation, the aggregates may grow in size and eventually settle to the bottom of the container, and the pharmaceutical composition is considered colloidally unstable. Once the plurality of particles in a pharmaceutical composition form aggregates, it is usually difficult to disrupt the aggregates into individual particles.

Certain pharmaceutical compositions of the invention show unexpected properties in that, among other things, the presence of one or more ionic tonicity agents (e.g., a salt, such as NaCl) in the pharmaceutical compositions at certain concentrations actually decreases or maintains the degree of aggregation of the particles present in the pharmaceutical compositions, and/or does not significantly increase aggregation. In certain embodiments, the polydispersity of the pharmaceutical composition decreases, is relatively constant, or does not change by an appreciable amount upon addition of one or more ionic tonicity agents into the pharmaceutical composition. For example, in some embodiments, the polydispersity of a pharmaceutical composition is relatively constant in the presence of added ionic strength and/or when the added ionic strength of the pharmaceutical composition is kept relatively constant or increased (e.g., during a formation and/or dilution process described herein). In certain embodiments, when the ionic strength increases by at least 50%, the polydispersity increases by less than about 300%, less than about 100%, less than about 30%, less than about 10%, less than about 3%, or less than about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100%. Combinations of the above-noted ranges are possible (e.g., an increase in polydispersity of less than 30% and greater than or equal to 3%), Other ranges are also possible.

The ionic strength of a pharmaceutical composition of the invention may be controlled (e.g., increased, decreased, or maintained) through a variety of means, such as the addition of one or more ionic tonicity agents (e.g., a salt, such as NaCl) to the pharmaceutical composition. In certain embodiments, the ionic strength of a pharmaceutical composition of the invention is greater than or equal to about 0M, greater than or equal to about 0.0003 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a pharmaceutical composition of the invention is less than about 10 M, less than about 3 M, less than about 1 M, less than about 0.3 M, less than about 0.1 M, less than about 0.03 M, less than about 0.01 M, less than about 0.003 M, less than about 0.001 M, or less than about 0.0003 M. Combinations of the above-noted ranges are possible (e.g., an ionic strength of greater than or equal to about 0.01 M and less than about 1 M). Other ranges are also possible. In certain embodiments, the ionic strength of a pharmaceutical composition of the invention is about 0.1 M, about 0.15 M, or about 0.3 M.

In certain embodiments, the polydispersity of a pharmaceutical composition does not change upon addition of one or more ionic tonicity agents into the pharmaceutical composition. In certain embodiments, the polydispersity does not significantly increase upon addition of one or more ionic tonicity agents into the pharmaceutical composition. In certain embodiments, the polydispersity increases to a level described herein upon addition of one or more ionic tonicity agents into the pharmaceutical composition.

The polydispersity of an inventive pharmaceutical composition that comprises a plurality of particles of the invention may be measured by the polydispersity index (PDI). In certain embodiments, the PDI of the pharmaceutical composition is less than about 1, less than about 0.8, less than about 0.6, less than about 0.4, less than about 0.3, less than about 0.2, less than about 0.15, less than about 0.1, less than about 0.05, less than about 0.01, or less than about 0.005. In certain embodiments, the PDI of the pharmaceutical composition is greater than or equal to about 0.005, greater than or equal to about 0.01, greater than or equal to about 0.05, greater than or equal to about 0.1, greater than or equal to about 0.15, greater than or equal to about 0.2, greater than or equal to about 0.3, greater than or equal to about 0.4, greater than or equal to about 0.6, greater than or equal to about 0.8, or greater than or equal to about 1. Combinations of the above-noted ranges are possible (e.g., a PDI of greater than or equal to about 0.1 and less than about 0.5). Other ranges are also possible. In certain embodiments, the PDI of the pharmaceutical composition is about 0.1, about 0.15, or about 0.2. In certain embodiments, the pharmaceutical composition is highly dispersible and does not tend to form aggregates. Even when the particles do form aggregates, the aggregates may be easily broken up into individual particles without rigorously agitating the pharmaceutical composition.

For example, in some embodiments, the polydispersity of a composition and/or formulation is relatively constant in the presence of added ionic strength and/or when the added ionic strength of the composition and/or formulation is kept relatively constant or increased (e.g., during a formation and/or dilution process). In certain embodiments, when the ionic strength increases by at least 50%, the polydispersity increases by less than or equal to about 200%, less than or equal to about 150%, less than or equal to about 100%, less than or equal to about 75%, less than or equal to about 50%, less than or equal to about 30%, less than or equal to about 20%, less than or equal to about 10%, less than or equal to about 3%, or less than or equal to about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100°10. Combinations of the above-noted ranges are possible (e.g., an increase in polydispersity of less than or equal to 50% and greater than or equal to 1%). Other ranges are also possible.

The ionic strength of a formulation described herein may be controlled (e.g., increased) through a variety of means, such as the addition of one or more ionic tonicity agents (e.g., a salt such as NaCl) to the formulation. In certain embodiments, the ionic strength of a formulation described herein is greater than or equal to about 0.0005 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a formulation described herein is less than or equal to about 10 M, less than or equal to about 3 M, less than or equal to about 1 M, less than or equal to about 0.3 M, less than or equal to about 0.1 M, less than or equal to about 0.03 M, less than or equal to about 0.01 M, less than or equal to about 0.003 M, less than or equal to about 0.001 M, or less than or equal to about 0.0005 M. Combinations of the above-noted ranges are possible (e.g., an ionic strength of greater than or equal to about 0.01 M and less than or equal to about 1 M). Other ranges are also possible. In certain embodiments, the ionic strength of a formulation described herein is about 0.1 M. In certain embodiments, the ionic strength of a formulation described herein is about 0.15 M. In certain embodiments, the ionic strength of a formulation described herein is about 0.3 M.

Generally, it is desired that a formulation is sterile before or upon administration to a subject. A sterile formulation is essentially free of pathogenic microorganisms, such as bacteria, microbes, fungi, viruses, spores, yeasts, molds, and others generally associated with infections. In some embodiments, compositions and/or formulations including the coated particles described herein may be subject to an aseptic process and/or other sterilization process. An aseptic process typically involves sterilizing the components of a formulation, final formulation, and/or container closure of a drug product through a process such as heat, gamma irradiation, ethylene oxide, or filtration and then combining in a sterile environment. In some cases, an aseptic process is preferred. In other embodiments, terminal sterilization is preferred.

Examples of other sterilization methods include radiation sterilization (e.g., gamma, electron, or x-ray radiation), heat sterilization, sterile filtration, and ethylene oxide sterilization. The terms "radiation" and "irradiation" are used herein interchangeably. Unlike other sterilization methods, radiation sterilization has the advantage of high penetrating ability and instantaneous effects, without the need to control temperature, pressure, vacuum, or humidity in some instances. In certain embodiments, the radiation used to sterilize the coated particles described herein is gamma radiation. Gamma radiation may be applied in an amount sufficient to kill most or substantially all of the microbes in or on the coated particles. The temperature of the coated particles described herein and the rate of radiation may be relatively constant during the entire gamma radiation period. Gamma irradiation may be performed at any suitable temperature (e.g., ambient temperature, about 40° C., between about 30 to about 50° C.). Unless otherwise indicated, measurements of gamma irradiation described herein refer to ones performed at about 40° C.

In embodiments in which a sterilization process is used, it may be desired that the process does not: (1) significantly change the particle size of the coated particles described herein; (2) significantly change the integrity of the active ingredient (such as a drug) of the coated particles described herein; and (3) generate unacceptable concentrations of impurities during or following the process. In certain embodiments, the impurities generated during or following the process are degradants of the active ingredient of the coated particles described herein.

In certain embodiments, a process used to sterilize a composition and/or formulation described herein results in the presence of one or more degradants in the formulation at less than or equal to about 10 wt % (relative to the weight of the undegraded drug), less than or equal to about 3 wt %, less than or equal to about 2 wt %, less than or equal to about 1.5 wt %, less than or equal to about 1 wt %, less than or equal to about 0.9 wt %, less than or equal to about 0.8 wt %, less than or equal to about 0.7 wt %, less than or equal to about 0.6 wt %, less than or equal to about 0.5 wt %, less than or equal to about 0.4 wt %, less than or equal to about 0.3 wt %, less than or equal to about 0.2 wt %, less than or equal to about 0.15 wt %, less than or equal to about 0.1 wt %, less than or equal to about 0.03 wt %, less than or equal to about 0.01 wt %, less than or equal to about 0.003 wt %, or less than or equal to about 0.001 wt %. In some embodiments, the process results in a degradant in the formulation at greater than or equal to about 0.001 wt %, greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, greater than or equal to about 3 wt %, or greater than or equal to about 10 wt %,Combinations of the above-referenced ranges are also possible (e.g., less than or equal to about 1 wt % and greater than or equal to about 0.01 wt %). Other ranges are also possible.

When gamma irradiation is used in a sterilization process, the cumulative amount of the gamma radiation used may vary. In certain embodiments, the cumulative amount of the gamma radiation is greater than or equal to about 0.1 kGy, greater than or equal to about 0.3 kGy, greater than or equal to about 1 kGy, greater than or equal to about 3 kGy, greater than or equal to about 10 kGy, greater than or equal to about 30 kGy, greater than or equal to about 100 kGy, or greater than or equal to about 300 kGy. In certain embodiments, the cumulative amount of the gamma radiation is less than or equal to about 0.1 kGy, less than or equal to about 0.3 kGy, less than or equal to about 1 kGy, less than or equal to about 3 kGy, less than or equal to about 10 kGy, less than or equal to about 30 kGy, less than or equal to about 100 kGy, or less than or equal to about 300 kGy. Combinations of the above-noted ranges are possible (e.g., greater than or equal to about 1 kGy and less than or equal to about 30 kGy). Other ranges are also possible. In certain embodiments, multiple doses of radiation are utilized to achieve a desired cumulative radiation dosage.

The compositions and/or formulations described herein may have any suitable pH values. The term "pH," unless otherwise provided, refers to pH measured at ambient temperature (e.g., about 20° C., about 23° C., or about 25° C.). The compositions and/or formulations have, for example, an acidic pH, a neutral pH, or a basic pH and may depend on, for example, where the compositions and/or formulations are to be delivered in the body. In certain embodiments, the compositions and/or formulations have a physiological pH. In certain embodiments, the pH value of the compositions and/or formulations is at least about 1, at least about 2, at least about 3, at least about 4, at least about 5, at least about 6, at least about 6.2, at least about 6.4, at least about 6.6, at least about 6.8, at least about 7, at least about 7.2, at least about 7.4, at least about 7.6, at least about 7.8, at least about 8, at least about 8.2, at least about 8.4, at least about 8.6, at least about 8.8, at least about 9, at least about 10, at least about 11, or at least about 12. In certain embodiments, the pH value of the compositions and/or formulations is less than or equal to about 12, less than or equal to about 11, less than or equal to about 10, less than or equal to about 9, less than or equal to about 8.8, less than or equal to about 8.6, less than or equal to about 8.4, less than or equal to about 8.2, less than or equal to about 8, less than or equal to about 7.8, less than or equal to about 7.6, less than or equal to about 7.4, less than or equal to about 7.2, less than or equal to about 7, less than or equal to about 6.8, less than or equal to about 6.6, less than or equal to about 6.4, less than or equal to about 6.2, less than or equal to about 6, less than or equal to about 5, less than or equal to about 4, less than or equal to about 3, less than or equal to about 2, or less than or equal to about 1. Combinations of the above-noted ranges are possible (e.g., a pH value of at least about 5 and less than or equal to about 8.2). Other ranges are also possible. In certain embodiments, the pH value of the compositions and/or formulations described herein is at least about 5 and less than or equal to about 8.

In some embodiments, the particles, compositions, and/or formulations described herein increase the ocular bioavailability of a pharmaceutical agent by at least about 10%, at least about 20%, at least about 30%, at least about 40%, at least about 50%, at least about 60%, at least about 70%, at least about 80%, at least about 90%, at least about 100%, at least about 150%, at least about 200%, at least about 5 fold, at least about 10 fold, at least about 20 fold, at least about 50 fold, at least about 100 fold, at least about 500 fold, or at least about 1000 fold. In certain embodiments the particles, compositions, and/or formulations described herein increase the ocular bioavailability of a pharmaceutical agent by less than or equal to about 1000 fold, less than or equal to about 500 fold, less than or equal to about 100 fold, less than or equal to about 50 fold, less than or equal to about 20 fold, less than or equal to about 10 fold, less than or equal to about 5 fold, less than or equal to about 200%, less than or equal to about 150%, less than or equal to about 100%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., an increase of at least about 10% and less than or equal to about 10 fold). Other ranges are also possible. In some instances, the AUC of a pharmaceutical agent increases at a tissue and/or fluid in the front of the eye. In other instances, the AUC of a pharmaceutical agent increases at a tissue and/or fluid in the back of the eye.

In general, an increase in ocular bioavailability may be calculated by taking the difference in the AUC measured in an ocular tissue of interest (e.g., in aqueous humor) between those of a test composition and a control composition, and dividing the difference by the bioavailability of the control composition. A test composition may include particles comprising a pharmaceutical agent, and the particles may be characterized as being mucus penetrating (e.g., having a relative velocity in mucus of greater than about 0.5, or another other relative velocity described herein). A control composition may include particles comprising the same pharmaceutical agent as that present in the test composition, the particles having a substantially similar size as those of the test composition, but which are not mucus penetrating (e.g., having a relative velocity in mucus of less than or equal to about 0.5, or another other relative velocity described herein).

Ocular bioavailability of a pharmaceutical agent may be measured in an appropriate animal model (e.g. in a New Zealand white rabbit model). The concentration of a pharmaceutical agent and, when appropriate, its metabolite(s), in appropriate ocular tissues or fluids is measured as a function of time after administration.

Other methods of measuring ocular bioavailability of a pharmaceutical agent are possible.

In some embodiments, the concentration of a pharmaceutical agent in an ocular tissue and/or fluid may be increased when the pharmaceutical agent is delivered (e.g., via topical administration to the eye) using the particles, compositions, and/or formulations described herein compared to when the pharmaceutical agent is delivered using certain existing particles, compositions, and/or formulations that contain the same the pharmaceutical agent (or compared to the delivery of the same pharmaceutical agent (e.g., of similar size) as the coated particle in question, but which does not include the coating). In certain embodiments, a dose of the particles, compositions, and/or formulations is administered, followed by the measurement of the concentration of the pharmaceutical agent in a tissue and/or fluid of the eye. For purposes of comparison, the amount of the pharmaceutical agent included in the administered dose of the particles, compositions, and/or formulations described herein may be similar or substantially equal to the amount of the pharmaceutical agent included in the administered dose of the existing particles, compositions, and/or formulations. In certain embodiments, the concentration of the pharmaceutical agent in a tissue and/or fluid of the eye is measured at a certain time subsequent to the administration ("time post-dose") of a dose of the particles, compositions, and/or formulations described herein or of the existing particles, compositions, and/or formulations. In certain embodiments, the time when the concentration is measured is about 1 min, about 10 min, about 30 min, about 1 h, about 2 h, about 3 h, about 4 h, about 5 h, about 6 h, about 7 h, about 8 h, about 9 h, about 10 h, about 11 h, about 12 h, about 18 h, about 24 h, about 36 h, or about 48 h, post-dose.

In some embodiments, the concentration of the pharmaceutical agent in a tissue and/or fluid may increase due to, at least in part, a coating on core particles comprising the pharmaceutical agent that renders the particles mucus penetrating, compared to particles of the same pharmaceutical agent (e.g., of similar size) as the coated particle in question, but which does not include the coating. In some embodiments, the particles, compositions, and/or formulations described herein increases the concentration of a pharmaceutical agent in a tissue and/or fluid by at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, or at least about 10 fold, at least about 20 fold, at least about 50 fold, at least about 100 fold, at least about 1000 fold, at least about $10^4$ fold, at least about $10^5$ fold, or at least about $10^6$ fold. In some cases, the particles, compositions, and/or formulations described herein increases the concentration of a pharmaceutical agent in a tissue and/or fluid by less than or equal to about $10^6$ fold, less than or equal to about $10^5$ fold, less than or equal to about $10^4$ fold, 1000 fold, less than or equal to about 100 fold, less than or equal to about 10 fold, less than or equal to about 500%, less than or equal to about 400%, less than or equal to about 300%, less than or equal to about 200%, less than or equal to about 100%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., an increase of greater than or equal to about 10% and less than or equal to about 90%). Other ranges are also possible. In some instances, the concentration of a pharmaceutical agent increases at a tissue and/or fluid in the front of the eye. In other instances, the concentration of a pharmaceutical agent increases at a tissue and/or fluid in the back of the eye.

The ocular concentration of a pharmaceutical agent, and, when appropriate, its metabolite(s), in appropriate ocular fluids or tissues may be measured as a function of time in vivo using an appropriate animal model. One method of determining the ocular concentration of a pharmaceutical agent involves dissecting of the eye to isolate tissues of interest (e.g., in a animal model comparable to the subject). The concentration of the pharmaceutical agent in the tissues of interest is then determined by HPLC or LC/MS analysis.

In certain embodiments, the period of time between administration of the particles described herein and obtaining a sample for measurement of concentration or AUC is less than about 1 hour, less than or equal to about 2 hours, less than or equal to about 3 hours, less than or equal to about 4 hours, less than or equal to about 6 hours, less than or equal to about 12 hours, less than or equal to about 36 hours, or less than or equal to about 48 hours. In certain embodiments, the period of time is at least about 1 hour, at least about 2 hours, at least about 3 hours, at least about 4 hours, at least about 6 hours, at least about 8 hours, at least about 12 hours, at least about 36 hours, or at least about 48 hours. Combinations of the above-referenced ranges are also possible (e.g., a period of time between consecutive doses of greater than or equal to about 3 hours and less than or equal to about 12 hours). Other ranges are also possible.

Other methods of measuring the concentration of a pharmaceutical agent in an eye of a subject or an animal model are also possible. In some embodiments, the concentration of a pharmaceutical agent may be measured in the eye of the subject directly or indirectly (e.g., taking a sample of fluid, such as vitreous humor, from an eye of the subject).

In general, an increase in concentration of a pharmaceutical agent in an ocular site may be calculated by taking the difference in concentration measured between those of a test composition and a control composition, and dividing the difference by the concentration of the control composition. A test composition may include particles comprising a pharmaceutical agent, and the particles may be characterized as being mucus penetrating (e.g., having a relative velocity of greater than about 0.5, or another other relative velocity described herein). A control composition may include particles comprising the same pharmaceutical agent as that present in the test composition, the particles having a substantially similar size as those of the test composition, but which are not mucus penetrating (e.g., having a relative velocity of less than about 0.5, or another other relative velocity described herein).

As described herein, in some embodiments, the particles, compositions, and/or formulations described herein, or a component thereof, is present in a sufficient amount to increase the bioavailability and/or concentration of a pharmaceutical agent in an ocular tissue, compared to the pharmaceutical agent administered to the ocular tissue in the absence of the particles, compositions, and formulations described herein, or a component thereof.

The ocular tissue may be an anterior ocular tissue (e.g., a palpebral conjunctiva, a bulbar conjunctiva, or a cornea). The pharmaceutical agent may be any suitable agent as described herein, such as the compounds of Formulae I-IV. In certain embodiments, the core particle of a formulation comprising a pharmaceutical agent is present in a sufficient amount to increase the bioavailability and/or concentration of the pharmaceutical agent in an ocular tissue. In certain embodiments, the coating on the core particle of a formulation comprising a pharmaceutical agent is present in a sufficient amount to increase the bioavailability and/or concentration of the pharmaceutical agent in an ocular tissue. In certain embodiments, the coating on the core particle of a formulation comprising a pharmaceutical agent is present in a sufficient amount to increase the concentration of the pharmaceutical agent in an ocular tissue after at least 10 minutes, at least 20 minutes, at least 30 minutes, at least 1 hour, at least 2 hours, at least 3 hours, at least 4 hours, at least 6 hours, at least 9 hours, at least 12 hours, at least 18 hours, or at least 24 hours after administration of the formulation to the ocular tissue. In certain embodiments, the coating on the core particle of a formulation comprising a pharmaceutical agent is present in a sufficient amount to increase the concentration of the pharmaceutical agent in an ocular tissue after less than or equal to 24 hours, less than or equal to 18 hours, less than or equal to 12 hours, less than or equal to 9 hours, less than or equal to 6 hours, less than or equal to 4 hours, less than or equal to 3 hours, less than or equal to 2 hours, less than or equal to 1 hour, less than or equal to 30 minutes, less than or equal to 20 minutes, or less than or equal to 10 minutes after administration of the formulation to the ocular tissue. Combinations of the above-referenced ranges are also possible (e.g., the concentration of the pharmaceutical agent increases after at least 10 minutes and less than or equal to 2 hours). Other ranges are also possible. In certain embodiments, the coating on the core particle of a formulation comprising a pharmaceutical agent is present in a sufficient amount to increase the concentration of the pharmaceutical agent in an ocular tissue after about 30 minutes after administration of the formulation to the ocular tissue.

In some embodiments, the particles, compositions, and/or formulations described herein can be administered topically to an eye of a subject in various forms of doses. For example, the particles, compositions, and/or formulations described herein may be administered in a single unit dose or repeatedly administered in a plurality of single unit doses. A unit dose is a discrete amount of the particles, compositions, and/or formulations described herein comprising a predetermined amount of a pharmaceutical agent. In some embodiments, fewer numbers of doses (e.g., ½, ⅓, or ¼ the number doses) are required using the particles described herein having a mucus-penetrating coating compared to particles that do not have such a coating.

The exact amount of the particles, compositions, and/or formulations described herein required to achieve a therapeutically or prophylactically effective amount will vary from subject to subject, depending, for example, on species, age, and general condition of a subject, severity of the side effects or disorder, identity of the particular compound, mode of administration, and the like. The particles, compositions, and/or formulations described herein can be delivered using repeated administrations where there is a period of time between consecutive doses. Repeated administration may be advantageous because it may allow the eye to be exposed to a therapeutically or prophylactically effective amount of a pharmaceutical agent for a period of time that is sufficiently long for the ocular condition to be treated, prevented, or managed. In certain embodiments, the period of time between consecutive doses is less than or equal to about 1 hour, less than or equal to about 2 hours, less than or equal to about 3 hours, less than or equal to about 4 hours, less than or equal to about 6 hours, less than or equal to about 12 hours, less than or equal to about 36 hours, or less than or equal to about 48 hours. In certain embodiments, the period of time between consecutive doses is at least about 1 hour, at least about 2 hours, at least about 3 hours, at least about 4 hours, at least about 6 hours, at least about 12 hours, at least about 36 hours, or at least about 48 hours. Combinations of the above-referenced ranges are also possible (e.g., a period of time between consecutive doses of greater than or equal to about 3 hours and less than or equal to about 12 hours). Other ranges are also possible.

Delivery of the particles, compositions, and/or formulations described herein to an ocular tissue may result in ophthalmically efficacious drug levels in the ocular tissue for an extended period of time after administration (e.g., topical administration or administration by direct injection). An ophthalmically efficacious level of a drug refers to an amount sufficient to elicit the desired biological response of an ocular tissue, i.e., treating an ocular disease. As will be appreciated by those skilled in this art, the ophthalmically efficacious level of a drug may vary depending on such factors as the desired biological endpoint, the pharmacokinetics of the drug, the ocular disease being treated, the mode of administration, and the age and health of the subject. In certain embodiments, the ophthalmically efficacious level of a drug is an amount of the drug, alone or in combination with other therapies, which provides a therapeutic benefit in the treatment of the ocular condition. The ophthalmically efficacious level of a drug can encompass a level that improves overall therapy, reduces or avoids symptoms or causes of the ocular condition, or enhances the therapeutic efficacy of another therapeutic agent.

In some embodiments, an ophthalmically efficacious drug level may be gauged, at least in part, by the maximum concentration ($C_{max}$) of the pharmaceutical agent in the ocular tissue after administration. In some cases, delivery of the particles, compositions, and/or formulations comprising a pharmaceutical agent as described herein to an ocular tissue may result in a higher $C_{max}$ of the pharmaceutical agent in the ocular tissue after administration, compared to marketed particles, compositions, and formulations at similar doses. In certain embodiments, the $C_{max}$ obtained from an administration of the particles, compositions, and/or formulations described herein is at least about 3%, at least about 10%, at least about 30%, at least about 100%, at least about 200%, at least about 300%, at least about 400%, at least about 500%, at least about 1000%, or at least about 3000%, higher than the $C_{max}$ obtained from an administration of the marketed particles, compositions, and/or formulations. In certain embodiments, the $C_{max}$ obtained from an administration of the particles, compositions, and/or formulations described herein is less than or equal to about 3000%, less than or equal to about 1000%, less than or equal to about 500%, less than or equal to about 400%, less than or equal to about 300%, less than or equal to about 200%, less than or equal to about 100%, less than or equal to about 30%, less than or equal to about 10%, or less than or equal to about 3%, higher than the $C_{max}$ obtained from an administration of the marketed particles, compositions, and/or formulations. Combinations of the above-referenced ranges are also possible (e.g., an increase in $C_{max}$ at least about 30% and less than or equal to about 500%). Other ranges are also possible.

In some embodiments, the ophthalmically efficacious drug levels are gauged, at least in part, by minimally efficacious concentrations of the drug, e.g., $IC_{50}$ or $IC_{90}$, as known in the art.

In certain embodiments in which ophthalmically efficacious drug levels (or $C_{max}$, $IC_{50}$, or $IC_{90}$) are present in the ocular tissue for an extended period of time after administration, the extended period of time after administration can range from hours to days. In certain embodiments, the extended period of time after administration is at least 1 hour, at least 2 hours, at least 4 hours, at least 6 hours, at least 9 hours, at least 12 hours, at least 1 day, at least 2 days, at least 3 days, at least 4 days, at least 5 days, at least 6 days, or at least 1 week. In certain embodiments, the extended period of time after administration is less than or equal to 1 week, less than or equal to 6 days, less than or equal to 5 days, less than or equal to 4 days, less than or equal to 3 days, less than or equal to 2 days, less than or equal to 1 day, less than or equal to 12 hours, less than or equal to 9 hours, less than or equal to 6 hours, less than or equal to 4 hours, less than or equal to 2 hours, less than or equal to 1 hour. Combinations of the above-referenced ranges are also possible (e.g., an extended period of time of at least about 4 hours and less than or equal to about 1 week). Other ranges are also possible.

In certain embodiments, the particles, compositions, and/or formulations described herein may be at dosage levels sufficient to deliver an effective amount of a pharmaceutical agent to an eye of a subject to obtain a desired therapeutic or prophylactic effect. In certain embodiments, an effective amount of a pharmaceutical agent that is delivered to an appropriate eye tissue is at least about $10^{-3}$ ng/g, at least about $10^{-2}$ ng/g, at least about $10^{-1}$ ng/g, at least about 1 ng/g, at least about $10^1$ ng/g, at least about $10^2$ ng/g, at least about $10^3$ ng/g, at least about $10^4$ ng/g, at least about $10^5$ ng/g, or at least about $10^6$ ng/g of tissue weight. In certain embodiments, an effective amount of a pharmaceutical agent that is delivered to the eye is less than or equal to about $10^6$ ng/g, less than or equal to about $10^5$ ng/g, less than or equal to about $10^4$ ng/g, less than or equal to about $10^3$ ng/g, less than or equal to about $10^2$ ng/g, less than or equal to about $10^1$ ng/g, less than or equal to about 1 ng/g, less than or equal to about $10^{-1}$ ng/g, less than or equal to about $10^{-2}$ ng/g, or less than or equal to about $10^{-3}$ ng/g of tissue weight. Combinations of the above-referenced ranges are also possible (e.g., an effective amount of a pharmaceutical agent of at least about $10^{-2}$ ng/g and less than or equal to about $10^3$ ng/g of tissue weight). Other ranges are also possible. In certain embodiments, the particles, compositions, and/or formulations described herein may be at dosage levels sufficient to deliver an effective amount of a pharmaceutical agent to the back of an eye of a subject to obtain a desired therapeutic or prophylactic effect.

It will be appreciated that dose ranges as described herein provide guidance for the administration of provided particles, compositions, and/or formulations to an adult. The amount to be administered to, for example, a child or an adolescent can be determined by a medical practitioner or person skilled in the art and can be lower or the same as that administered to an adult.

The particles, compositions, and/or formulations described herein may be topically administered by any method, for example, as by drops, powders, ointments, or creams. Other topical administration approaches or forms are also possible.

In certain embodiments, the compositions and/or formulations described herein are packaged as a ready to use shelf stable suspension. Eye drop formulations are traditionally liquid formulations (solutions or suspensions) which can be packaged in dropper bottles (which dispense a standard drop volume of liquid) or in individual use droppers (typically used for preservative free drops; used once and disposed). These formulations are ready to use and can be self-administered. In some cases the bottle should be shaken before use to ensure homogeneity of the formulation, but no other preparation may be necessary. This may be the simplest and most convenient method of ocular delivery. The compositions and/or formulations described herein can be packaged in the same way as traditional eye drop formulations. They can be stored in suspension and may retain the characteristics which allow the particles to avoid adhesion to mucus.

Methods of Preparing Particles and Pharmaceutical Compositions Thereof

In one aspect, the present invention provides methods of preparing the particles of the invention. Methods of preparing similar particles have been described in U.S. patent application Ser. No. 13/886,493, filed May 3, 2013, and U.S. Ser. No. 13/886,602, filed May 3, 2013, and U.S. Ser. No. 13/886,658, filed May 3, 2013, each of which is incorporated by reference herein in its entirety.

The core of the particle may be formed by any suitable method. Suitable methods may include, for example, top-down techniques, i.e. techniques based on size reduction of relatively large particles into smaller particles (e.g., milling or homogenization) or bottom-up techniques, i.e. techniques based on the growth of particles from smaller particles or individual molecules (e.g., precipitation or spray-freezing into liquid).

In some embodiments, the core of the particle may be coated with a coating. For example, the core may be provided or formed in a first step, and then the core may be coated in a second step. In some embodiments, the core particle is formed and coated substantially simultaneously (e.g., in a single step).

In some embodiments, the particle is formed by a method that involves using a formulation process, a milling process, and/or a dilution process. In certain embodiments, a method of forming the particle includes a milling process, optionally with a formulation process and/or a dilution process. A formulation process may be used to form a suspension comprising a core material, one or more surface-altering agents, and other components, such as solvents, tonicity agents, chelating agents, salts, and/or buffers (e.g., a sodium citrate and citric acid buffer), each of which is as described herein. The formulation process may be performed using a formulation vessel. The core material and other components may be added into the formulation vessel at the same time or different times. A mixture of the core material and/or one or more other components may be stirred and/or shaken, or otherwise agitated in the vessel to facilitate suspending the components to form the suspension. The temperature and/or pressure of the core material, other components, and/or mixture may also be individually increased or decreased to facilitate the suspending process. In some embodiments, the core material and other components are processed as described herein in the formulation vessel under an inert atmosphere (e.g., nitrogen or argon) and/or protected from light. The suspension obtained from the formulation vessel may be subsequently subject to a milling process which may be followed by a dilution process.

In some embodiments involving a core comprising a solid material (e.g., crystalline compound of the invention) a milling process may be used to reduce the size of the solid material to form particles in a micrometer to nanometer size range. The milling process may be performed using a mill or other suitable apparatus. Dry and wet milling processes such as jet milling, cryo-milling, ball milling, media milling, sonication, and homogenization are known and can be used in methods of the invention. For example, in a wet milling process, a suspension of the solid material to be used to form the core ("core material") is agitated with or without excipients to reduce the size of the core to be formed. Dry milling is a process wherein the core material is mixed with milling media with or without excipients to reduce the size of the core to be formed. In a cryo-milling process, a suspension of the core material is mixed with milling media with or without excipients under cooled temperatures. In certain embodiments, when surface-altering agents are employed, a suspension comprising coated particles is obtained from the milling process. In certain embodiments, when surface-altering agents are not employed, a suspension comprising uncoated particles is obtained from the milling process.

The suspension of particles (coated or uncoated) of the invention obtained from a milling process may be further processed with a dilution process. A dilution process may be used to achieve a target dosing concentration by diluting a suspension of particles that were formed during a milling process, with or without surface-altering agents and/or other components. In certain embodiments, when a suspension of coated particles that comprise a first surface-altering agent is processed with a dilution process involving a second surface-altering agent, a suspension of coated particles that comprise the second surface-altering agent is obtained from the dilution process. In certain embodiments, when a suspension of coated particles that comprise a surface-altering agent is processed with a dilution process involving no or the same surface-altering agent, a suspension of coated particles that comprise the surface-altering agent is obtained from the dilution process. In certain embodiments, when a suspension of uncoated particles is processed with a dilution process involving a surface-altering agent, a suspension of coated particles comprising the surface-altering agent is obtained from the dilution process. The dilution process may be performed using a product vessel or any other suitable apparatus. In certain embodiments, the suspension of the particles is diluted, i.e., mixed or otherwise processed with a diluent, in the product vessel. The diluent may contain solvents, surface-altering agents, tonicity agents, chelating agents, salts, anti-microbial agents or a combination thereof, as described herein. The suspension and the diluent may be added into the product vessel at the same time or different times. In certain embodiments when the suspension is obtained from a milling process involving milling media, the milling media may be separated from the suspension before the suspension is added into the product vessel. The suspension, the diluent, or the mixture of the suspension and the diluent may be stirred and/or shaken, or otherwise agitated, to form the particles and/or pharmaceutical compositions of the invention. The temperature and/or pressure of the suspension, the diluent, or the mixture may also be individually increased or decreased to form the coated particles. In some embodiments, the suspension and the diluent are processed in the product vessel under an inert atmosphere (e.g., nitrogen or argon) and/or protected from light.

In some embodiments, the core and/or coated particles may be produced by milling of a solid material (e.g., a pharmaceutical agent) in the presence of one or more surface-altering agents. Small particles of a solid material may require the presence of one or more surface-altering agents, which may function as a stabilizer in some embodiments, in order to stabilize a suspension of particles without agglomeration or aggregation in a liquid solution. In some such embodiments, the stabilizer may act as a surface-altering agent, forming the coated particles of the invention.

As described herein, a method of forming the core and/or the coated particles, may involve choosing a surface-altering agent that is suitable for both milling and forming a coating on the core, wherein the coating renders the particle mucus penetrating.

In a wet milling process, milling may be performed in a dispersion (e.g., an aqueous dispersion) containing at least one surface-altering agent, a grinding medium, a solid to be milled (e.g., a solid pharmaceutical agent), and a solvent. The solvent described herein includes a single solvent or a mixture of different solvents. Any suitable amount of a surface-altering agent can be included in the solvent. In some embodiments, the surface-altering agent may be present in the solvent in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the surface-altering agent may be present in the solvent in an amount of about 100% (e.g., in an instance where the surface-altering agent is the solvent). In other embodiments, the surface-altering agent may be present in the solvent in an amount of less than about 100% less than about 60%, less than about 30%, less than about 10%, less than about 3%, or less than about 1% of the solvent. Combinations of the above-referenced ranges are also possible (e.g., an amount of less than about 3% and at least about 1% of the solvent). Other ranges are also possible. In certain embodiments, the surface-altering agent is present in the solvent in an amount of about 0.01-2%, about 0.2-20%, about 0.1%, about 0.4%, about 1%, about 2%, about 5%, or about 10% of the solvent.

The particular range chosen may influence factors that may affect the ability of the particles to penetrate mucus such as the stability of the coating of the surface-altering agent on the particle surface, the average thickness of the coating of the surface-altering agent on the particles, the orientation of the surface-altering agent on the particles, the density of the surface altering agent on the particles, the ratio of the surface-altering agent to pharmaceutical agent, the concentration of the pharmaceutical agent, the size, dispersibility, and polydispersity of the particles formed, and the morphology of the particles formed.

The pharmaceutical agent may be present in the solvent in any suitable amount. In some embodiments, the pharmaceutical agent is present in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the pharmaceutical agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 30% and at least about 1% of the solvent).

The ratio of surface-altering agent to pharmaceutical agent in a solvent may also vary. In some embodiments, the ratio of the surface-altering agent to pharmaceutical agent is at least about 0.001:1 (weight ratio, molar ratio, or w:v), at least about 0.01:1, at least about 0.01:1, at least about 1:1, at least about 2:1, at least about 3:1, at least about 5:1, at least about 10:1, at least about 30:1, at least about 100:1, or at least about 1000:1. In some embodiments, the ratio of the surface-altering agent to pharmaceutical agent is less than 1000:1 (weight ratio, molar ratio, or vv:v), less than about 100:1, less than about 30:1, less than about 10:1, less than about 5:1, less than about 3:1, less than about 2:1, less than about 1:1, or less than about 0.1:1. Combinations of the above-referenced ranges are possible (e.g., a ratio of at least about 5:1 and less than about 30:1). Other ranges are also possible.

The surface-altering agents described herein that may act as stabilizers may be, for example, polymers or surfactants. Examples of polymers include those suitable for use in the coating of the particles of the invention, such as polyvinyl alcohol) and Pluronics®. Examples of surfactants include L-α-phosphatidylcholine (PC), 1,2-dipalmitoylphosphatidycholine (DPPC), oleic acid, sorbitan trioleate, sorbitan mono-oleate, sorbitan monolaurate, polyoxylene sorbitan fatty acid esters (Tweens), polysorbates (e.g., polyoxyethylene sorbitan monooleate) (e.g., Tween 80®), polyoxyethylene sorbitan monostearate (e.g., Tween 60®), polyoxyethylene sorbitan monopalmitate (e.g., Tween 40®), polyoxyethylene sorbitan monolaurate (e.g., Tween 20®), natural lecithin, oleyl polyoxyethylene ether, stearyl polyoxyethylene ether, lauryl polyoxyethylene ether, polyoxyethylene alkyl ethers, block copolymers of oxyethylene and oxypropylene, polyoxyethylene sterates, polyoxyethylene castor oil and their derivatives, Vitamin-PEG and their derivatives, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, cetyl pyridinium chloride, benzalkonium chloride, olive oil, glyceryl monolaurate, corn oil, cotton seed oil, and sunflower seed oil. Derivatives of the above-noted compounds are also possible. Combinations of the above-noted compounds and others described herein may also be used as surface-altering agents in the inventive particles. As described herein, in some embodiments a surface-altering agent may act as a stabilizer, a surfactant, and/or an emulsifier. In some embodiments, the surface altering agent may aid particle transport in mucus.

A stabilizer used for milling may form the coating of a particle of the invention, wherein the coating renders the particle mucus penetrating. The stabilizer may also be exchanged with one or more other surface-altering agents after the particle has been formed. For example, a first stabilizer/surface-altering agent may be used during a milling process and may form a first coating of the particle of the invention, and all or part of the first stabilizer/surface-altering agent may then be exchanged with a second stabilizer/surface-altering agent to form a second coating of the particle. In some embodiments, the second stabilizer/surface-altering agent may render the particle mucus penetrating more than the first stabilizer/surface-altering agent. In some embodiments, a particle comprising multiple coatings that include multiple surface-altering agents is formed by a method of the invention.

Any suitable grinding medium can be used for milling. In some embodiments, a ceramic and/or polymeric material and/or a metal can be used. Examples of suitable materials include zirconium oxide, silicon carbide, silicon oxide, silicon nitride, zirconium silicate, yttrium oxide, glass, alumina, alpha-alumina, aluminum oxide, polystyrene, poly (methyl methacrylate), titanium, and steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than about 5 mm, less than about 2 mm, less than about 1 mm, less than about 0.8, less than about 0.5 mm, or less than about 0.2 mm. Combinations of the above-referenced ranges are also possible (e.g., an average diameter of at least about 0.5 millimeters and less than about 1 mm). Other ranges are also possible.

A solvent may be used for milling. The choice of the solvent suitable for milling may depend on factors like the solid material (e.g., a solid pharmaceutical agent) being milled, the particular type of stabilizer/surface-altering agent (e.g., one that may render the particle mucus penetrating), and the grinding material. The solvent suitable for milling may be one of those solvents that do not substantially dissolve the solid material or the grinding material, but dissolve the stabilizer/surface-altering agent to a suitable degree. Examples of the solvents suitable for milling include water, aqueous solutions, buffered solutions, alcohols (e.g., ethanol, methanol, and butanol), and mixtures thereof, each of which may optionally include other components, such as one or more pharmaceutical excipients, polymers, pharmaceutical agents, salts, preservative agents, viscosity modifiers, tonicity modifiers, taste masking agents, antioxidants, and pH modifiers. In some embodiments, the solvent suitable for milling is an organic solvent.

A pharmaceutical agent described herein (e.g., a compound of the invention) may have a suitable solubility in a solvent suitable for milling, such as a solubility in one or more ranges described herein for aqueous solubility or for solubility in a coating solution. A pharmaceutical agent having a relatively low solubility in a solvent (e.g., water or a coating solution) may be preferred because a milling process described herein typically requires a material (e.g., a pharmaceutical agent) to be in a solid form in order for the material to be milled. In some cases, if the material to be milled has a relatively high soluble in a solvent (e.g., water or a coating solution) used in the milling process, milling may not be conducted because significant or complete dissolution of the material to be milled in the solvent will occur. In certain embodiments, a relatively high solubility of a solid material (e.g., a solid pharmaceutical agent) in a solvent is at least about 1 mg/mL, at least about 3 mg/mL, or at least about 10 mg/mL at 25° C. In certain embodiments, a relatively low solubility of a substance (e.g., a pharmaceutical agent) in a solvent is less than about 1 mg/mL, less than about 0.3 mg/mL, less than about 0.1 mg/mL, less than about 0.03 mg/mL, less than about 0.01 mg/mL, less than about 0.003 mg/mL, or less than about 0.001 mg/mL at 25° C. The solid material may have these or other ranges of solubilities at any point throughout the pH range (e.g., from pH 1 to pH 14). A pharmaceutical agent that has a relatively high solubility in the solvent used in the milling process may be modified to form a prodrug of the pharmaceutical agent. The prodrug may have a relatively low solubility and thus may be suitable for the milling process. Upon or after the particles or pharmaceutical compositions comprising the prodrug are administered to a subject, the prodrug may be converted and form or, in other words, "release," the pharmaceutical agent.

In other embodiments, the core and/or coated particles may be formed by an emulsification process or technique (emulsification) known in the art. See, e.g., U.S. patent application Ser. No. 13/886,602. Generally, emulsification techniques may involve dissolving or dispersing a material to be used as the core in a solvent; this solution or dispersion is then emulsified in a second immiscible solvent, thereby forming a plurality of particles comprising the material. Suitable emulsification techniques may include formation of oil-in-water emulsions, water-in-oil emulsions, water-oil-water emulsions, oil-water-oil emulsions, solid-in-oil-in-water emulsions, and solid-in-water-in-oil emulsions, etc., with or without subsequent solvent removal, for example, by evaporation or extraction. Emulsification techniques are versatile and may be useful for preparing core particles comprising pharmaceutical agents having a relatively low aqueous solubility as well as pharmaceutical agents having a relatively high aqueous solubility.

In some embodiments, the core particles described herein may be produced by emulsification in the presence of one or more surface-altering agents. In some such embodiments, the stabilizer may act as a surface-altering agent, forming a coating on the particle (i.e., the emulsification and coating steps may be performed substantially simultaneously).

In some embodiments, a method of forming a core particle by emulsification involves choosing a stabilizer that is suitable for both emulsification and for forming a coating on the particle and rendering the particle mucus penetrating. For example, as described in more detail below, it has been demonstrated that 200-500 nm nanoparticles of a model polymer PLA produced by emulsification in the presence of certain PVA polymers resulted in particles that can penetrate physiological mucus samples at the same rate as well-established PEGylated polymeric MPP. Interestingly, it was observed that only a subset of PVA polymers tested fit the criteria of being suitable for both emulsification and for forming a coating on the particle that renders the particle mucus penetrating, as described in more detail below.

In other embodiments, the particles are first formed using an emulsification technique, following by coating of the particles with a surface-altering agent.

Any suitable solvent and solvent combinations can be used for emulsification. Some examples of solvents which can serve as oil phase are organic solvents such chloroform, dichloromethane, ethyl acetate, ethyl ether, petroleum ether (hexane, heptane), and oils such as peanut oil, cottonseed oil; safflower oil; sesame oil; olive oil; corn oil soybean oil, and silicone oil. Some examples of solvents which can serve as water phase are water and aqueous buffers. Other solvents are also possible.

The core and/or coated particles may also be formed by a precipitation process or technique (precipitation). Precipitation techniques (e.g., microprecipitation, nanoprecipitation, crystallization, and controlled crystallization) may involve forming a first solution comprising the material that is to form the core (e.g., a pharmaceutical agent) and a first solvent, wherein the material has a relatively high solubility in the first solvent. The first solution may be added to a second solution comprising a second solvent that is an anti-solvent, in which the material has a relatively low solubility, thereby forming a plurality of particles comprising the material. In certain embodiments, the second solvent is miscible with the first solvent. In some embodiments, one or more surface-altering agents and/or surfactants may be present in the first and/or second solutions. A coating may be formed during the process of precipitating the core (e.g., the coating of the particles may be formed substantially simultaneously when the precipitation is performed) to form the coated particles of the invention.

In other embodiments, the core of the particles of the invention is first formed using a precipitation technique, following by coating of the core with a surface-altering agent to form the coated particles of the invention.

In some embodiments, a precipitation technique may be used to form polymeric core of the particles of the invention with or without a pharmaceutical agent. Generally, a precipitation technique involves dissolving a polymer that is to form the core in a first solvent, in the presence or absence of a pharmaceutical agent, to form a solution. The solution is then added to a second solvent that is an anti-solvent and is miscible with the first solvent, in the presence or absence of one or more excipients, to form the core of the particles. In some embodiments, precipitation is useful for preparing a polymeric core comprising one or more pharmaceutical agents having a relatively low aqueous solubility.

The precipitation described herein involves the use of a first solvent. Examples of suitable first solvents for precipitation include organic solvents (e.g., acetone, acetonitrile, dimethylformamide, dimethylsulfoxide, N-methyl-2-pyrrolidone, 2-pyrrolidone, and tetrahydrofuran) and nonorganic solvents.

The precipitation described herein also involves the use of a second solvent. In certain embodiments, the second solvent suitable for precipitation is an anti-solvent. Examples of second solvents suitable for precipitation include the solvents described herein that may be used for milling. In some embodiments, the second solvents suitable for precipitation is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

Surface-altering agents for the emulsification and precipitation described herein may be polymers or surfactants, including the surface-altering agents described herein that may be used for milling.

Examples of polymers suitable for forming all or part of the core of the particles of the invention by the emulsification or precipitation may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, polyarylates, polypeptides, polynucleotides, and polysaccharides. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly (D, L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone, bovine serum albumin, human serum albumin, collagen, DNA, RNA, carboxymethyl cellulose, chitosan, dextran.

Polymers suitable for forming all or portions of a core and/or surface-altering agent may also include a poly(ethylene glycol)-vitamin E conjugate (hereinafter, "PEG-VitE conjugate"). The particles, compositions, and/or formulations including a PEG-VitE conjugate, and methods of making and using the particles, compositions, and/or formulations, are provided in more detail in international PCT application publication WO2012/061703, which is incorporated herein by reference in its entirety for all purposes. In some cases, the molecular weight of the PEG portion of the PEG-VitE conjugate is greater than about 2 kDa. The molecular weight of the PEG portion of the PEG-VitE conjugate may be selected so as to aid in the formation and/or transport of the particle across a mucosal barrier as described herein. In some embodiments, use of a PEG-VitE conjugate with a PEG portion having a molecular weight greater than about 2 kDa may allow for greater penetration of the particles through a mucosal barrier as compared to use of a PEG-VitE conjugate with a PEG portion having a molecular weight less than about 2 kDa. Additionally, in certain embodiments a higher molecular weight PEG portion may facilitate drug encapsulation. The combined ability to act as a surfactant and to reduce mucoadhesion provides important benefits as compared to other commonly used surfactants for drug encapsulation. In some cases, the molecular weight of the PEG portion of the PEG-VitE conjugate is between about 2 kDa and about 8 kDa, or between about 3 kDa and about 7 kDa, or between about 4 kDa and about 6 kDa, or between about 4.5 kDa and about 6.5 kDa, or about 5 kDa.

In some embodiments, a precipitation technique may be used to form particles comprised predominantly of a pharmaceutical agent (e.g., a compound of the invention). In certain embodiments, the particles of the invention formed by the precipitation technique comprise predominantly of a pharmaceutical agent that is a nanocrystal. Generally, such a precipitation technique involves dissolving the pharmaceutical agent that is to form the core in a first solvent, which is then added to a second solvent that is an anti-solvent, in which the pharmaceutical agent has a relatively low solubility, in the presence or absence of one or more pharmaceutical excipients, to form the core or uncoated particle. In some embodiments, this technique may be useful for preparing, for example, particles of pharmaceutical agents that are slightly soluble (1-10 mg/mL), very slightly soluble (0.1-1 mg/mL) or practically insoluble (<0.1 mg/mL) in aqueous solutions (e.g., agents having a relatively low aqueous solubility).

A pharmaceutical agent described herein (e.g., a compound of the invention) may have a suitable solubility in the first and second solvents suitable for precipitation, such as a solubility in one or more ranges described herein for aqueous solubility or for solubility in a coating solution. A pharmaceutical agent having a relatively high solubility in the first solvent (e.g., an organic solvent) may be preferred. In certain embodiments, the pharmaceutical agent substantially or completely dissolves in the first solvent. A pharmaceutical agent having a relatively low solubility in the second solvent (e.g., water or a coating solution) may also be preferred. In certain embodiments, the solubility of the pharmaceutical agent in a mixture of the first and second solvents is lower than the solubility of the pharmaceutical agent in the first solvent. The relatively high solubility and relatively low solubility are as described herein. A pharmaceutical agent that has a relatively high solubility in the second solvent may be modified to form a prodrug of the pharmaceutical agent. The prodrug may have a relatively low solubility in the second solvent and still have a relatively high solubility in the first solvent and thus may be suitable for precipitation. Upon or after the particles or pharmaceutical compositions comprising the prodrug are administered to a subject, the prodrug may be converted and form or, in other words, "release," the pharmaceutical agent.

Precipitation by formation of a salt or complex may also be used to form particles comprised predominantly of a salt or complex of a pharmaceutical agent. In certain embodiments, the particles formed by this specific precipitation technique comprise predominantly of a pharmaceutical agent that is a nanocrystal. Generally, precipitation by formation of a salt or complex involves dissolving a pharmaceutical agent that is to form the core in a solvent, in the presence or absence of one or more excipients, followed by the addition of a counterion or a complexing agent, which forms a salt or a complex with the pharmaceutical agent to form the core. A variety of counter-ions can be used to form salt complexes, including metals (e.g., alkali metals, alkali earth metals and transition metals). Non-limiting examples of cationic counter-ions include zinc, calcium, aluminum, zinc, barium, and magnesium. Non-limiting examples of anionic counter-ions include phosphate, carbonate, and fatty acids. Counter-ions may be, for example, monovalent, divalent, or trivalent. Other counter-ions are known in the art and can be used in the embodiments described herein. Other ionic and non-ionic complexing agents are also possible. This technique may be useful for preparing particles comprising pharmaceutical agents that have a relatively high solubility in the second solvent (e.g., water or a coating solution). In certain embodiments, the pharmaceutical agent has a relatively high solubility in the second solvent, and the salt or complex of the pharmaceutical agent has a relatively low solubility in the second solvent. The relatively high solubility and relatively low solubility are as described herein. In some embodiments, pharmaceutical agents having one or more charged or ionizable groups interact with a counterion (e.g., a cation or an anion) to form a salt or complex.

A variety of different acids may be used in a precipitation process involving formation of a salt or complex. Examples of acids suitable for precipitation include deconoic acid, hexanoic acid, mucic acid, octanoic acid. In other embodiments, a suitable acid may include acetic acid, adipic acid, L-ascorbic acid, L-aspartic acid, capric acid (decanoic acid), carbonic acid, citric acid, fumaric acid, galactaric acid, D-glucoheptonic acid, D-gluconic acid, D-glucuronic acid, glutamic acid, glutaric acid, glycerophosphoric acid, glycolic acid, hippuric acid, hydrochloric acid, DL-lactic acid, lauric acid, maleic acid, (−)-L-malic acid, palmitic acid, phosphoric acid, sebacic acid, stearic acid, succinic acid, sulfuric acid, (+)-L-tartaric acid, or thiocyanic acid. In other embodiments, a suitable acid may include alginic acid, benzenesulfonic acid, benzoic acid, (+)-camphoric acid, caprylic acid (octanoic acid), cyclamic acid, dodecylsulfuric acid, ethane-1,2-disulfonic acid, ethanesulfonic acid, ethanesulfonic acid, 2-hydroxy-, gentisic acid, glutaric acid, 2-oxo-, isobutyric acid, lactobionic acid, malonic acid, methanesulfonic acid, naphthalene-1,5-disulfonic acid, naphthalene-2-sulfonic acid, 2-naphthoic acid, 1-hydroxy-, nicotinic acid, oleic acid, orotic acid, oxalic acid, pamoic acid, (embonic acid), propionic acid, (−)-L-pyroglutamic acid, or p-toluenesulfonic acid. In yet other embodiments, a suitable acid may include acetic acid, 2,2-dichloro-, benzoic acid, 4-acetamido-, (+)-camphor-10-sulfonic acid, caproic acid (hexanoic acid), cinnamic acid, formic acid, hydrobromic acid, DL-mandelic acid, nitric acid, salicylic acid, salicylic acid, 4-amino-, and undecylenic acid (undec-10-enoic acid). Mixtures of two or more acids can also be used.

A variety of different bases may also be used in a precipitation process involving formation of a salt or complex. Examples of bases suitable for precipitation include ammonia, L-arginine, calcium hydroxide, choline, glucamine, N-methyl-, lysine, magnesium hydroxide, potassium hydroxide, or sodium hydroxide. In other embodiments, a suitable base may include benethamine, benzathine, betaine, deanol, diethylamine, ethanol, 2-(diethylamino)-, hydrabamine, morpholine, 4-(2-hydroxyethyl)-, pyrrolidine, 1-(2-hydroxyethyl)-, or tromethamine. In other embodiments, a suitable base may include diethanolamine (2,2'-iminobis(ethanol)), ethanolamine (2-aminoethanol), ethylenediamine, IH-imidazole, piperazine, triethanolamine (2,2', 2"-nitrilotris(ethanol)), and zinc hydroxide. Mixtures of two or more bases can also be used.

Examples of solvents suitable for precipitation involving formation of a salt or complex include the solvents described herein that may be used for milling. In some embodiments, the first or second solvent suitable for precipitation involving formation of a salt or complex is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

The first or second solvent suitable for precipitation may include one or more surface-altering agents as described herein, and therefore, a coating comprising the one or more surface-altering agents may be formed around the core to provide the coated particles of the invention as they precipitate out of solution. The one or more surface-altering agents may be present in the first or second solvent at any suitable concentration, such as a concentration of at least about 0.001% (w/v), at least about 0.003% (w/v), at least about 0.01% (w/v), at least about 0.03% (w/v), at least about 0.1% (w/v), at least about 0.3% (w/v), at least about 1% (w/v), or at least about 3% (w/v). In some embodiments, the one or more surface-altering agents are present in the first or second solvent at a concentration of less than about 3% (w/v), less than about 1% (w/v), less than about 0.3% (w/v), less than about 0.1% (w/v), less than about 0.05% (w/v), less than about 0.01% (w/v), or less than about 0.003% (w/v). Combinations of the above-referenced ranges are also possible (e.g., a concentration of at least about 0.01 (w/v) and less than about 1% (w/v), Other ranges are also possible. In certain embodiments, the one or more surface-altering agents are present in the first solvent but absent in the second solvent. In certain embodiments, the one or more surface-altering agents are present in the second solvent but absent in the first solvent. In certain embodiments, the one or more surface-altering agents are present in both the first and second solvents.

In the precipitation process, the salt may have a lower aqueous solubility (or solubility in the solvent containing the salt) than the pharmaceutical agent in the non-salt form. The aqueous solubility (or solubility in the solvent) of the salt may be, for example, less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, or less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the salt may have an aqueous solubility (or solubility in the solvent) of at least about 1 µg/mL, at least about 10 pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility (or solubility in the solvent) of at least about 0.001 mg/mL and less than or equal to about 1 mg/mL). Other ranges are also possible. The salt may have these or other ranges of aqueous solubilities at any point throughout the pH range (e.g., from pH 1 to pH 14).

Another exemplary method of forming the core and/or coated particle is a freeze-drying process or technique known in the art. See, e.g., U.S. patent application Ser. No. 13/886,602. In this technique, a pharmaceutical agent or salt thereof may be dissolved in an aqueous solution, optionally containing a surface-altering agent. A counter-ion may be added to the solution, and the solution may be immediately flash frozen and freeze dried. Dry powder can be reconstituted in a suitable solvent (e.g., an aqueous solution such as water) at a desired concentration.

A counter-ion may be added to a solvent for freeze-drying in any suitable range. In some cases, the ratio of counter-ion to pharmaceutical agent (e.g., salt) may be at least 0.1:1 (weight ratio or molar ratio), at least 1:1, at least 2:1, at least 3:1, at least 5:1, at least 10:1, at least 25:1, at least 50:1, or at least 100:1. In some cases, the ratio of counter-ion to pharmaceutical agent (e.g., salt) may be less than or equal to 100:1 (weight ratio or molar ratio), less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

If the surface-altering agent is present in the solvent prior to freeze drying, it may be present at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (wiv), less than or equal to about 0.5% (w/v), less than or equal to about 0.1% (wiv), less than or equal to about 0.05% (w/v), less than or equal to about 0.01% (w/v), or less than or equal to about 0.005% (w/v). Combinations of the above-referenced ranges are also possible (e.g., a concentration of at least about 0.01% (w/v) and less than or equal to about 1% (w/v). Other ranges are also possible.

The concentration of surface-altering agent present in the solvent may be above or below the critical micelle concentration (CMC) of the surface-altering agent, depending on the particular surface-altering agent used. In other embodiments, stable particles can be formed by adding excess counter-ion to a solution containing a pharmaceutical agent. The precipitate can then be washed by various methods such as centrifugation. The resultant slurry may be sonicated. One or more surface-altering agents may be added to stabilize the resultant particles.

Other methods of forming core particles are also possible. For example, additional techniques of forming the core and/or coated particles include coacervation-phase separation, melt dispersion, interfacial deposition, in situ polymerization, self-assembly of macromolecules (e.g., formation of polyelectrolyte complexes or polyelectrolyte-surfactant complexes), spray-drying and spray-congealing, electrospray, air suspension coating, pan and spray coating, freeze-drying, air drying, vacuum drying, fluidized-bed drying, precipitation (e.g., nanoprecipitation, microprecipitation), critical fluid extraction, and lithographic approaches (e.g., soft lithography, step and flash imprint lithography, interference lithography, and photolithography). Combinations of the methods described herein are also possible. In some embodiments, a core of a pharmaceutical agent is first formed by precipitation, and then the size of the core is reduced by a milling process, optionally a coating is form on the core by the milling process.

Following the formation of the core of the particles including a pharmaceutical agent, the core may be optionally exposed to a solution comprising a (second) surface-altering agent that may associate with and/or coat the core. In embodiments in which the pharmaceutical agent already includes a coating of a first surface-altering agent, all or part of the first surface-altering agent may be exchanged with a second surface-altering agent. In some embodiments, the second surface-altering agent renders the particle mucus penetrating more than the first surface-altering agent does. In some embodiments, a particle having a coating including multiple surface-altering agents is formed (e.g., in a single layer or in multiple layers). In some embodiments, a particle having multiple coatings (e.g., each coating optionally comprising different surface-altering agents) may be formed. In some embodiments, the coating is in the form of a monolayer of a surface-altering agent. Other configurations are also possible.

In any of the methods described herein, a coating comprising a surface-altering agent may be formed on a core of the particles of the invention by incubating the core in a solution including the surface-altering agent for a period of at least about 1 minute, at least about 3 minutes, at least about 10 minutes, at least about 20 minutes, at least about 30 minutes, at least about 60 minutes, or more. In some cases, incubation may take place for a period of less than about 10 hours, less than about 3 hours, or less than about 60 minutes. Combinations of the above referenced ranges are also possible (e.g., an incubation period of less than 60 minutes and at least about 1 minute).

Methods of Treatment and Uses

A range of diseases may result when the body of a subject loses control over angiogenesis, i.e., new blood vessels grow abnormally (i.e., excessively or insufficiently) or grow as a result of a tumor. Excessive angiogenesis is often observed in subjects with diseases such as proliferative diseases (e.g., cancers, benign neoplasms, inflammatory diseases, autoimmune diseases) and ocular diseases, especially with cancer, diabetic retinopathy, macular degeneration, rheumatoid arthritis, and psoriasis. In these diseases, new blood vessels feed abnormal tissues and/or destroy normal tissues. Excessive angiogenesis may occur when there are abnormal amounts of angiogenic growth factors present, overwhelming the effects of natural angiogenesis inhibitors. Therefore, inhibiting new blood vessel growth may be useful to treat diseases associated with excessive angiogenesis. Insufficient angiogenesis is typically observed in subjects with a disease such as coronary artery disease, stroke, or chronic wounds. In these diseases, blood vessel growth is inadequate, and circulation is not properly restored, which may lead to tissue death.

VEGFs have been found to play a major role in angiogenesis, for example, by increasing the number of capillaries in a given network. In vitro studies have demonstrated that bovine capillary endothelial cells proliferated and showed signs of tube structures upon stimulation with VEGF. Upregulation of VEGF is a major component of the physiological response to exercise and its role in angiogenesis is suspected to be a possible treatment in vascular injuries. In vitro studies have showed that VEGFs are a potent stimulator of angiogenesis because, among other things, in the presence of this growth factor, plated endothelial cells will proliferate and migrate, eventually forming tube structures resembling capillaries. VEGFs may cause a massive signaling cascade in endothelial cells. Binding to VEGF receptor-2 starts a tyrosine kinase signaling cascade that stimulates the production of factors that variously stimulate vessel permeability, proliferation/survival, migration, and finally differentiation into mature blood vessels. Mechanically, VEGF is upregulated with muscle contractions as a result of increased blood flow to affected areas. The increased flow also causes a large increase in the mRNA production of VEGF receptors 1 and 2. The increase in receptor production indicates that muscle contractions could cause upregulation of the signaling cascade relating to angiogenesis.

In one aspect, the present invention provides methods of treating and/or preventing a disease associated with abnormal angiogenesis in a subject in need thereof. In certain embodiments, the disease being treated and/or prevented by the inventive methods is associated with excessive and/or pathological angiogenesis.

In another aspect, the present invention provides methods of treating and/or preventing a disease associated with aberrant signaling of a growth factor in a subject in need thereof. In certain embodiments, the disease is associated with excessive signaling of the growth factor. In certain embodiments, the disease being treated and/or prevented by the inventive methods is associated with aberrant signaling of VEGF. In certain embodiments, the disease is associated with excessive or aberrant signaling of VEGF-A, VEGF-B, VEGF-C, VEGF-D, VEGF-F, and/or placental growth factor (PGF).

In certain embodiments, the disease being treated and/or prevented by the inventive methods is a proliferative disease. All types of proliferative diseases described herein may be treated and/or prevented by the inventive methods. In certain embodiments, the disease being treated and/or prevented by the inventive methods is cancer. All types of cancer described herein may be treated and/or prevented by the inventive methods. In certain embodiments, the cancer is an ocular cancer. In certain embodiments, the ocular cancer is retinoblastoma, medulloepithelioma, uveal melanoma, ciliary body melanoma, or primary intraocular lymphoma. In certain embodiments, the disease being treated and/or prevented by the inventive methods is a benign neoplasm. All types of benign neoplasm described herein may be treated and/or prevented by the inventive methods. In certain embodiments, the benign neoplasm is an ocular benign neoplasm. In certain embodiments, the benign neoplasm is orbital dermoid cysts.

In certain embodiments, the disease being treated and/or prevented by the inventive methods is an inflammatory disease. All types of inflammatory diseases described herein may be treated and/or prevented by the inventive methods. In certain embodiments, the inflammatory disease is an ocular inflammatory disease. In certain embodiments, the ocular inflammatory disease is post-surgical inflammation. In certain embodiments, the disease being treated and/or prevented by the inventive methods is an autoimmune disease. All types of autoimmune diseases described herein may be treated and/or prevented by the inventive methods. In certain embodiments, the autoimmune disease is rheumatoid arthritis. In certain embodiments, the disease being treated and/or prevented by the inventive methods is diabetes. In certain embodiments, the disease is type 1 diabetes. In certain embodiments, the disease is type 2 diabetes. In certain embodiments, the disease is gestational diabetes.

The disease being treated and/or prevented by the inventive methods may be an ocular disease. In some embodiments, the ocular disease being treated and/or prevented by the inventive methods is an anterior ocular disease that occurs at the anterior portion or "front" of the eye of a subject. The anterior portion of the eye includes the cornea, iris, conjunctiva, tear film, corneal epithelium, anterior chamber, lens, ciliary body, ciliary zonule, posterior chamber, retina, macula, sclera, an optic nerve, choroid, and vitreous chamber. In certain embodiments, the anterior ocular disease being treated and/or prevented by the inventive methods is allergy, post-surgical inflammation, uveitis, an infection (e.g., a viral, bacterial, or fungal infection), aphakia, pseudophakia, astigmatism, blepharospasm, cataract, a conjunctival disease, conjunctivitis, a corneal disease, corneal oedema, meibomiam gland disease, corneal transplant surgery, corneal ulcer, dry eye (e.g., dry eye syndrome), an eyelid disease, a lacrimal apparatus disease, lacrimal duct obstruction, laser induced exudation, myopia, presbyopia, pterygium, pupil disorders, corneal neovascularization, a refractive disorder, strabismus, or glaucoma. In some embodiments, the ocular disease being treated and/or prevented by the inventive methods is a posterior ocular disease that occurs at the posterior portion or "back" of the eye. The posterior portion of the eye includes the choroid, sclera, vitreous humor, vitreous chamber, retina, macula, optic nerve, and blood vessels and nerves which vascularize or innervate a posterior ocular region or site. In certain embodiments, the posterior ocular disease being treated and/or prevented by the inventive methods is intraocular melanoma, acute macular neuroretinopathy, an exudative eye disease, Behcet's disease, exudative retinopathy, macular oedema, retinopathy of prematurity, an epiretmal membrane disorder, choroidal neovascularization, uveitis, diabetic uveitis, histoplasmosis, an infection (e.g., a viral, bacterial, or fungal infection), macular degeneration (e.g., acute macular degeneration and age-related macular degeneration (AMD, such as non-exudative age-related macular degeneration and exudative age-related macular degeneration)), edema (e.g., macular edema, such as cystoid macular edema (CME) and diabetic macular edema (DME)), multifocal choroiditis, ocular trauma which affects a posterior ocular site or location, ocular cancer, a retinal disorder (e.g., central retinal vein occlusion), diabetic retinopathy (e.g., proliferative diabetic retinopathy and non-proliferative diabetic retinopathy), proliferative vitreoretinopathy (PVR), retinal arterial occlusive disease, retinal detachment, uveitic retinal disease, sympathetic opthalmia, Vogt Koyanagi-Harada (VKH) syndrome, uveal diffusion, a posterior ocular condition caused by or influenced by an ocular laser treatment, a posterior ocular condition caused by or influenced by a photodynamic therapy, photocoagulation, radiation retinopathy, an epiretinal membrane disorder, branch retinal vein occlusion, anterior ischemic optic neuropathy, non-retinopathy diabetic retinal dysfunction, retinitis pigmentosa, retinoblastoma, or glaucoma. In certain embodiments, the ocular disease being prevented and/or treated by the inventive methods is macular degeneration. In certain embodiments, the ocular disease is age-related macular degeneration (AMD). In certain embodiments, the ocular disease is glaucoma. In certain embodiments, the ocular disease is diabetic retinopathy. In certain embodiments, the ocular disease is retinoblastoma. In certain embodiments, the ocular disease is edema. In certain embodiments, the ocular disease is cystoid macular edema (CME). In certain embodiments, the ocular disease is diabetic macular edema (DME). In certain embodiments, the ocular disease is an ocular inflammatory disease. In certain embodiments, the ocular disease is post-surgical inflammation. In certain embodiments, the ocular disease is uveitis (e.g., anterior uveitis, intermediate uveitis, and posterior uveitis). In certain embodiments, the ocular disease is blepharitis. In certain embodiments, the ocular disease is panuveitis. In certain embodiments, the ocular disease is scleritis. In certain embodiments, the ocular disease is dry eye. In certain embodiments, the ocular disease is Sjögren's syndrome. In certain embodiments, the ocular disease is an eye surgery.

Another aspect of the present invention relates to methods of inhibiting the aberrant signaling of a growth factor signaling pathway (e.g., VEGF) in a subject or cell.

In another aspect, the present invention provides methods of inhibiting abnormal or pathological angiogenesis in a subject in need thereof.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

In certain embodiments, the cell described herein is in vivo. In certain embodiments, the cell is in vitro. In certain embodiments, the cell is ex vitro.

In certain embodiments, the methods of the invention include administering to a subject in need thereof an effective amount of a compound, particle, or pharmaceutical composition of the invention. In certain embodiments, the methods of the invention include contacting a cell with an effective amount of a compound, particle, or pharmaceutical composition of the invention.

In certain embodiments, the inventive methods are in vivo methods. In certain embodiments, the inventive methods are in vitro methods. In certain embodiments, the inventive methods are ex vitro methods.

Another aspect of the invention relates to methods of screening a library of compounds to identify one or more compounds that are useful in the methods of the invention.

In certain embodiments, the one or more compounds identified are useful for treating and/or preventing a disease associated with abnormal or pathological angiogenesis in a subject in need thereof. In certain embodiments, the one or more compounds identified are useful for treating and/or preventing a disease associated with aberrant signaling of a growth factor in a subject in need thereof. In certain embodiments, the one or more compounds identified are useful for inhibiting abnormal or pathological angiogenesis in a subject in need thereof. In certain embodiments, the one or more compounds identified are useful for inhibiting aberrant signaling of a growth factor in a subject or cell in need thereof. In certain embodiments, the library of compounds is a library of compounds of the invention. In certain embodiments, the methods of screening a library include providing at least two different compounds of the invention; and performing at least one assay using the different compounds of the invention, to identify one or more compounds that are useful in the inventive methods.

Typically, the methods of screening a library of compounds involve at least one assay. In certain embodiments, the assay is performed to detect one or more characteristics associated with the treatment and/or prevention of a disease described herein, with the inhibition of abnormal angiogenesis, and/or with the inhibition of aberrant signaling of a growth factor. The characteristics may be desired (e.g., a disease being treated or prevented, abnormal angiogenesis being inhibited, or aberrant signaling of a growth factor being inhibited) or undesired (e.g., a disease not being treated or prevented, abnormal angiogenesis not being inhibited, or aberrant signaling of a growth factor not being inhibited) characteristics. The assay may be an immunoassay, such as a sandwich-type assay, competitive binding assay, one-step direct test, two-step test, or blot assay. The step of performing at least one assay may be performed robotically or manually.

In another aspect, the present invention provides the compounds, particles, and pharmaceutical compositions of the invention for use in the treatment and/or prevention of a disease described herein in a subject in need thereof.

In yet another aspect, the present invention provides the compounds, particles, and pharmaceutical compositions of the invention for use in the inhibition of abnormal angiogenesis in a subject in need thereof.

In still another aspect, the present invention provides the compounds, particles, and pharmaceutical compositions of the invention for use in the inhibition of aberrant signaling of a growth factor in a subject or cell in need thereof.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

General Preparation of the Compounds

Compounds of Formula (I) may be prepared by the synthetic sequences outlined below in Schemes 1 and 2, wherein X, Y, Ring A, Ring Y, $R^A$, $R^B$, $R^C$, $R^D$, $R^L$, a, l, and m are as defined herein, and each one of $LG^1$ to $LG^3$ is independently a leaving group as described herein. Alternatively, compounds of Formula (I) may be prepared by other methods described herein or known in the art.

Scheme 1. Exemplary synthesis of compounds of Formula (I).

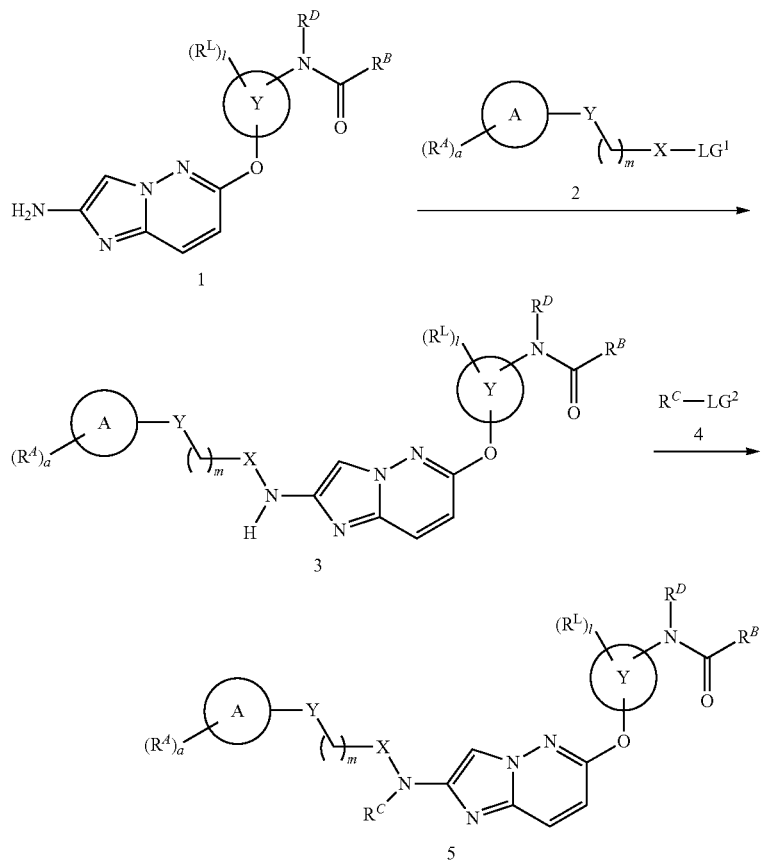

In Scheme 1, the starting point of the synthesis compounds of Formula (I) is compounds of Formula 1. Synthesis of compounds of Formula 1, such as compound 6 (below), is known in the art. See, e.g., international POT application publication, WO 2008/016192; Okaniwa et al., *Journal of Medicinal Chemistry*, 55(7), 3452-3478; 2012: international POT application publication, WO 2008/016131; each of which is incorporated herein by reference.

6

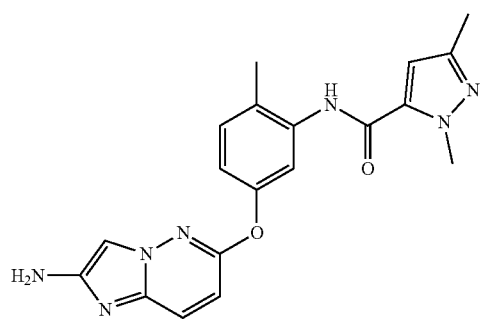

In an exemplary synthesis of a compound of Formula (I), a compound of Formula 1 is reacted with a compound of Formula 2. The leaving group $LG^1$ of the compound of Formula 2 is displaced by the nucleophilic amino moiety of the compound of Formula 1 to give a compound of Formula 3, which is a compound of Formula (I) where $R^C$ is H. The compound of Formula 3 undergoes a nucleophilic displacement reaction with a compound of Formula 4 that includes leaving group $LG^2$, yielding a compound of Formula 5, which is a compound of Formula (I) where $R^C$ is not H. Alternatively, a compound of Formula 1 may react with a compound of Formula 4, and the resulting product may react with a compound of Formula 2 to yield a compound of Formula 5.

In another exemplary synthesis of a compound of Formula (e.g., a compound of Formula 11 in Scheme 2 below) where Ring A includes a nitrogen atom, a compound of Formula 1 reacts with a compound of Formula 8, which includes leaving group $LG^3$, and the reaction product reacts with a compound of Formula 4 to give a compound of Formula 9 (Scheme 2). A compound of Formula 9 may alternatively be prepared by reacting a compound of Formula 1 with a compound of Formula 4 and reacting the resulting product with a compound of Formula 8. A compound of Formula 10, which includes a nucleophilic secondary amino moiety, displaces $LG^3$ of the compound of Formula 9 to furnish the compound of Formula 11. A compound of Formula 11 may alternatively be synthesized by reacting a compound of formula 1 with a compound of Formula 8, followed by a reaction with a compound of Formula 10 and then by a reaction with a compound of Formula 4.

Scheme 2. Exemplary synthesis of certain compounds of Formula (I).

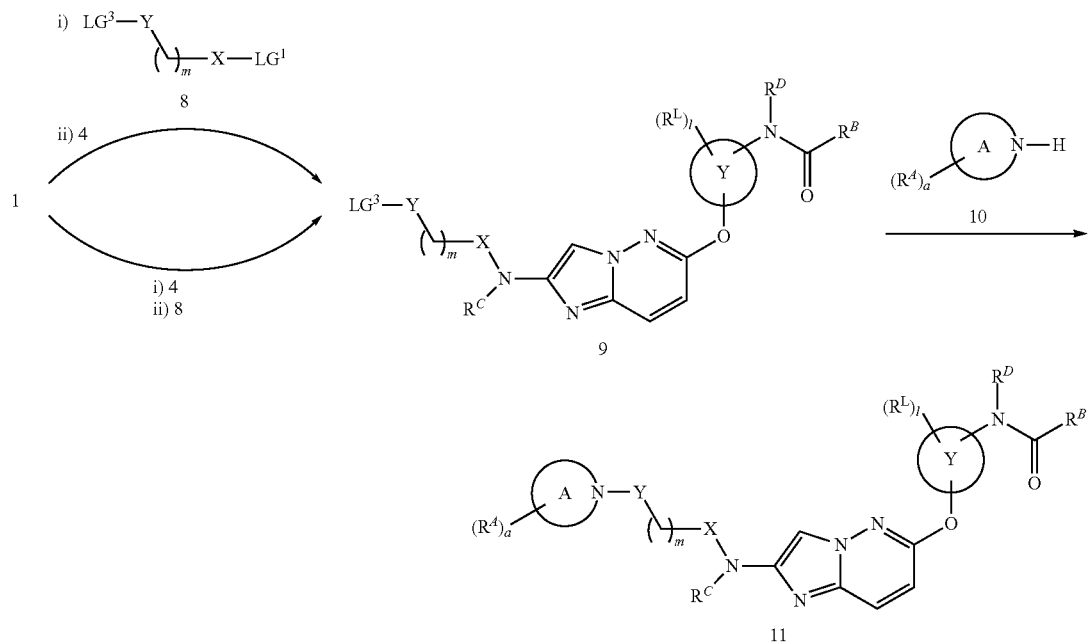

Following are examples of the synthesis of exemplary compounds of Formula (I), starting from compound 6.

Example 1

Preparation of Compound I-1

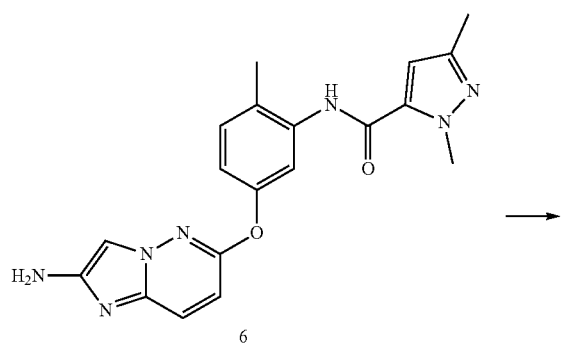

N-(5-(2-Aminoimidazo[1,2-b]pyridazin-6-yloxy)-2-methylphenyl)-1,3-dimethyl-1H-pyrazole-5-carboxamide (compound 6, 189 mg, 0.5 mmol) was dissolved in dichloromethane. 2-(Oxetan-3-yl)acetic acid (87 mg, 0.75 mmol) was added followed by 1-ethyl-3-(3-dimethylaminopropyl) carbodiimide (EDCI, 155 mg, 1.0 mmol) and 4-dimethylaminopyridine (DMAP, 5 mg). The resulting mixture was stirred for 3 hours, diluted with ethyl acetate (25 mL), and washed with saturated sodium bicarbonate (10 mL). The organic phase was separated, dried with anhydrous magnesium sulfate, and evaporated. The resulting residue was purified by flash chromatography eluting with a gradient from ethyl acetate to ethyl acetate-methanol (70:30). The fractions were concentrated, and the resulting residue was suspended in dichloromethane (1 mL) and diethyl ether (20 mL) was added. The resulting precipitate was filtered and dried in high vacuum to yield compound I-1 as a white solid (82 mg). MS: m/z 476.3 (M+1) (positive ionization mode). $^1$H NMR: (DMSO-d6): 10.85 (s, 1H), 9.78 (s, 1H), 8.01 (d, J=9.5 Hz, 1H), 7.92 (s, 1H), 7.33 (s, J=8.5 Hz, 1H), 7.26 (d, J=2.5 Hz, 1H), 7.08 (dd, J=8.5, 2.5 Hz, 1H), 7.03 (d, J=9.5 Hz, 1H), 6.80 (s, 1H), 4.67 (dd, J=6.0, 7.5 Hz, 2H), 4.31 (dd, J=6.0, 6.0 Hz, 2H), 3.96 (s, 3H), 3.40-3.25 (m, 2H), 2.77 (d, J=8.0 Hz, 2H), 2.23 (s, 3H), 2.18 (s, 3H).

Example 2

Preparation of Compound I-2

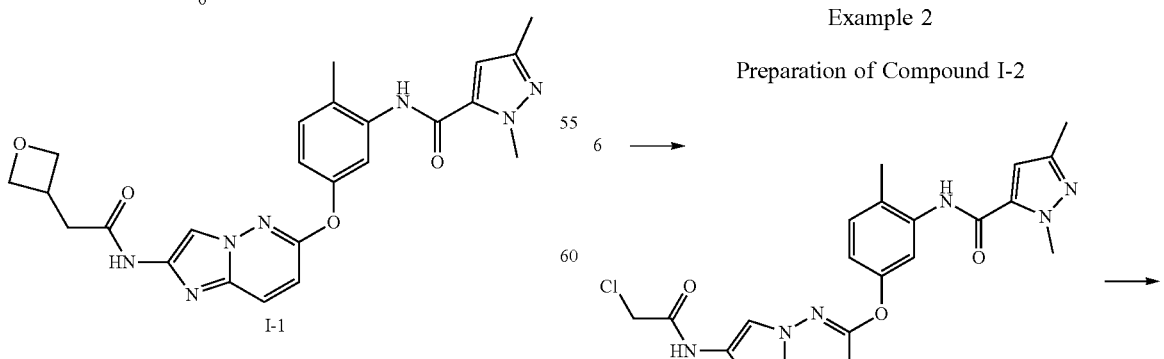

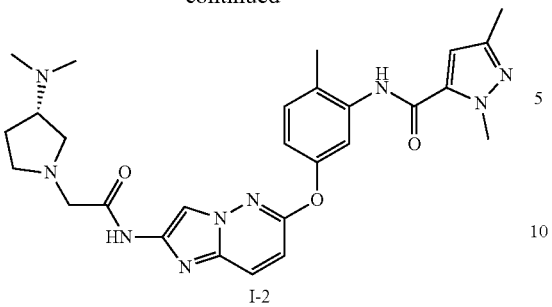

I-2

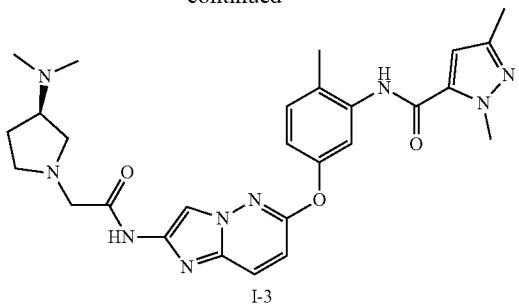

I-3

N-(5-(2-Aminoimidazo[1,2-b]pyridazin-6-yloxy)-2-methylphenyl)-1,3-dimethyl-1H-pyrazole-5-carboxamide (compound 6, 189 mg, 0.5 mmol) was dissolved in tetrahydrofuran. Triethylamine (0.5 mL, 3.5 mmol) was added followed by chloroacetyl chloride (96 mg, 0.85 mmol), then the resulting mixture was stirred for 1 hour to generate intermediate 12. (S)—N,N-dimethylpyrrolidin-3-amine (171 mg, 1.5 mmol) was added. The resulting mixture was heated to 60° C. for 2 hours. The volatiles were evaporated, and the residue was dissolved in dichloromethane (25 mL) and washed with saturated sodium bicarbonate (10 mL). The organic phase was directly purified by flash chromatography eluted with a gradient from dichloromethane to dichloromethane-methanol-triethylamine (80:10:10). The fractions were concentrated, leaving a yellow foam (200 mg). Further purification was performed using reverse phase chromatography (8-gram $C_{18}$ column, gradient from 5:95 water-acetonitrile to 95:5 water-acetonitrile; both water and acetonitrile contained 0.01% of formic acid modifier). The product obtained from the reverse phase chromatography was converted to free base using dichloromethane-aqueous sodium bicarbonate, dried with sodium sulfate, and concentrated. Hexane was added to the resulting residue to precipitate out compound I-2 as a yellow solid (15 mg). MS m/z: 532.3 (M+1) (positive ionization mode). $^1$H NMR: (DMSO-d6): 10.33 (s, 1H), 9.79 (s, 1H), 8.02 (d, J=9.5 Hz, 1H), 7.98 (s, 2H), 7.33 (d, J=8.5 Hz, 1H) 7.26 (d, J=2.5 Hz, 1H), 7.08 (dd, J=2.5, 8.5 Hz, 1H), 7.05 (d, J=9.5 Hz, 1H) 6.80 (s, 1H), 3.96 (s, 3H), 3.31 (d, J=15.5 Hz, 1H), 3.21 (d, J=5.5 Hz, 1H), 2.79-2.60 (m, 4H), 2.59-2.53 (m, 1H), 2.48-2.40 (m, 1H), 2.34 (s, 3H), 2.18 (s, 3H), 2.08 (s, 3H). 1.89-1.80 (m, 1H), 1.66-1.58 (m, 1H).

Example 3

Preparation of Compound I-3

6 ⟶

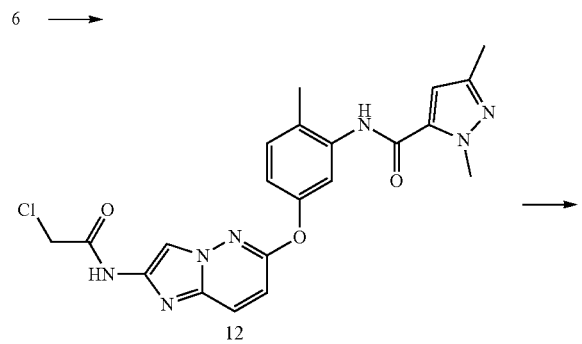

12

Compound I-3 was prepared in the same manner as compound I-2 except that (R)-N,N-dimethylpyrrolidin-3-amine was used instead of (S)—N,N-dimethylpyrrolidin-3-amine. Compound I-3 was obtained as a yellow solid (32 mg). MS: m/z 532.3 (M+1) (positive ionization mode). $^1$H NMR: (DMSO-d6): 10.35 (s, 1H), 9.79 (s, 1H), 8.14-7.79 (m, 2H), 7.37-7.26 (m, 2H), 7.12-7.02 (m, 2H). 6.80 (s, 1H), 3.96 (s, 3H), 3.42-3.16 (m, 2H), 2.79-2.60 (m, 4H), 2.59-2.53 (m, 1H), 2.48-2.40 (m, 1H), 2.34 (s, 3H), 2.17 (s, 3H), 2.09 (s, 3H), 1.89-1.80 (m, 1H), 1.66-1.58 (m, 1H).

Example 4

Preparation of Compound I-4

6 ⟶

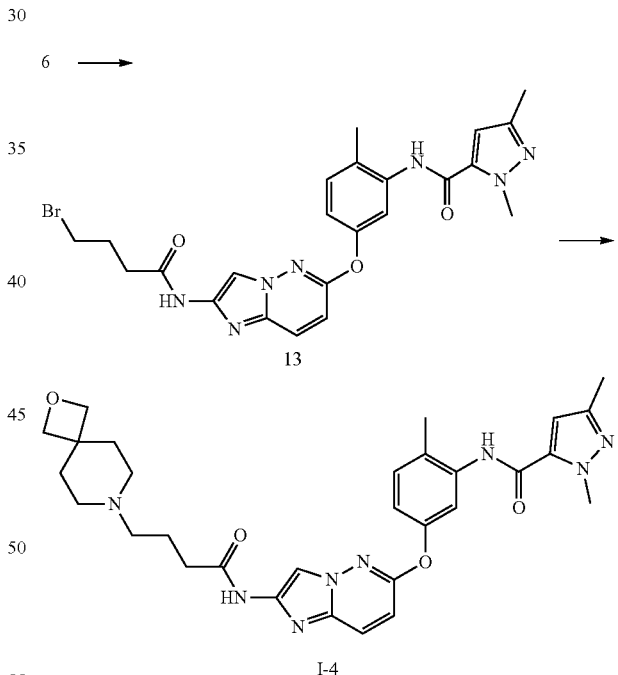

N-(5-(2-Aminoimidazo[1,2-b]pyridazin-6-yloxy)-2-methylphenyl)-1,3-dimethyl-1H-pyrazole-5-carboxamide (compound 6, 189 mg, 0.5 mmol) was dissolved in tetrahydrofuran. Triethylamine (0.3 mL, 2.1 mmol) was added followed by 4-bromobutanoyl chloride (95 mg, 0.50 mmol), and the resulting mixture was stirred for 2 hours to generate intermediate 13. The volatiles were evaporated, and the residue was re-dissolved in DMF (3 mL). 2-Oxa-7-azaspiro[3.5]nonane (generated from 2-oxa-7-azaspiro[3.5]nonane hemioxalate (0.5 g, 5.8 mmol) using 10M NaOH and ethyl acetate extraction) was added followed by potassium carbonate (138 mg, 1.0 mmol). The resulting mixture was heated to 60° C. for 3 hours. The volatiles were evaporated, and the residue was dissolved in ethyl acetate (25 mL) and washed with saturated sodium bicarbonate (10 mL). The organic phase was evaporated, leaving a yellow oil (239 mg). Purification was performed using reverse phase chromatography (8 gram $C_8$ column, gradient from 5:95 water-acetonitrile to 95:5 water-acetonitrile; both water and acetonitrile contained 0.01% of formic acid modifier). The obtained product was converted to free base using dichloromethane-aqueous sodium bicarbonate, dried with sodium sulfate, and concentrated. Hexane was added to the resulting residue to yield compound I-4 as a yellow solid (32 mg). MS: m/z 573.3 (M+1) (positive ionization mode). $^1$H NMR: (DMSO-d6): 9.78 (s, 1H), 9.09 (s, 1H), 7.96 (d, J=10.0 Hz, 1H), 7.68 (s, 1H), 7.32 (d, J=8.5 Hz, 1H), 7.2-7.20 (m, 2H), 7.06 (dd, J=8.5, 2.5 Hz, 1H), 6.97 (d, J=10.0 Hz, 1H), 6.79 (s, 1H), 4.83-4.68 (m, 3H), 4.41 (dd, J=5.5, 5.5 Hz, 2H), 3.96 (s, 3H), 2.23 (s, 3H), 2.17 (s, 2.17).

Example 5

Preparation of Compound I-5

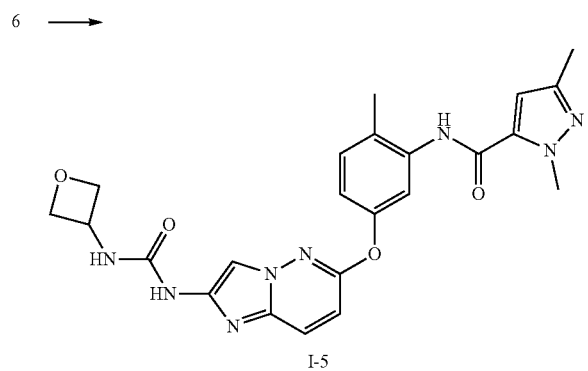

N-(5-(2-Aminoimidazo[1,2-b]pyridazin-6-yloxy)-2-methylphenyl)-1,3-dimethyl-1H-pyrazole-5-carboxamide (compound 6, 189 mg, 0.5 mmol) was dissolved in dichloromethane. Triethylamine (0.5 mL, 3.5 mmol) was added. The resulting mixture was cooled to −78° C., and phosgene (0.5 mL, 15% solution in toluene, 1.0 mmol) was added. The resulting mixture was stirred for 1 hour, warmed up to room temperature, and stirred further for 1 hour. 2-Oxetanyl amine (183 mg, 5.0 mmol) and DMF (3 mL) were added, and the resulting mixture was stirred for 4 hours at 60° C. The volatiles were evaporated. The residue was stirred with aqueous sodium bicarbonate (10 mL), and the resulting yellow precipitate was filtered and briefly dried in high vacuum. Purification was performed using reverse phase chromatography (8 gram $C_{18}$ column, gradient from 5:95 water-acetonitrile to 95:5 water-acetonitrile; both water and acetonitrile contained 0.01% of formic acid modifier). The obtained product was converted to free base by partitioning in dichloromethane-aqueous sodium bicarbonate, dried with sodium sulfate, and concentrated. Hexane was added to the resulting residue to yield compound I-5 as a yellow solid (15 mg). MS: m/z 477.2 (M+1) (positive ionization mode). $^1$H NMR: (DMSO-d6): 10.75 (s, 1H) 9.79 (s, 1H), 8.00 (d, J=9.5 Hz, 1H), 7.95 (s, 1H), 7.33 (d, J=8.5 Hz, 1H), 7.26 (d, J=2.5 Hz, 1H), 7.08 (dd, J=8.5. 2.5 Hz, 1H), 7.02 ((d, J=9.5 Hz, 1H), 6.80 (s, 1H), 4.22 (s, 4H), 3.96 (s, 3H), 2.35-2.15 (m, 8H), 2.24 (s, 3H), 2.18 (s, 3H), 1.85-1.65 (m, 6H).

Example 6

Preparation of Compound I-6

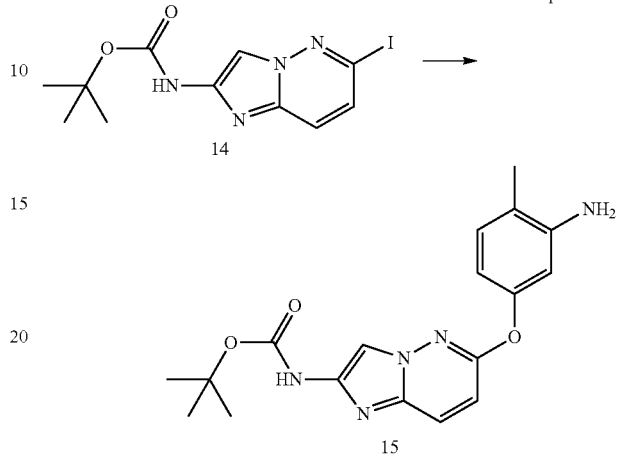

3-Amino-4-methylphenol (28.7 g, 233.3 mmol), N,N-dimethylformamide (2 L), and potassium tert-butoxide (26.13 g, 232.86 mmol) were placed in a 3-L round-bottom flask, purged and maintained with nitrogen. The resulting solution was stirred for 2 hours at room temperature. tert-Butyl N-[6-iodoimidazo[1,2-b]pyridazin-2-yl]carbamate (compound 14, 80 g, 222.13 mmol) was added to the reaction solution. The solution was allowed to react, with stirring, for an additional 12 hours at 80° C. The reaction was then quenched by the addition of ice water (6 L) and the solids were collected by filtration. The solids were washed with water (3 × 500 mL) and petroleum ether (3×500 mL). This reaction was repeated four times and the crude product was combined (total of 600 g). This material was dissolved in tetrahydrofuran (6 L). The solution was applied on silica column (6 kg, 100-200 mesh). The column was eluted with dichloromethane tetrahydrofuran mixture (gradient from 30:1 to 20:1). Fractions were analyzed by TLC ($R_f$ of the product=0.5 in ethyl acetate:petroleum ether 3:2). The fractions containing product were combined and evaporated and the material was dried in vacuum for 12 hours at 33° C., leaving a light yellow solid (50.0 g). The solid was washed with ether (2×500 mL) and dried in an oven under reduced pressure to give compound 15 as a light yellow powder (39.7 g). m/z: 356.2 (M+1) (positive ionization mode).

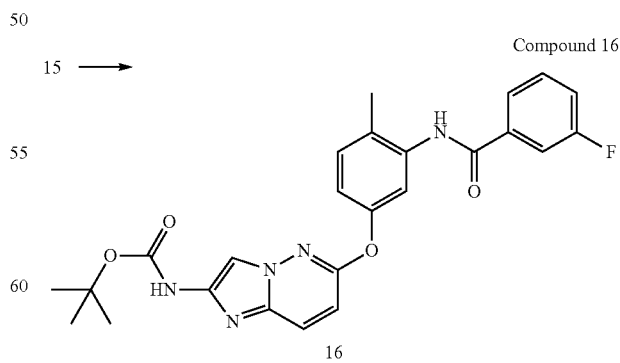

tert-Butyl N-[6-(3-amino-4-methylphenoxy)imidazo[1,2-b]pyridazin-2-yl]carbamate (compound 15, 1.77 g, 5.0 mmol) was dissolved in tetrahydrofuran (200 mL). 3-Fluorobenzoic acid (1.00 g, 7.5 mmol) was added followed by 1-ethyl-3(3-dimethylaminopropyl)carbodiimide hydrochloride (1.44 g, 7.5 mmol) and DMAP (61 mg, 0.5 mmol). The solution was stirred overnight. The solvent was evaporated and the residue was partitioned between saturated sodium bicarbonate (100 mL) and ethyl acetate with 5% methanol (200 mL). The organic solution was separated and dried with magnesium sulfate. Removal of the solvent provided compound 16 as a thick oil (2.4 g) m/z: 478.6 (M+1) (positive ionization mode).

Compound 17

16 →

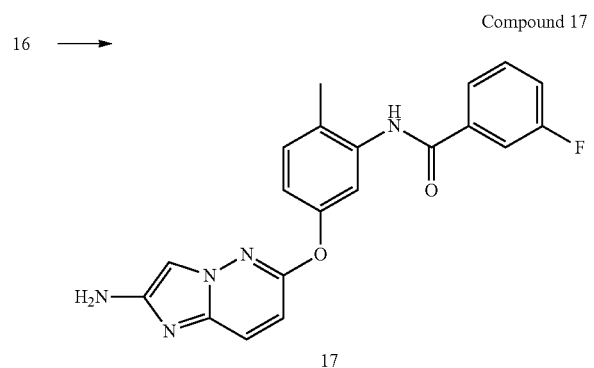

17

N-(5-(2-tert-Butoxycarbamoylimidazo[1,2-b]pyridazin-6-yloxy)-2-methylphenyl)-3-fluorobenzamide (compound 16, 2.4 g, 5.0 mmol) was dissolved in mixture of dichloromethane (25 mL) and trifluoroacetic acid (25 mL). The solution was stirred for 1 h. The solvent was evaporated and the remainder was partitioned between 2 M sodium hydroxide (200 mL) and 5% methanol in dichloromethane (200 mL). The organic solution was separated and dried with magnesium sulfate. The solvent was evaporated leaving compound 17 as a yellow foam (1.51 g) m/z: 378.5 (M+1) (positive ionization mode).

Compound I-6

17 →

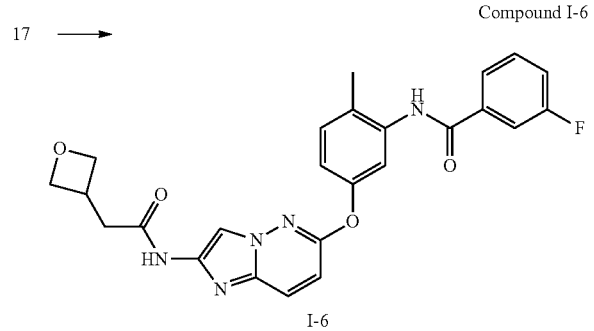

I-6

N-(5-(2-Aminoimidazo[1,2-b]pyridazin-6-yloxy)-2-methylphenyl)-3-fluorobenzamide (compound 17, 1.51 g, 4.0 mmol) and lithium 2-(oxetan-3-yl)acetate (0.58 g, 4.77 mmol) were dissolved in N-methylpyrrolidone (15 mL). N,N-Diisopropylethylamine (2.0 mL, 11.50 mmol) was added followed by TBTU (2.55 g, 7.94 mmol). The solution was stirred overnight. The solvent was evaporated and the remainder was partitioned between saturated sodium bicarbonate (100 mL) and 5% methanol in dichloromethane (200 mL). The organic solution was separated and dried with magnesium sulfate. The solvent was evaporated leaving a yellow oil that was purified by flash chromatography (Isco, 24 g column, 16 column volumes, gradient from dichloromethane to ethyl acetate). The fractions were collected and evaporated leaving a white solid (530 mg). Further purification was achieved using reverse phase flash chromatography (Isco, 120 g C18 column, gradient from 10:90 to 90:10 water acetonitrile with 0.1% formic acid). The fractions were collected, basified with saturated sodium bicarbonate and the organic solvent was evaporated. The aqueous suspension was extracted with 5% methanol in dichloromethane (200 mL), dried with magnesium sulfate and evaporated. The residue was dissolved in ethyl acetate and slowly diluted with hexane while sonicating. The precipitate was filtered off and dried in high vacuum overnight to yield compound I-6 as white solid (0.30 g) m/z: 476.2 (M+1) (positive ionization mode). $^1$H NMR: (DMSO-d6): 10.83 (s, 1H), 10.00 (s, 1H), 8.01 (d, J=10.0 Hz, 1H), 7.93 (s, 1H), 7.82-7.72 (m, 2H), 7.81-7.53 (m, 1H), 7.47-7.40 (m, 1H), 7.36-7.27 (m, 2H), 7.11-7.01 (m, 2H), 4.65 (dd, J=8.0, 6.0 Hz, 2H), 4.31 (dd, J=6.0, 6.0 Hz, 2H), 3.21-3.35 (m, 1H), 2.71 (d, J=7.0 Hz, 2H), 2.51 (s, 3H).

Example 7

Preparation of Compound 24

Compound 22

15 →

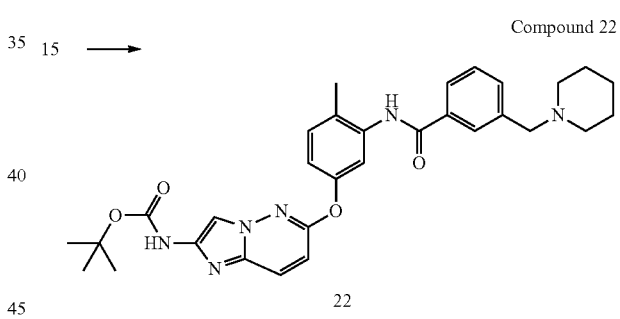

22

3-(Bromomethyl)benzoic acid (1.075 g, 5.0 mmol) was dissolved in dichloromethane (20 mL). Oxalyl chloride (1.26 g, 10.0 mmol) was added followed by catalytic amount of N,N-dimethylformamide (0.1 mL). The solution was stirred for 2 h. The solvent was removed and the residue was re-dissolved in dichloromethane (10 mL). The solvent was again removed, leaving an oil (1.15 g). The material was dissolved in dichloromethane (10 mL) and added to the solution of tert-butyl N-[6-(3-amino-4-methylphenoxy)imidazo[1,2-b]pyridazin-2-yl]carbamate (compound 15, 1.77 g, 5.0 mmol) dissolved in tetrahydrofuran (50 mL). The solution was stirred 1 h and piperidine (4.25 g, 50.0 mmol) was added. The solution was stirred 2 h. The solvent was evaporated and the residue was partitioned between ethyl acetate and saturated sodium bicarbonate. The organic phase was separated and dried with magnesium sulfate. Removal of the solvent provided compound 22 as a yellow foam (2.3 g). MS: m/z 557.2 (M+1) (positive ionization mode).

22 →

Compound 23

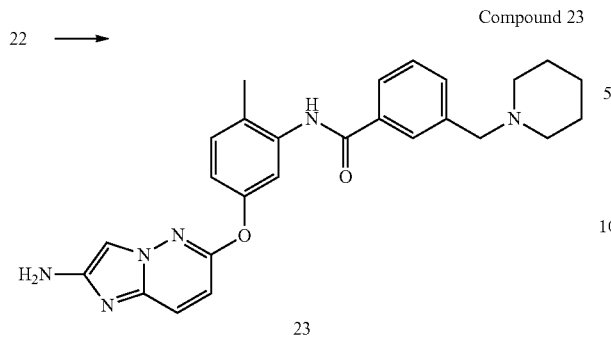

23 tert-butyl N-(5-(2-aminoimidazo[1,2-b]pyridazin-6-yloxy)-2-methylphenyl)-3-((piperidin-1-yl)methyl)benzamide carbamate (compound 22, 2.3 g, 4.14 mmol) was dissolved in dichloromethane (20 mL). Trifluoroacetic acid (20 mL) was added and the solution was stirred for 2 h. The solvent was evaporated and the remainder was suspended in water (50 mL) and neutralized with 10 M sodium hydroxide solution. The suspension was extracted with ethyl acetate containing 10% methanol. The organic phase was separated and dried with magnesium sulfate. Removal of the solvent provided compound 23 as a yellow foam (2.1 g). MS: m/z 457.2 (M+1) (positive ionization mode).

23 →

Compound 24

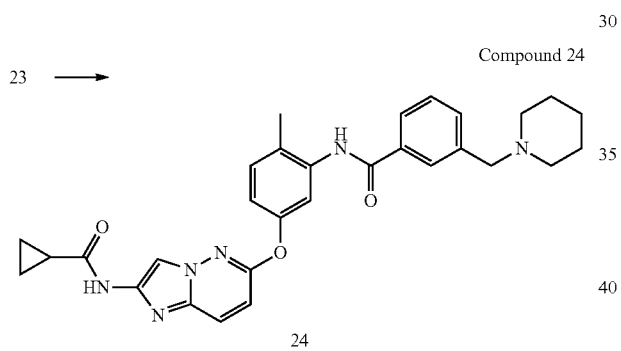

24

N-(5-(2-aminoimidazo[1,2-b]pyridazin-6-yloxy)-2-methylphenyl)-3-((piperidin-1-yl)methyl)benzamide (crude compound 23, 2.1 g, 4.6 mmol) was dissolved in tetrahydrofuran (50 mL). Triethylamine (3.22 mL, 23.0 mmol) was added followed by cyclopropylcarbonyl chloride (478 mg, 4.6 mmol). The solution was stirred for 2 h. The solvent was evaporated and the residue was partitioned between ethyl acetate and saturated sodium bicarbonate. The organic phase was separated and dried with magnesium sulfate. Removal of the solvent provided crude compound 24 as a yellow foam (2.2 g). Purification was performed using flash chromatography eluting with a gradient from dichloromethane to ethyl acetate with 20% methanol followed by ethyl acetate with 10% methanol and 10% triethylamine. The organic solution was evaporated and dried in high vacuum giving compound 24 as a greenish amorphous foam (0.50 g). MS: m/z 525.3 (M+1) (positive ionization mode). $^1$H NMR: (DMSO-d6): 11.05 (s, 1H), 9.89 (s, 1H), 8.01 (d, J=9.5 Hz, 1H), 7.29 (s, 1H), 7.87-7.81 (m, 2H), 7.51-7.41 (m, 2H), 7.36-7.27 (m, 2H), 7.06 (dd, J=8.5. 2.5 Hz, 1H), 7.03 (d, J=9.5 Hz, 1H), 3.37 (s, 2H), 2.32 (br. s, 4H), 2.25 (s, 3H), 1.94-1.87 (m, 1H), 1.51-1.43 (m, 4H), 1.41-1.31 (m, 2H), 0.81-0.75 (m, 4H).

Example 8

Preparation of Compound 27

15 →

Compound 25

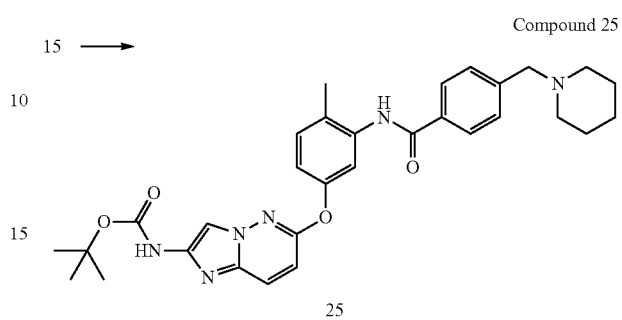

25

Compound 25 was synthesized from 4-(bromomethyl)benzoic (1.075 g, 5.0 mmol) acid and tert-butyl N-[6-(3-amino-4-methylphenoxy)imidazo[1,2-b]pyridazin-2-yl]carbamate (compound 15, 1.77 g, 5.0 mmol) as described for the synthesis of compound 22, resulting in the production of a yellow foam (3.51 g). MS: m/z 557.3 (M+1) (positive ionization mode).

25 →

Compound 26

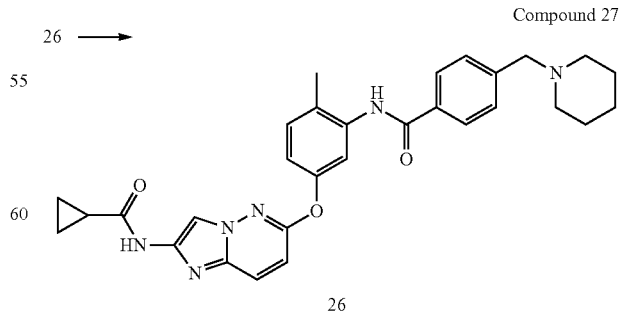

26

Compound 26 was synthesized from tert-butyl N-(5-(2-aminoimidazo[1,2-b]pyridazin-6-yloxy)-2-methylphenyl)-4-((piperidin-1-yl)methyl)benzamide carbamate (compound 25, 3.51 g) following the same procedure as the synthesis of compound 23, resulting in a y&low foam (2.65 g). MS: m/z 457.3 (M+1) (positive ionization mode).

26 →

Compound 27

26

Compound 27 was synthesized from N-(5-(2-aminoimidazo[1,2-b]pyridazin-6-yloxy)-2-methylphenyl)-4-((piperidin-1-yl)methyl)benzamide (compound 26, 2.65 g) using the procedure described for the synthesis of compound 24. The crude material (2.54 g) was purified by preparative HPLC using Varian PrepStar with water-acetonitrile solvent system each containing 0.1% formic acid as modifier and "Load & Lock" 50×250 mm column with C18 reverse phase silica gel. The obtained solution of the product was converted to free base using dichloromethane with 10% methanol and aqueous sodium bicarbonate, dried with sodium sulfate, and concentrated. The product was a yellow solid (84 mg). MS: m/z 525.3 (M+1) (positive ionization mode) $^1$H NMR: (DMSO-d6): 11.06 (s, 1H), 9.85 (s, 1H), 8.02 (d, J=9.5 Hz, 1H), 7.95-7.87 (m, 3H), 7.40 (d, J=8.5 Hz, 2H), 7.35-7.29 (m, 2H), 7.06 (dd, J=8.5, 2.5 Hz, 1H), 7.03 (d, J=9.5 Hz, 1H), 3.48 (s, 2H), 2.31 (br. s, 4H), 2.25 (s, 3H), 1.95-1.87 (m, 1H), 1.51-1.45 (m, 4H), 1.42-1.33 (m, 2H), 0.83-0.75 (m, 4H).

Example 9

Preparation of Compound 30

15 ⟶

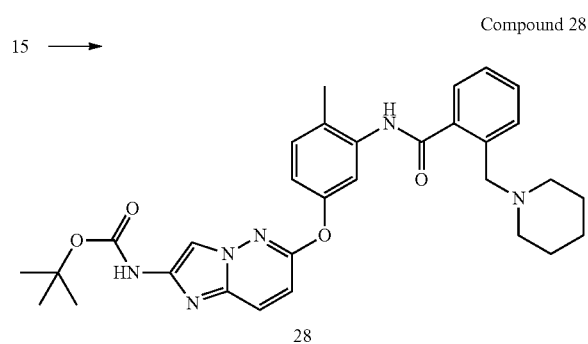

Compound 28

28

Compound 28 was synthesized from 2-(bromomethyl)benzoic (1.075 g, 5.0 mmol) acid and tert-butyl N-[6-(3-amino-4-methylphenoxy)imidazo[1,2-b]pyridazin-2-yl]carbamate (compound 15, 1.77 g, 5.0 mmol) as described for the synthesis of compound 22, resulting in a yellow foam (5.57 g). MS: m/z 557.3 (M+1) (positive ionization mode).

Compound 29

28 ⟶

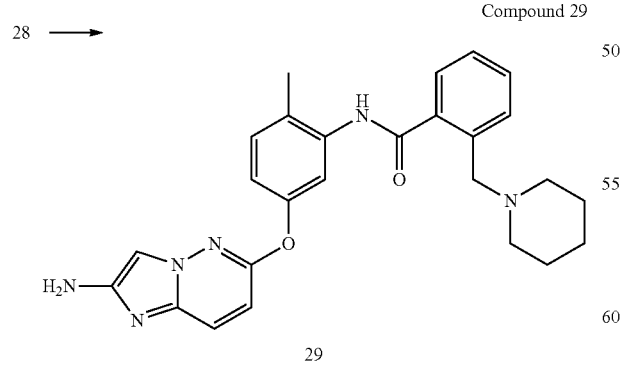

29

Compound 29 was synthesized from tert-butyl N-(5-(2-aminoimidazo[1,2-b]pyridazin-6-yloxy)-2-methylphenyl)-4-((piperidin-1-yl)methyl)benzamide carbamate (compound 28, 5.57 g) following the same procedure as the synthesis of compound 23, resulting in a yellow foam (2.33 g). MS: m/z: 457.3 (M+1) (positive ionization mode).

Compound 30

29 ⟶

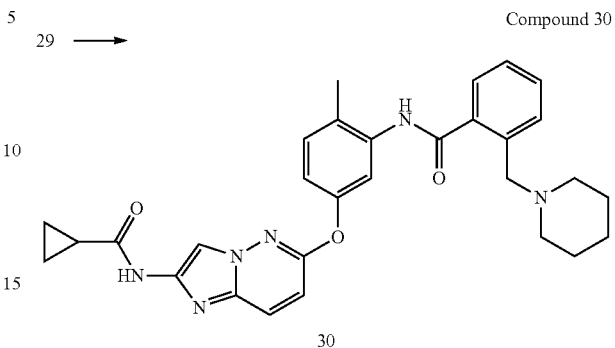

30

Compound 30 was synthesized from N-(5-(2-aminoimidazo[1,2-b]pyridazin-6-yloxy)-2-methylphenyl)-2-((piperidin-1-yl)methyl)benzamide (compound 29, 2.33 g) as described for the synthesis of compound 24. The crude material (2.92 g) was purified by preparative HPLC using Varian PrepStar with water-acetonitrile solvent system (each solvent containing 0.1% formic acid modifier) and "Load and Lock" 50×250 mm column with C18 reverse phase silica gel. The obtained solution of the product was converted to free base using dichloromethane with 10% methanol and aqueous sodium bicarbonate, dried with sodium sulfate, and concentrated. The product was a yellow solid (110 mg). MS: m/z 525.3 (M+1) (positive ionization mode) $^1$H NMR: (DMSO-d6): 11.14 (s, 1H), 10.00 (s, 1H), 8.01 (d, J=9.5 Hz, 1H), 7.92 (s, 1H), 7.69-7.62 (m, 1H), 7.46-7.29 (m, 7H), 7.07-7.00 (m, 2H), 3.60 (s, 2H), 2.36-2.22 (m, 7H), 1.94-1.86 (m, 1H), 1.38-1.21 (m, 6H), 0.84-0.75 (m, 4H).

Example 10

Preparation of Compound 33

Compound 31

15 ⟶

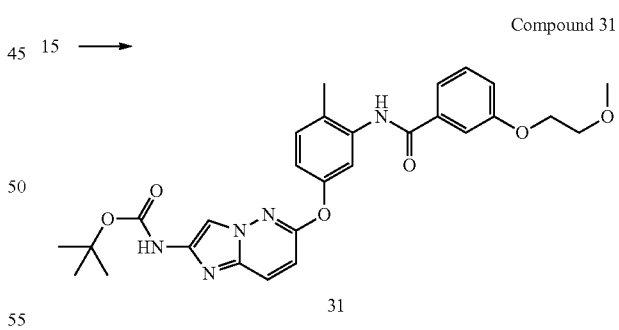

31

Compound 31. 3-(2-Methoxyethoxy)benzoic acid (0.975 g, 5.0 mmol) was dissolved in dichloromethane (20 mL). Oxalyl chloride (1.26 g, 10.0 mmol) was added followed by catalytic amount of N,N-dimethylformamide (0.1 mL). The solution was stirred for 2 h. The solvent was removed and the residue was re-dissolved in dichloromethane (10 mL). The solvent was again removed leaving an oil (1.0 g). The material was dissolved in dichloromethane (10 mL) and added to the solution of tert-butyl N-[6-(3-amino-4-methylphenoxy)imidazo[1,2-b]pyridazin-2-yl]carbamate (compound 15, 1.77 g, 5.0 mmol) and triethylamine (2.8 mL, 20.0 mmol) dissolved in tetrahydrofuran (50 mL). The solution was stirred 2 h. The solvent was evaporated and the residue was partitioned between ethyl acetate and saturated sodium bicarbonate. The organic phase was separated and dried with magnesium sulfate. Removal of the solvent provided compound 31 as a yellow foam (2.76 g). MS: m/z 534.2 (M+1) (positive ionization mode).

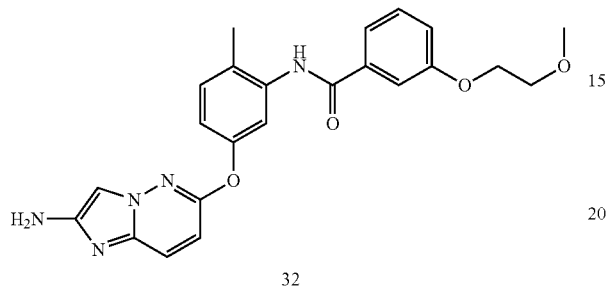

Compound 32 was synthesized from tert-butyl N-(5-(2-aminoimidazo[1,2-b]pyridazin-6-yloxy)-2-methylphenyl)-3-(2-methoxyethoxy)benzamide carbamate (compound 31, 2.76 g) following the same procedure as the synthesis of compound 23, resulting in a yellow foam (1.70 g). MS: m/z 434.3 (M+1) (positive ionization mode).

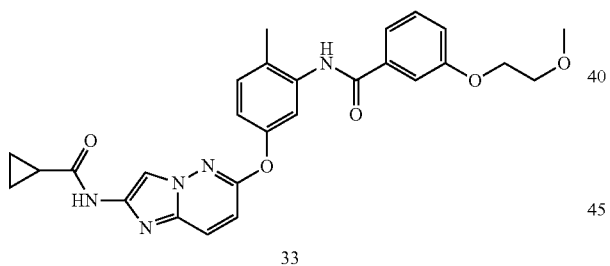

Compound 33 was synthesized from N-(5-(2-aminoimidazo[1,2-b]pyridazin-6-yloxy)-2-methylphenyl)-3-(2-methoxyethoxy)benzamide (compound 32, 1.70 g) as described for the synthesis of compound 24. The crude material (1.95 g) was purified by flash chromatography eluting with a gradient from dichloromethane to ethyl acetate with 10% methanol. The organic solution was evaporated and dried in high vacuum giving compound 33 as a greenish foam (1.19 g). MS: m/z 502.2 (M+1) (positive ionization mode). $^1$H NMR: (DMSO-d6): 11.06 (s, 1H), 9.88 (s, 1H), 8.01 (d, J=10.0 Hz, 1H), 7.93 (s, 1H), 7.56-7.49 (m, 2H), 7.41 (dd, J=8.5 Hz, 8.5 Hz, 1H), 7.33 (d, J=8.5 Hz, 1H), 7.29 (d, J=2.5 Hz, 1H), 7.15 (dd, J=8.0 Hz, 2.5 Hz, 1H), 7.08 (dd, J=8.5 Hz. 3.0 Hz, 1H), 7.03 (d, J=9.5 Hz, 1H), 4.18-4.13 (m, 2H), 3.69-3.65 (m, 2H), 3.30 (s, 3H), 2.25 (s, 3H), 1.94-1.87 (m, 1H), 0.82-0.77 (m, 4H).

Example 11

Preparation of Compound 36

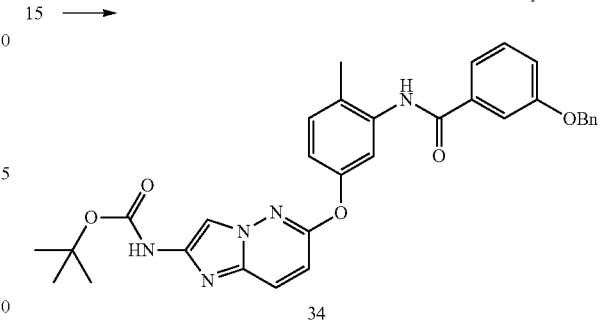

Compound 34. 3-Benzyloxybenzoic acid (2.28 g, 10.0 mmol) was dissolved in dichloromethane (50 mL). Oxalyl chloride (2.02 g, 20.0 mmol) was added followed by catalytic amount of N,N-dimethylformamide (0.2 mL). The solution was stirred for 2 h. The solvent was removed and the residue was re-dissolved in dichloromethane (50 mL). The solvent was again removed leaving an oil (2.3 g). The material was dissolved in dichloromethane (20 mL) and added to the solution of tert-butyl N-[6-(3-amino-4-methylphenoxy)imidazo[1,2-b]pyridazin-2-yl]carbamate (compound 15, 3.55 g, 10.0 mmol) and triethylamine (4.2 mL mL, 30.0 mmol) dissolved in tetrahydrofuran (100 mL). The solution was stirred for 2 h. The solvent was evaporated and the residue was treated with saturated sodium bicarbonate and briefly sonicated. The precipitate was filtered off and washed with water. Drying in high vacuum overnight furnished off-white solid (5.70 g). MS: m/z 566.2 (M+1) (positive ionization mode).

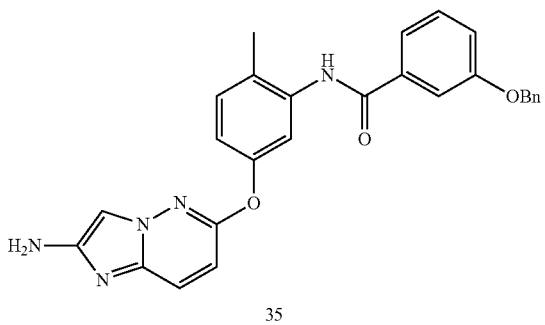

Compound 35 was synthesized from tert-butyl N-(5-(2-aminoimidazo[1,2-b]pyridazin-6-yloxy)-2-methylphenyl)-3-benzyloxybenzamide carbamate (compound 34, 1.00 g) following the same procedure as the synthesis of compound 23, resulting in a yellow foam (0.80 g). MS: m/z 466.2 (M+1) (positive ionization mode).

35 → Compound 36

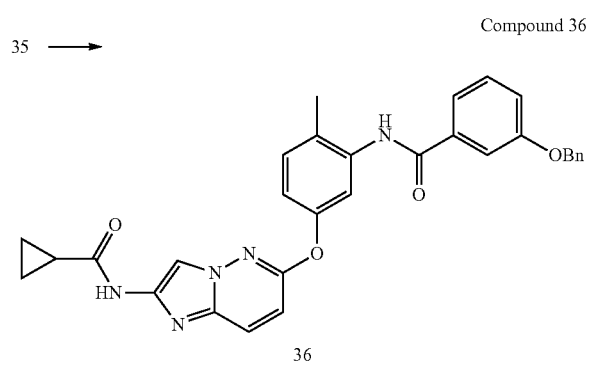 [SMILES: Cc1ccc(Oc2ccc3nc(NC(=O)C4CC4)cn3n2)cc1NC(=O)c1cccc(OCc2ccccc2)c1]

36

Compound 36 was synthesized from N-(5-(2-aminoimidazo[1,2-b]pyridazin-6-yloxy)-2-methylphenyl)-3-benzyloxybenzamide (compound 35, 1.00 g) following the same procedure as the synthesis of compound 24. The crude material (0.80 g) was purified by flash chromatography (gradient from dichloromethane to ethyl acetate with 10% methanol). The organic solution was evaporated and dried in high vacuum giving compound 36 as a greenish foam (0.31 g). MS: m/z 534.2 (M+1) (positive ionization mode). $^1$H NMR: (DMSO-d6): 11.06 (s, 1H), 9.89 (s, 1H), 8.01 (d, J=10.0 Hz, 1H), 7.29 (s, 1H), 7.61-7.52 (m, 2H), 7.48-7.20 (m, 9H), 7.07 (dd, J=8.5 Hz, 2.5 Hz, 1H), 7.04 (d, J=10.0 Hz, 1H), 5.17 (s, 2H), 2.24 (s, 3H), 1.93-1.87 (m, 1H), 0.83-0.76 (m, 4H).

Example 12

Preparation of Compound 40

34 → Compound 37

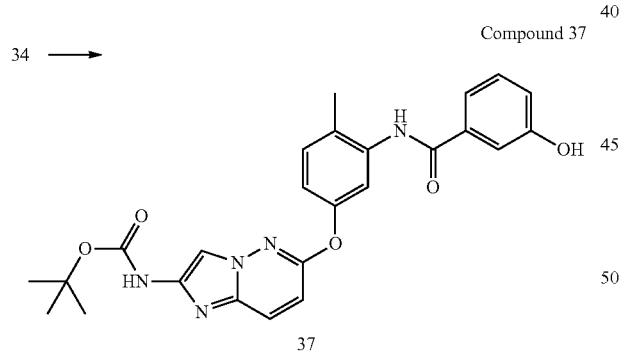

37 tert-butyl N-(5-(2-aminoimidazo[1,2-b]pyridazin-6-yloxy)-2-methylphenyl)-3-benzyloxybenzamide carbamate (compound 34, 1.00 g, 1.70 mmol) was dissolved in N,N-dimethylformamide (20 mL). Ammonium formate (5.00 g, 79.40 mmol) was added followed by palladium hydroxide (0.20 g, 20% Pd(OH)$_2$, wet). The suspension was heated at 80° C. for 3 h, The catalyst was filtered off on cellite pad and the solvent was evaporated. The residue was treated with saturated sodium bicarbonate and the resulting white solid was filtered off and washed with water. Drying in high vacuum overnight gave white solid (Compound 37, 1.01 g). MS: m/z 476.2 (M+1) (positive ionization mode).

37 → Compound 38

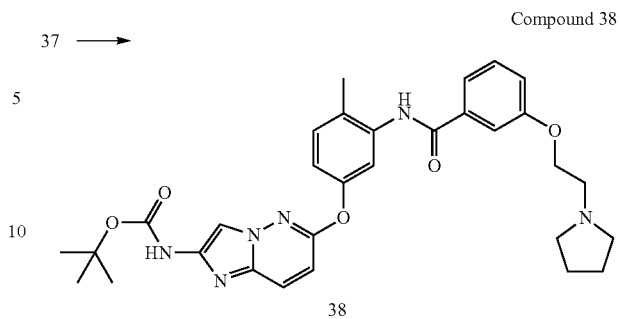

38 tert-butyl N-(5-(2-aminoimidazo[1,2-b]pyridazin-6-yloxy)-2-methylphenyl)-3-hydroxybenzamide carbamate (compound 37, 1.70 g, 3.57 mmol) was dissolved in N,N-dimethylformamide (50 mL). 1-(2-Chloroethyl)pyrrolidine hydrochloride (6.10 g, 35.9 mmol) was added followed by cesium carbonate (10.0 g, 30.7 mmol). The suspension was heated at 60° C. for 3 h. The solvent was evaporated and the remainder was partitioned between ethyl acetate and brine. The organic solution was separated, dried with magnesium sulfate and evaporated. The crude material was purified by flash chromatography using gradient of dichloromethane to ethyl acetate:methanol:triethylamine 90:5:5. The solvent was evaporated leaving yellow foam (0.53 g). MS: m/z 573.3 (M+1) (positive ionization mode).

38 → Compound 39

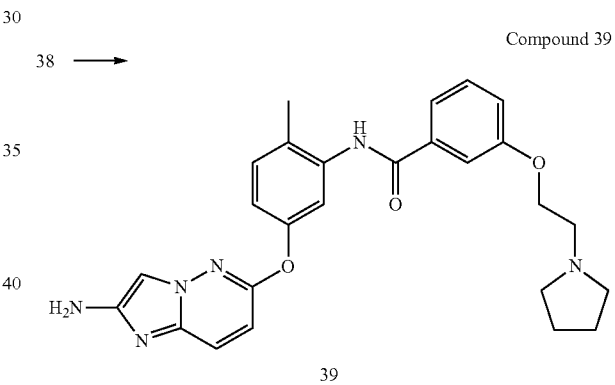

39

Compound 39 was synthesized from tert-butyl 3-(2-(pyrrolidin-1-yl)ethoxy)-N-(5-(2-aminoimidazo[1,2-b]pyridazin-6-yloxy)-2-methylphenyl)benzamide carbamate (compound 38, 0.53 g) following the same procedure as the synthesis of compound 23, resulting in a yellow foam (0.32 g). MS: m/z 473.3 (M+1) (positive ionization mode).

39 → Compound 40

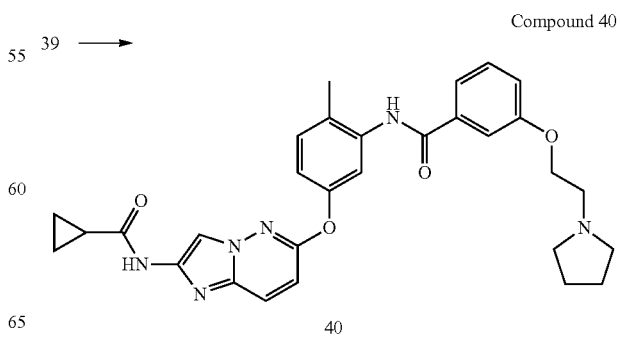

40

3-(2-(Pyrrolidin-1-yl)ethoxy)-N-(5-(2-aminoimidazo[1,2-b]pyridazin-6-yloxy)-2-methylphenyl)benzamide (compound 39, 0.32 g, 0.60 mmol) was dissolved in tetrahydrofuran (10 mL). Triethylamine (0.28 mL, 1.98 mmol) was added followed by cyclopropylcarbonyl chloride (68 mg, 0.66 mmol). The solution was stirred for 1 h. The solvent was evaporated and the residue was partitioned between ethyl acetate and saturated sodium bicarbonate. The organic phase was separated and dried with magnesium sulfate. Removal of the solvent provided crude compound a yellow foam. The crude material was purified by flash chromatography (gradient from dichloromethane to ethyl acetate with 10% 7M ammonia in methanol). The organic solution was evaporated and dried in high vacuum giving a yellow foam (0.18 g). Further purification was performed by preparative HPLC using Varian PrepStar with water-acetonitrile solvent system each containing 0.1% formic acid as modifier and "Load & Lock" 50×250 mm column with C18 reverse phase silica gel. The obtained solution of the product was converted to free base using dichloromethane with 10% methanol and aqueous sodium bicarbonate, dried with sodium sulfate, and concentrated. The product was a yellow solid (86 mg). MS: m/z 541.3 (M+1), (positive ionization mode) $^1$H NMR: (DMSO-d6): 11.06 (s, 1H), 9.88 (s, 1H), 8.02 (d, J=9.5 Hz, 1H), 7.93 (s, 1H), 7.55-7.48 (m, 2H), 7.41 (dd, J=8.0 Hz, 8.0 Hz, 1H), 7.33 (d, J=9.0 Hz, 1H), 7.28 (d, J=2.5 Hz, 1H), 7.17-7.12 (m, 1H), 7.08 (dd, J=8.5 Hz, 2.5 Hz, 1H), 7.03 (d, J=9.5 Hz, 1H), 4.12 (t, J=6.0 Hz, 2H), 2.80 (t, J=6.0 Hz, 2H), 2.25 (s, 3H), 1.94-1.88 (m, 1H), 1.69-1.63 (m, 4H), 0.83-0.73 (m, 4H).

Example 13

Vascular Endothelial Growth Factor Receptor 2 (VEGF-R2) Cellular Assay

The Human Umbilical Endothelial (HUE) cell line expresses high levels of VEGF-R2, Compounds of the invention are tested for the ability to inhibit tyrosine auto-phosphorylation of this receptor after stimulation with vascular endothelial growth factor A (VEGF-A). HUE cells are plated into 48-well cell culture plates in Endothelial Cell Growth Medium (ECGM) supplemented with 10% fetal calf serum (FCS). The cells are incubated overnight at 37° C. in Endothelial Cell Basal Medium (ECBM) supplemented with 10% FCS, On the day of the assay the compounds are 1:3 serial diluted from 10 mM stocks in 100% DMSO and then 1:100 diluted to each well of cells in ECBM without FCS to create final solutions containing 1% DMSO and an 8-point compound dose response curve starting at 1.0E-07 M, 1.0E-08 M, or 1.0E-09 M. Compounds of the invention are added in duplicate to rows A, B, E, and F of the 48-well cell culture plate. Cells in Row C are treated with 1% DMSO to serve as High control, and cells in row D are treated with 1.0E-05 M Staurosporine to serve as Low Control for the assay. Cells are incubated for 90 minutes at 37° C. in ECBM with the serial diluted compounds of the invention and then stimulated for 3 minutes with 100 ng/ml VEGF-A. Cells are lysed, and then levels of phosphorylated VEGF-R2 are determined in a sandwich ELISA assay formatted in a 96-well plate using a VEGF-R2 specific capture antibody and an anti-phosphotyrosine VEGF-R2 detection antibody. The raw data are converted to percent tyrosine phosphorylated VEGF-R2 with respect to the on plate High and Low controls. IC$_{50}$ values are determined by fitting the converted 8-point dose response data to a four-parameter logistic equation using GraphPad Prism® 5.01 software.

Example 14

Platelet-Derived Growth Factor Receptor-beta (PDGFR-beta) Cellular Assay

The murine embryonal fibroblast cell line NIH3T3 expresses endogenously high levels of PDGFR-beta. Compounds of the invention are tested for the ability to inhibit tyrosine auto-phosphorylation of this receptor after stimulation with platelet-derived growth factor BB (PDGF-BB). The NIH3T3 cells are plated into 48-well cell culture plates in Dulbecco's Modified Eagle Medium (DMEM) supplemented with 10% FCS. The medium is removed and then replaced with DMEM and cells serum starved overnight at 37° C. On the day of the assay the compounds are 1:3 serial diluted from 10 mM stocks in 100% DMSO and then are 1:100 diluted to each well of cells in DMEM without FCS to create final DMSO solutions containing 1% DMSO and an 8-point compound dose response curve starting at 1.0E-06 M, 1.0E-07 M, or 1.0E-08 M. Compounds of the invention are added in duplicate to rows A, B, E, and F of the 48-well plate. Cells in Row C are treated with 1% DMSO to serve as High control, and cells in row D are treated with 1.0E-05 M Staurosporine to serve as Low Control for the assay. Cells are incubated for 90 minutes at 37° C. in DMEM with the serial diluted compounds and then stimulated for 3 minutes with 100 ng/ml PDGF-BB. Cells are lysed, and then levels of phosphorylated PDGFR-beta are determined in a sandwich ELISA assay formatted in a 96-well plate using a PDGFR-beta specific capture antibody and an anti-phosphotyrosine PDGFR-beta detection antibody. The raw data are converted to percent phosphorylated PDGFR-beta with respect to the on plate High and Low controls. IC$_{50}$ values are determined by fitting the converted 8-point dose response data to a four-parameter logistic equation using GraphPad Prism® 5.01 software.

Example 15

VEGF-R2 Binding Assay

A competition binding assay (DiscoveRx KINOMEscan™) was used to measure the ability of the compound to compete for binding of an immobilized adenosine triphosphate (ATP) site directed ligand using a DNA-tagged vascular endothelial growth receptor 2 (VEGFR2) as the target. The ability of the test compound to compete with the immobilized ligand was measured using quantitative polymerase chain reaction (qPCR) of the DNA tag (Fabian, et al, *Nature Biotechnology* (2005) 23, 329-336; Karaman, et al, *Nature Biotechnology* (2008) 26, 127-132).

A VEGFR2 tagged T7 phage strain was prepared in an *Escherichia coli* (*E. coli*) derived from the BL21 strain. The *E. coli* were grown to log-phase, infected with VEGFR2 tagged T7 phage and then incubated with shaking at 32° C. until lysis. The lysate containing the kinase was then centrifuged and filtered to remove cell debris. Affinity resin for the VEGFR2 assay was prepared by treating Streptavidin-coated magnetic beads with a biotinylated small molecule ligand for 30 minutes at room temperature. The beads were blocked with excess biotin and then washed with blocking buffer (SeaBlock (Pierce), 1% bovine serum albumin, 0.17% phosphate buffered saline, 0.05% Tween 20, 6 mM dithiothreitol). The binding reaction was initiated by combining in a well of a polystyrene 96-well plate, DNA tagged VEGFR2, liganded affinity beads and the serial diluted test compound in 1× binding buffer (20% SeaBlock, 0.17× phosphate buffered saline, 0.05% Tween 20, 6 mM dithiothreitol) in a final volume of 0.135 ml. The assay plates were incubated at room temperature with shaking for 1 hour and then the beads were washed with wash buffer (1× phosphate buffered saline, 0.05% Tween 20). The beads were re-suspended in elution buffer (1× phosphate buffered saline, 0.05% Tween 20, 0.05 pM non-biotinylated affinity ligand) and incubated at room temperature with shaking for 30 minutes. The VEGFR2 concentration in the eluate was measured using qPCR.

An 11-point dose response curve of 3-fold serial diluted test compound starting at 1 μM was used to determine the VEGFR2 binding constant (Kd). The compounds were prepared in 100% DMSO at 100× the final test concentration and then diluted to 1× in the assay for final DMSO concentration of 1%. Binding constants were calculated with standard dose-response curve using the Hill equation with Hill slope set to −1. Curves were fit using a non-linear least square fit with the Levenberg-Marquardt algorithm.

TABLE 3

$K_d$ values of selected compounds.

| Compound ID | $K_d$ |
|---|---|
| I-1 | 1.1 |
| I-2 | 1.6 |
| I-4 | 1.3 |
| I-5 | 1.1 |
| I-6 | 0.41 |
| 24 | 2.5 |
| 27 | 1.9 |
| 30 | 110 |
| 33 | 0.44 |
| 36 | 6.1 |
| 40 | 1 |

Example 16

Novel Compounds Prepared as Mucus Penetrating Particles (MPP)

Compounds of the present invention synthesized in accordance with the preceding Examples were formulated as mucus penetrating particles (MPP). Specifically, compounds I-2, compound I-5, and compound I-6 were each milled in the presence of Pluronic F127 (F127) to determine whether F127 1) aids particle size reduction to several hundreds of nanometers and 2) physically (non-covalently) coats the surface of generated nanoparticles with a mucoinert coating that would minimize particle interactions with mucus constituents and prevent mucus adhesion.

A milling procedure was employed in which an aqueous dispersion containing coarse drug particles and Pluronic F127 (F127) was milled with grinding medium until particle size was reduced below 400 nm as measured by dynamic light scattering. Table 4 lists the size of particles and polydispersity index (a measure of the width of the particle size distribution) generated using this technique. In this example suspensions were buffered using DPBS (Dulbecco's Phosphate-Buffered Saline) which yields a suspension that is both isotonic and has a physiologically relevant pH.

TABLE 4

Particle Size for Compounds Formulated as MPP

| Compound ID | Particle Size (nm) | Polydispersity Index (PDI) |
|---|---|---|
| I-2 | 259 | 0.292 |
| I-5 | 276 | 0.160 |
| I-6 | 245 | 0.206 |

In order to determine whether the generated nanoparticles have reduced interactions with mucins and are therefore able to move within mucus without becoming trapped, particles were incubated with human cervicovaginal mucus (CVM) and observed via dark field microscopy. In a typical experiment, ≤1 μL of the nanoparticle suspension was added to 20 μl of CVM. Observations were made in a minimum of three distinct and randomly selected areas of the CVM sample. Control particles with known behavior were used to qualify the CVM sample as appropriate for the assay. For compound I-5 and compound I-6, mobility in mucus was observed and therefore the nanoparticles were deemed to be effective MPP. Compound I-2 is soluble in the low pH of CVM, which is only an issue in the assay, not in intended target sites such as the eye, which has a neutral pH.

Example 17

Compound I-2 Formulated as Solution

Solutions of I-2 were formulated with F127 or Tween 80, and under a range of pH values. Briefly, I-2 was first completely solubilized using an acidic solution (0.1 N HCl) at a high concentration of ~5% (w/v). The final formulation was diluted to a solution consisting of 0.5% (w/v) I-2 into buffered solution containing F127 or Tween 80 as described in Table 5. Following dilution, the pH of the formulations was measured using pH indicator strips (PEHANON) and confirmed to be within expected range (±0.5 units of target pH).

TABLE 5

Solutions of I-2 at 0.5% (w/v) combined with solubilizers Tween 80 or F127, and buffers. The values listed are final concentration of each constituent in the formulation.

| I-2 % (w/v) | Solubilizer % (w/v) | Buffer | Target pH |
|---|---|---|---|
| 0.5 | Tween 80 (0.5) | 20 mM Citrate | 6 |
| | F127 (0.5) | 20 mM Citrate | 6 |
| | | 1× Phosphate buffered saline (PBS) | 7 |
| | | 20 mM Borate | 8 |
| | | 40 mM Borate | 8 |
| | | 20 mM Tris | 8 |

Physical and chemical stability of the solutions at room temperature (20-25° C.) were assessed after 7-10 days ($t_{final}$). Physical instability in a solution can manifest as the precipitation and sedimentation of the drug of interest and excipients over time. To assess physical stability, the formulations at $t_{final}$ were first filtered through a 300 kDa modified polyethersulfone filter membrane (Nanosep) to remove any precipitate in the solution. The concentration of I-2 in the filtrates was then measured and compared to that at t=0. The purity of I-2 in the unfiltered solution was also evaluated at $t_{final}$, to further confirm chemical stability. This parameter is defined by the area under the signal peak that is attributed to compound I-2 as a percentage of all peaks reported by in the sample by HPLC (% peak area). The content and purity results for all formulations are reported in Table 6.

TABLE 6

Chemical stability and purity of various solutions containing Compound I-2.

| Solubilizer % (W/V) | Buffer | API % (w/v) at t = 0 | API % (w/v) at t = $t_{final}$* | % concentration change** | API % peak area at t = $t_{final}$ |
|---|---|---|---|---|---|
| Tween 80 (0.5%) | 20 mM Citrate | 0.45 | 0.44 | −2.2 | 97.1 |
| F127 (0.5%) | 20 mM Citrate | 0.52 | 0.50 | −3.8 | 98.0 |
| | 1x PBS | 0.52 | 0.51 | −1.9 | 98.3 |
| | 20 mM Borate | 0.54 | 0.51 | −5.6 | 98.5 |
| | 40 mM Borate | 0.52 | 0.52 | 0.0 | 98.5 |
| | 20 mM Tris | 0.52 | not determined | not determined | not determined |

*($t_{final}$ = 10 days for formulation in Tween 80, and 7 days for formulations in F127).
**% concentration change = 100 * ($API_{t=final}$ − $API_{t=0}$)/$API_{t=0}$ The majority of the solution formulations of I-2 were physically and chemically stable, with the exception of the formulation buffered in 20 mM Tris (pH 8). This formulation exhibited major physical instability (i.e., precipitation), and was not evaluated at $t_{final}$. In all other formulations, the concentrations of I-2 after 7-10 days storage were maintained at >94% of their respective original concentrations measured at t=0. The purities of I-2 in these formulations, as defined by % peak area for all solutions, were also comparable to that of the bulk API (% peak area=98.0).

Example 18

Exposure in the Back of the Eye from Topical Administration of Compound I-2 Solution In order to demonstrate that topical administration of novel compound solution results in drug exposure at the back of the eye, pharmacokinetic (PK) studies were performed with a solution of compound I-2 as described in Example 17. In this example, the formulation consisted of 0.5% I-2, 0.5% F127, in 20 mM citrate buffer pH 6.0 and NaCl (added to produce isotonic formulation). Dutch-belted rabbits were treated with a multi-dose regimen of compound I-2 solution as shown in Table 7.

TABLE 7

Study design for PK evaluation of Compound I-2 solution

| Group | Test Article | Number of Animals (n/time point) | Dose Volume | Frequency/ Duration | Terminal Time points (hours) |
|---|---|---|---|---|---|
| 1 | solution, 0.5% | 4 | 50 µL | BID 5 days | 0.5 |
| 2 | solution, 0.5% | 4 | 50 µL | BID 5 days | 1 |
| 3 | solution, 0.5% | 4 | 50 µL | BID 5 days | 2 |
| 4 | solution, 0.5% | 4 | 50 µL | BID 5 days | 4 |
| 5 | solution, 0.5% | 6 | 50 µL | BID 5 days | 8 |
| 6 | solution, 0.5% | 6 | 50 µL | BID 5 days | 12 |

BID = twice a day

The resulting drug exposure in the back of the eye is shown in Table 8. The portion of the retina and choroid collected and analyzed was an 8-mm round punch where the macula is located in humans. These results demonstrate that topical administration of a solution of compound I-2 results in drug exposure in the retina and choroid in vivo. Draize-Ocular Irritation assessments were also performed during these studies and no irritation was seen for any of the formulations.

TABLE 8

PK parameters of I-2

| PK Parameters | Plasma | Retina | Choroid |
|---|---|---|---|
| Tmax (hours) | 0.5 | 0.5 | 2.0 |
| Cmax (nM) | 5.96 | 218 | 1790 |
| $t^{1/2}$ (hours) | 3.63 | NC | NC |
| AUC0-12 hr (nM * h) | 25.6 | 2055 | 12500 |

Tmax: time at maximum concentration;
Cmax: maximum concentration in tissue;
$t^{1/2}$: drug elimination half-life;
AUC0-12 hr: the area under the curve vs. time integrated between time = 0-12 hrs;
NC: Not Calculated.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

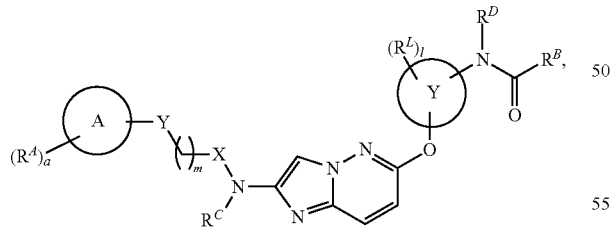

(I)

or a pharmaceutically acceptable salt thereof;
wherein:
X is a bond, —C(=O)—, —S(=O)—, or —S(=O)$_2$—;
Y is a bond, —C(=O)—, —S(=O)—, or —S(=O)$_2$—;
Ring A is substituted or unsubstituted, 4-membered, monocyclic heterocyclyl, substituted or unsubstituted, 7-membered, monocyclic heterocyclyl, or substituted or unsubstituted, 7- to 10-membered, spiro bicyclic heterocyclyl, wherein one or two atoms in the heterocyclic ring are independently selected from the group consisting of oxygen and nitrogen;

Ring Y is substituted or unsubstituted carbocyclyl, substituted or unsubstituted heterocyclyl, substituted or unsubstituted aryl, or substituted or unsubstituted heteroaryl;

each instance of $R^A$ is independently hydrogen, halogen, substituted or unsubstituted alkyl, —OR$^{A1}$, —N(R$A^{A1}$)$_2$, oxo, or a nitrogen protecting group when attached to a nitrogen atom;

each instance of RA$^{A1}$ is independently hydrogen, substituted or unsubstituted alkyl, a nitrogen protecting group when attached to a nitrogen atom, or an oxygen protecting group when attached to an oxygen atom, or two instances of RA$^{A1}$ are joined to form substituted or unsubstituted heterocyclyl;

a is 0, 1, 2, or 3;
$R^B$ is substituted or unsubstituted alkyl or of the formula:

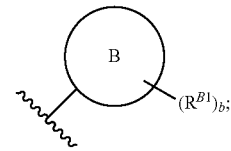

Ring B is substituted or unsubstituted carbocyclyl, substituted or unsubstituted heterocyclyl, substituted or unsubstituted aryl, or substituted or unsubstituted heteroaryl;

each instance of RB$^{B1}$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1a}$, —N(R$^{B1a}$)$_2$, —SR$^{B1a}$, —CN, —SCN, —C(=NR$^{B1a}$)R$^{B1a}$, —C(=NR$^{B1a}$)OR$^{B1a}$, —C(=NR$^{B1a}$)N(R$^{B1a}$)$_2$, —C(=O)R$^{B1a}$, —C(=O) OR$^{B1a}$, —C(=O)N(R$^{B1a}$)$_2$, —NO$_2$, —NR$^{B1a}$C (=O)R$^{B1a}$, —NR$^{B1a}$C(=O)OR$^{B1a}$, —NR$^{B1a}$C (=O)N(R$^{B1a}$)$_2$, —OC(=O)R$^{B1a}$, —OC(=O) OR$^{B1a}$, —OC(=O)N(R$^{B1a}$)$_2$, or a nitrogen protecting group when attached to a nitrogen atom, or two instances of R$^{B1}$ are joined to form substituted or unsubstituted carbocyclyl, substituted or unsubstituted heterocyclyl, substituted or unsubstituted aryl, or substituted or unsubstituted heteroaryl;

each instance of R$^{B1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{B1a}$ are joined to form substituted or unsubstituted heterocyclyl;

b is 0, 1, 2, 3, 4, or 5;

$R^C$ is hydrogen, substituted or unsubstituted $C_{1-6}$ alkyl, or a nitrogen protecting group;

$R^D$ is hydrogen, substituted or unsubstituted $C_{1-6}$ alkyl, or a nitrogen protecting group;

each instance of $R^L$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{L1}$, —$N(R^{L1})_2$, —$SR^{L1}$, —CN, —SCN, —C(=NR^{L1})R^{L1}, —C(=NR^{L1})OR^{L1}, —C(=NR^{L1})N(R^{L1})_2, —C(=O)R^{L1}, —C(=O)OR^{L1}, —C(=O)N(R^{L1})_2, —NO_2, —NR^{L1}C(=O)R^{L1}, —NR^{L1}C(=O)OR^{L1}, —NR^{L1}C(=O)N(R^{L1})_2, —OC(=O)R^{L1}, —OC(=O)OR^{L1}, or —OC(=O)N(R^{L1})_2, or two instances of RL are joined to form substituted or unsubstituted carbocyclyl, substituted or unsubstituted heterocyclyl, substituted or unsubstituted aryl, or substituted or unsubstituted heteroaryl;

each instance of $R^{L1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{L1}$ are joined to form substituted or unsubstituted heterocyclyl;

l is 0, 1, 2, 3, or 4; and m is 0, 1, 2, 3, 4, or 5.

2. The compound of claim 1, wherein the compound is of the formula:

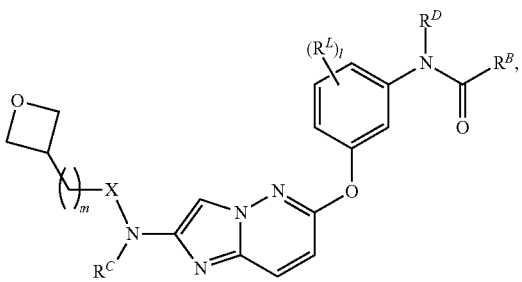

or a pharmaceutically acceptable salt thereof.

3. The compound of claim 1, wherein the compound is of the formula:

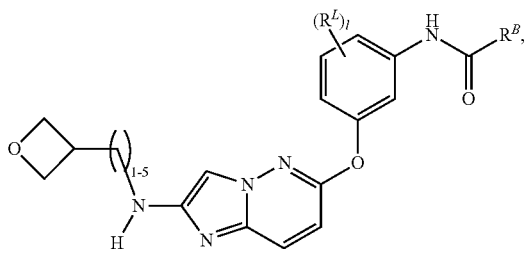

or a pharmaceutically acceptable salt thereof.

4. The compound of claim 1, wherein the compound is of the formula:

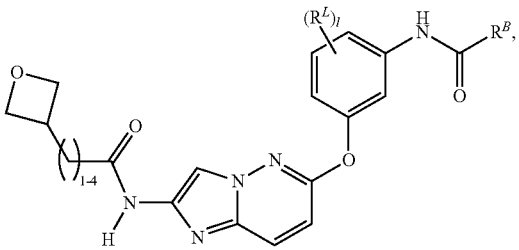

or a pharmaceutically acceptable salt thereof.

5. The compound of claim 1, wherein the compound is of the formula:

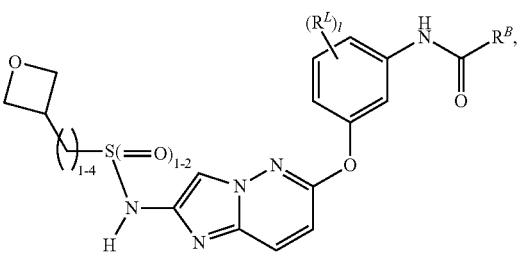

or a pharmaceutically acceptable salt thereof.

6. The compound of claim 1, wherein the compound is of the formula:

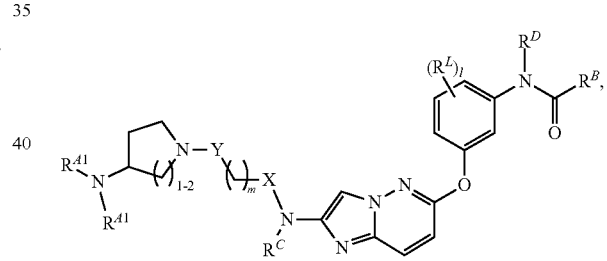

or a pharmaceutically acceptable salt thereof.

7. The compound of claim 1, wherein the compound is of the formula:

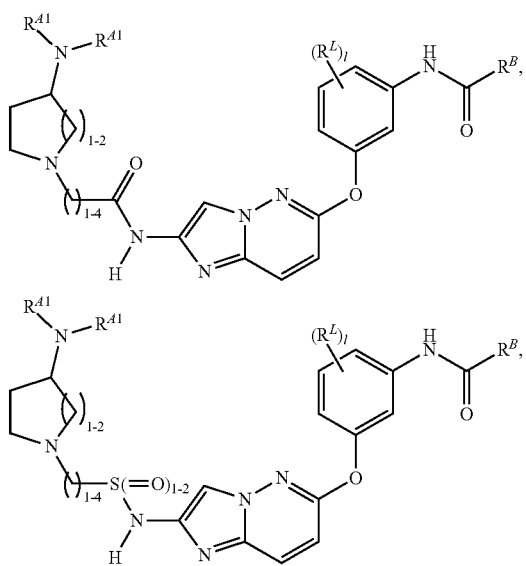

or a pharmaceutically acceptable salt thereof.

8. The compound of claim 1, wherein the compound is of the formula:

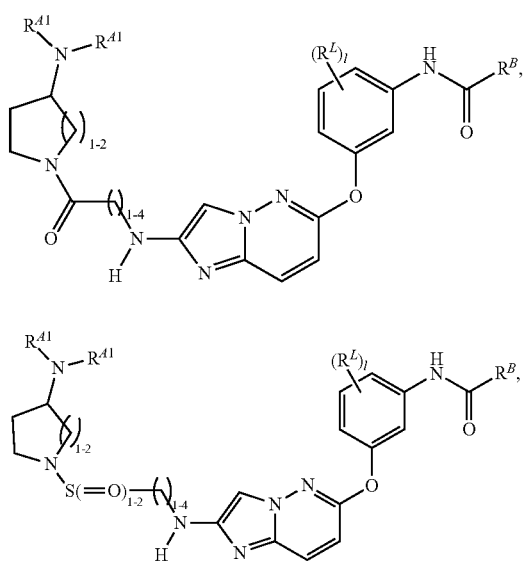

or a pharmaceutically acceptable salt thereof.

9. The compound of claim 1, wherein the compound is of the formula:

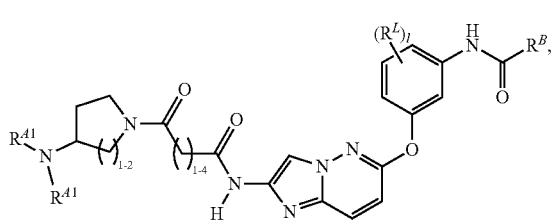

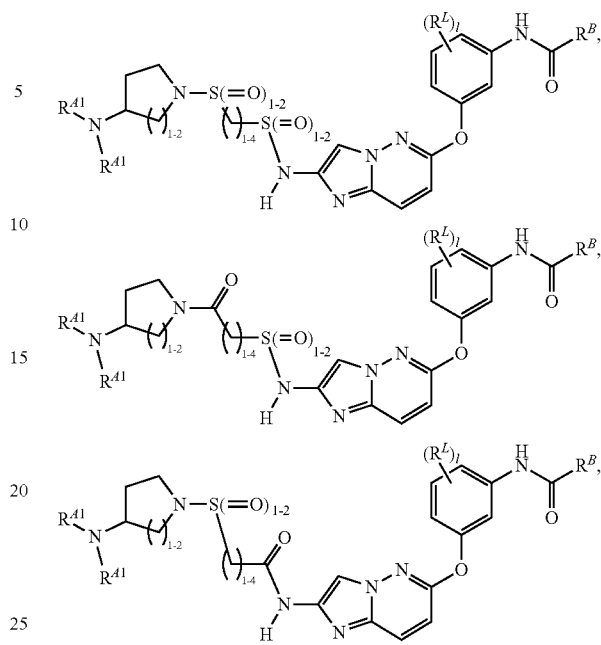

or a pharmaceutically acceptable salt thereof.

10. The compound of claim 1, wherein the compound is of the formula:

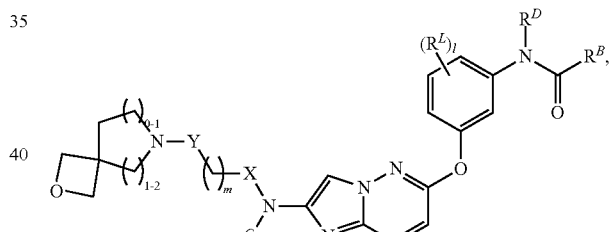

or a pharmaceutically acceptable salt thereof.

11. The compound of claim 1, wherein the compound is of the formula:

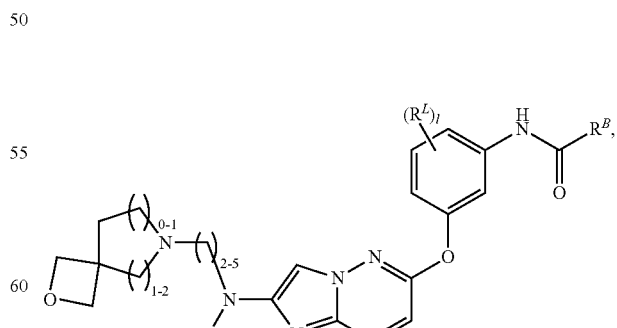

or a pharmaceutically acceptable salt thereof.

12. The compound of claim 1, wherein the compound is of the formula:

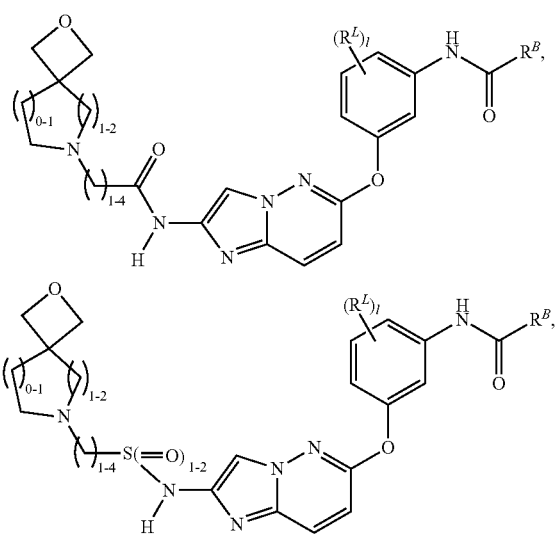

or a pharmaceutically acceptable salt thereof.

13. The compound of claim 1, wherein the compound is of the formula:

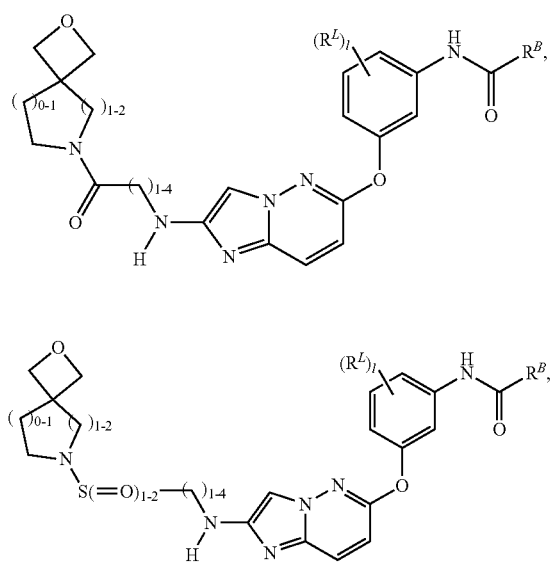

or a pharmaceutically acceptable salt thereof.

14. The compound of claim 1, wherein the compound is of the formula:

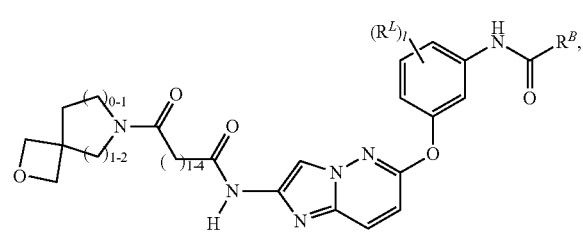

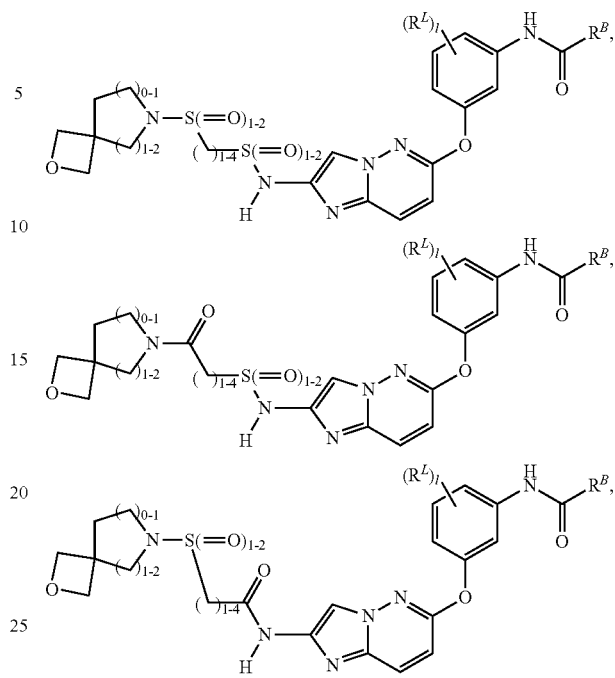

or a pharmaceutically acceptable salt thereof.

15. The compound of claim 1, wherein the compound is of the formula:

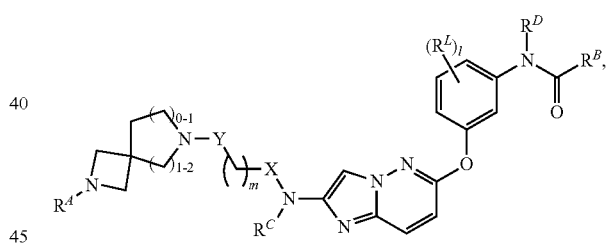

or a pharmaceutically acceptable salt thereof.

16. The compound of claim 1, wherein the compound is of the formula:

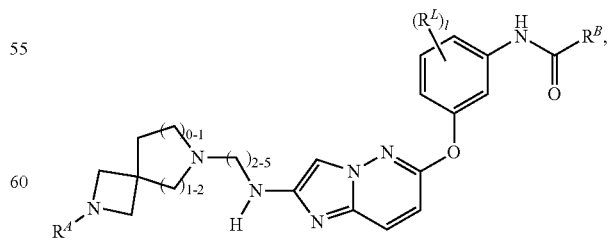

or a pharmaceutically acceptable salt thereof.

17. The compound of claim 1, wherein the compound is of the formula:

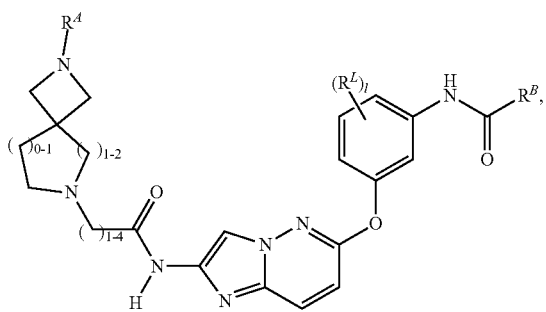

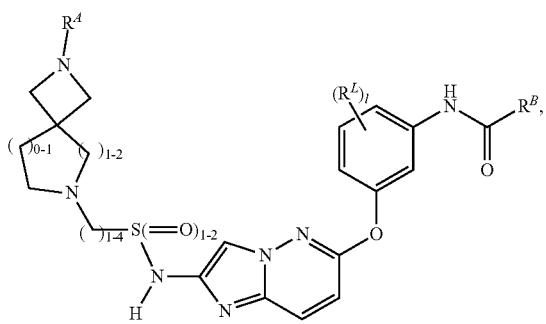

or a pharmaceutically acceptable salt thereof.

18. The compound of claim 1, wherein the compound is of the formula:

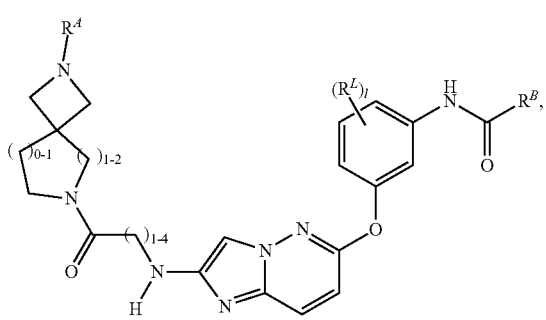

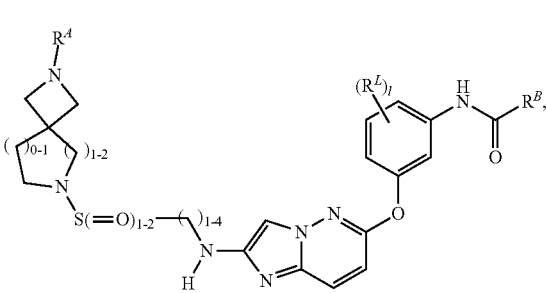

or a pharmaceutically acceptable salt thereof.

19. The compound of claim 1, wherein the compound is of the formula:

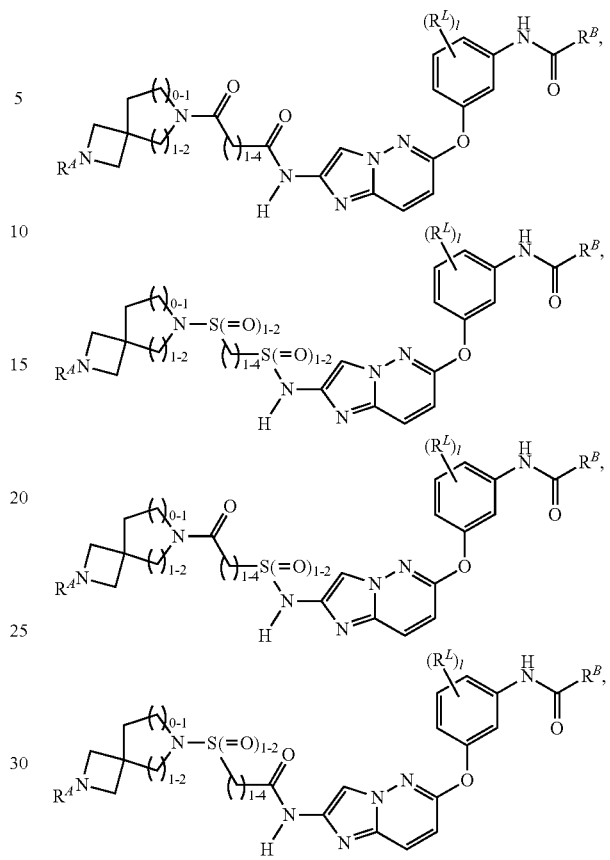

or a pharmaceutically acceptable salt thereof.

20. The compound of claim 1, wherein the compound is of the formula:

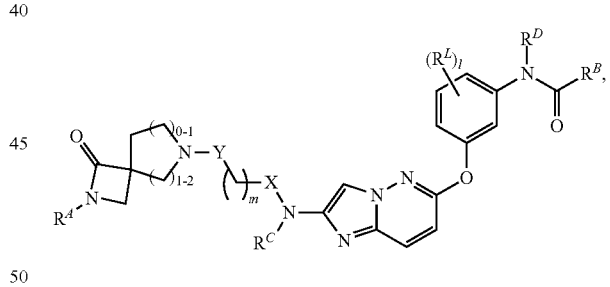

or a pharmaceutically acceptable salt thereof.

21. The compound of claim 1, wherein the compound is of the formula:

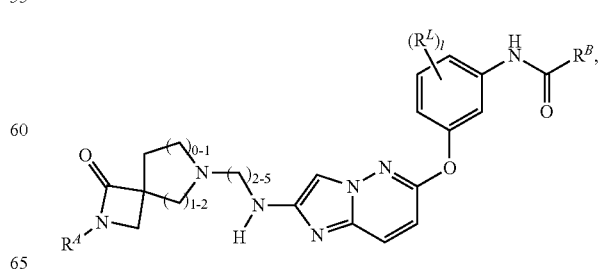

or a pharmaceutically acceptable salt thereof.

22. The compound of claim 1, wherein the compound is of the formula:

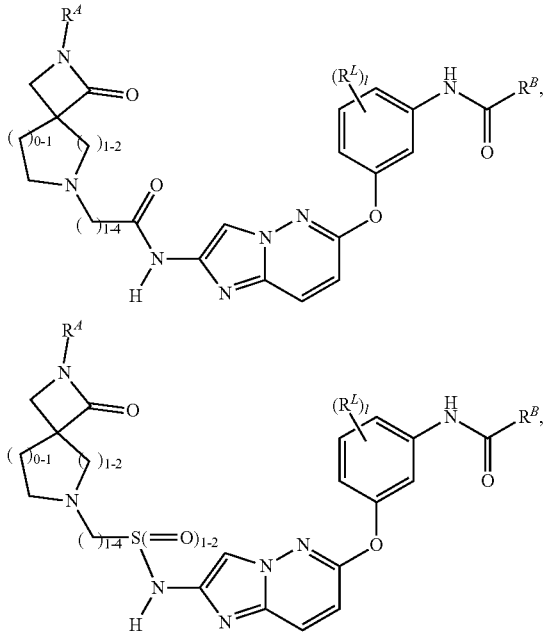

or a pharmaceutically acceptable salt thereof.

23. The compound of claim 1, wherein the compound is of the formula:

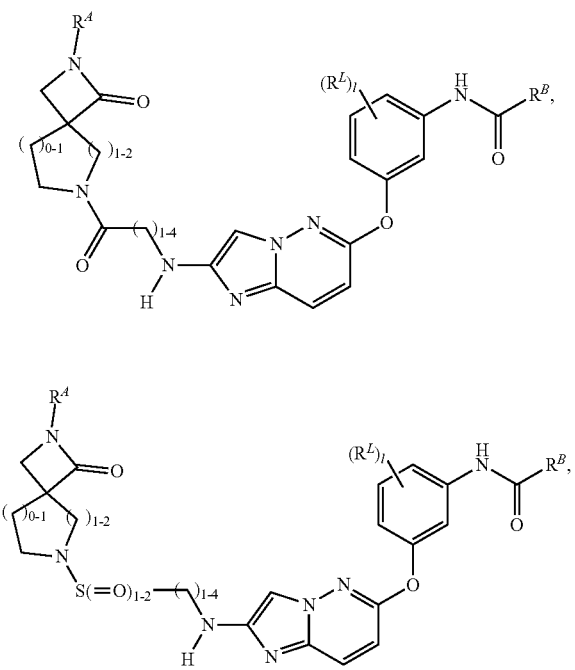

or a pharmaceutically acceptable salt thereof.

24. The compound of claim 1, wherein the compound is of the formula:

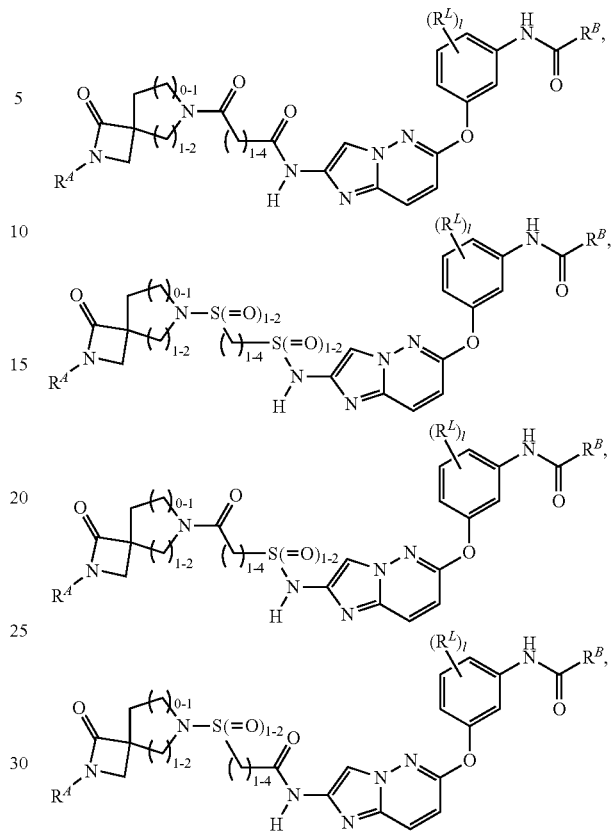

or a pharmaceutically acceptable salt thereof.

25. A pharmaceutical composition comprising the compound of claim 1, and optionally a pharmaceutically acceptable excipient.

26. The pharmaceutical composition of claim 25, wherein the pharmaceutical composition is suitable for topical administration to the eye of a subject.

27. A method of treating an ocular disease in a subject in need thereof comprising: administering to the subject a therapeutically effective amount of the compound of claim 1.

28. The method of claim 27, wherein the subject is a human.

29. The method of claim 27, wherein the ocular disease is macular degeneration, diabetic retinopathy, retinoblastoma, edema, diabetic macular edema or retinal vein occlusion.

30. The method of claim 27, wherein the ocular disease is age-related macular degeneration.

31. The method of claim 27, wherein the ocular disease is corneal neovascularization.

32. The method of 27, wherein the compound is administered to an eye of the subject.

33. The method of 27, wherein the compound is administered topically to an eye of the subject.

34. A method of inhibiting growth factor signaling in a subject in need thereof comprising:
administering to the subject a therapeutically effective amount of the compound of claim 1.

35. A method of inhibiting growth factor signaling in a cell comprising:
contacting the cell with an effective amount of the compound of claim 1.

36. The method of claim 34, wherein the cell is in vitro.

37. A kit comprising:
the compound of claim 1; and
instructions for using the kit.

38. The compound of claim 1, wherein the compound is,

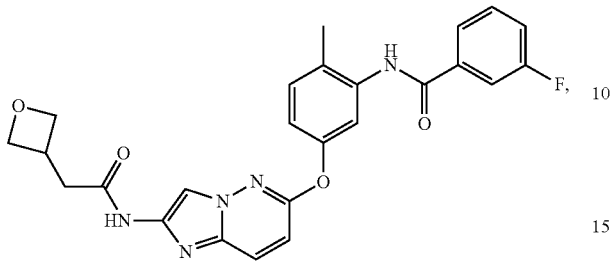

or a pharmaceutically acceptable salt thereof.

39. The compound of claim 1, wherein:
each one of $R^C$ and $R^D$ is hydrogen or unsubstituted $C_{1-6}$ alkyl; and
each of $R^L$ is halogen or unsubstituted $C^{1-6}$ alkyl.

40. The compound of claim 39, wherein:
each $R^{A1}$ is independently hydrogen or substituted or unsubstituted alkyl; and
each $R^{B1}$ is independently hydrogen, halogen, substituted or unsubstituted alkyl, substituted or unsubstituted heterocyclyl, substituted or unsubstituted heteroaryl, —$OR^{B1a}$, or —$N(R^{B1a})_2$ or two instances of $R^{B1}$ are joined to form substituted or unsubstituted heterocyclyl; and
each $R^{B1a}$ is independently hydrogen or unsubstituted $C_{1-6}$ alkyl.

41. The compound of claim 40, wherein:
each $R^{A1}$ is independently hydrogen, unsubstituted $C_{1-6}$ alkyl, —$CH_2F$, —$CHF_2$, or —$CF_3$; and each $R^{B1}$ is independently hydrogen, halogen, unsubstituted $C_{1-6}$ alkyl, —$CH_2F$, —$CHF_2$, or —$CF_3$.

42. The compound of claim 39, wherein:
each $R^{A1}$ is independently hydrogen, unsubstituted $C_{1-6}$ alkyl, —$CH_2F$, —$CHF_2$, —$CF_3$, —$(CH_2)_2Ph$, or Bn.

43. The compound of claim 42, wherein $R^B$ is

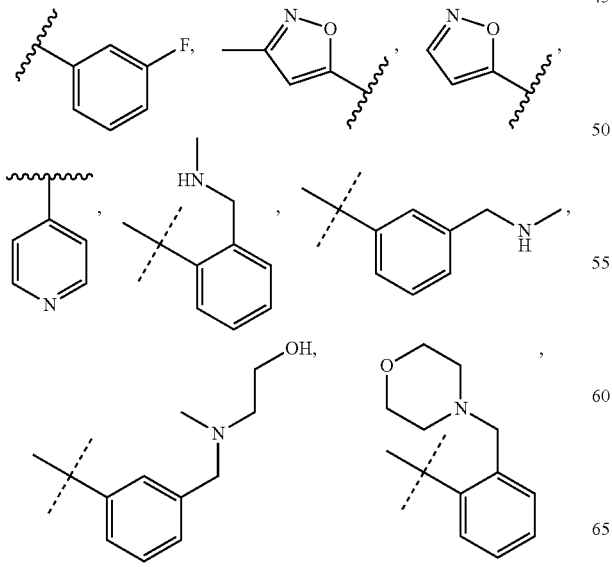

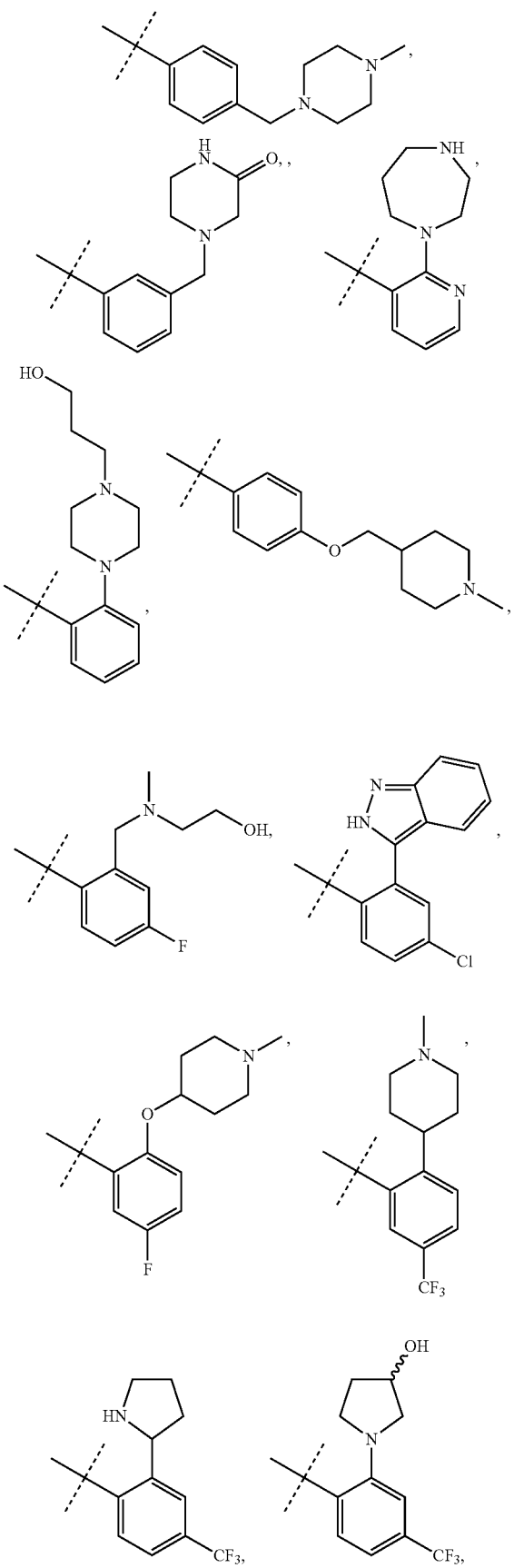

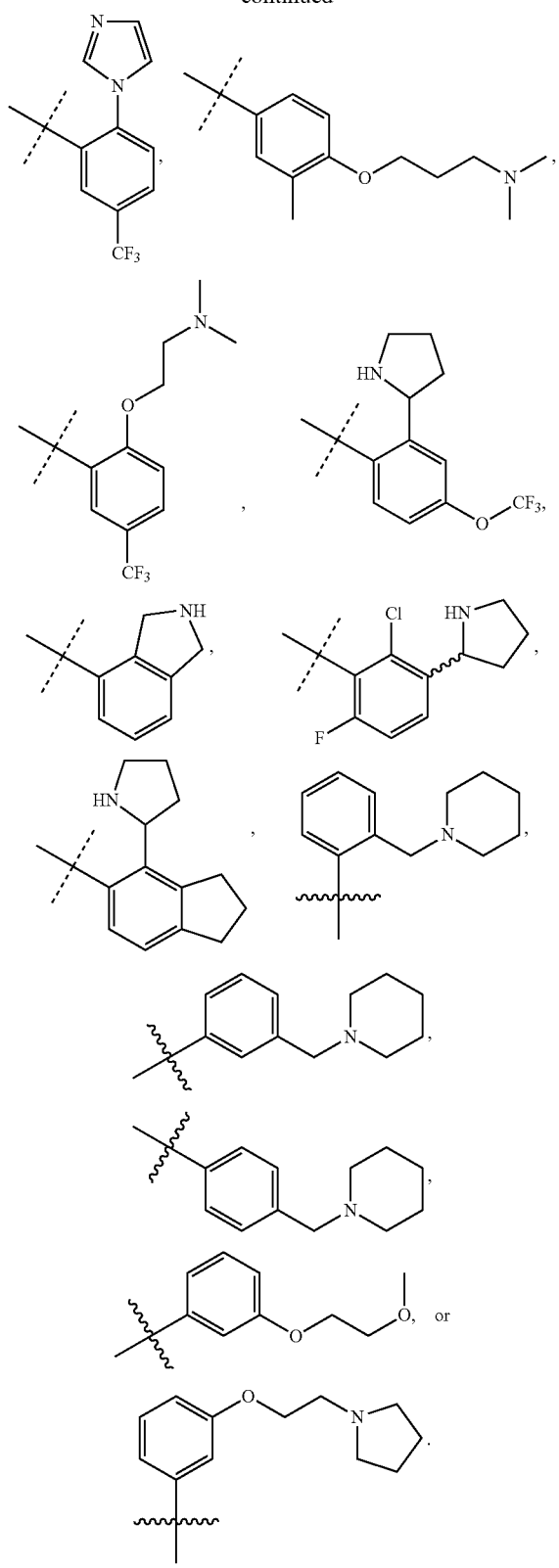
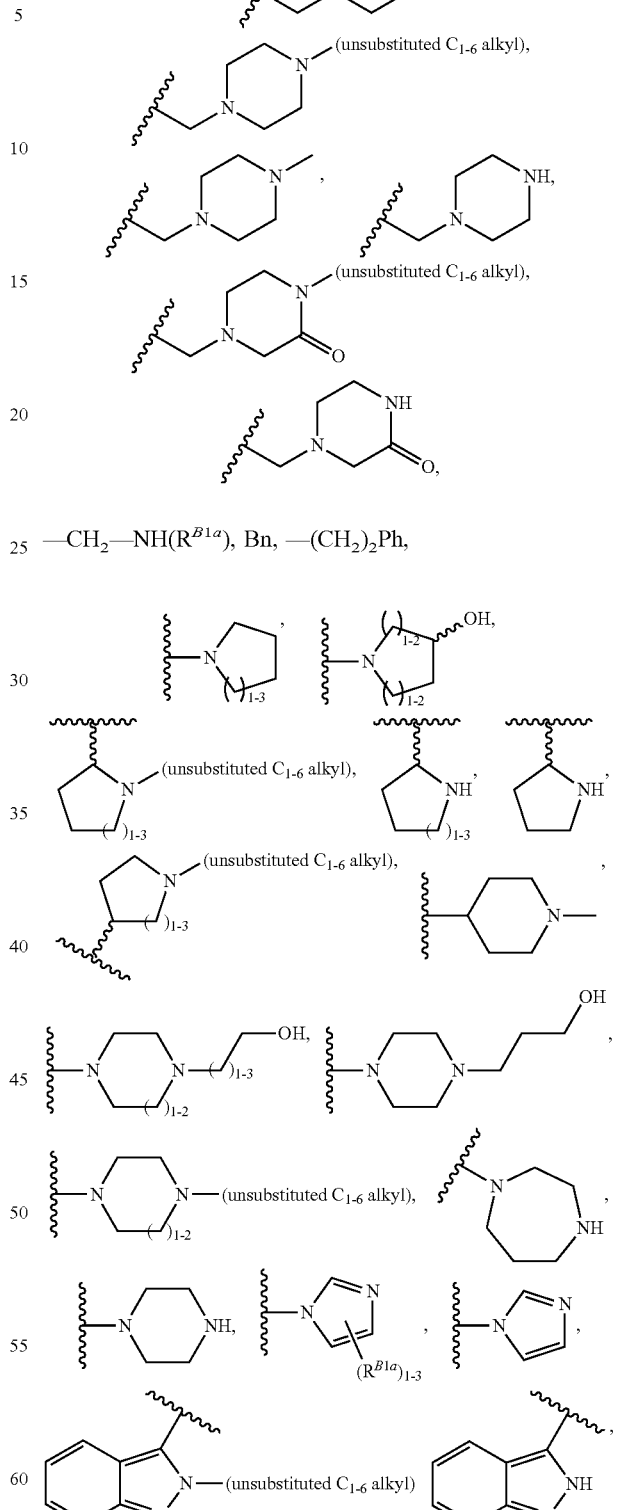
—CH$_2$—NH(R$^{B1a}$), Bn, —(CH$_2$)$_2$Ph,
44. The compound of claim 42, wherein each R$^{B1}$ is independently hydrogen, halogen, unsubstituted C$_{1-6}$ alkyl, —CH$_2$F, —CHF$_2$, —CF$_3$, —CH$_2$—N(R$^{B1a}$)$_2$, —CH$_2$—N(unsubstituted C$_{1-6}$ alkyl)—(CH$_2$)$_{2-4}$—OH, —OR$^{B1a}$, —OPh, —OBn, —O(CH$_2$)$_2$Ph, —O—CF$_3$, —O—(CH$_2$)$_{2-4}$—N(R$^{B1a}$)$_2$, —O—(CH$_2$)—N(unsubstituted C$_{1-6}$ alkyl)$_2$, —O—(CH$_2$)$_2$—N(CH$_3$)$_2$, —O—(CH$_2$)$_3$—N(CH$_3$)$_2$,

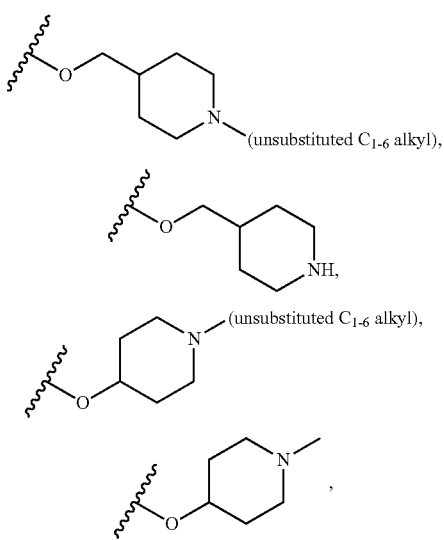
—N($R^{B1a}$)$_2$, or —CN, wherein each $R^{B1a}$ is independently hydrogen or unsubstituted $C_{1-6}$ alkyl.
45. the compound of claim 44, wherein each $RB^{B1}$ is, independently, —CH$_2$—N(CH$_3$)—(CH$_2$)$_2$—OH, —CH$_2$—NH(unsubstituted $C_{1-6}$ alkyl),
or —O—(CH$_2$)$_{2-4}$—N(unsubstituted $C_{1-6}$ alkyl)$_2$, or
46. The compound of claim 45, wherein each $R^{B1}$ is, independently, —O—(CH$_2$)$_2$—N(CH$_3$)$_2$, or —O—(CH$_2$)$_3$—N(CH$_3$)$_2$.
\* \* \* \* \*